United States Patent
Ghosh et al.

(10) Patent No.: US 9,808,527 B2
(45) Date of Patent: Nov. 7, 2017

(54) METHODS AND COMPOSITIONS FOR TREATING HIV INFECTIONS

(75) Inventors: Arun K. Ghosh, West Lafayette, IN (US); Hiroaki Mitsuya, Kumamoto (JP); Yasuhiro Koh, Kumamoto (JP)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 12/515,886

(22) PCT Filed: Nov. 20, 2007

(86) PCT No.: PCT/US2007/085265
§ 371 (c)(1),
(2), (4) Date: Jan. 12, 2010

(87) PCT Pub. No.: WO2008/133734
PCT Pub. Date: Nov. 6, 2008

(65) Prior Publication Data
US 2010/0113582 A1     May 6, 2010

Related U.S. Application Data

(60) Provisional application No. 60/866,786, filed on Nov. 21, 2006, provisional application No. 60/945,708, filed on Jun. 22, 2007.

(51) Int. Cl.
| | |
|---|---|
| *A61K 31/34* | (2006.01) |
| *A61K 31/35* | (2006.01) |
| *A61K 31/402* | (2006.01) |
| *A61K 45/06* | (2006.01) |
| *A61K 31/4025* | (2006.01) |
| *A61K 31/366* | (2006.01) |

(52) U.S. Cl.
CPC ............. *A61K 45/06* (2013.01); *A61K 31/34* (2013.01); *A61K 31/35* (2013.01); *A61K 31/366* (2013.01); *A61K 31/4025* (2013.01)

(58) Field of Classification Search
None
See application file for complete search history.

(56) References Cited

U.S. PATENT DOCUMENTS

| | | |
|---|---|---|
| 5,723,490 A | 3/1998 | Tung |
| 5,728,718 A | 3/1998 | Randad et al. |
| | (Continued) | |

FOREIGN PATENT DOCUMENTS

| | | |
|---|---|---|
| EP | 2120562 A2 | 11/2009 |
| WO | WO1996/022087 | 7/1996 |
| | (Continued) | |

OTHER PUBLICATIONS

"Short-course induction with boosted saquinavir monotherapy for naive patients with late-stage infection" by Ebrahim et al., AIDS 19, 211-12 (2005).*

(Continued)

*Primary Examiner* — Theodore R. West
(74) *Attorney, Agent, or Firm* — Schwegman Lundberg & Woessner, P.A.

(57) ABSTRACT

Described herein are compounds and compositions that are useful in the treatment of HIV, AIDS, and AIDS-related diseases. In addition, compounds are described herein that are capable of inhibiting the dimerization of HIV proteases.

2 Claims, 25 Drawing Sheets

(56) References Cited

U.S. PATENT DOCUMENTS

| | | | |
|---|---|---|---|
| 6,248,775 B1* | 6/2001 | Vazquez et al. | 514/445 |
| 6,313,345 B1 | 11/2001 | Vazquez et al. | |
| 6,649,641 B2 | 11/2003 | Wigerinck et al. | |
| 6,649,651 B1 | 11/2003 | Wigerinck et al. | |
| 7,470,506 B1* | 12/2008 | Erickson et al. | 435/5 |
| 8,501,961 B2* | 8/2013 | Ghosh | C07D 273/01 548/453 |
| 2003/0171423 A1* | 9/2003 | Erickson | A61K 31/337 514/452 |
| 2004/0039016 A1* | 2/2004 | Ghosh et al. | 514/311 |
| 2004/0122000 A1 | 6/2004 | Hale et al. | |
| 2005/0159469 A1 | 7/2005 | Randolph et al. | |
| 2005/0214890 A1 | 9/2005 | Tan et al. | |
| 2006/0293286 A1 | 12/2006 | Erickson et al. | |
| 2007/0082883 A1 | 4/2007 | Ghosh et al. | |
| 2007/0117793 A1 | 5/2007 | Ghosh et al. | |
| 2008/0096942 A1 | 4/2008 | Tenbrink et al. | |

FOREIGN PATENT DOCUMENTS

| | | |
|---|---|---|
| WO | WO 96/33187 | 10/1996 |
| WO | WO1996/33187 | 10/1996 |
| WO | WO-9633187 A1 | 10/1996 |
| WO | WO 99/67254 | 12/1999 |
| WO | WO1999/067254 | 12/1999 |
| WO | WO-9967254 A2 | 12/1999 |
| WO | WO 0076961 A1 * | 12/2000 |
| WO | WO 01/25240 | 4/2001 |
| WO | WO2001/25240 | 4/2001 |
| WO | WO-0125240 A1 | 4/2001 |
| WO | WO 03/078438 | 9/2003 |
| WO | WO-2008133734 A2 | 11/2008 |
| WO | WO 2009/091941 | 7/2009 |
| WO | WO 2010/002994 | 1/2010 |
| WO | WO 2010/006050 | 1/2010 |

OTHER PUBLICATIONS

"Analysis of the protease sequences of HIV-1 infected individuals after Indinavir monotherapy" by Sa-Filho et al., J. Clin. Virol. 28, 186-202 (2003).*

"Tipranavir" by Plosker et al., Drugs 63, 1611-18 (2003).*

"A Phase I/II Study of the Protease Inhibitor Indinavir in Children with HIV Infection" by Mueller et al., Pediatrics 102, 101-09 (1998).*

"A Preliminary Evaluation of Nelfinavir Mesylate, an Inhibitor of Human Immunodeficiency Virus (HIV)-1 Protease, to Treat HIV Infection" by Markowitz et al., J. Infect. Dis. 177, 1533-40 (1998).*

"Ritonavir boosted indinavir treatment as a simplified maintenance 'mono'-therapy for HIV infection" by Kahlert et al., AIDS 18, 955-57 (2004).*

"Lopinavir/ritonavir maintenance monotherapy after successful viral suppression with standard highly active antiretroviral therapy in HIV-1 infected patients" by Campo et al., AIDS 19, 447-52 (2005).*

"Regimen Simplification to Atazanavir-Ritonavir Alone as Maintenance Antiretroviral Therapy After Sustained Virologic Suppression" by Swindells et al., JAMA 296, 806-14 (2006).*

"A Pilot Study of Switch to Lopinavir/Ritonavir (LPV/r) Monotherapy from Nonnucleoside Reverse Transcriptase Inhibitor-Based Therapy" by Pierone et al., HIV Clin. Trials 7, 237-45 (2006).*

"Long-term efficacy of darunavir/ritonavir monotherapy in patients with HIV-1 viral suppression: week 96 results from the MONOI ANRS 136 study" by Valantin et al., J. Antimicrob. Chemother. 67, 691-95 (2012).*

Brecanavir Registry Record (retrieved Nov. 2014).*

Nakamurah et al., "Inhibitory Effects of Polyethers on Human Immunodeficiency Virus Replication," Antimicrob. Agents Chemother., 1992, 36(2), 492-494.

Ghosh et al., "Structure Based Design: Synthesis and Biological Evaluation of a Series of Novel Cycloamide-Derived HIV-1 Protease Inhibitors," J. Med. Chem., 2005, 48(10), 3576-3585.

Ghosh, et al. "TiCl4 Promoted Multi-component Reaction: A New Entry to the Functionalized α-Amino Acids," Organic Letters, vol. 7, 2005, pp. 7-10.

Ghosh et al., "Stereocontrolled Synthesis of HIV-1 Protease Inhibitors with C2-Axis of Symmetry," Tetrahedron Letters 1991, 32, 5729-33.

Ghosh et al., "An Efficient Synthesis of Hydroxyethylene Dipeptide Isosteres: The Core Unit of Potent HIV-1 Protease Inhibitors," J. Org. Chem. 1991, 56, 6500-03.

Ghosh et al., "HIV-1 Protease Inhibitors: Synthesis and biological Evalution of Glycopeptides," Drug Design and Discovery 1993, 10, 77-86.

Ghosh et al., "Potent HIV-1 Protease Inhibitors : Stereoselective Synthesis of a New Dipeptide Mimic," J. Org. Chem. 1993, 58, 1025-32.

W. J. Thompson et al., "3'-Tetrahydrofuranglycine as a Novel, Unnatural Amino Acid Surrogate for Asparagine in the Design of Inhibitors of the HIV Protease," J. Am. Chem. Soc. 1993, 115, 801-03.

Ghosh et al., "3-Tetrahydrofuran and pyranyl Urethanes as High Affinity P2-Ligands for HIV-1 Protease Inhibitors," J. Med. Chem. 1993, 36, 292-94.

Ghosh et al., "Cyclic sulfones as novel and High Affinity P2-Ligands for HIV Protease Inhibitors," J. Med. Chem. 1993, 36, 924-27.

Ghosh et al., "Potent HIV Protease Inhibitors: The Development of Tetrahydrofuranylglycines as Novel $P_2$-Ligands and Pyrazine Amides as $P_3$-Ligands," J. Med. Chem., 1993, 36, 2300-10.

Ghosh et al., "Structure Based Design of High Affinity Ligands for HIV-1 Protease Inhibitor: Replacements of Two Amides and a 10π Electron Aromatic System by a Fused Bis-tetrahydrofuran," J. Med. Chem. 1994, 37, 2506-08.

Ghosh et al., "The Development of Cyclic Sulfolanes as Novel and High Affinity P2-Ligands for HIV-1 Protease Inhibitors," J. Med. Chem. 1994, 37, 1177-86.

M. K. Holloway et al., "A Priori Prediction of Activity for HIV-1 Protease Inhibitors Employing Energy Minimization in the Active Site," J. Med. Chem., 1995, 38, 305-12.

Ghosh et al., "Synthesis and Optical Resolution of High Affinity P2-Ligands for HIV-1 Protease Inhibitors," Tetrahedron Letters, 1995, 36, 505-08.

Ghosh et al., "Cyclic Sulfone-3-Carboxamide as Novel P2-ligands for HIV-1 Protease Inhibitors," Bioorganic and Med. Chem. Letters, 1995, 5, 83-88.

Ghosh et al., "Chiral Auxiliary Mediated Conjugate reduction and Asymmetric Protonation: Synthesis of High Affinity Ligands for HIV Protease Inhibitors," J. Org. Chem. 1995, 60, 6198-6201.

Ghosh et al., "A Convenient Enzymatic Route to Optically Active 1-Aminoindan-2-ol: Versatile Ligands for HIV-1 Protease Inhibitors and Asymmetric Syntheses," Synthesis 1997, 541-44.

Ghosh et al., "Asymmetric Aldol Route to Hydroxyethylamine Dipeptide Isostere: Stereoselective Synthesis of the Core Unit of Saquinavir," J. Org. Chem. 1997, 62, 6080-82.

Ghosh et al., "Ring-Closing Metathesis Strategy to α,β-unsaturated γ- and δ-Lactones: Synthesis of Hydroxyethylamine Isosteres for HIV Protease Inhibitors," Tetrahedron Letters, 1998, 8, 4651-54.

Ghosh et al., "Transition-State Mimetics for HIV Protease Inhibitors: Stereocontrolled Synthesis of Hydroxyethylene and Hydroxyethylamine Isosteres by Ester Derived Titanium Enolate Syn- and Anti-aldol Reactions," J. Org. Chem. 1998, 63, 6146-52.

Ghosh et al., "Asymmetric dihydroxylation route to a dipeptide isostere of a protease inhibitor: enantioselective synthesis of the core unit of ritonavir," Chem. Commun. 1999, 1025-26.

Ghosh et al., "2,5-Anhydro Sugar Diacid and 2,5-Anhydro Sugar Diamine Based C2-Symmetric Peptidomimetics as Potential HIV-1 Protease Inhibitors," Tetrahedron Letters 2001, 42, 10121-24.

Ghosh et al., "Structure-based Design of Nonpeptide HIV Protease Inhibitors," Farmaco 2001, 56, 29-32.

Ghosh et al., "Syntheses of FDA Approved HIV Protease Inhibitors," Synthesis, 2001, 2203-29.

(56) References Cited

OTHER PUBLICATIONS

Ghosh et al., "Antiviral Activity of UIC-PI, a Novel Inhibitor of the Human Immunodeficiency Virus Type 1 Protease," Antiviral Research , 2002, 54, 29-36.
Ghosh et al., "Stereoselective Photochemical 1,3-Dioxolane Addition to 5-Alkoxymethyl-2(5H)-furanone: Synthesis of Bis-tetrahydrofuranyl Ligand for HIV Protease Inhibitor UIC-94017 (TMC-114)," J. Org. Chem. 2004, 69, 7822-29.
H. Gataniga et al., "Altered HIV-1 gag Protein Interactions with Cyclophilin A (CypA) on the Acquisitionof H219Qand H219P Substitutios in the CypA Binding Loop," J. Biol. Chem. 2006, 281, 1241.
Ghosh et al., "Bis-Tetrahydrofuran: A Privileged Ligand for Darunavir and a New Generation of HIV-Protease Inhibitors That Combat Drug-Resistance. Bis-Tetrahydrofuran," ChemMedChem 2006, 1, 939-950.
Ghosh et al., "A Stereoselective Anti-aldol Route to (3R,3aS,6aR)-Tetrahydro-2H-furo[2,3-b]furan-3-ol: A Key Ligand for a New Generation of HIV Protease Inhibitors," Synthesis 2006, 3015-3019.
Tie et al., "Atomic Resolution crystal Structures of HIV-1 Protease and MutantsV82A and I84V with Saquinavir," Proteins 2007, 67, 232-242.
Wang et al., "Potent New Antiviral Compound Shows Similar inhibition and Structural Interactions with Drug Resistant Mutants and Wild Type HIV-1 Protease," J. Med. Chem. 2007, 50, 4509.
Ghosh et al., "Darunavir, a Conceptually New HIV-1 Protease Inhibitor for the Treatment of Drug-resistant HIV," Bioorg. Med. Chem. 2007, 15, 7576.
Mitsuya et al., "Development of Protease Inhibitors and the Fight with Drug-Resistant HIV-1 Variants," Advances in Pharmacology, 2007, 56, 169-197.
Ghosh et al., "Design of HIV Protease Inhibitors Targeting Protein Backbone: An Effective Strategy for Combating Drug Resistance," Acc. Chem. Res. 2008, 41, 78-86.
Ghosh et al., "Enantioselective Synthesis of Cyclopentyltetrahydrofuran (Cp-THF), an Important High-Affinity P2-Ligand for HIV-1 Protease Inhibitors," Tet. Lett. 2008, 49, 3409-2412.
Ghosh et al., "Potent HIV-1 Protease Inhibitors Incorporating meso-Bicyclic Urethanes as P2-ligands: Structure-Based Design, Synthesis, Biological Evaluation and Protein-Ligand X-Ray Studies," Org. Biomol. Chem., 2008, 6, 3703-3713.
Liu et al., "Effect of Flap Mutations on Structure of HIV-1 Protease and Inhibition by Saquinavir and Darunavir," J. Mol. Biol. 2008, 381, 102-115.
Ghosh et al., "Flexible Cyclic Ethers/Polyethers as Novel P2-Ligands for HIV-1 Protease Inhibitors: Design, Synthesis, Biological Evaluation and Protein-ligand X-ray Studies," J. Med. Chem. 2008, 51, 6021-33.
Kovalevsky et al., "Solution Kinetics Measurements Suggest HIV-1 Protease Has Two Binding Sites for Darunavir and Amprenavir," J. Med. Chem. 2008, 51, 6599-03.
Kovalevsky et al., "Structural Evidence for Effectiveness of Darunavir and Two Related Antiviral Inhibitors against HIV-2 Protease," J.Mol. Biol. 2008, 384, 178-192.
Ghosh et al., "Design and Synthesis of Stereochemically Defined Novel Spirocyclic P¬ 2-Ligands for HIV-1 Protease Inhibitors," Org. Lett. 2008, 10, 5135-38.
Koh et al., "GRL-02031: A Novel Nonpeptide Protease Inhibitor (PI) Containing A Stereochemistry Defined Fused Cyclopentanyltetrahydrofuran (Cp-THF) Potent Against Multi-PI-Resistant HIV-1 In Vitro," Antimicrobial Agents Chemother. 2009, 53, 987-996.
Ghosh et al., "Harnessing Nature's Insight: Design of Aspartyl Protease Inhibitors from Treatment of Drug-Resistant HIV to Alzheimer's Disease," J. Med. Chem. 2009, 52(8), 2163-2176.
Ghosh et al., "Design of HIV-1 Protease Inhibitors with Pyrrolidinones and Oxazolidinones as Novel P1'-Ligands to Enhance Backbone-binding interactions with Protease: Synthesis, Biological Evaluation and Protein-ligand X-ray Studies," J. Med. Chem. 2009, 52, 3902-3914.
Ghosh et al., "Structure-Based Design, Synthesis, and Biological Evaluation of a Series of Novel and Reversible Inhibitors for the Severe Acute Respiratory Syndrome—Coronavirus Papain-Like Protease," J. Med. Chem. 2009, 52 (16), 5228-5240.
Ghosh et al., "Design, Synthesis, Protein-Ligand X-ray Structure, and Biological Evaluation of a Series of Novel Macrocyclic Human Immunodeficiency Virus-1 Protease Inhibitors to Combat Drug Resistance," J. Med. Chem. 2009, 52 (23), 7689-7705.
Das et al.,"Prediction of Potency of Protease Inhibitors Using Free Energy Simulations with Polarizable Quantum Mechanics-Based Ligand Charges and a Hybrid Water Model," J. Chem. Info. Model, 2009, 49, 2851-2862.
Ghosh et al.,"Synthesis and biological evaluation of novel allophenylnorstatine-based HIV-1 protease inhibitors incorporating high affinity P2-ligands," Bioorg. Med. Chem. Lett. 2010, 20, 1241-1246.
Clementz et al., "Deubiquitinating and Interferon Antagonism Activities of Coronavirus Papain-Like Proteases," J. Virol. 2010, 84, 4619-4629.
Tojo et al.,"Novel Protease Inhibitors (PIs) Containing Macrocyclic Components and 3(R),3a(S),6a(R)-bis-Tetrahydrofuranylurethane (bis-THF) That Are Potent Against Multi-PI-Resistant HIV-1 Variants In Vitro," Antimicrobial Agents and Chemotherapy, 2010, 54, 3460-3470.
Ghosh et al., "Severe Acute Respiratory Syndrome Coronavirus Papain-like Novel Protease Inhibitors: Design, Synthesis, Protein—Ligand X-ray Structure and Biological Evaluation," J. Med. Chem. 2010, 53, 4968-4979.
Ghosh et al., "Darunavir (Prezista): A HIV-1 Protease Inhibitor for Treatment of Multidrug-Resistant HIV," Modern Drug Synthesis, Wiley, Edited by J. J. Li and D. S. Johnson, 2010, 29-44.
Ghosh et al., "Probing Multidrug-Resistance and Protein-Ligand Interactions with Oxatricyclic Designed Ligands in HIV-1 Protease Inhibitors," ChemMedChem 2010, 5, 1850-1854.
European Search Report for EP07874304 completed Dec. 1, 2009.
Hicks, Charles B., et al., "Durable Efficacy of Tipranavir-Ritonavir in Combination With an Optimised Background Regimen Of Antiretroviral Drugs For Treatment-Experienced HIV-1-Infected Patients At 48 Weeks In The Randomized Evaluation Of Strategic Intervention In Multi-Drug ReSistant Patients With Tipranavir (RESIST) Studies: An Analysis of Combined Data From Two Randomised Open-Label Trials", Aug. 5, 2006, The Lancet, vol. 368, pp. 466-475.
Koh, Yasuhiro, et al., "Potent Inhibitation of HIV-1 Replication by Novel Non-Peptidyl Small Molecule Inhibitors Of Protease Dimerization", Sep. 28, 2007, The Journal of Biological Chemistry, vol. 282, No. 39, pp. 28709-28720.
Amano et al., "A Novel Bis-Tetrahydrofuranylurethane-containing Nonpeptidic Protease Inhibitor (PI), GRL-98065, is Potent against Multiple-PI-Resistant Human Immunodeficiency Virus In Vitro," Antimicrobial Agents and Chemotherapy. vol. 51. No. 6 2143-2155 (2007).
Ami et al., "Synthesis of Novel Amino Acids, L-Bis-Tetrahydrofuranylglycines," Tetrahedron Letters, vol. 43, 2931-2934 (2002).
Babe et al., "Synthetic "interface" Peptides Alter Dimeric Assembly of the HIV 1 and 2 Proteases," Protein Science, vol. 1, No. 10, 1244-1253 (1992).
Bannwarth et al., "Molecular Tongs Containing Amino Acid Mimetic Fragments: New Inhibitors of Wild-Type and Mutated HIV-1 Protease Dimerization," J. Med. Chem., vol. 49, No. 15, 4657-4664 (2006).
Bastiaens et al., "Imaging the Intracellular Trafficking and State of the $AB_5$ Quaternary Structure of Cholera Toxin," EMBO Journal, vol. 15, No. 16, 4246-4253 (1996).
Bowman et al., "Switching between Allosteric and Dimerization Inhibition of HIV-1 Protease," Chemistry & Biology, vol. 12, No. 4, 439-444 (2005).
Carr, "Toxicity of antiretroviral therapy and implications for drug development," Nature Reviews Drug Disc, vol. 2, 624-634 (2003).

(56) References Cited

OTHER PUBLICATIONS

Chen et al., "Syntheses of a New Cerebroside Isolated from Typhonium Giganteum Engl," Chinese Journal of Chemistry, vol. 21, 937-943 (2003).

Davis et al., "Inhibition of HIV-1 Replication by a Peptide Dimerization Inhibitor of HIV-1 Protease", Antiviral Research, vol. 72, No. 2, 89-99 (2006).

De Clercq, "Strategies in the design of antiviral drugs," Nature Reviews Drug Disc, vol. 1, 13-25 (2002).

De Meyer et al., "TMC114, a Novel Human Immunodeficiency Virus Type 1 Protease Inhibitor Active against Protease Inhibitor-Resistant Viruses, Including a Broad Range of Clinical Isolates," Antimicrobial Agents and Chemotherapy, vol. 49, No. 6, 2314-2321 (2005).

Fang et al., "PCR-Mediated Recombination: A General Method Applied to Construct Chimeric Infectious Molecular Clones of Plasma-Derived HIV-1 RNA," Nature Medicine, vol. 5, No. 2, 239-242 (1999).

Firulli et al., "Altered Twist1 and Hand2 Dimerization is Associated with Saethre-Chotzen Syndrome and Limb Abnormalities," Nature genetics, vol. 37, No. 4, 373-381 (2005).

Friesner et al., "Glide: a new approach for rapid, accurate docking and scoring. 1. Method and assessment of docking accuracy," J. Med. Chem., vol. 47, 1739-1749 (2004).

Frutos et al., "Disruption of the HIV-1 Protease Dimer with Interface Peptides: Structural Studies Using NMR Spectroscopy Combined with [2-$^{13}$C]-Trp Selective Labeling," Peptide Science, vol. 88, No. 2, 164-173 (2007).

Fumero et al., "New patterns of HIV-1 resistance during HAART," European Society of Clinical Microbiology and Infectious Diseases, vol. 9, 1077-1084 (2003).

Gatanaga et al., "Amino Acid Substitutions in Gag Protein and Non-Cleavage Sites are Indispensable for the Development of a High Multitude of HIV-1 Resistance Against Protease Inhibitors," Journal of Biological Chemistry, vol. 277, No. 8, 5952-5961 (2002).

Ghosh et al., "Potent HIV protease inhibitors incorporating high-affinity P2-ligands and (R)-(hydroxyethylamino)sulfonamide isostere," Bioorganic & Medicinal Chemistry Letters, vol. 8, 687-690 (1998).

Ghosh et al., "Structure based design: novel spirocyclic ethers as nonpeptidal P2-ligands for HIV protease inhibitors," Bioorganic & Medicinal Chemistry Letters, vol. 8, 979-982 (1998).

Ghosh et al., "Design and synthesis of novel HIV-1 protease inhibitors incorporating oxyindoles as the P'2-ligands," Bioorganic & Medicinal Chemistry Letters, vol. 16, 1869-1873 (2006).

Ghosh et al., "Nonpeptidal P2 Ligands for HIV Protease Inhibitors: Structure-Based Design, Synthesis, and Biological Evaluation," J. Med. Chem., vol. 39, 3278-3290 (1996).

Grabar et al., "HIV infection in older patients in the HAART era," Journal of Antimicrobial Chemotherapy, vol. 57, 4-7 (2005).

Hirsch et al., "Immune reconstitution in HIV-infected patients," Clinical Infectious Diseases, vol. 38, 1159-1166 (2004).

Hong et al., "Crystal structure of an in vivo HIV-1 protease mutant in complex with saquinavir: insights into the mechanisms of drug resistance," Protein Science, vol. 9, 1898-1904 (2000).

Ishima et al., "Solution Structure of the Mature HIV-1 Protease Monomer," J. Biol. Chem., vol. 278, No. 44, 43311-43319 (2003).

Ishima et al., "Folded Monomer of HIV-1 Protease," J. Biol. Chem., vol. 276, No. 52, 49110-49116 (2001).

Kaplan et al., "Selection of multiple human immunodeficiency virus type 1 variants that encode viral proteases with decreased sensitivity to an inhibitor of the viral protease," Proc. Natl. Acad. Sci. USA, vol. 91, 5597-5601 (1994).

Koh et al., "Novel bis tetrahydrofuranylurethane-containing nonpeptidic protease inhibitor (PI) UIC-94017 (TMC114) with potent activity against multi-PI-resistant human immunodeficiency virus in vitro," Antimicrobial Agents and Chemotherapy, vol. 47, No. 10, 3123-3129 (2003).

Konvalinka et al., "An Active-Site Mutation in the Human Immunodeficiency Virus Type 1 Proteinase (PR) Causes Reduced PR Activity and Loss of PR-Mediated Cytotoxicity without Apparent Effect on Virus Maturation and Infectivity," Journal of Virology, vol. 69, No. 11, 7180-7186 (1995).

Kovalevsky et al., "Effectiveness of nonpeptide clinical inhibitor TMC-114 on HIV-1 protease with highly drug resistant mutations D3ON, I50V, and L90M," J. Med. Chem., vol. 49, 1379-1387 (2006).

Kovalevsky et al., "Ultra-High Resolution Crystal Structure of HIV-1 Protease Mutant Reveals Two Binding Sites for Clinical Inhibitor TMC114," J. Mol. Biol., vol. 363, No. 1, 161-173 (2006).

Lapatto et al., "X-Ray Analysis of HIV-1 Proteinase and 2.7 Å Resolution Confirms Structural Homology Among Retroviral Enzymes," Nature, vol. 342, 299-302 (1989).

Levy et al., "The Folding and Dimerization of HIV-1 Protease: Evidence for a Stable Monomer from Simulations," J. Mol. Biol., vol. 340, No. 1, 67-79 (2004).

Little et al., "Antiretroviral-drug resistance among patients recently infected with HIV," New England Journal of Medicine, vol. 347, No. 6, 385-394 (2002).

Louis et al., "Revisiting Monomeric HIV-1 Protease," J. Biol. Chem., vol. 278, No. 8, 6085-6092 (2003).

Maibaum et al., "Inhibition of Porcine Pepsin by Two Substrate Analogues Containing Statine. The Effect of Histidine at the P2 Subsite on the Inhibition of Aspartic Proteinases," J. Med. Chem., vol. 31, No. 34, 625-629 (1988).

Miller et al., "Ultra-potent P1 modified arylsulfonamide HIV protease inhibitors: the discovery of GW0385," Bioorganic & Medicinal Chemistry Letters, vol. 16, 1788-1794 (2006).

Miyawaki et al., "Fluorescent Indicators for $Ca^{2+}$ Based on Green Fluorescent Proteins and Calmodulin," Nature, vol. 388, No. 6645, 882-887 (1997).

Patick et al., "Antiviral and Resistance Studies of AG1343, an Orally Bioavailable Inhibitor of Human Immunodeficiency Virus Protease," Antimicrobial Agents and Chemotherapy, vol. 40, No. 2, 292-297 (1996).

Poveda et al., "Successful rescue therapy with darunabir (TMC114) in HIV-infected patients who have failed several ritonavir-boosted protease inhibitors," AIDS, vol. 20, No. 11, 1558-1560 (2006).

Prabu-Jeyabalan et al., "Mechanism of Substrate Recognition by Drug-Resistant Human Immunodeficiency Virus Type 1 Protease Variants Revealed by a Novel Structural Intermediate," Journal of Virology. vol. 80, No. 7, 3607-3616 (2006).

Sekar et al., "Fluorescence Resonance Energy Transfer (FRET) Microscopy Imaging of Live Cell Protein Localizations," J. Cell Biology, vol. 160, No. 5, 629-633 (2003).

Sepkowitz, "AIDS—the first 20 years," New England Journal of Medicine, vol. 344, No. 23, 1764-1772 (2001).

Siegel et al., "Fas Preassociation Required for Apoptosis Signaling and Dominant Inhibition by Pathogenic Mutations", Science, 2354 (2000).

Siliciano et al., "A long-term latent reservoir for HIV-1: discovery and clinical implications," Journal of Antimicrobial Chemotherapy. vol. 54. 6-9 (2004).

Simon, et al., "HIV-1 dynamics in vivo: implications for therapy," Nature Reviews Microbiology, vol. 1, 181-190 (2003).

Staszewski et al., "Efavirenz plus zidovudine and lamivudine, efavirenz plus indinavir, and indinavir plus zidovudine and lamivudine in the treatment of HIV-1 infection in adults," New England Journal of Medicine, vol. 341, No. 25, 1865-1873 (1999).

Szczesna-Skorupa et al., "Fluorescence Resonance Energy Transfer Analysis of Cytochromes P450 2C2 and 2E1 Molecular Interactions in Living Cells," Journal of Biological Chemistry, vol. 278, No. 33, 31269-31276 (2003).

Thaisrivongs et al., "Structure-Based Design of HIV Protease Inhibitors: Sulfonamide-Containing 5,6 Dihydro-4-hydroxy-2-pyrones as Non-Peptidic Inhibitors," J. Med. Chem., vol. 39, No. 22, 4349-4353 (1996).

Tie et al., "High resolution crystal structures of HIV-1 protease with a potent non-peptide inhibitor (UIC-94017) active against multi-drug-resistant clinical strains," J. Mol. Biol., vol. 338, 341-352 (2004).

(56) References Cited

OTHER PUBLICATIONS

Wainberg et al., "Public health implications of antiretroviral therapy and HIV drug resistance," J. Am. Med. Assoc., vol. 279, 1977-1983 (1998).

Wlodawer et al., "Conserved Folding in Retroviral Proteases: Crystal Structure of a Synthetic HIV-1 Protease," Science, vol. 245, 616-621 (1989).

Yoshimura et al., "JE-2147: a dipeptide protease inhibitor (PI) that potently inhibits multi-PI-resistant HIV-1," Proc. Natl. Acad. Sci. USA, vol. 96, 8675-8680 (1999).

Yoshimura et al., "Potent Human Immunodeficiency Virus Type 1 Protease Inhibitor, UIC-94003 (TMC-126), and Selection of a Novel (A28S) Mutation in the Protease Active Site," Journal of Virology, vol. 76, No. 3, 1349-1358 (2002).

Youle et al., "Concomitant Use of an Active Boosted Protease Inhibitor with Enfuvirtide in Treatment-Experienced, HIV-Infected Individuals: Recent Data Consensus Recommendations," HIV Clin. Trials, vol. 7, No. 2, 86-96 (2006).

International Search Report and Written Opinion for PCT/US2007/085265 completed Oct. 25, 2008 (Oct. 25, 2008).

Prezista Label, Jun. 2006.

Ghosh et al., "Novel Cyclourethane-Derived HIV Protease Inhibitors: A Ring Closing Olefin Metathesis Based Strategy," Bioorg. Med. Chem. Lett., 2002, 12, 1993-96.

Ghosh et al., "Structure-Based Design of Novel HIV-1 Protease Inhibitors to Combat Drug Resistance," J. Med. Chem., vol. 49, 5252-5261 (2006).

"European Application Serial No. 07874304.4, Extended European Search Report dated Dec. 14, 2009", 14 pgs.

"European Application Serial No. 07874304.4, Office Action dated Aug. 3, 2009", 2 pgs.

"European Application Serial No. 10173554.6, Extended European Search Report dated Aug. 1, 2012", 10 pgs.

"International Application Serial No. PCT/US2007/085265, International Preliminary Report on Patentability dated May 26, 2009", 6 pgs.

Koh, Yasuhiro, et al., "Potent Inhibition of HIV-1 Replication by Novel Non-peptidyl Small Molecule Inhibitors of Protease Dimerization", J. Bioi. Chem, (2007), 28709-28720.

European Search Report for EP Application No. EP 10173554.6, dated Aug. 1, 2012, 10 pages.

Arun K Ghosh et al: "Structure-based design of novel HIV-1 protease inhibitors to combat drug resistance," Journal Of Medicinal Chemistry, American Chemical Society, US, vol. 49, No. 17, Aug. 24, 2006 (Aug. 24, 2006), pp. 5252-5261.

Ghosh A K et al: "Structure based design: Novel spirocyclic ethers as nonpeptidal P2-ligands for HIV protease inhibitors," Bioorganic & Medicinal Chemistry Letters, Pergamon, Elsevier Science, GB, vol. 8, No. 8, Apr. 21, 1998 (Apr. 21, 1998), pp. 979-982.

Ghosh A K et al: "Potent HIV protease inhibitors incorporating high-affinity P2-ligands and (R)-(hydroxyethylamino) sulfonamide isostere," Bioorganic & Medicinal Chemistry Letters, Pergamon, Elsevier Science, GB, vol. 8, No. 6, Mar. 17, 1998 (Mar. 17, 1998), pp. 687-690.

Koh Yasuhiro et al: "Potent inhibition of HIV-1 replication by novel non-peptidyl small molecule inhibitors of protease dimerization," Journal Of Biological Chemistry, vol. 1282, No. 39, Sep. 2007 (Sep. 2007), pp. 28709-28720.

\* cited by examiner

| NO: | 10 | 20 | 30 | 40 | 50 | 60 | 70 | 80 | 90 | 99 | | SEQ ID |
|---|---|---|---|---|---|---|---|---|---|---|---|---|
| pNL4-3 | | | | | | | | | | | | |
| PR | PQITLWQRPL | VTIKIGGQLK | EALLDTGADD | TVLEEMNLPG | RWKPKMIGGI | GGFIKVRQYD | QILIEICGHK | AIGTVLVGPT | PVNIIGRNLL | TQIGCTLNF | | 1 |
| 5P-1 | PQITLWQRPL | VTIKIGGQLK | EALLDTGADD | TVLEEMNLPG | RWKPKMIGGI | GGFIKVRQYD | QILIEICGHK | AIGTVLVGPT | PVNIIGRNLL | TQIGCTLNF | 9/13 | 2 |
| 5P-2 | PQITLWQRPL | VTIKIGGQLK | EALLDTGADD | TVLEEMNLPG | RWKPKMIGGI | GGFIEVRQYD | QILIEICGHK | AIGTVLVGPT | PVNIIGRNLL | TQIGCTLNF | 1/13 | 3 |
| 5P-3 | PQITLWQRPL | VTIKIGGQLK | EALLDAGADD | TVLEEMNLPG | RWKPKMIGGI | GGFIKVRQYD | QILIEICGHK | AIGTVLVGPT | PVNIIGRNLL | TQIGCTLNF | 1/13 | 4 |
| 5P-4 | PQITLWQRPL | VTIKIGGQLK | EALLDTGADD | TVLEEMNLPG | RWKPKMVGGI | GGFIKVRQYD | QILIEICGHK | AIGTVLVGPT | PVNIIGRNLL | TQIGCTLNF | 1/13 | 5 |
| 5P-5 | PQITLWQRPL | VTIKIGGQLK | EALLDTGADD | TVLEEMNLPE | RWKPKMIGGI | GGFIKVRQYD | QILIEICGHK | AIGTVLVGPT | PVNIIGRNLL | TQIGCTLNF | 1/13 | 6 |
| 10P-1 | PQITLWQRPL | VTIKIGGQLK | EALLDTGADD | TVLEEMNLPG | RWKPKMIGGI | GGFIKVRQYD | QILIEICGHK | AIGTVLVGPT | PVNIIGRNLL | TQIGCTLNF | 8/13 | 7 |
| 10P-2 | PQITLWQRPL | VTIKIGGQLK | EALLDTGADD | TVLEEMNLPG | RWKPKMIGGI | GGFIKVRQYD | QILIEICGHK | AIGTVLVGPT | PVNIIGRNLL | THIGCTLNF | 1/13 | 8 |
| 10P-3 | PQITLCQRPL | VTIKIGGQLK | EALLDTGADD | TVLEEMNLPG | RWKPKMIGGI | GGFIKVRQYD | QILIEICGHK | AIGTVLVGPT | PVNIIGRNLL | TQIGCTLNF | 1/13 | 9 |
| 10P-4 | PQITPWQRPL | VTIKIGGQLK | EALLDTGADD | TVLEEMNLPG | RWKPKMIGGI | GGFIKVRQYD | QILIEICGHK | AIGTVLVGPT | PVNIIGRNLL | TQIGCTLNF | 1/13 | 10 |
| 10P-5 | PQITLWQRPL | VTIKIGGQLK | EALLDTGADD | TVLEEMNLPE | RWKPKMIGGI | GGFIKVRQYD | QILIEICGHK | AIGTVLVGPT | PVNIIGRNLL | TQIGCTLNF | 1/13 | 11 |
| 10P-6 | PQITLWQRPL | VTIKIGGQLK | EALLDTGADD | TVLEEMNLPG | RLKPKMIGGI | GGFIKVRQYD | QILIEICGHK | AIGTVLVGPT | PINIIGRNLL | TQIGCTLNF | 1/13 | 12 |
| 15P-1 | PQITLWQRPL | VTIKIGGQLK | EALLDTGADD | TVLEEMNLPG | RWIPKMIGGI | GGFIKVRQYD | QILIEICGHK | AIGTVLVGPT | PVNIIGRNLL | TQIGCTLNF | 5/11 | 13 |
| 15P-2 | PQITLWQRPL | VTIKIGGQLK | EALLDTGADD | TVLEEMNSPG | RWIPKMIGGI | GGFIKVRQYD | QILIEICGHK | AIGTVLVGPT | PVNIVGRNLL | TQIGCTLNF | 1/11 | 14 |
| 15P-3 | PQITLWQRPL | VTIKIGGQLK | EALLDTGADD | TVLEEMNLPG | RWIPKMIGGI | GGFIKVRQYD | QILIEICGHK | AIGTVLVGPT | PVNIVGRNLL | TQIGCTLNF | 1/11 | 15 |
| 15P-4 | PQITLWQRPL | VTIKIGGQLK | EALLDTGADD | TVLEEMNLPG | RWIPKMIGGI | GDFIKVRQYD | QILIEICGHK | AIGTVLVGPT | PVNIVGRNML | TQIGCTLNF | 1/11 | 16 |
| 15P-5 | PQVTLWQRPL | VTIKIGGQLK | EALLDTGADD | TVLEEMNLPG | RWIPKMIGGI | GGFIKVRQYD | QILIEICGHK | AIGTVLVGPT | PVNIVGRNML | TQIGCTLNF | 1/11 | 17 |
| 15P-6 | PQITLWQRPL | VTIKIGGQLK | EALLDTGADD | TVLEEMNLPG | RWIPKMIGGI | GGFIKVRQYD | QILIEICGHK | AIGTVLVGPT | PVNIIGRNLL | TQIGYTLNF | 1/11 | 18 |
| 15P-7 | PQITLWQRPL | VTIKIGGQLK | EALLDTGADD | TVLEEMNLPG | RWIPKMIGGI | GGFIKVRQYD | QILIEICGHK | ALGTVLVGPT | PVNIIGRNLL | TQIGCTLNF | 1/11 | 19 |
| 20P-1 | PQITLWQRPL | VTIKIGGQLK | EALLDTGADD | TVLEEMNLPG | RWIPKMIGGI | GGFIKVRQYD | QILIEICGHK | AIGTVLVGPT | PINIVGRNLL | TQIGCTLNF | 8/19 | 20 |
| 20P-2 | PQITLWQRPL | VTIKIGGQLK | EALLDTGSDD | TVLEEMNLPG | RWIPKMIGGI | GGFIKVRQYD | QILIEIYGHK | AIGTVLVGPT | PINIIGRNML | TQIGCTLNF | 2/19 | 21 |
| 20P-3 | PQITLWQRPL | VTIKIGGQLK | EALLDTGSDD | TVLEEMNLPG | RWIPKMIGGI | GGFIKVRQYD | RILIEIYGHK | AIGTVLVGPT | PINIIGRNML | TQIGCTLNF | 1/19 | 22 |
| 20P-4 | PQITLWQRPL | VTIRIGGQLK | EALLDTGSDD | TVLEEMNLPG | RWIPKMIGGI | GGFIKVRQYD | QILIEICGHK | AIGTVLVGPT | PINIVGRNML | TQIGCTLNF | 1/19 | 23 |
| 20P-5 | PQVTLWQRPL | VTIKIGGQLK | EALLDTGAED | TVLEEMNLPG | SWIPKMIGGI | GGFIKVRQYD | QILIEICGHK | AIGTVLVGPT | PINIVGRNML | TQIGCTLNF | 1/19 | 24 |
| 20P-6 | PQITLWQRPL | VTIKIGGQLK | EALLDTGADD | TVLEEMNLPG | RWIPKMIGGI | GGFIKVRQYD | QILIEIYGHK | AIGTVLVGPT | PINIIGRNML | TQIGCTLNF | 1/19 | 25 |
| 20P-7 | PQITLWQRPL | VTIKIGGQLK | EALLDTGADD | TVLEEMNLPG | RWIPKMIGGI | GGFIKVRQCD | QILIEICGHK | AIGTVLVGPT | PINIIGRNLL | TQIGCTLNF | 1/19 | 26 |
| 20P-8 | PQITLWQRPL | VTIKIGGQLK | EALLDTGADD | TVLEEMNLPG | RWIPKMIGGI | GGFIKVGQYD | QILIEIYGHK | AIGTVLVGPT | PINIGRNML | TQIGCTLNF | 1/19 | 27 |
| 20P-9 | PQITLWQRPL | VTIKIGGQLK | EALLDTGADD | IVLEEMNLPG | RWIPKMIGGI | GGFIKVRQYD | QILIEICGHK | AIGTVLVGPT | PINIVGRNLL | TQIGCTLNF | 1/19 | 28 |
| 20P-10 | PQITLWQRPL | VTIKIGGQLK | EALLDTGADD | TVLEEMNLPG | RWIPKMIGGI | GGFIKVRQYD | QILIEICGHK | AIGTVLVGPT | PINIVGRNLL | TQIGCTLNF | 1/19 | 29 |
| 20P-11 | PQITLWQRPL | VTIKIGGQLK | EALLDTGADD | TVLEEMNLPG | RWIPKMLGGI | GGFIKVRQYD | QILIEICGHK | AIGTVLVGPT | PINIVGRNLL | TQIGCTLNF | 1/19 | 30 |
| 25P-1 | PQITLWQRPL | VTIKIGGQLK | EALLDTGSDD | TVLEEMNLPG | RWIPKIIGGI | GGFIKVRQYD | QILIEICGHK | AIGTVLVGPT | PINIVGRNLL | TQIGCTLNF | 4/20 | 31 |
| 25P-2 | PQITLWQRPL | VTIKTGGQLK | EALLDTGADD | TVLEEMNLPG | RWIPKMIGGI | GGFIKVRQYD | QILIEICGHK | AIGTVLVGPT | PINIIGRNML | TQIGCTLNF | 3/20 | 32 |
| 25P-3 | PQITLWQRPL | VTIKIGGQLK | EALLDTGADD | TVLEEMNLPG | RWIPKMIGGI | GGFIKVRQYD | VILIEICGHK | AIGTVLVGPT | PINIVGRNLL | TQIGCTLNF | 2/20 | 33 |
| 25P-4 | PQITLWQRPL | VTIKIGGQLK | EALLDTGADD | TVLEEMNLPG | RWIPKIIGGI | GGFIKVRQYD | QILIEICGHK | AIGTVLVGPT | PINVIGRNLL | TQIGCTLNF | 2/20 | 34 |

FIG. 4

| NO: | | 10 | 20 | 30 | 40 | 50 | 60 | 70 | 80 | 90 | 99 | | SEQ ID |
|---|---|---|---|---|---|---|---|---|---|---|---|---|---|
| pNL4-3 | | | | | | | | | | | | | |
| PR | PQITLWQRPL | VTIKIGGQLK | EALLDTGADD | TVLEEMNLPG | RWKPKMIGGI | GGFIKVRQYD | QILIEICGHK | AIGTVLVGPT | PVNIIGRNLL | TQIGCTLNF | | | 1 |
| 25P-5 | PQITLWQRPL | VTIKIGGQLK | EALLDTGSDD | TVLEEMNLPG | RWIPKMIGGI | GGFIKVRQYD | QILIEICGHK | TIGTVLVGPT | PINIIGRNML | TQIGCTLNF | 1/20 | | 35 |
| 25P-6 | PQITLWQRPL | VAIKIGGQLK | EALLDTGSDD | TVLEEMNLPG | RWIPKIIGGI | GGFIKVRQYD | QILIEICGHK | AIGTVLVGPT | PINIVGRNLL | TQIGCTLNF | 1/20 | | 36 |
| 25P-7 | PQITLWQRPL | VTIKIGGQLK | EALLDTGADD | TVLEEMNLPG | RWIPKIIGGI | GGFIKVRQYD | QILIEICGHK | AIGTVLVGPT | PINIIGRNML | TQIGCTLNF | 1/20 | | 37 |
| 25P-8 | PQITLWQRPL | VTIKIGGQLK | EALLDTGADD | TVLEEMNLPG | RWIPKMIGGI | GGFIKVRQYD | QILIEICGHK | VIGTVLVGPT | PINIIGRNML | TQIGCTLNF | 1/20 | | 38 |
| 25P-9 | PQITLWQRPL | VTIKIGGQLK | EALLDTGADD | TVLEEMNLPG | RWIPKMIGGI | GGFIKVRQYD | QILIEICGHK | AIGTVLVGPT | PINIIGRNML | TQIGCTLNF | 1/20 | | 39 |
| 25P-10 | PQITLWQRPL | VTIKIGGQLK | EALLDTGADD | TVLEEMNLPG | RWIPKIIGGI | GGFIKVRQYD | QILIEICGHK | AIGTVLVGPT | PTNIVGRNLL | TQIGCTLNF | 1/20 | | 40 |
| 25P-11 | PQITLWQRPL | VTIKIGGQLK | EALLDDAGADD | TVLEEMNLPG | RWIPKIIGGI | GGFIKVRQYD | QILIEICGHK | AIGTVLVGPT | PINIVGRNLL | TQIGCTLNF | 1/20 | | 41 |
| 25P-12 | PQITLWQRPL | VTIKIGGQLK | EALLDTGADD | TVLEEMNLPG | RWIPKIIGGI | GGFIKVRQYD | QILMEICGHK | AIGTVLVGPT | PINIVGRNLL | TQIGCTLNF | 1/20 | | 42 |
| 25P-13 | PQITLWQRPL | VTIKIGGQLK | EALLDTGADD | TVLEEMNLPG | RWTPKIIGGI | GGFIKVRQYD | QILIEICGHK | AIGTVLVGPT | PINIVGRNLL | TQIGCTLNF | 1/20 | | 43 |
| 30P-1 | PQITLWQRPL | VIIKIGGQLK | EALLDTGADD | TVLKEMNLPG | RWIPKMIGGI | GGFIKVRQYD | QILIEICGHK | AIGTVLVGPT | PINIVGRNLL | TQIGCTLNF | 2/10 | | 44 |
| 30P-2 | PQITLWQRPL | VTIKIGGQLK | KALLDTGSDD | TVLEEMNLPG | RWIPKIIGGI | GGFIKVRQYD | QILIEICGHK | AIGTVLVGPT | PINIVGRNLL | TQIGCTLNF | 2/10 | | 45 |
| 30P-3 | PQITLRQRPL | VTIKIGGQLK | EALLDTGSDD | TVLKEMNLPG | RWIPKMIGGI | GGFVKVRQYD | QILIEICGHK | VIGTVLVGPT | PINIVGRNLL | TQIGCTLNF | 1/10 | | 46 |
| 30P-4 | PQITLWQRPL | VTIKIGGQLK | KALLDTGSDD | TVLEEMNLPG | RWIPKIIGGI | GGFIKVRQYD | QILIEICGHK | AIGTVLVGPT | PINIVGRNLL | TQIGCTLNF | 1/10 | | 47 |
| 30P-5 | PQITLWQRPL | VTIKIGGQLK | KALLDTGSDD | TVLEEMNLPG | RWIPKMIGGI | GGFIKVRQYD | QILIEICGHK | AIGTVLVGPT | PINIVGRNLL | TQIGCTLNF | 1/10 | | 48 |
| 30P-6 | PQITLWQRPL | VIIKIGGQLK | EALLDTGSDD | AVLKEMNLPG | RWIPKMIGGI | GGFIKVRQYD | QILIEICGHK | AIGTVLVGPT | PINIVGRNML | TQIGCTLNF | 1/10 | | 49 |
| 30P-7 | PQITLWQRPL | VTIKIGGQLK | EALLDTGADD | TVLEEMNLPG | RWIPKMIGGI | GGFIKVRQYD | QILIEICGHK | AIGTVLVGPT | PINIVGRNLL | TQIGCTLNF | 1/10 | | 50 |
| 30P-8 | PQITLWQRPL | VTIKIGGQLK | EALLDTGADD | TVLEEMNLPG | RWIPKMIGGI | GGFIKVRQYD | QILIEICGHK | AIGTVLVGPT | PINIVGRNML | TQIGCTLNF | 1/10 | | 51 |
| 33P-1 | PQITLWQRPL | VTIKIGGQLK | EALLDTGADD | TVLEEMNLPG | RWIPKIIGGI | GGFIKVRQYN | QILIEICGHK | AIGTVLVGPT | PINIIGRNML | TQIGCTLNF | 2/11 | | 52 |
| 33P-2 | PQITLWQRPL | VTIKIGGQLK | KALLDTGSDD | TVLEEMNLPG | RWIPKIIGGI | GGFIKVRQYN | QILIEICGHK | AIGTVLVGPT | PINIVGRNML | TQIGCTLNF | 2/11 | | 53 |
| 33P-3 | PQITLWQRPL | VTIKIGGQLK | KALLDTGSDD | TVLEEMNLPG | RWIPKIIGGI | GGFTKVRQYD | QILIEICGHK | AIGTVLVGPT | PINIVGRNML | TQIGCTLNF | 1/11 | | 54 |
| 33P-4 | PQITLWQRPL | ITIKIGGQLK | KALLDTGSDD | AVLEEMNLPG | RWIPKIIGGI | GGFIKVRQYN | QILIEICGHK | AIGTVLVGPT | PINIIGRNML | TQIGCTLNF | 1/11 | | 55 |
| 33P-5 | PQITLWQRPL | VTIKIGGQLK | EALLDTGADD | TVLEEMNLPG | RWIPKIIGGI | GGFINVRQYG | QILIEICGHK | AIGTVLVGPT | PINIVGRNML | TQIGCTLNF | 1/11 | | 56 |
| 33P-6 | PQITLWQRPL | VTIKIGGQLK | EALLDTGADD | TVLEEMNLPG | RWIPKIIGGI | GGFIKVRQYD | QILIEICGHK | AIGTVLVGPT | PINIVGRNML | TQIGCTLNF | 1/11 | | 57 |
| 33P-7 | PQITLWQRPL | VTIKIGGQLK | EALLDDAGADD | TVLEEMNLPG | RWIPKIIGGI | GGFIKVRQYD | QILIEICGHK | AIGTVLVGPT | PINIVGRNML | TQIGCTLNF | 1/11 | | 58 |
| 33P-8 | PQITLWQRPL | VTIKIGGQLK | EALLDTGADD | TVLEEMNLPG | RWIPKIIGGI | GGFIKVRQYD | QILIEICGHK | AIGTVLVGPT | PINIVGRNLL | TQIGCTLNF | 1/11 | | 59 |
| 33P-9 | PQITLWQRPL | VTIKIGGQLK | EALLDTGADD | TVLEEMNLPG | RWIPKMIGGI | GGFIKVRQYD | QMLIEICGHK | AIGTVLVGPT | PINIVGRNML | TQIGCTLNF | 1/11 | | 60 |
| 40P-1 | PQITLWQRPL | VTIKIGGQLK | KALLDTGSDD | TVLEEMNLPG | RWIPKIIGGI | GGFIKVRQYN | QILIEICGHK | VIGTVLVGPT | PINIIGRNML | TQIGCTLNF | 3/11 | | 61 |
| 40P-2 | PQITLWQRPL | VTIKIGGQLK | KALLDTGSDD | TVLEEMNLPG | RWIPKIIGGI | GGFIKVRQYD | QILIEICGHK | VISTVLVGPT | PINIVGRNML | TQIGCTLNF | 2/11 | | 62 |
| 40P-3 | PQITLWQRPL | VTIKIGGQLK | KALLDTGSDD | TVLEEMNLPG | RWIPKIIGGI | GGFIKVRQYN | QILIEICGHK | VIGTILVGPT | PINIVGRNML | TQIGCTLNF | 1/11 | | 63 |
| 40P-4 | PQITLWQRPL | VTIKIGGQLK | KALLDTGSDA | TVLEEMNLPG | RWIPKIIGGI | GGFIKVRQYD | QILIEICGHK | AIGTVLVGPT | PINIIGRNML | TQIGCTLNF | 1/11 | | 64 |
| 40P-5 | PQITLWQRPL | VTIKIGGQLK | EALLDTGADD | TVLEEMNLPG | RWIPKIIGGV | GGFIKVRQYD | QILIEICGHK | AIGTVLVGPT | PINIVGRNML | TQIGCTLNF | 1/11 | | 65 |
| 40P-6 | PQITLWQRPL | VTIKIGGQLK | EALLDTGADD | TVLEEMNLPG | RWIPKIIGGV | GGFIKVRQYD | QILIEICGHK | AIGTVLVGPT | PINIVGRNML | TQIGCTLNF | 1/11 | | 66 |
| 40P-7 | PQITLWQRPL | VTIKIGGQLK | EALLDTGVDD | TVLEEMNLPG | RWIPKIIGGV | GGFIKVRQYD | QILIEICGHK | AIGTVLVGPT | PINIVGRNML | TQIGCTLNF | 1/11 | | 67 |
| 40P-8 | PQITLWQRPL | VTINTGGQLK | EALLDTGADD | TVLEEMNLPG | RWIPKIIGGV | GGFIKVRQYN | QILIEICGHK | AIGTVLVGPT | PINIIGRNML | TQIGCTLNF | 1/11 | | 68 |

SEQUENCE LISTING

```
<160> NUMBER OF SEQ ID NOS: 82

<210> SEQ ID NO 1
<211> LENGTH: 99
<212> TYPE: PRT
<213> ORGANISM: Human immunodeficiency virus type 1

<400> SEQUENCE: 1

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30
```

```
Leu Glu Glu Met Asn Leu Pro Gly Arg Trp Lys Pro Lys Met Ile Gly
         35                  40                  45

Gly Ile Gly Gly Phe Ile Lys Val Arg Gln Tyr Asp Gln Ile Leu Ile
 50                  55                  60

Glu Ile Cys Gly His Lys Ala Ile Gly Thr Val Leu Val Gly Pro Thr
 65                  70                  75                  80

Pro Val Asn Ile Ile Gly Arg Asn Leu Leu Thr Gln Ile Gly Cys Thr
             85                  90                  95

Leu Asn Phe

<210> SEQ ID NO 2
<211> LENGTH: 99
<212> TYPE: PRT
<213> ORGANISM: Human immunodeficiency virus type 1

<400> SEQUENCE: 2

Pro Gln Ile Thr Leu Trp Gln Arg Pro Leu Val Thr Ile Lys Ile Gly
 1               5                  10                  15

Gly Gln Leu Lys Glu Ala Leu Leu Asp Thr Gly Ala Asp Asp Thr Val
             20                  25                  30

Leu Glu Glu Met Asn Leu Pro Gly Arg Trp Lys Pro Lys Met Ile Gly
         35                  40                  45

Gly Ile Gly Gly Phe Ile Lys Val Arg Gln Tyr Asp Gln Ile Leu Ile
 50                  55                  60

Glu Ile Cys Gly His Lys Ala Ile Gly Thr Val Leu Val Gly Pro Thr
 65                  70                  75                  80

Pro Val Asn Ile Ile Gly Arg Asn Leu Leu Thr Gln Ile Gly Cys Thr
             85                  90                  95

Leu Asn Phe

<210> SEQ ID NO 3
<211> LENGTH: 99
<212> TYPE: PRT
<213> ORGANISM: Human immunodeficiency virus type 1

<400> SEQUENCE: 3

Pro Gln Ile Thr Leu Trp Gln Arg Pro Leu Val Thr Ile Lys Ile Gly
 1               5                  10                  15

Gly Gln Leu Lys Glu Ala Leu Leu Asp Thr Gly Ala Asp Asp Thr Val
             20                  25                  30

Leu Glu Glu Met Asn Leu Pro Gly Arg Trp Lys Pro Lys Met Ile Gly
         35                  40                  45

Gly Ile Gly Gly Phe Ile Glu Val Arg Gln Tyr Asp Gln Ile Leu Ile
 50                  55                  60

Glu Ile Cys Gly His Lys Ala Ile Gly Thr Val Leu Val Gly Pro Thr
 65                  70                  75                  80

Pro Val Asn Ile Ile Gly Arg Asn Leu Leu Thr Gln Ile Gly Cys Thr
             85                  90                  95

Leu Asn Phe

<210> SEQ ID NO 4
<211> LENGTH: 99
<212> TYPE: PRT
<213> ORGANISM: Human immunodeficiency virus type 1

<400> SEQUENCE: 4

Pro Gln Ile Thr Leu Trp Gln Arg Pro Leu Val Thr Ile Lys Ile Gly
```

```
                1               5                   10                  15
Gly Gln Leu Lys Glu Ala Leu Leu Asp Ala Gly Ala Asp Asp Thr Val
                20                  25                  30

Leu Glu Glu Met Asn Leu Pro Gly Arg Trp Lys Pro Lys Met Ile Gly
            35                  40                  45

Gly Ile Gly Gly Phe Ile Lys Val Arg Gln Tyr Asp Gln Ile Leu Ile
        50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 5
<211> LENGTH: 99
<212> TYPE: PRT
<213> ORGANISM: Human immunodeficiency virus type 1

<400> SEQUENCE: 5

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
                20                  25                  30

Leu Glu Glu Met Asn Leu Pro Gly Arg Trp Lys Pro Lys Met Val Gly
            35                  40                  45

Gly Ile Gly Gly Phe Ile Lys Val Arg Gln Tyr Asp Gln Ile Leu Ile
        50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 6
<211> LENGTH: 99
<212> TYPE: PRT
<213> ORGANISM: Human immunodeficiency virus type 1

<400> SEQUENCE: 6

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
                20                  25                  30

Leu Glu Glu Met Asn Leu Pro Gly Glu Arg Trp Lys Pro Lys Met Ile Gly
            35                  40                  45

Gly Ile Gly Gly Phe Ile Lys Val Arg Gln Tyr Asp Gln Ile Leu Ile
        50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 7
<211> LENGTH: 99
<212> TYPE: PRT
```

<213> ORGANISM: Human immunodeficiency virus type 1

<400> SEQUENCE: 7

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 8
<211> LENGTH: 99
<212> TYPE: PRT
<213> ORGANISM: Human immunodeficiency virus type 1

<400> SEQUENCE: 8

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr His Ile Gly Cys Thr
                85                  90                  95

Leu Asn Phe

<210> SEQ ID NO 9
<211> LENGTH: 99
<212> TYPE: PRT
<213> ORGANISM: Human immunodeficiency virus type 1

<400> SEQUENCE: 9

Pro Gln Ile Thr Leu Cys Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

```
<210> SEQ ID NO 10
<211> LENGTH: 99
<212> TYPE: PRT
<213> ORGANISM: Human immunodeficiency virus type 1

<400> SEQUENCE: 10

Pro Gln Ile Thr Pro Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 11
<211> LENGTH: 99
<212> TYPE: PRT
<213> ORGANISM: Human immunodeficiency virus type 1

<400> SEQUENCE: 11

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Glu Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 12
<211> LENGTH: 99
<212> TYPE: PRT
<213> ORGANISM: Human immunodeficiency virus type 1

<400> SEQUENCE: 12

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Leu Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80
```

```
Pro Ile Asn Ile Ile Gly Arg Asn Leu Leu Thr Gln Ile Gly Cys Thr
                85                  90                  95

Leu Asn Phe

<210> SEQ ID NO 13
<211> LENGTH: 99
<212> TYPE: PRT
<213> ORGANISM: Human immunodeficiency virus type 1

<400> SEQUENCE: 13

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 14
<211> LENGTH: 99
<212> TYPE: PRT
<213> ORGANISM: Human immunodeficiency virus type 1

<400> SEQUENCE: 14

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Ser Pro Gly Arg Trp Ile Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 15
<211> LENGTH: 99
<212> TYPE: PRT
<213> ORGANISM: Human immunodeficiency virus type 1

<400> SEQUENCE: 15

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Met Ile Gly
        35                  40                  45
```

```
Gly Ile Gly Gly Phe Ile Lys Val Arg Gln Tyr Asp Gln Ile Leu Ile
            50                  55                  60

Glu Ile Cys Gly His Lys Ala Ile Gly Thr Val Leu Val Gly Pro Thr
 65                  70                  75                  80

Pro Val Asn Ile Val Gly Arg Asn Leu Leu Thr Gln Ile Gly Cys Thr
                85                  90                  95

Leu Asn Phe

<210> SEQ ID NO 16
<211> LENGTH: 99
<212> TYPE: PRT
<213> ORGANISM: Human immunodeficiency virus type 1

<400> SEQUENCE: 16

Pro Gln Ile Thr Leu Trp Gln Arg Pro Leu Val Thr Ile Lys Ile Gly
 1               5                  10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Met Ile Gly
        35                  40                  45

Gly Ile Gly Asp Phe Ile Lys Val Arg Gln Tyr Asp Gln Ile Leu Ile
            50                  55                  60

Glu Ile Cys Gly His Lys Ala Ile Gly Thr Val Leu Val Gly Pro Thr
 65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 17
<211> LENGTH: 99
<212> TYPE: PRT
<213> ORGANISM: Human immunodeficiency virus type 1

<400> SEQUENCE: 17

Pro Gln Val Thr Leu Trp Gln Arg Pro Leu Val Thr Ile Lys Ile Gly
 1               5                  10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Met Ile Gly
        35                  40                  45

Gly Ile Gly Gly Phe Ile Lys Val Arg Gln Tyr Asp Gln Ile Leu Ile
            50                  55                  60

Glu Ile Cys Gly His Lys Ala Ile Gly Thr Val Leu Val Gly Pro Thr
 65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 18
<211> LENGTH: 99
<212> TYPE: PRT
<213> ORGANISM: Human immunodeficiency virus type 1

<400> SEQUENCE: 18

Pro Gln Ile Thr Leu Trp Gln Arg Pro Leu Val Thr Ile Lys Ile Gly
 1               5                  10                  15

Gly Gln Leu Lys Glu Ala Leu Leu Asp Thr Gly Ala Asp Asp Thr Val
```

```
                    20                  25                  30

Leu Glu Glu Met Asn Leu Pro Gly Arg Trp Ile Pro Lys Met Ile Gly
                35                  40                  45

Gly Ile Gly Gly Phe Ile Lys Val Arg Gln Tyr Asp Gln Ile Leu Ile
            50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Tyr Thr
                85                  90                  95

Leu Asn Phe

<210> SEQ ID NO 19
<211> LENGTH: 99
<212> TYPE: PRT
<213> ORGANISM: Human immunodeficiency virus type 1

<400> SEQUENCE: 19

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
                20                  25                  30

Leu Glu Glu Met Asn Leu Pro Gly Arg Trp Ile Pro Lys Met Ile Gly
                35                  40                  45

Gly Ile Gly Gly Phe Ile Lys Val Arg Gln Tyr Asp Gln Ile Leu Ile
            50                  55                  60

Glu Ile Cys Gly His Lys Ala Leu Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 20
<211> LENGTH: 99
<212> TYPE: PRT
<213> ORGANISM: Human immunodeficiency virus type 1

<400> SEQUENCE: 20

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
                20                  25                  30

Leu Glu Glu Met Asn Leu Pro Gly Arg Trp Ile Pro Lys Met Ile Gly
                35                  40                  45

Gly Ile Gly Gly Phe Ile Lys Val Arg Gln Tyr Asp Gln Ile Leu Ile
            50                  55                  60

Glu Ile Cys Gly His Lys Ala Ile Gly Thr Val Leu Val Gly Pro Thr
65                  70                  75                  80

Pro Ile Asn Ile Val Gly Arg Asn Leu Leu Thr Gln Ile Gly Cys Thr
                85                  90                  95

Leu Asn Phe

<210> SEQ ID NO 21
<211> LENGTH: 99
<212> TYPE: PRT
<213> ORGANISM: Human immunodeficiency virus type 1

<400> SEQUENCE: 21
```

```
Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ser Asp Asp Thr Val
            20                  25                  30

Leu Glu Glu Met Asn Leu Pro Gly Arg Trp Ile Pro Lys Met Ile Gly
        35                  40                  45

Gly Ile Gly Gly Phe Ile Lys Val Arg Gln Tyr Asp Gln Ile Leu Ile
    50                  55                  60

Glu Ile Tyr Gly His Lys Ala Ile Gly Thr Val Leu Val Gly Pro Thr
65                  70                  75                  80

Pro Ile Asn Ile Ile Gly Arg Asn Met Leu Thr Gln Ile Gly Cys Thr
                85                  90                  95

Leu Asn Phe

<210> SEQ ID NO 22
<211> LENGTH: 99
<212> TYPE: PRT
<213> ORGANISM: Human immunodeficiency virus type 1

<400> SEQUENCE: 22

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ser Asp Asp Thr Val
            20                  25                  30

Leu Glu Glu Met Asn Leu Pro Gly Arg Trp Ile Pro Lys Met Ile Gly
        35                  40                  45

Gly Ile Gly Gly Phe Ile Lys Val Arg Gln Tyr Asp Arg Ile Leu Ile
    50                  55                  60

Glu Ile Tyr Gly His Lys Ala Ile Gly Thr Val Leu Val Gly Pro Thr
65                  70                  75                  80

Pro Ile Asn Ile Ile Gly Arg Asn Met Leu Thr Gln Ile Gly Cys Thr
                85                  90                  95

Leu Asn Phe

<210> SEQ ID NO 23
<211> LENGTH: 99
<212> TYPE: PRT
<213> ORGANISM: Human immunodeficiency virus type 1

<400> SEQUENCE: 23

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ser Asp Asp Thr Val
            20                  25                  30

Leu Glu Glu Met Asn Leu Pro Gly Arg Trp Ile Pro Lys Met Ile Gly
        35                  40                  45

Gly Ile Gly Gly Phe Ile Lys Val Arg Gln Tyr Asp Gln Ile Leu Ile
    50                  55                  60

Glu Ile Tyr Gly His Lys Ala Ile Gly Thr Val Leu Val Gly Pro Thr
65                  70                  75                  80

Pro Ile Asn Ile Val Gly Arg Asn Met Leu Thr Gln Ile Gly Cys Thr
                85                  90                  95

Leu Asn Phe

<210> SEQ ID NO 24
```

```
<211> LENGTH: 99
<212> TYPE: PRT
<213> ORGANISM: Human immunodeficiency virus type 1

<400> SEQUENCE: 24

Pro Gln Ile Thr Leu Trp Gln Arg Pro Leu Val Thr Ile Arg Ile Gly
1               5                   10                  15

Gly Gln Leu Lys Glu Ala Leu Leu Asp Thr Gly Ala Glu Asp Thr Val
            20                  25                  30

Leu Glu Glu Met Asn Leu Pro Gly Ser Trp Ile Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Val Gly Arg Asn Leu Leu Thr Gln Ile Gly Cys Thr
                85                  90                  95

Leu Asn Phe

<210> SEQ ID NO 25
<211> LENGTH: 99
<212> TYPE: PRT
<213> ORGANISM: Human immunodeficiency virus type 1

<400> SEQUENCE: 25

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Met Ile Gly
        35                  40                  45

Gly Ile Gly Gly Phe Ile Lys Val Arg Gln Tyr Asp Gln Ile Leu Ile
    50                  55                  60

Glu Ile Tyr Gly His Lys Ala Ile Gly Thr Val Leu Val Gly Pro Thr
65                  70                  75                  80

Pro Ile Asn Ile Ile Gly Arg Asn Met Leu Thr Gln Ile Gly Cys Thr
                85                  90                  95

Leu Asn Phe

<210> SEQ ID NO 26
<211> LENGTH: 99
<212> TYPE: PRT
<213> ORGANISM: Human immunodeficiency virus type 1

<400> SEQUENCE: 26

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Met Ile Gly
        35                  40                  45

Gly Ile Gly Gly Phe Ile Lys Val Arg Gln Cys Asp Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Val Gly Arg Asn Leu Leu Thr Gln Ile Gly Cys Thr
                85                  90                  95
```

Leu Asn Phe

<210> SEQ ID NO 27
<211> LENGTH: 99
<212> TYPE: PRT
<213> ORGANISM: Human immunodeficiency virus type 1

<400> SEQUENCE: 27

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Ile Gly Arg Asn Met Leu Thr Gln Ile Gly Cys Thr
                85                  90                  95

Leu Asn Phe

<210> SEQ ID NO 28
<211> LENGTH: 99
<212> TYPE: PRT
<213> ORGANISM: Human immunodeficiency virus type 1

<400> SEQUENCE: 28

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Met Ile Gly
        35                  40                  45

Gly Ile Gly Gly Phe Ile Lys Val Gly Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Val Gly Arg Asn Leu Leu Thr Gln Ile Gly Cys Thr
                85                  90                  95

Leu Asn Phe

<210> SEQ ID NO 29
<211> LENGTH: 99
<212> TYPE: PRT
<213> ORGANISM: Human immunodeficiency virus type 1

<400> SEQUENCE: 29

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Ile Val
            20                  25                  30

Leu Glu Glu Met Asn Leu Pro Gly Arg Trp Ile Pro Lys Met Ile Gly
        35                  40                  45

Gly Ile Gly Gly Phe Ile Lys Val Arg Gln Tyr Asp Gln Ile Leu Ile
    50                  55                  60

```
Glu Ile Cys Gly His Lys Ala Ile Gly Thr Val Leu Val Gly Pro Thr
 65                  70                  75                  80

Pro Ile Asn Ile Val Gly Arg Asn Leu Leu Thr Gln Ile Gly Cys Thr
                 85                  90                  95

Leu Asn Phe

<210> SEQ ID NO 30
<211> LENGTH: 99
<212> TYPE: PRT
<213> ORGANISM: Human immunodeficiency virus type 1

<400> SEQUENCE: 30

Pro Gln Ile Thr Leu Trp Gln Arg Pro Leu Val Thr Ile Lys Ile Gly
  1               5                  10                  15

Gly Gln Leu Lys Glu Ala Leu Leu Asp Thr Gly Ala Asp Asp Thr Val
                 20                  25                  30

Leu Glu Glu Met Asn Leu Pro Gly Arg Trp Ile Pro Lys Met Leu Gly
             35                  40                  45

Gly Ile Gly Gly Phe Ile Lys Val Arg Gln Tyr Asp Gln Ile Leu Ile
         50                  55                  60

Glu Ile Cys Gly His Lys Ala Ile Gly Thr Val Leu Val Gly Pro Thr
 65                  70                  75                  80

Pro Ile Asn Ile Val Gly Arg Asn Leu Leu Thr Gln Ile Gly Cys Thr
                 85                  90                  95

Leu Asn Phe

<210> SEQ ID NO 31
<211> LENGTH: 99
<212> TYPE: PRT
<213> ORGANISM: Human immunodeficiency virus type 1

<400> SEQUENCE: 31

Pro Gln Ile Thr Leu Trp Gln Arg Pro Leu Val Thr Ile Lys Ile Gly
  1               5                  10                  15

Gly Gln Leu Lys Glu Ala Leu Leu Asp Thr Gly Ser Asp Asp Thr Val
                 20                  25                  30

Leu Glu Glu Met Asn Leu Pro Gly Arg Trp Ile Pro Lys Ile Ile Gly
             35                  40                  45

Gly Ile Gly Gly Phe Ile Lys Val Arg Gln Tyr Asp Gln Ile Leu Ile
         50                  55                  60

Glu Ile Cys Gly His Lys Ala Ile Gly Thr Val Leu Val Gly Pro Thr
 65                  70                  75                  80

Pro Ile Asn Ile Val Gly Arg Asn Leu Leu Thr Gln Ile Gly Cys Thr
                 85                  90                  95

Leu Asn Phe

<210> SEQ ID NO 32
<211> LENGTH: 99
<212> TYPE: PRT
<213> ORGANISM: Human immunodeficiency virus type 1

<400> SEQUENCE: 32

Pro Gln Ile Thr Leu Trp Gln Arg Pro Leu Val Thr Ile Lys Ile Gly
  1               5                  10                  15

Gly Gln Leu Lys Glu Ala Leu Leu Asp Thr Gly Ser Asp Asp Thr Val
                 20                  25                  30

Leu Glu Glu Met Asn Leu Pro Gly Arg Trp Ile Pro Lys Met Ile Gly
```

```
                35                  40                  45
Gly Ile Gly Gly Phe Ile Lys Val Arg Gln Tyr Asp Gln Ile Leu Ile
         50                  55                  60
Glu Ile Cys Gly His Lys Ala Ile Gly Thr Val Leu Val Gly Pro Thr
 65                  70                  75                  80
Pro Ile Asn Ile Ile Gly Arg Asn Met Leu Thr Gln Ile Gly Cys Thr
                 85                  90                  95
Leu Asn Phe
```

<210> SEQ ID NO 33
<211> LENGTH: 99
<212> TYPE: PRT
<213> ORGANISM: Human immunodeficiency virus type 1

<400> SEQUENCE: 33

```
Pro Gln Ile Thr Leu Trp Gln Arg Pro Leu Val Thr Ile Lys Ile Gly
 1               5                  10                  15
Gly Gln Leu Lys Glu Ala Leu Leu Asp Thr Gly Ala Asp Asp Thr Val
                20                  25                  30
Leu Glu Glu Met Asn Leu Pro Gly Arg Trp Ile Pro Lys Met Ile Gly
            35                  40                  45
Gly Ile Gly Gly Phe Ile Lys Val Arg Gln Tyr Asp Val Ile Leu Ile
         50                  55                  60
Glu Ile Cys Gly His Lys Ala Ile Gly Thr Val Leu Val Gly Pro Thr
 65                  70                  75                  80
Pro Ile Asn Ile Val Gly Arg Asn Leu Leu Thr Gln Ile Gly Cys Thr
                 85                  90                  95
Leu Asn Phe
```

<210> SEQ ID NO 34
<211> LENGTH: 99
<212> TYPE: PRT
<213> ORGANISM: Human immunodeficiency virus type 1

<400> SEQUENCE: 34

```
Pro Gln Ile Thr Leu Trp Gln Arg Pro Leu Val Thr Ile Lys Ile Gly
 1               5                  10                  15
Gly Gln Leu Lys Glu Ala Leu Leu Asp Thr Gly Ala Asp Asp Thr Val
                20                  25                  30
Leu Glu Glu Met Asn Leu Pro Gly Arg Trp Ile Pro Lys Ile Ile Gly
            35                  40                  45
Gly Ile Gly Gly Phe Ile Lys Val Arg Gln Tyr Asp Gln Ile Leu Ile
         50                  55                  60
Glu Ile Cys Gly His Lys Ala Ile Gly Thr Val Leu Val Gly Pro Thr
 65                  70                  75                  80
Pro Ile Asn Val Ile Gly Arg Asn Leu Leu Thr Gln Ile Gly Cys Thr
                 85                  90                  95
Leu Asn Phe
```

<210> SEQ ID NO 35
<211> LENGTH: 99
<212> TYPE: PRT
<213> ORGANISM: Human immunodeficiency virus type 1

<400> SEQUENCE: 35

```
Pro Gln Ile Thr Leu Trp Gln Arg Pro Leu Val Thr Ile Lys Ile Gly
 1               5                  10                  15
```

Gly Gln Leu Lys Glu Ala Leu Leu Asp Thr Gly Ser Asp Asp Thr Val
            20                  25                  30

Leu Glu Glu Met Asn Leu Pro Gly Arg Trp Ile Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Thr Ile Gly Thr Val Leu Val Gly Pro Thr
65                  70                  75                  80

Pro Ile Asn Ile Ile Gly Arg Asn Met Leu Thr Gln Ile Gly Cys Thr
                85                  90                  95

Leu Asn Phe

<210> SEQ ID NO 36
<211> LENGTH: 99
<212> TYPE: PRT
<213> ORGANISM: Human immunodeficiency virus type 1

<400> SEQUENCE: 36

Pro Gln Ile Thr Leu Trp Gln Arg Pro Leu Val Ala Ile Lys Ile Gly
1               5                   10                  15

Gly Gln Leu Lys Glu Ala Leu Leu Asp Thr Gly Ser Asp Asp Thr Val
            20                  25                  30

Leu Glu Glu Met Asn Leu Pro Gly Arg Trp Ile Pro Lys Ile Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Val Gly Arg Asn Leu Leu Thr Gln Ile Gly Cys Thr
                85                  90                  95

Leu Asn Phe

<210> SEQ ID NO 37
<211> LENGTH: 99
<212> TYPE: PRT
<213> ORGANISM: Human immunodeficiency virus type 1

<400> SEQUENCE: 37

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Ile Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Ile Gly Arg Asn Met Leu Thr Gln Ile Gly Cys Thr
                85                  90                  95

Leu Asn Phe

<210> SEQ ID NO 38
<211> LENGTH: 99
<212> TYPE: PRT
<213> ORGANISM: Human immunodeficiency virus type 1

<400> SEQUENCE: 38

```
Pro Gln Ile Thr Leu Trp Gln Arg Pro Leu Val Thr Ile Lys Ile Gly
1               5                   10                  15
Gly Gln Leu Lys Glu Ala Leu Leu Asp Thr Gly Ala Asp Asp Thr Val
                20                  25                  30
Leu Glu Glu Met Asn Leu Pro Gly Arg Trp Ile Pro Lys Met Ile Gly
            35                  40                  45
Gly Ile Gly Gly Phe Thr Lys Val Arg Gln Tyr Asp Gln Ile Leu Ile
        50                  55                  60
Glu Ile Cys Gly His Lys Val Ile Gly Thr Val Leu Val Gly Pro Thr
65                  70                  75                  80
Pro Ile Asn Ile Ile Gly Arg Asn Leu Leu Thr Gln Ile Gly Cys Thr
                85                  90                  95
Leu Asn Phe
```

<210> SEQ ID NO 39
<211> LENGTH: 99
<212> TYPE: PRT
<213> ORGANISM: Human immunodeficiency virus type 1

<400> SEQUENCE: 39

```
Pro Gln Ile Thr Leu Trp Gln Arg Pro Leu Val Thr Ile Lys Ile Gly
1               5                   10                  15
Gly Gln Leu Lys Glu Ala Leu Leu Asp Thr Gly Ala Asp Asp Thr Val
                20                  25                  30
Leu Glu Glu Met Asn Leu Pro Gly Arg Trp Ile Pro Lys Met Ile Gly
            35                  40                  45
Gly Ile Gly Gly Phe Ile Lys Val Arg Gln Tyr Asp Gln Ile Leu Ile
        50                  55                  60
Glu Ile Cys Gly His Lys Ala Ile Gly Thr Val Leu Val Gly Pro Thr
65                  70                  75                  80
Pro Ile Asn Ile Ile Gly Arg Asn Met Leu Thr Gln Ile Gly Cys Thr
                85                  90                  95
Leu Asn Phe
```

<210> SEQ ID NO 40
<211> LENGTH: 99
<212> TYPE: PRT
<213> ORGANISM: Human immunodeficiency virus type 1

<400> SEQUENCE: 40

```
Pro Gln Ile Thr Leu Trp Gln Arg Pro Leu Val Thr Ile Lys Ile Gly
1               5                   10                  15
Gly Gln Leu Lys Glu Ala Leu Leu Asp Thr Gly Ala Asp Asp Thr Val
                20                  25                  30
Leu Glu Glu Met Asn Leu Pro Gly Arg Trp Ile Pro Lys Ile Ile Gly
            35                  40                  45
Gly Ile Gly Gly Phe Ile Lys Val Arg Gln Tyr Asp Gln Ile Leu Ile
        50                  55                  60
Glu Ile Cys Gly His Lys Ala Ile Gly Thr Val Leu Val Gly Pro Thr
65                  70                  75                  80
Pro Thr Asn Ile Val Gly Arg Asn Leu Leu Thr Gln Ile Gly Cys Thr
                85                  90                  95
Leu Asn Phe
```

```
<210> SEQ ID NO 41
<211> LENGTH: 99
<212> TYPE: PRT
<213> ORGANISM: Human immunodeficiency virus type 1

<400> SEQUENCE: 41

Pro Gln Ile Thr Leu Trp Gln Arg Pro Leu Val Thr Ile Lys Ile Gly
1               5                   10                  15

Gly Gln Leu Lys Glu Ala Leu Leu Asp Ala Gly Ala Asp Asp Thr Val
            20                  25                  30

Leu Glu Glu Met Asn Leu Pro Gly Arg Trp Ile Pro Lys Ile Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Ile Gly Arg Asn Met Leu Thr Gln Ile Gly Cys Thr
                85                  90                  95

Leu Asn Phe

<210> SEQ ID NO 42
<211> LENGTH: 99
<212> TYPE: PRT
<213> ORGANISM: Human immunodeficiency virus type 1

<400> SEQUENCE: 42

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Ile Ile Gly
        35                  40                  45

Gly Ile Gly Gly Phe Ile Lys Val Arg Gln Tyr Asp Gln Ile Leu Met
    50                  55                  60

Glu Ile Cys Gly His Lys Ala Ile Gly Thr Val Leu Val Gly Pro Thr
65                  70                  75                  80

Pro Ile Asn Ile Val Gly Arg Asn Leu Leu Thr Gln Ile Gly Cys Thr
                85                  90                  95

Leu Asn Phe

<210> SEQ ID NO 43
<211> LENGTH: 99
<212> TYPE: PRT
<213> ORGANISM: Human immunodeficiency virus type 1

<400> SEQUENCE: 43

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Thr Pro Lys Ile Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80
```

```
Pro Ile Asn Ile Val Gly Arg Asn Leu Leu Thr Gln Ile Gly Cys Thr
                85                  90                  95

Leu Asn Phe

<210> SEQ ID NO 44
<211> LENGTH: 99
<212> TYPE: PRT
<213> ORGANISM: Human immunodeficiency virus type 1

<400> SEQUENCE: 44

Pro Gln Ile Thr Leu Trp Gln Arg Pro Leu Val Ile Ile Lys Ile Gly
1               5                   10                  15

Gly Gln Leu Lys Glu Ala Leu Leu Asp Thr Gly Ala Asp Asp Thr Val
            20                  25                  30

Leu Lys Glu Met Asn Leu Pro Gly Arg Trp Ile Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Val Gly Arg Asn Met Leu Thr Gln Ile Gly Cys Thr
                85                  90                  95

Leu Asn Phe

<210> SEQ ID NO 45
<211> LENGTH: 99
<212> TYPE: PRT
<213> ORGANISM: Human immunodeficiency virus type 1

<400> SEQUENCE: 45

Pro Gln Ile Thr Leu Trp Gln Arg Pro Leu Val Ile Ile Lys Ile Gly
1               5                   10                  15

Gly Gln Leu Lys Lys Ala Leu Leu Asp Thr Gly Ser Asp Asp Thr Val
            20                  25                  30

Leu Glu Glu Met Asn Leu Pro Gly Arg Trp Ile Pro Lys Ile Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Val Gly Arg Asn Leu Leu Thr Gln Ile Gly Cys Thr
                85                  90                  95

Leu Asn Phe

<210> SEQ ID NO 46
<211> LENGTH: 99
<212> TYPE: PRT
<213> ORGANISM: Human immunodeficiency virus type 1

<400> SEQUENCE: 46

Pro Gln Ile Thr Leu Arg Gln Arg Pro Leu Val Thr Ile Lys Ile Gly
1               5                   10                  15

Gly Gln Leu Lys Glu Ala Leu Leu Asp Thr Gly Ser Asp Asp Thr Val
            20                  25                  30

Leu Glu Glu Met Asn Leu Pro Gly Arg Trp Ile Pro Lys Met Ile Gly
        35                  40                  45

Gly Ile Gly Gly Phe Val Lys Val Arg Gln Tyr Asp Gln Ile Leu Ile
```

```
            50                  55                  60
Glu Ile Cys Gly His Lys Val Ile Gly Thr Val Leu Val Gly Pro Thr
 65                  70                  75                  80

Pro Ile Asn Ile Ile Gly Arg Asn Leu Leu Thr Gln Ile Gly Cys Thr
                 85                  90                  95

Leu Asn Phe

<210> SEQ ID NO 47
<211> LENGTH: 99
<212> TYPE: PRT
<213> ORGANISM: Human immunodeficiency virus type 1

<400> SEQUENCE: 47

Pro Gln Ile Thr Leu Trp Gln Arg Pro Leu Val Thr Ile Lys Ile Gly
 1               5                  10                  15

Gly Gln Leu Lys Lys Ala Leu Leu Asp Thr Gly Ser Asp Asp Thr Val
                20                  25                  30

Leu Lys Glu Met Asn Leu Pro Gly Arg Trp Ile Pro Lys Ile Ile Gly
             35                  40                  45

Gly Ile Gly Gly Phe Ile Lys Val Arg Gln Tyr Asp Gln Ile Leu Ile
         50                  55                  60

Glu Ile Cys Gly His Lys Ala Ile Gly Thr Val Leu Val Gly Pro Thr
 65                  70                  75                  80

Pro Ile Asn Ile Val Gly Arg Asn Leu Leu Thr Gln Ile Gly Cys Thr
                 85                  90                  95

Leu Asn Phe

<210> SEQ ID NO 48
<211> LENGTH: 99
<212> TYPE: PRT
<213> ORGANISM: Human immunodeficiency virus type 1

<400> SEQUENCE: 48

Pro Gln Ile Thr Leu Trp Gln Arg Pro Leu Val Thr Ile Lys Ile Gly
 1               5                  10                  15

Gly Gln Leu Lys Lys Ala Leu Leu Asp Thr Gly Ser Asp Asp Thr Val
                20                  25                  30

Leu Glu Glu Met Asn Leu Pro Gly Arg Trp Ile Pro Lys Met Ile Gly
             35                  40                  45

Gly Ile Gly Gly Phe Ile Lys Val Arg Gln Tyr Asp Gln Ile Leu Ile
         50                  55                  60

Glu Ile Cys Gly His Lys Ala Ile Gly Thr Val Leu Val Gly Pro Thr
 65                  70                  75                  80

Pro Ile Asn Ile Val Gly Arg Asn Leu Leu Thr Gln Ile Gly Cys Thr
                 85                  90                  95

Leu Asn Phe

<210> SEQ ID NO 49
<211> LENGTH: 99
<212> TYPE: PRT
<213> ORGANISM: Human immunodeficiency virus type 1

<400> SEQUENCE: 49

Pro Gln Ile Thr Leu Trp Gln Arg Pro Leu Val Ile Ile Lys Ile Gly
 1               5                  10                  15

Gly Gln Leu Lys Glu Ala Leu Leu Asp Thr Gly Ser Asp Asp Ala Val
                20                  25                  30
```

```
Leu Lys Glu Met Asn Leu Pro Gly Arg Trp Ile Pro Lys Ile Ile Gly
            35                  40                  45

Gly Ile Gly Gly Phe Ile Lys Val Arg Gln Tyr Asp Gln Ile Leu Ile
        50                  55                  60

Glu Ile Cys Gly His Lys Ala Ile Gly Thr Val Leu Val Gly Pro Thr
65                  70                  75                  80

Pro Ile Asn Ile Ile Gly Arg Asn Met Leu Thr Gln Ile Gly Cys Thr
                85                  90                  95

Leu Asn Phe

<210> SEQ ID NO 50
<211> LENGTH: 99
<212> TYPE: PRT
<213> ORGANISM: Human immunodeficiency virus type 1

<400> SEQUENCE: 50

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Met Ile Gly
            35                  40                  45

Gly Ile Gly Gly Phe Ile Lys Val Arg Gln Tyr Asp Gln Ile Leu Ile
        50                  55                  60

Glu Ile Cys Gly His Lys Ala Ile Gly Thr Val Leu Val Gly Pro Thr
65                  70                  75                  80

Pro Ile Asn Ile Val Gly Arg Asn Met Leu Thr Gln Ile Gly Cys Thr
                85                  90                  95

Leu Asn Phe

<210> SEQ ID NO 51
<211> LENGTH: 99
<212> TYPE: PRT
<213> ORGANISM: Human immunodeficiency virus type 1

<400> SEQUENCE: 51

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Met Ile Gly
            35                  40                  45

Gly Ile Gly Gly Phe Ile Lys Val Arg Gln Tyr Asp Gln Ile Leu Ile
        50                  55                  60

Glu Ile Cys Gly His Lys Ala Ile Gly Thr Val Leu Val Gly Pro Thr
65                  70                  75                  80

Pro Ile Asn Ile Val Gly Arg Asn Met Leu Thr Gln Ile Gly Cys Thr
                85                  90                  95

Leu Asn Phe

<210> SEQ ID NO 52
<211> LENGTH: 99
<212> TYPE: PRT
<213> ORGANISM: Human immunodeficiency virus type 1

<400> SEQUENCE: 52
```

```
Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Ile Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Ile Gly Arg Asn Met Leu Thr Gln Ile Gly Cys Thr
                85                  90                  95

Leu Asn Phe

<210> SEQ ID NO 53
<211> LENGTH: 99
<212> TYPE: PRT
<213> ORGANISM: Human immunodeficiency virus type 1

<400> SEQUENCE: 53

Pro Gln Ile Thr Leu Trp Gln Arg Pro Leu Val Thr Ile Lys Ile Gly
1               5                   10                  15

Gly Gln Leu Lys Lys Ala Leu Leu Asp Thr Gly Ser Asp Asp Thr Val
            20                  25                  30

Leu Glu Glu Met Asn Leu Pro Gly Arg Trp Ile Pro Lys Ile Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Val Gly Arg Asn Met Leu Thr Gln Ile Gly Cys Thr
                85                  90                  95

Leu Asn Phe

<210> SEQ ID NO 54
<211> LENGTH: 99
<212> TYPE: PRT
<213> ORGANISM: Human immunodeficiency virus type 1

<400> SEQUENCE: 54

Pro Gln Ile Thr Leu Trp Gln Arg Pro Leu Val Thr Ile Lys Ile Gly
1               5                   10                  15

Gly Gln Leu Lys Lys Ala Leu Leu Asp Thr Gly Ser Asp Asp Thr Val
            20                  25                  30

Leu Glu Glu Met Asn Leu Pro Gly Arg Trp Ile Pro Lys Ile Ile Gly
        35                  40                  45

Gly Ile Gly Gly Phe Thr Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Val Gly Arg Asn Met Leu Thr Gln Ile Gly Cys Thr
                85                  90                  95

Leu Asn Phe

<210> SEQ ID NO 55
<211> LENGTH: 99
```

-continued

```
<212> TYPE: PRT
<213> ORGANISM: Human immunodeficiency virus type 1

<400> SEQUENCE: 55

Pro Gln Ile Thr Leu Trp Gln Arg Pro Leu Ile Thr Ile Lys Ile Gly
1               5                   10                  15

Gly Gln Leu Lys Lys Ala Leu Leu Asp Thr Gly Ser Asp Asp Ala Val
            20                  25                  30

Leu Glu Glu Met Asn Leu Pro Gly Arg Trp Ile Pro Lys Ile Ile Gly
        35                  40                  45

Gly Ile Gly Gly Phe Ile Lys Val Arg Gln Tyr Asn Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Ile Gly Arg Asn Met Leu Thr Gln Ile Gly Cys Thr
                85                  90                  95

Leu Asn Phe

<210> SEQ ID NO 56
<211> LENGTH: 99
<212> TYPE: PRT
<213> ORGANISM: Human immunodeficiency virus type 1

<400> SEQUENCE: 56

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Ile Ile Gly
        35                  40                  45

Gly Ile Gly Gly Phe Ile Lys Val Arg Gln Tyr Asn Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Val Gly Arg Asn Met Leu Thr Gln Ile Gly Cys Thr
                85                  90                  95

Leu Asn Phe

<210> SEQ ID NO 57
<211> LENGTH: 99
<212> TYPE: PRT
<213> ORGANISM: Human immunodeficiency virus type 1

<400> SEQUENCE: 57

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Ile Ile Gly
        35                  40                  45

Gly Ile Gly Gly Phe Ile Asn Val Arg Gln Tyr Gly Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Ile Gly Arg Asn Met Leu Thr Gln Ile Gly Cys Thr
                85                  90                  95
```

-continued

Leu Asn Phe

<210> SEQ ID NO 58
<211> LENGTH: 99
<212> TYPE: PRT
<213> ORGANISM: Human immunodeficiency virus type 1

<400> SEQUENCE: 58

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Ile Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Val Gly Arg Asn Met Leu Thr Gln Ile Gly Cys Thr
                85                  90                  95

Leu Asn Phe

<210> SEQ ID NO 59
<211> LENGTH: 99
<212> TYPE: PRT
<213> ORGANISM: Human immunodeficiency virus type 1

<400> SEQUENCE: 59

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Ile Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Ile Asn Ile Val Gly Arg Asn Leu Leu Thr Gln Ile Gly Cys Thr
                85                  90                  95

Leu Asn Phe

<210> SEQ ID NO 60
<211> LENGTH: 99
<212> TYPE: PRT
<213> ORGANISM: Human immunodeficiency virus type 1

<400> SEQUENCE: 60

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Met Ile Gly
        35                  40                  45

Gly Ile Gly Gly Phe Ile Lys Val Arg Gln Tyr Asp Gln Met Leu Ile
    50                  55                  60

Glu Ile Cys Gly His Lys Ala Ile Gly Thr Val Leu Val Gly Pro Thr

```
                65                 70                  75                  80
Pro Ile Asn Ile Val Gly Arg Asn Met Leu Thr Gln Ile Gly Cys Thr
                85                  90                  95

Leu Asn Phe

<210> SEQ ID NO 61
<211> LENGTH: 99
<212> TYPE: PRT
<213> ORGANISM: Human immunodeficiency virus type 1

<400> SEQUENCE: 61

Pro Gln Ile Thr Leu Trp Gln Arg Pro Leu Val Thr Ile Lys Ile Gly
1               5                   10                  15

Gly Gln Leu Lys Lys Ala Leu Leu Asp Thr Gly Ser Asp Asp Thr Val
            20                  25                  30

Leu Glu Glu Met Asn Leu Pro Gly Arg Trp Ile Pro Lys Ile Ile Gly
        35                  40                  45

Gly Ile Gly Gly Phe Ile Lys Val Arg Gln Tyr Asn Gln Ile Leu Ile
    50                  55                  60

Glu Ile Cys Gly His Lys Val Ile Gly Thr Val Leu Val Gly Pro Thr
65                  70                  75                  80

Pro Ile Asn Ile Val Gly Arg Asn Met Leu Thr Gln Ile Gly Cys Thr
                85                  90                  95

Leu Asn Phe

<210> SEQ ID NO 62
<211> LENGTH: 99
<212> TYPE: PRT
<213> ORGANISM: Human immunodeficiency virus type 1

<400> SEQUENCE: 62

Pro Gln Ile Thr Leu Trp Gln Arg Pro Leu Val Thr Ile Lys Ile Gly
1               5                   10                  15

Gly Gln Leu Lys Lys Ala Leu Leu Asp Thr Gly Ser Asp Asp Thr Val
            20                  25                  30

Leu Glu Glu Met Asn Leu Pro Gly Arg Trp Ile Pro Lys Ile Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Val Ile Ser Thr Val Leu Val Gly Pro Thr
65                  70                  75                  80

Pro Ile Asn Ile Val Gly Arg Asn Met Leu Thr Gln Ile Gly Cys Thr
                85                  90                  95

Leu Asn Phe

<210> SEQ ID NO 63
<211> LENGTH: 99
<212> TYPE: PRT
<213> ORGANISM: Human immunodeficiency virus type 1

<400> SEQUENCE: 63

Pro Gln Ile Thr Leu Trp Gln Arg Pro Leu Val Thr Ile Lys Ile Gly
1               5                   10                  15

Gly Gln Leu Lys Lys Ala Leu Leu Asp Thr Gly Ser Asp Asp Thr Val
            20                  25                  30

Leu Glu Glu Met Asn Leu Pro Gly Arg Trp Ile Pro Lys Ile Ile Gly
        35                  40                  45
```

-continued

Gly Ile Gly Gly Phe Ile Lys Val Arg Gln Tyr Asn Gln Ile Leu Ile
            50                  55                  60

Glu Ile Cys Gly His Lys Val Ile Gly Thr Ile Leu Val Gly Pro Thr
 65                  70                  75                  80

Pro Ile Asn Ile Val Gly Arg Asn Met Leu Thr Gln Ile Gly Cys Thr
                85                  90                  95

Leu Asn Phe

<210> SEQ ID NO 64
<211> LENGTH: 99
<212> TYPE: PRT
<213> ORGANISM: Human immunodeficiency virus type 1

<400> SEQUENCE: 64

Pro Gln Ile Thr Leu Trp Gln Arg Pro Leu Val Thr Ile Lys Ile Gly
 1               5                  10                  15

Gly Gln Leu Lys Lys Ala Leu Leu Asp Thr Gly Ser Asp Ala Thr Val
            20                  25                  30

Leu Glu Glu Met Asn Leu Pro Gly Arg Trp Ile Pro Lys Ile Ile Gly
        35                  40                  45

Gly Ile Gly Gly Phe Ile Lys Val Arg Gln Tyr Asp Gln Ile Leu Ile
            50                  55                  60

Glu Ile Cys Gly His Lys Ala Ile Gly Thr Val Leu Val Gly Pro Thr
 65                  70                  75                  80

Pro Ile Asn Ile Val Gly Arg Asn Met Leu Thr Gln Ile Gly Cys Thr
                85                  90                  95

Leu Asn Phe

<210> SEQ ID NO 65
<211> LENGTH: 99
<212> TYPE: PRT
<213> ORGANISM: Human immunodeficiency virus type 1

<400> SEQUENCE: 65

Pro Gln Ile Thr Leu Trp Gln Arg Pro Leu Val Thr Ile Lys Ile Gly
 1               5                  10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Ile Ile Gly
        35                  40                  45

Gly Val Gly Gly Phe Ile Lys Val Arg Gln Tyr Asn Gln Ile Leu Ile
            50                  55                  60

Glu Ile Cys Gly His Lys Ala Ile Gly Thr Val Leu Val Gly Pro Thr
 65                  70                  75                  80

Pro Ile Asn Ile Ile Gly Arg Asn Met Leu Thr Gln Ile Gly Cys Thr
                85                  90                  95

Leu Asn Phe

<210> SEQ ID NO 66
<211> LENGTH: 99
<212> TYPE: PRT
<213> ORGANISM: Human immunodeficiency virus type 1

<400> SEQUENCE: 66

Pro Gln Ile Thr Leu Trp Gln Arg Pro Leu Val Thr Ile Lys Ile Gly
 1               5                  10                  15

Gly Gln Leu Lys Glu Ala Leu Leu Asp Thr Gly Ala Asp Thr Val
            20                  25                  30

Leu Glu Glu Met Asn Leu Pro Gly Arg Trp Ile Pro Lys Ile Ile Gly
        35                  40                  45

Gly Val Gly Gly Phe Ile Lys Val Arg Gln Tyr Asp Gln Ile Leu Ile
50                  55                  60

Glu Ile Cys Gly His Lys Ala Ile Gly Thr Val Leu Val Gly Pro Thr
65                  70                  75                  80

Pro Ile Asn Ile Val Gly Arg Asn Met Leu Thr Gln Ile Gly Cys Thr
                85                  90                  95

Leu Asn Phe

<210> SEQ ID NO 67
<211> LENGTH: 99
<212> TYPE: PRT
<213> ORGANISM: Human immunodeficiency virus type 1

<400> SEQUENCE: 67

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Val Asp Asp Thr Val
            20                  25                  30

Leu Glu Glu Met Asn Leu Pro Gly Arg Trp Ile Pro Lys Ile Ile Gly
        35                  40                  45

Gly Val Gly Gly Phe Ile Lys Val Arg Gln Tyr Asp Gln Ile Leu Ile
50                  55                  60

Glu Ile Cys Gly His Lys Ala Ile Gly Thr Val Leu Val Gly Pro Thr
65                  70                  75                  80

Pro Ile Asn Ile Val Gly Arg Asn Met Leu Thr Gln Ile Gly Cys Thr
                85                  90                  95

Leu Asn Phe

<210> SEQ ID NO 68
<211> LENGTH: 99
<212> TYPE: PRT
<213> ORGANISM: Human immunodeficiency virus type 1

<400> SEQUENCE: 68

Pro Gln Ile Thr Leu Trp Gln Arg Pro Leu Val Thr Ile Asn Thr Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Ile Pro Lys Ile Ile Gly
        35                  40                  45

Gly Val Gly Gly Phe Ile Lys Val Arg Gln Tyr Asn Gln Ile Leu Ile
50                  55                  60

Glu Ile Cys Gly His Lys Ala Ile Gly Thr Val Leu Val Gly Pro Thr
65                  70                  75                  80

Pro Ile Asn Ile Ile Gly Arg Asn Met Leu Thr Gln Ile Gly Cys Thr
                85                  90                  95

Leu Asn Phe

<210> SEQ ID NO 69
<211> LENGTH: 22
<212> TYPE: DNA
<213> ORGANISM: Human immunodeficiency virus type 1

```
<400> SEQUENCE: 69
gatgctacat ataagcagct gc                                              22

<210> SEQ ID NO 70
<211> LENGTH: 24
<212> TYPE: DNA
<213> ORGANISM: Human immunodeficiency virus type 1

<400> SEQUENCE: 70
ctcgtgacaa atttctacta atgc                                            24

<210> SEQ ID NO 71
<211> LENGTH: 22
<212> TYPE: DNA
<213> ORGANISM: Human immunodeficiency virus type 1

<400> SEQUENCE: 71
gagactctgg taactagaga tc                                              22

<210> SEQ ID NO 72
<211> LENGTH: 28
<212> TYPE: DNA
<213> ORGANISM: Human immunodeficiency virus type 1

<400> SEQUENCE: 72
ccatcccggg ctttaatttt actggtac                                        28

<210> SEQ ID NO 73
<211> LENGTH: 23
<212> TYPE: DNA
<213> ORGANISM: Human immunodeficiency virus type 1

<400> SEQUENCE: 73
ttgcagggcc cctaggaaaa agg                                             23

<210> SEQ ID NO 74
<211> LENGTH: 38
<212> TYPE: DNA
<213> ORGANISM: Human immunodeficiency virus type 1

<400> SEQUENCE: 74
ggctgctgcg gcagcaaaat ttaaagtgca gccaatct                             38

<210> SEQ ID NO 75
<211> LENGTH: 36
<212> TYPE: DNA
<213> ORGANISM: Human immunodeficiency virus type 1

<400> SEQUENCE: 75
gctgccgcag cagccgtgag caagggcgag gagctg                               36

<210> SEQ ID NO 76
<211> LENGTH: 34
<212> TYPE: DNA
<213> ORGANISM: Human immunodeficiency virus type 1

<400> SEQUENCE: 76
actaatggga aacttgtaca gctcgtccat gccg                                 34

<210> SEQ ID NO 77
<211> LENGTH: 27
<212> TYPE: DNA
<213> ORGANISM: Human immunodeficiency virus type 1
```

<400> SEQUENCE: 77
tttcccatta gtcctattga gactgta                                      27

<210> SEQ ID NO 78
<211> LENGTH: 24
<212> TYPE: DNA
<213> ORGANISM: Human immunodeficiency virus type 1

<400> SEQUENCE: 78
ccagaaatct tgagttctct tatt                                         24

<210> SEQ ID NO 79
<211> LENGTH: 23
<212> TYPE: DNA
<213> ORGANISM: Human immunodeficiency virus type 1

<400> SEQUENCE: 79
ttgcagggcc cctaggaaaa agg                                          23

<210> SEQ ID NO 80
<211> LENGTH: 24
<212> TYPE: DNA
<213> ORGANISM: Human immunodeficiency virus type 1

<400> SEQUENCE: 80
ccagaaatct tgagttctct tatt                                         24

<210> SEQ ID NO 81
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Pro Gln Ile Thr Leu Arg Lys Lys Arg Arg Gln Arg Arg Pro Pro
1               5                   10                  15

Gln Val Ser Phe Asn Phe Ala Thr Leu Asn Phe
            20                  25

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Lys Lys Arg Arg Gln Arg Arg Pro Pro Gln Val Ser Phe Asn
1               5                   10                  15

Phe

METHODS AND COMPOSITIONS FOR TREATING HIV INFECTIONS

CROSS REFERENCE TO RELATED APPLICATIONS

This application is a U.S. national stage application under 35 U.S.C. §371 of international application serial no. PCT/US2007/085265 filed Nov. 20, 2007, which claims priority to U.S. Provisional Patent Application Ser. No. 60/866,786 filed on Nov. 21, 2006, and U.S. Provisional Patent Application Ser. No. 60/945,708 filed on Jun. 22, 2007, the entire disclosure of each of which is hereby incorporated by reference.

GOVERNMENT RIGHTS

This invention was made with government support under grant number GM053386 awarded by the National Institutes of Health. The government has certain rights in the invention.

BACKGROUND

The AIDS epidemic is one of the most challenging problems in medicine in the 21st century (United Nations. 2004 Report on the global HIV/AIDS Epidemic: 4th global report. New York, U.S.A., 2004). The disclosure of the foregoing is incorporated herein in its entirety by reference. In addition, the entirety of the disclosures of each of the publications cited herein are also incorporated herein by reference. Among many strategies to combat this disease, highly active antiretroviral therapy (HAART) with HIV protease inhibitors (PIs) in combination with reverse transcriptase inhibitors (RTIs) continues to be the first line treatment for control of HIV infection (Sepkowitz, K. A. AIDS—the first 20 years. N. Engl. J. Med. 2001, 344, 1764-1772). This treatment regimen has definitely improved quality of life, enhanced HIV management, and halted the progression of the disease. However, despite these impressive successes, there remain many challenges to treating this devastating disease, including decreasing both the toxicity of and complexity of these treatment regimens. In addition, there is a growing population of patients that are developing multi-drug resistant strains of HIV, and there is ample evidence that these strains can be further transmitted (Staszewski et al., Efavirenz plus zidovudine and lamivudine, efavirenz plus indinavir, and indinavir plus zidovudine and lamivudine in the treatment of HIV-1 infection in adults. N. Engl. J. Med. 1999, 341, 1865-1873; Wainberg et al., Public health implications of antiretroviral therapy and HIV drug resistance. J. Am. Med. Assoc. 1998, 279, 1977-1983).

HAART has had a major impact on the AIDS epidemic in industrially advanced nations; however, eradication of human immunodeficiency virus type 1 (HIV 1) appears to be currently unachieved, in part due to the viral reservoirs remaining in blood and infected tissues. The limitation of antiviral therapy of AIDS is also exacerbated by complicated regimens, the development of drug-resistant HIV-1 variants, and a number of inherent adverse effects.

However, a number of challenges have nonetheless been encountered in bringing about the optimal benefits of the currently available therapeutics of AIDS and HIV-1 infection to individuals receiving HAART (De Clercq 2002. Strategies in the design of antiviral drugs. Nat Rev Drug Discov 1:13-25; Siliciano et al. 2004. A long-term latent reservoir for HIV-1: discovery and clinical implications. J Antimicrob Chemother 54:6-9; Simon, et al. 2003. HIV-1 dynamics in vivo: implications for therapy. Nat Rev Microbiol 1:181-90). They include (i) drug-related toxicities; (ii) partial restoration of immunologic functions once individuals developed AIDS; (iii) development of various cancers as a consequence of survival prolongation; (iv) flame-up of inflammation in individuals receiving HAART or immune re-construction syndrome (IRS); and (v) increased cost of antiviral therapy. Such limitations of HAART are exacerbated by the development of drug-resistant HIV-1 variants (Carr 2003. Toxicity of antiretroviral therapy and implications for drug development. Nat Rev Drug Discov 2:624-34; Fumero et al. 2003. New patterns of HIV-1 resistance during HAART. Clin Microbiol Infect 9:1077-84; Grabar et al. 2006. HIV infection in older patients in the HAART era. J Antimicrob Chemother 57:4-7; Hirsch et al. 2004. Immune reconstitution in HIV-infected patients. Clin Infect Dis 38:1159-66; Little et al. 2002. Antiretroviral-drug resistance among patients recently infected with HIV. N Engl J Med 347:385-94.

Successful antiviral drugs, in theory, exert their virus-specific effects by interacting with viral receptors, virally encoded enzymes, viral structural components, viral genes, or their transcripts without disturbing cellular metabolism or function. However, at present, no antiretroviral drugs or agents are likely to be completely specific for HIV-1 or to be devoid of toxicity or side effects in the therapy of AIDS, which has been an issue because patients with AIDS and its related diseases will have to receive antiretroviral therapy for a long period of time, perhaps for the rest of their lives.

The design and synthesis of non-peptidyl protease inhibitors (NPPIs) that are potent against HIV-1 variants resistant to the currently approved PIs has yielded one successful anti-HIV-1 agent, darunavir (DRV)/TMC114. DRV includes the structure-based designed nonpeptidic P2 ligand, 3(R),3a(S),6a(R)-bis tetrahydrofuranylurethane (bis-THF) (Ghosh et al. 1998. Potent HIV protease inhibitors incorporating high-affinity P2-ligands and (R)-(hydroxyethylamino)sulfonamide isostere. Bioorg Med Chem Lett 8:687-90; Ghosh et al. 1998. Structure based design: novel spirocyclic ethers as nonpeptidal P2-ligands for HIV protease inhibitors. Bioorg Med Chem Lett 8:979-82; Koh et al. 2003. Novel bis tetrahydrofuranylurethane-containing nonpeptidic protease inhibitor (PI) UIC-94017 (TMC114) with potent activity against multi-PI-resistant human immunodeficiency virus in vitro. Antimicrob Agents Chemother 47:3123-9). DRV has recently been approved as a therapeutic agent for the treatment of individuals who harbor multi-drug-resistant HIV-1 variants and do not respond to previously existing HAART regimens.

Incorporation of bis-THF also conferred on other NPPIs including brecanavir (BCV)/GW640385, which has potent antiviral activity against a wide spectrum of PI-resistant HIV-1 variants (Ghosh et al. 2006. Design and synthesis of novel HIV-1 protease inhibitors incorporating oxyindoles as the P2'-ligands. Bioorg Med Chem Lett 16:1869-73; Ghosh et al. 2006. Structure-Based Design of Novel HIV-1 Protease Inhibitors To Combat Drug Resistance. J Med Chem 49:5252-5261; Miller et al. 2006. Ultra-potent P1 modified arylsulfonamide HIV protease inhibitors: the discovery of GW0385. Bioorg Med Chem Lett 16:1788-94). BCV is currently undergoing phase III clinical trials.

However, the foregoing examples have only been exploited for their protease inhibition activity. Thus, the identification of new class of antiretroviral drugs which have one or more new mechanisms of action and advantageously produce fewer side effects remains an important therapeutic objective.

SUMMARY OF THE INVENTION

Described herein are novel compounds and compositions for treating patients in need of relief from HIV, AIDS, and AIDS-related diseases. Also described herein are methods for treating such diseases that include inhibition of HIV protease dimerization. Also described herein are assays for screening and determining the activity and potency of compounds capable of inhibiting protease dimerization.

In one embodiment, compositions are described herein for use in treatment methods for HIV infection, AIDS, and AIDS-related diseases and disorders. The compositions include two or more compounds, each in a therapeutically effective amount, where the two compounds exhibit different modes of action in their ability to ameliorate the disease or the symptoms of the disease. In one aspect, the first compound is an inhibitor of the dimerization of one or more HIV proteases. In another aspect, the first compound is a dimerization inhibitor that is also a protease inhibitor. In another aspect, the mode of action of the second compound is illustratively, protease inhibition, integrase inhibition, reverse transcriptase inhibition, CCR-5 antagonism, and the like. Additional modes of action include other interactions with viral receptors, virally encoded enzymes, viral structural components, viral genes, or their transcripts. It is appreciated that those interactions that negatively affect HIV act advantageously without disturbing cellular metabolism or function. It is to be understood, that in some cases, a particular drug or therapeutic compound will have multiple modes of action. Such drugs are included in the compositions contemplated herein. Illustratively, a composition is described that includes a protease inhibitor with a protease dimerization inhibitor. It is appreciated that such protease inhibitors may also be dimerization inhibitors, and such dimerization inhibitors may also be protease inhibitors.

In one illustrative embodiment, the protease dimerization inhibitor is a compound of the following structure:

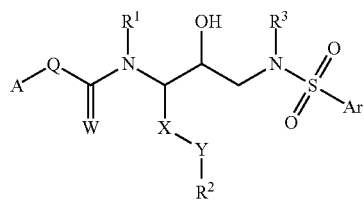

wherein A is heterocyclyl, heterocyclylalkyl, or heteroarylalkyl, each of which is optionally substituted; or A-O—C(O) is taken together to form an optionally substituted arylcarbonyl;

Q is oxygen, sulfur, nitrogen, or $C(R^aR^b)$; where each of $R^a$ and $R^b$ is independently selected in each instance from the group consisting of hydrogen, alkyl, and alkoxy;

W is oxygen or sulfur;

$R^1$ is hydrogen, a nitrogen protecting group, or a pro-drug substituent;

X is $C(R^aR^b)_n$, where each of $R^a$ and $R^b$ is independently selected in each instance from the group consisting of hydrogen, alkyl, and alkoxy;

Y is oxygen, sulfur, $N(R^e)$, or $N(R^e)$—$S(O)_2$; or Y represents a single bond connecting X and $R^2$; where $R^e$ is hydrogen or alkyl, or a nitrogen protecting group;

$R^2$ is alkyl, cycloalkyl, cycloalkylalkyl, aryl, heteroaryl, arylalkyl, or heteroarylalkyl, each of which is optionally substituted;

$R^3$ is alkyl, cycloalkyl, heterocyclyl, nitrogen-containing heterocyclyl attached at the heterocyclyl nitrogen, heterocyclylalkyl, hydroxy, alkoxy, cycloalkoxy, heterocyclyloxy, heterocyclylalkoxy, acyloxy, amino, mono or dialkylamino, cycloalkylamino, heterocyclylamino, heterocyclylalkylamino, or acylamino, each of which is optionally substituted.

In another illustrative embodiment, the protease dimerization inhibitor is a compound of the following structure:

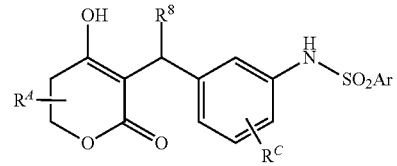

wherein Ar is an aryl or heteroaryl group, with is optionally substituted, $R^C$ is hydrogen or represents one or more aryl substituents, $R^B$ is hydrogen, alkyl, cycloalkyl, or arylalkyl, each of which is optionally substituted, and $R^A$ is hydrogen, or one or more substituents selected from alkyl, cycloalkyl, heterocyclyl, aryl, arylalkyl, heteroaryl, and heteroarylalkyl, each of which is optionally substituted.

In another aspect, the protease dimerization inhibitors are the compounds shown in FIG. 1.

The compounds described herein that are inhibitors of protease dimerization may be included in the pharmaceutical compositions described herein. Such pharmaceutical compositions include (a) one or more inhibitors of protease dimerization; (b) one or more additional therapeutic agents, where the additional one or more therapeutic agents exhibit their activity primarily by one or more modes of action different from dimerization inhibition; and (c) a pharmaceutically acceptable carrier, excipient, diluent, or combination thereof.

In another illustrative embodiment, methods for treating HIV infection, AIDS, and AIDS-related diseases and disorders are described using the compounds and pharmaceutical compositions described herein.

Also described herein are methods for treating HIV, AIDS, or an AIDS-related disease state, the method comprising the step of administering to patient in need of relief from AIDS or the AIDS-related disease state a therapeutically effective amount of a protease dimerization inhibitor.

Also described herein are methods for treating HIV, AIDS, or an AIDS-related disease state, the method comprising the step of administering to patient in need of relief from AIDS or the AIDS-related disease state a therapeutically effective amount of a protease dimerization inhibitor capable of hydrogen bonding to both monomers of HIV protease, where the hydrogen bonds occur at least one of residues 29 or 30 of each monomer Also described herein are nucleic acids comprising the coding sequence for (a) an HIV-1 protease and (b) enhanced cyan fluorescent protein (CFP). Also described herein are nucleic acids comprising the coding sequence for (a) an HIV-1 protease and (b) yellow fluorescent protein (YFP) protease. Also described herein are vectors comprising the nucleic acids described herein. Also described herein are proteins comprising a sequence encoded by the nucleic acids described herein. Also described herein are transformed cell comprising the nucleic acids described herein.

Also described herein are methods for measuring the inhibitory activity of a test compound or a library of test compounds, the method comprising the steps of (a) treating transformed cell described herein with the test compound or the library of test compounds; (b) measuring the fluorescence of the treated cell; and (c) comparing the fluorescence of the treated cell with the fluorescence of an untreated cell.

In one embodiment, an assay system is described that enables the discovery and examination of activity of test compounds to block the dimerization of HIV-1 protease, employing intermolecular fluorescence resonance energy transfer (FRET)-based probes. The probes consist of two different protease monomers, enhanced cyan fluorescent protein (CFP)-tagged and yellow fluorescent protein (YFP)-tagged HIV-1 protease subunits.

In another embodiment compounds that exhibit positive results in the FRET assay are also described. Such compounds inhibit the dimerization of HIV-1 protease and may show anti-HIV activity. Also described herein are pharmaceutical compositions that include those compounds.

BRIEF DESCRIPTION OF THE DRAWINGS

FIG. 2A-1 shows images of cells showing FRET after inhibition of protease dimerization by dimerization inhibitors; images of cells co-transfected with pNLPRwt-CFP and pNLPRwt-YFP viewed by fluorescence, and images of co-transfected cells prior to and after photobleaching. Cos-7 cells plated on EZ view cover-glass bottom culture plate (IWAKI, TOKYO, JAPAN) were transfected with two plasmids, pNLPRwt-CFP and pNLPRwt-YFP, using Lipofectamine 2000 (Invitrogen, Carlsbad, Calif.) according to manufacturer's instructions, cultured for 48-72 hrs, and analyzed under Fluoview FV500 confocal laser scanning microscope (OLYMPUS Optical Corp) at room temperature. Both NL-PRwt-ECFP and NL-PRwt-EYFP proteins were well visualized prior to photobleaching. The fluorescence pattern of the proteins was diffuse and a slightly punctuate staining pattern mostly in cytoplasmic regions within cells, and was not concentrated at the plasma membrane as CCR5-EYFP/ECFP. Photobleaching of the cells dramatically reduced EYFP fluorescence and increased ECFP emission from NL-PRwt-ECFP, signifying that dimerization of both YFP- and CFP-tagged protease subunits were dimerized. All the determinations were conducted in a double-blind fashion.

FIG. 2A-2 shows fluorescent images of co-transfected cells prior to and after acceptor photobleaching. Cos-7 cells plated on EZ view cover-glass bottom culture plate were transfected with two plasmids, $pPR_{WT}^{CFP}$ and $pPR_{WT}^{YFP}$, using Lipofectamine, cultured for 72 hrs, and analyzed under Fluoview FV500 confocal laser scanning microscope. Both $PR_{WT}^{CFP}$ and $PR_{WT}^{YFP}$ proteins were visualized prior to photobleaching. Photobleaching of the cells dramatically reduced YFP fluorescence with a $YFP^{A/B}$ ratio of 0.17 and increased CFP emission with a $CFP^{A/B}$ ratio of 1.38, signifying the dimerization of both YFP- and CFP-tagged protease subunits.

FIG. 4 shows the amino acid sequences of the protease-encoding region of HIV-1$_{NL4-3}$ variants selected in the presence of GRL-98065. The amino acid sequence of protease, deduced from the nucleotide sequence of the protease-encoding region of each proviral DNA isolated at an indicated time, is shown. The amino acid sequence of wild-type HIV-1$_{NL4-3}$ protease is illustrated at the top as a reference.

DETAILED DESCRIPTION

Described herein are compounds that exhibit dimerization inhibition of HIV proteases. In one aspect, the compound also exhibit protease inhibition. In one embodiment, protease dimerization inhibiting compounds of the following formula are described:

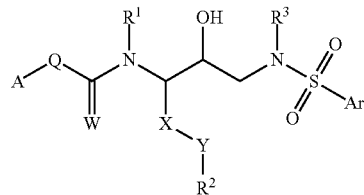

wherein A is heterocyclyl, heterocyclylalkyl, or heteroarylalkyl, each of which is optionally substituted; or A-O—C(O) is taken together to form an optionally substituted arylcarbonyl;

Q is oxygen, sulfur, nitrogen, or $C(R^a R^b)$; where each of $R^a$ and $R^b$ is independently selected in each instance from the group consisting of hydrogen, alkyl, and alkoxy;

W is oxygen or sulfur;

$R^1$ is hydrogen, a nitrogen protecting group, or a pro-drug substituent;

X is $C(R^a R^b)_n$, where each of $R^a$ and $R^b$ is independently selected in each instance from the group consisting of hydrogen, alkyl, and alkoxy;

Y is oxygen, sulfur, $N(R^e)$, or $N(R^e)$—$S(O)_2$; or Y represents a single bond connecting X and $R^2$; where $R^e$ is hydrogen or alkyl, or a nitrogen protecting group;

$R^2$ is alkyl, cycloalkyl, cycloalkylalkyl, aryl, heteroaryl, arylalkyl, or heteroarylalkyl, each of which is optionally substituted;

$R^3$ is alkyl, cycloalkyl, heterocyclyl, nitrogen-containing heterocyclyl attached at the heterocyclyl nitrogen, heterocyclylalkyl, hydroxy, alkoxy, cycloalkoxy, heterocyclyloxy, heterocyclylalkoxy, acyloxy, amino, mono or dialkylamino, cycloalkylamino, heterocyclylamino, heterocyclylalkylamino, or acylamino, each of which is optionally substituted.

Figure 1:
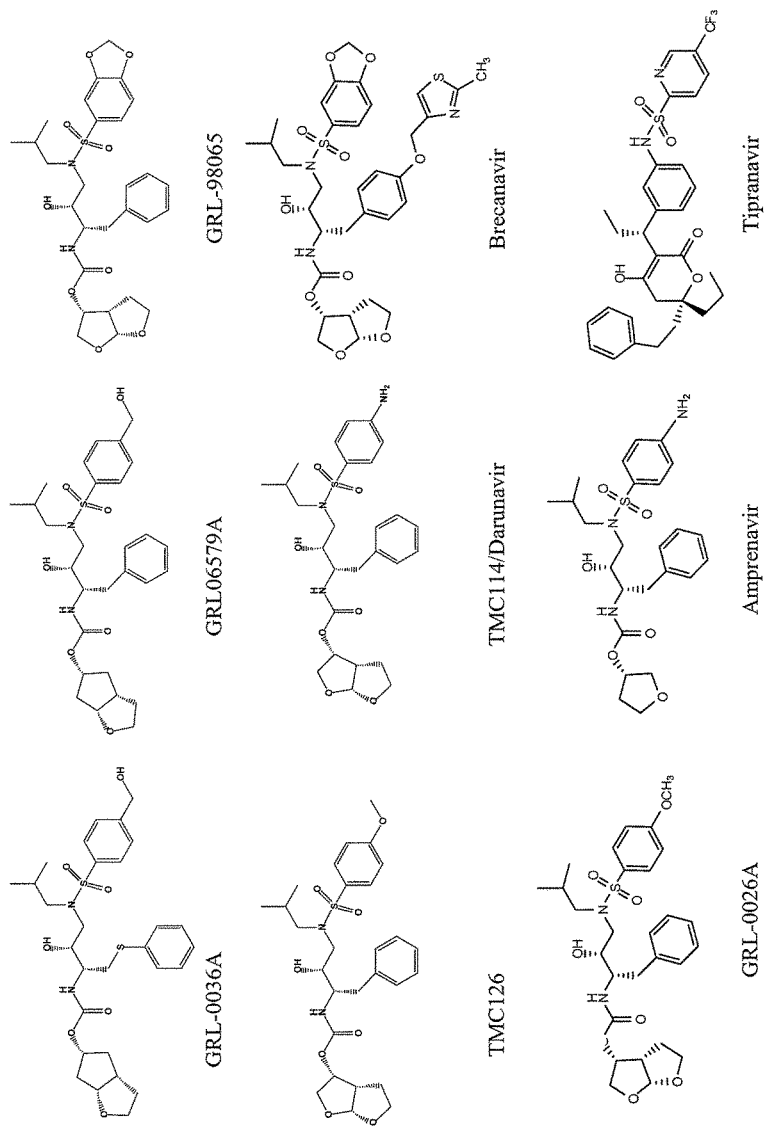
FIG. 1 shows structures of illustrative dimerization inhibitors. The $IC_{50}$ values for activity against HIV-1 in acute HIV-1 infection assays using MT-2 cells and 100 $TCID_{50}$ of HIV-$1_{LAI}$ were 0.005, 0.001, 0.0004, 0.0003, 0.003, 0.0002, 0.48 and 0.10 µM for GRL-0036A, GRL-06579A, GRL-98065, TMC126, DRV, brecanavir (BCV), GRL-0026A and tipranavir (TPV), respectively

In one aspect, the compounds described herein of the above formula are novel and not a compound shown in FIG. 1.

Such protease dimerization inhibitors may be used alone or in conjunction with a wide variety of other therapeutically active compounds. In one embodiment, the additional therapeutically active compounds exhibit their activity primarily by one or more modes of action different from dimerization inhibition.

As used herein, the term "heterocylclyl" includes monocyclic and polycyclic rings that have at least one nitrogen, oxygen, or sulfur atom, where it is to be understood that the polycyclic rings may be fused and/or spiro ring systems. Illustratively, monocyclic heterocyclyls include, but are not limited to 5-, 6-, and 7-membered cyclic ethers and diethers, such as tetrahydrofurans, pyrans, 1,3-dioxolanes, 1,3-dixoxanes, 1,4-dioxanes, 1,3-dioxepanes, and the like; pyrrolidines, piperidines, piperazines, and the like; and tetrahydrothiophenes, thiopyrans, including oxidized variations thereof, and the like. Illustratively, polycyclic heterocyclyls include, but are not limited to, the foregoing monocyclic rings fused to each other, or to cycloalkyls, and alternatively the spiro variations thereof. As indicated herein, it is also to be understood that where such fused or spiro ring systems include chiral centers, any and all possible stereoisomers are contemplated to be included herein. In addition, both the pure enantiomers and diastereomers, as well as various mixtures of pure enantiomers and diastereomers are contemplated to be included herein. It is also to be understood that the point of attachment of the heterocylclyl groups described herein may be at any locus of the ring system.

As used herein, the term "heteroaryl" includes monocyclic and polycyclic aromatic groups that have at least one nitrogen, oxygen, or sulfur atom. Illustrative monocyclic heteroaryl include furyl, pyrrolyl, thienyl, isoxazolyl, oxazolyl, pyrazolyl, imidazolyl, isothiazolyl, thiazolyl, pyridinyl, pyridazinyl, pyrimidinyl, pyrazinyl, and the like. It is to be understood that monocyclic heteroaryl also includes those ring systems that have three heteroatoms, such as oxadiazolyl, triazinyl, and the like. Illustrative polycyclic heteroaryls include, but are not limited to, the foregoing monocyclic rings fused to each other, or to phenyl. It is also to be understood that the point of attachment of the heteroaryl groups described herein may be at any locus of the ring system.

As used herein, the term "optionally substituted" includes a wide variety of groups that replace one or more hydrogens on a carbon, nitrogen, oxygen, or sulfur atom, including monovalent and divalent groups. Illustratively, optional substitution of carbon includes, but is not limited to, halo, hydroxy, alkyl, alkoxy, haloalkyl, haloalkoxy, aryl, arylalkyl, acyl, acyloxy, and the like. In one aspect, optional substitution of aryl carbon includes, but is not limited to, halo, amino, hydroxy, alkyl, alkenyl, alkoxy, arylalkyl, arylalkyloxy, hydroxyalkyl, hydroxyalkenyl, alkylene dioxy, aminoalkyl, where the amino group may also be substituted with one or two alkyl groups, arylalkylgroups, and/or acylgroups, nitro, acyl and derivatives thereof such as oximes, hydrazones, and the like, cyano, alkylsulfonyl, alkylsulfonylamino, and the like. Illustratively, optional substitution of nitrogen, oxygen, and sulfur includes, but is not limited to, alkyl, haloalkyl, aryl, arylalkyl, acyl, and the like, as well as protecting groups, such as alkyl, ether, ester, and acyl protecting groups, and pro-drug groups. Illustrative protecting groups contemplated herein are described in Greene & Wuts "Protective Groups in Organic Synthesis," 2d Ed., John Wiley & Sons, (NY, 1991). It is further understood that each of the foregoing optional substituents may themselves be additionally optionally substituted, such as with halo, hydroxy, alkyl, alkoxy, haloalkyl, haloalkoxy, and the like.

Also described herein are compounds that exhibit hydrogen bonding to the backbone of each monomer of HIV protease. Without being bound by theory, it is believed that the compounds described herein exert their potent anti-viral efficacy by disruption of the viral replication cycle by inhibiting the dimerization of HIV protease. This new mode of action has not specifically used in the treatment of HIV infections, AIDS, or AIDS-related diseases and disorders. Therefore, it is believed that this new mode of action may be an important addition to the arsenal of treatments by finding particular utility in resistant strains of the virus.

In one embodiment of the compounds described herein, the group A is a cyclic ether, such the following structures:

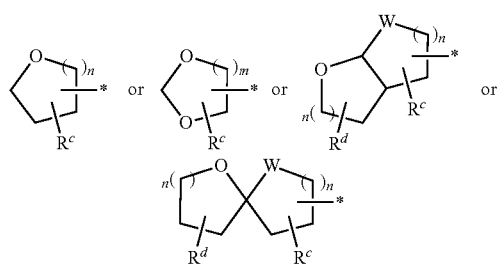

where (*) indicates the point of attachment of the group A; n is an integer that is independently selected in each instance from 0, 1, 2, or 3; m is an integer from 1 to 5; W is $C(R^aR^b)$ or oxygen; $R^a$ and $R^b$ are independently selected in each instance as described herein for the various embodiments and aspects; and $R^c$ and $R^d$ each represent one or more optional substituents, each of which is independently selected in each instance from hydrogen, alkyl, alkenyl, alkynyl, cycloalkyl, cycloalkylalkyl, aryl, arylalkyl, heterocyclyl, heterocyclylalkyl, heteroaryl, heteroarylalkyl, alkoxy, alkenyloxy, alkynyloxy, cycloalkoxy, cycloalkylalkoxy, aryl, arylalkoxy, heterocyclyloxy, heterocyclylalkoxy, heteroaryloxy, and heteroarylalkoxy, each of which is itself optionally substituted In one aspect, $R^a$ and $R^b$ are both hydrogen. In another aspect, $R^c$ and $R^d$ are both hydrogen. In another aspect, $R^a$, $R^b$, $R^c$, and $R^d$ are each hydrogen. In another aspect, one or more of $R^c$ and $R^d$ is alkoxy.

It is appreciated that when the integer n is in each case 0 or 1, the ring fusion is syn, whereas when in one instance the integer n is 2 and in the other instance the integer n is 1 or 2, the ring fusion may be syn or anti. It is further appreciated that in each of these relative stereochemical configurations, there are potentially two absolute stereochemical configurations. Unless otherwise indicated by specific reference to a relative or absolute stereochemical configuration, the structures described herein refer both individually to each enantiomer, as well as collectively to all possible mixtures of such enantiomers. It is appreciated that the foregoing cyclic ethers may be optionally substituted with one or more groups $R^a$ and/or $R^b$, each of which is independently selected, and is as described in the various embodiments and aspects disclosed herein.

Illustrative groups A include, but are not limited to:

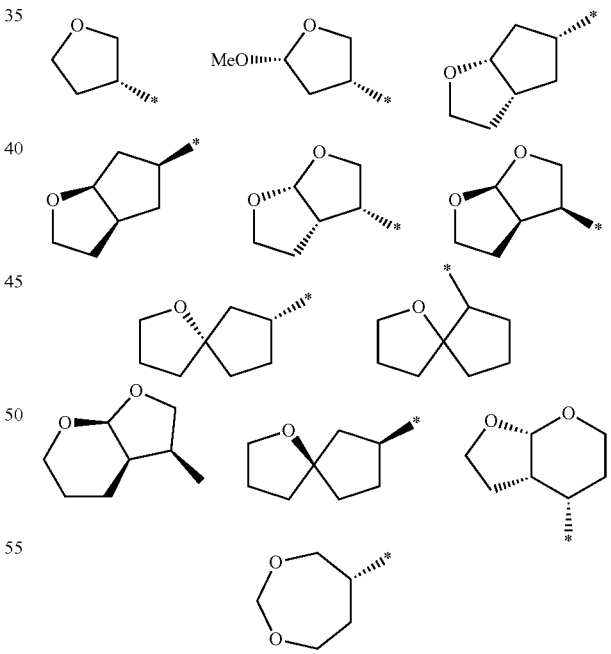

and stereoisomers thereof and mixtures thereof. where (*) indicates the point of attachment of A. It is therefore appreciated that such groups are attached to the group Q, which is oxygen, sulfur, nitrogen, or $C(R^aR^b)$; where each of $R^a$ and $R^b$ is independently selected in each instance, as defined in the various embodiments and aspects disclosed herein.

In another embodiment, the group A is heterocyclylalkyl or heteroarylalkyl of the formula Het-(CH$_2$)$_m$—; where m is an integer selected from 1, 2, or 3; and Het is heterocyclyl or heteroaryl, each of which is optionally substituted. In one aspect, Het is pyrazolyl, thienyl, isoxazolyl, isothiazolyl, oxazolyl, thiazolyl, pyridinyl, pyrimidinyl, and the like, each of which is optionally substituted. In another aspect, Het is oxazolidine, thiazolidine, pyrollidine, piperidine, piperazine, and the like, each of which is optionally substituted, including oxo substituents that form the corresponding oxazolidinones, thiazolidinones, pyrollidinones, piperidinones, piperazinones, and the like.

In another embodiment of the compounds described herein, the group A taken in combination with the attached oxygen, is replaced with optionally substituted aryloyl, including benzoyl, napthyloyl, and the like, or heteroaryloyl, each of which is optionally substituted.

In another embodiment of the compounds described herein, R$^3$ alkyl, cycloalkyl, heterocyclyl, heterocyclylalkyl, hydroxy, alkoxy, cycloalkoxy, heterocyclyloxy, heterocyclylalkoxy, amino, mono or dialkylamino, cycloalkylamino, heterocyclylamino, or heterocyclylalkylamino, each of which is optionally substituted. In one aspect, R$^3$ is amino substituted alkyl or heterocycyl, or heterocyclylalkyl. In one variation of this aspect, the nitrogen atom of the amino group is mono or disubstituted with alkyl, cycloalkyl, or acyl, or is included in another heterocyclic group such as a pyrrolidinyl, piperidinyl, or piperazinyl group. In another variation of this aspect, the nitrogen atom of the heterocylclyl group is substituted with alkyl, cycloalkyl, or acyl. In another aspect, R$^3$ is optionally substituted alkyl or cycloalkyl, including both linear and branched variations thereof, such as methyl, ethyl, butyl, isobutyl, and the like, and cyclobutyl, cyclopentyl, 3-methylcyclopentyl, and the like. In another aspect, R$^3$ is optionally substituted heterocyclyl or heterocyclylalkyl, where the heterocyclic portions includes, but is not limited to, tetrahydrofuranyl, azetidinyl, pyrrolidinyl, piperidinyl, morpholinyl, piperazinyl, and the like.

In another embodiment, compounds of the following formula are described herein:

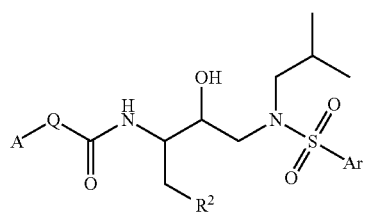

wherein A, R$^2$ and Ar are as described in the various embodiments and aspects disclosed herein.

In another embodiment, compounds having the following relative and/or absolute stereochemistry are described herein:

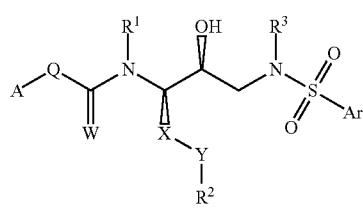

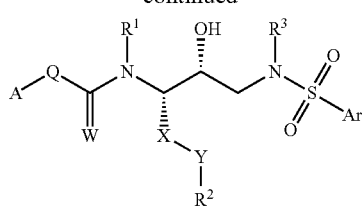

In another embodiment compounds of the following formula are described herein:

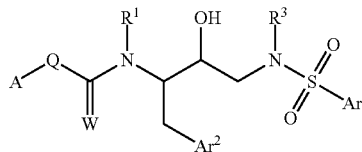

where Ar$^2$ is substituted aryl or substituted heteroaryl having one or more of the following illustrative substituents; halo, amino, hydroxy, alkyl, alkenyl, alkoxy, arylalkyl, arylalkyloxy, hydroxyalkyl, hydroxyalkenyl, alkylene dioxy, aminoalkyl, where the amino group may also be substituted with one or two alkyl groups, arylalkylgroups, and/or acylgroups, nitro, acyl and derivatives thereof such as oximes, hydrazones, and the like, cyano, alkylsulfonyl, alkylsulfonylamino, and the like and A, Q, R$^1$, R$^3$ and Ar have the meanings disclosed above.

In another embodiment compounds of the following formula are described herein:

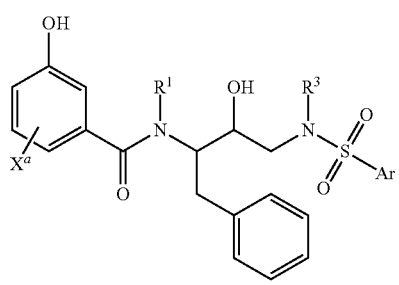

where X$^a$ is one or more of the following illustrative substituents; halo, amino, hydroxy, alkyl, alkenyl, alkoxy, arylalkyl, arylalkyloxy, hydroxyalkyl, hydroxyalkenyl, alkylene dioxy, aminoalkyl, where the amino group may also be substituted with one or two alkyl groups, arylalkylgroups, and/or acylgroups, nitro, acyl and derivatives thereof such as oximes, hydrazones, and the like, cyano, alkylsulfonyl, alkylsulfonylamino, and the like and R$^1$, R$^3$ and Ar have the meanings disclosed above In another embodiment compounds of the following formula are described herein:

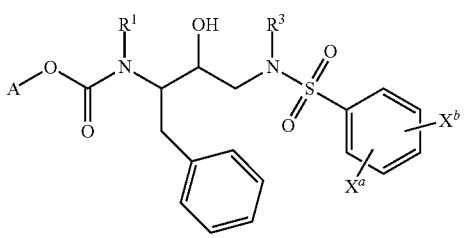

where $X^a$ and $X^b$ are each independently selected from halo, amino, hydroxy, alkyl, alkenyl, alkoxy, arylalkyl, arylalkyloxy, hydroxyalkyl, hydroxyalkenyl, alkylene dioxy, aminoalkyl, where the amino group may also be substituted with one or two alkyl groups, arylalkylgroups, and/or acylgroups, nitro, acyl and derivatives thereof such as oximes, hydrazones, and the like, cyano, alkylsulfonyl, alkylsulfonylamino, and the like and A, $R^1$, $R^3$ and Ar have the meanings disclosed above.

In another embodiment compounds of the following formula are described herein:

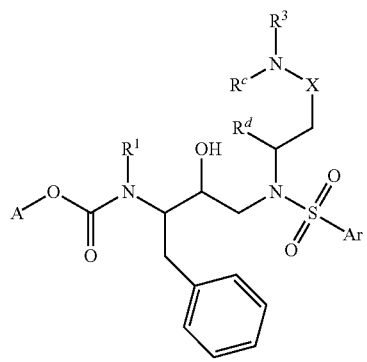

where X is $C(R^aR^b)$ where each of $R^a$ and $R^b$ is independently selected in each instance from the group consisting of hydrogen, alkyl, and alkylaryl; $R^c$ and $R^d$ are independently selected in each instance from the group consisting of hydrogen, alkyl, and alkylaryl, each which may be optionally substituted, or $R^c$ and $R^d$ and the atoms to which they are attached form a ring; A, $R^1$ and Ar have the meanings disclosed above.

In another embodiment compounds of the following formula are described herein:

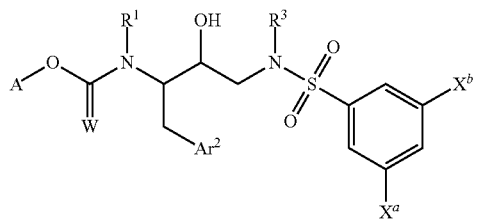

where Xa and Xb are independently selected from OH or $OR^4$, where $R^4$ is alkyl, alkylaryl, an oxygen protecting group or a pro-drug substituent; and A, Q, $R^1$, $Ar^2$ and $R^3$ have the meanings disclosed above.

In another embodiment compounds of the following formula are described herein:

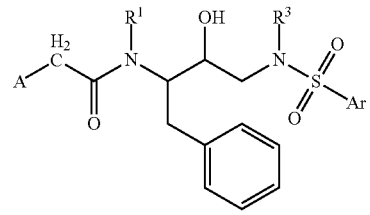

where $R^1$, $R^3$ and Ar have the meanings disclosed above and A is a cyclic ether, such the following structures:

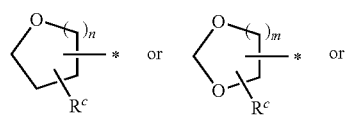

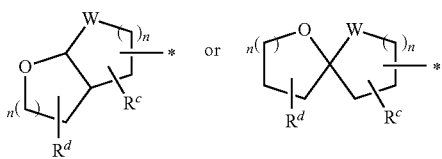

where (*) indicates the point of attachment of the group A; n is an integer that is independently selected in each instance from 0, 1, 2, or 3; m is an integer from 1 to 5; W is $C(R^aR^b)$ or oxygen; $R^a$ and $R^b$ are independently selected in each instance as described herein for the various embodiments and aspects; and $R^c$ and $R^d$ each represent one or more optional substituents, each of which is independently selected in each instance from hydrogen, alkyl, alkenyl, alkynyl, cycloalkyl, cycloalkylalkyl, aryl, arylalkyl, heterocyclyl, heterocyclylalkyl, heteroaryl, heteroarylalkyl, alkoxy, alkenyloxy, alkynyloxy, cycloalkoxy, cycloalkylalkoxy, aryl, arylalkoxy, heterocyclyloxy, heterocyclylalkoxy, heteroaryloxy, and heteroarylalkoxy, each of which is itself optionally substituted In one aspect, $R^a$ and $R^b$ are both hydrogen. In another aspect, $R^c$ and $R^d$ are both hydrogen. In another aspect, $R^a$, $R^b$, $R^c$, and $R^d$ are each hydrogen. In another aspect, one or more of $R^c$ and $R^d$ is alkoxy.

The compounds of the following formulae have been previously reported to be potent HIV protease inhibitors:

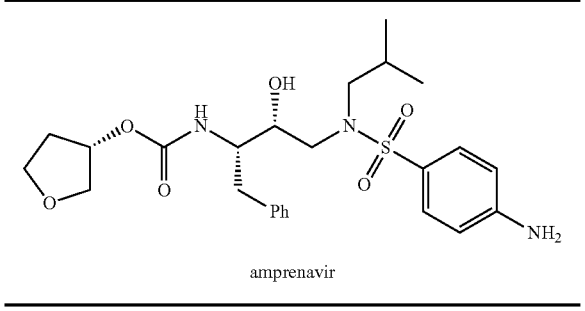

amprenavir

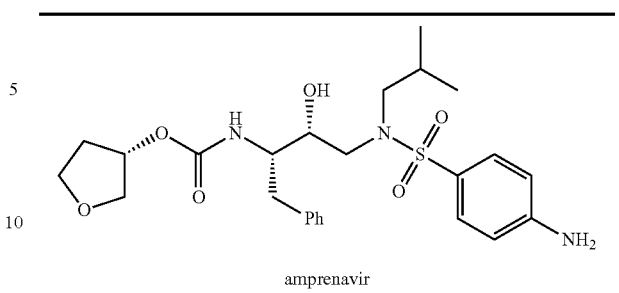

amprenavir

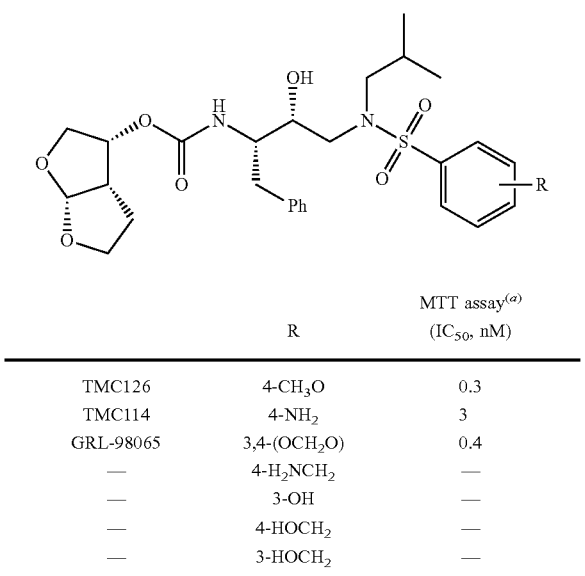

| | R | MTT assay[a] (IC$_{50}$, nM) |
|---|---|---|
| TMC126 | 4-CH$_3$O | 0.3 |
| TMC114 | 4-NH$_2$ | 3 |
| GRL-98065 | 3,4-(OCH$_2$O) | 0.4 |
| — | 4-H$_2$NCH$_2$ | — |
| — | 3-OH | — |
| — | 4-HOCH$_2$ | — |
| — | 3-HOCH$_2$ | — |

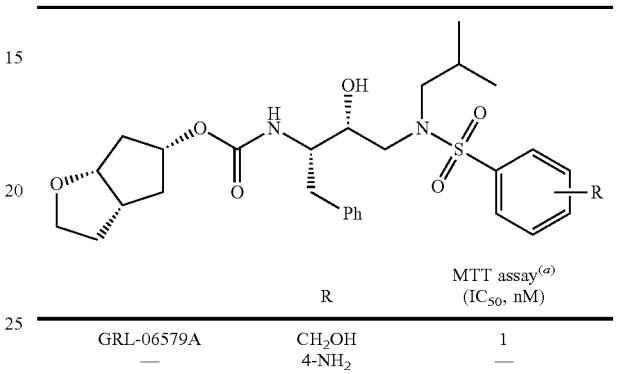

| | R | MTT assay[a] (IC$_{50}$, nM) |
|---|---|---|
| GRL-06579A | CH$_2$OH | 1 |
| | 4-NH$_2$ | — |

[a] Human CD4$^+$ MT-2 cells (2 × 10$^4$/mL) were exposed to 100 TCID$_{50}$ of HIV-1$_{LAI}$ and cultured in the presence of various concentrations of the compounds, and the IC$_{50}$ values were determined using the MTT assay on day 7 of culture. All assays were conducted in duplicate, and the data represent the results of three independent experiments.

It has been discovered herein that the foregoing compounds also possess potent dimerization inhibition. Each of the foregoing compounds may be included as a dimerization inhibitor in the compositions described herein. In addition, the following compounds have been previously reported to be potent HIV protease inhibitors (WO 99/67254):

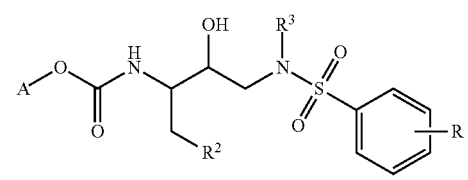

| A | R$^2$ | R$^3$ | R | K$_i$ (nM) | ID$_{50}$ (nM) |
|---|---|---|---|---|---|
| 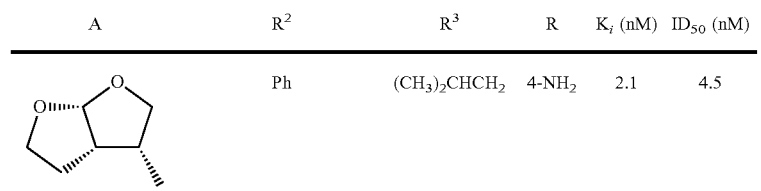 | Ph | (CH$_3$)$_2$CHCH$_2$ | 4-NH$_2$ | 2.1 | 4.5 |
| 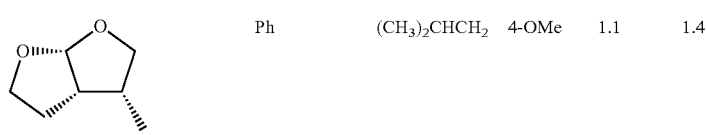 | Ph | (CH$_3$)$_2$CHCH$_2$ | 4-OMe | 1.1 | 1.4 |
| 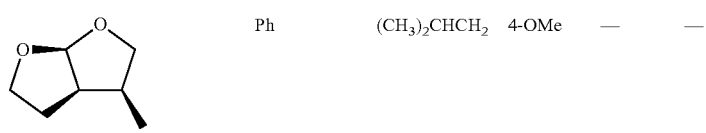 | Ph | (CH$_3$)$_2$CHCH$_2$ | 4-OMe | — | — |

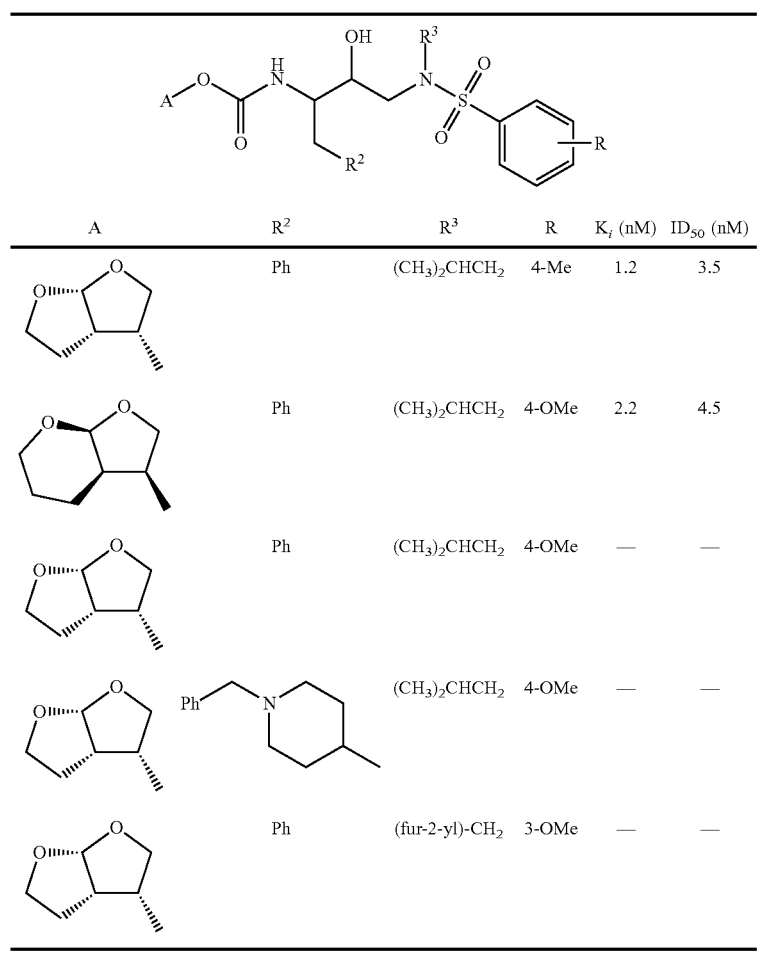

where $K_i$ is activity against wild-type HIV protease. Additional details of the biological evaluation of the compounds is described in Ghosh et al., J Bioorg Med Chem Lett 9:687-690 (1998). It has also been discovered herein that the foregoing compounds also possess potent dimerization inhibition. Each of the foregoing compounds may be included as a dimerization inhibitor in the compositions described herein.

In one aspect, the non-peptidic HIV-1 protease inhibitor GRL-98065, which also contains bis-THF and a sulfonamide isostere is found to exert highly potent activity against a wide spectrum of laboratory HIV-1 strains and primary clinical isolates including multi-PI-resistant variants with minimal cytotoxicity. GRL-98065 is also active against HIV-1 isolates of various subtypes as well as HIV-1 isolates examined. Structural analyses revealed that the close contact of GRL-98065 with the main chain of the protease active site amino acids (Asp-29 and Asp-30) is a diagnostic for its potency and wide-spectrum activity against multi-PI-resistant HIV-1 variants.

Additional, illustrative compounds that may be included in the pharmaceutical compositions described herein include, but are not limited to, ritonavir, amprenavir, saquinavir, indinavir, AZT, ddI, ddC, D4T, lamivudine, 3TC, and others, and combinations thereof.

Also described herein are synthetic processes useful for the preparation of compounds. In one embodiment, the following processes are described:

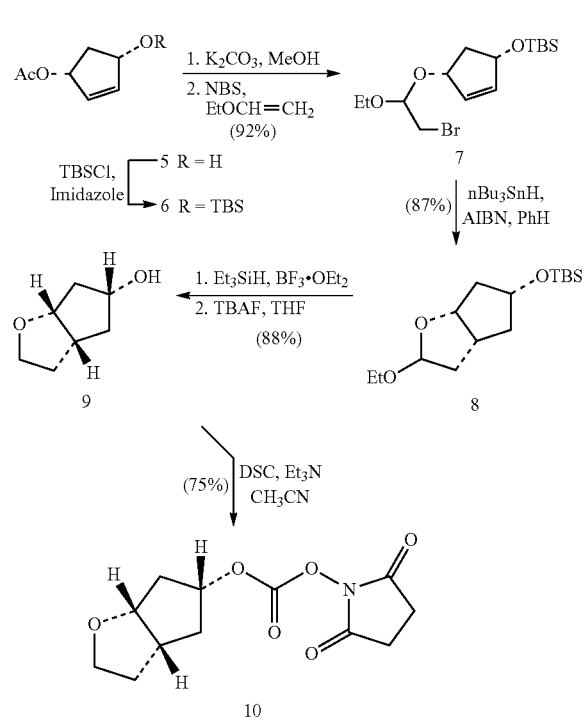

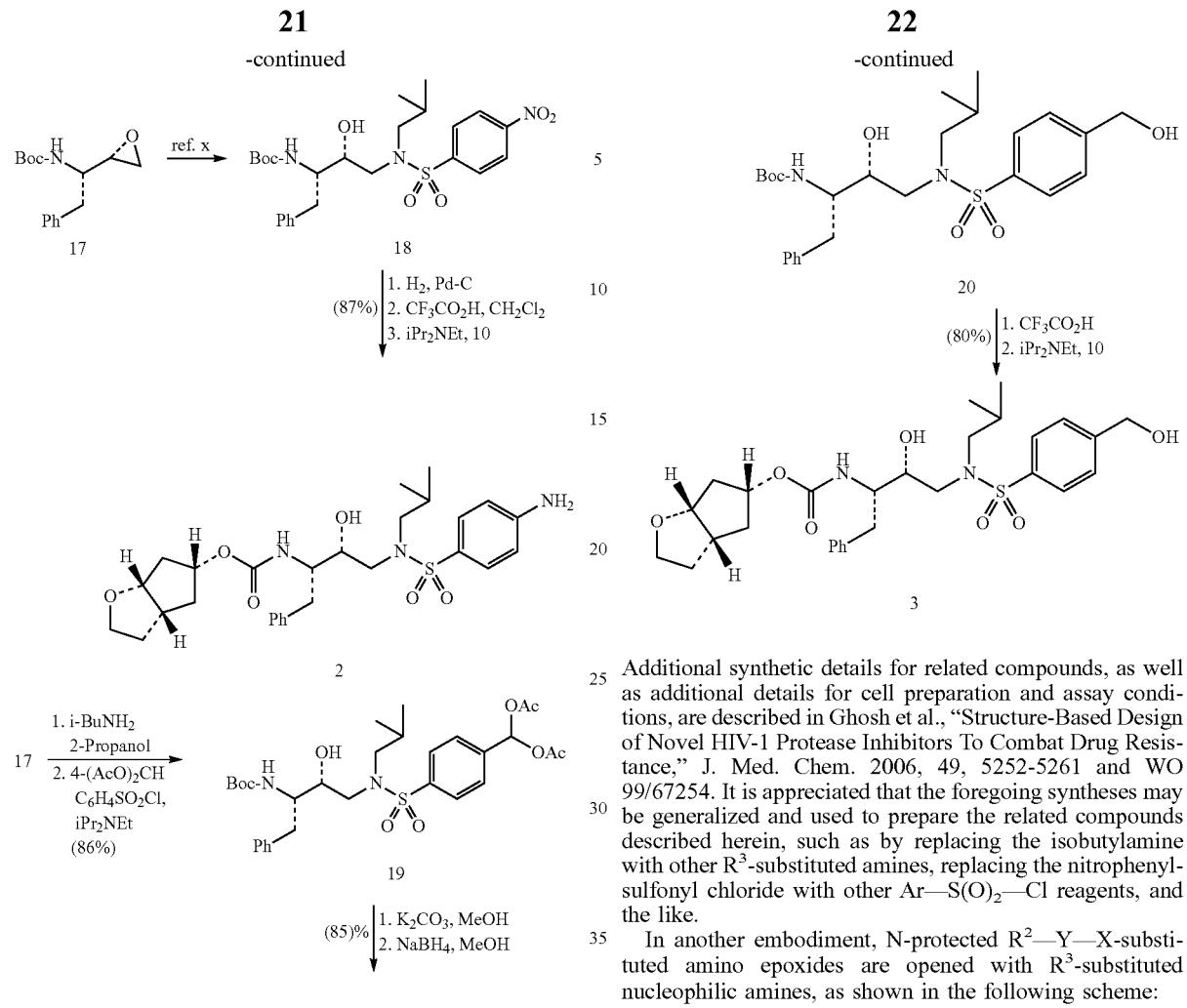

Additional synthetic details for related compounds, as well as additional details for cell preparation and assay conditions, are described in Ghosh et al., "Structure-Based Design of Novel HIV-1 Protease Inhibitors To Combat Drug Resistance," J. Med. Chem. 2006, 49, 5252-5261 and WO 99/67254. It is appreciated that the foregoing syntheses may be generalized and used to prepare the related compounds described herein, such as by replacing the isobutylamine with other $R^3$-substituted amines, replacing the nitrophenyl-sulfonyl chloride with other Ar—S(O)$_2$—Cl reagents, and the like.

In another embodiment, N-protected $R^2$—Y—X-substituted amino epoxides are opened with $R^3$-substituted nucleophilic amines, as shown in the following scheme:

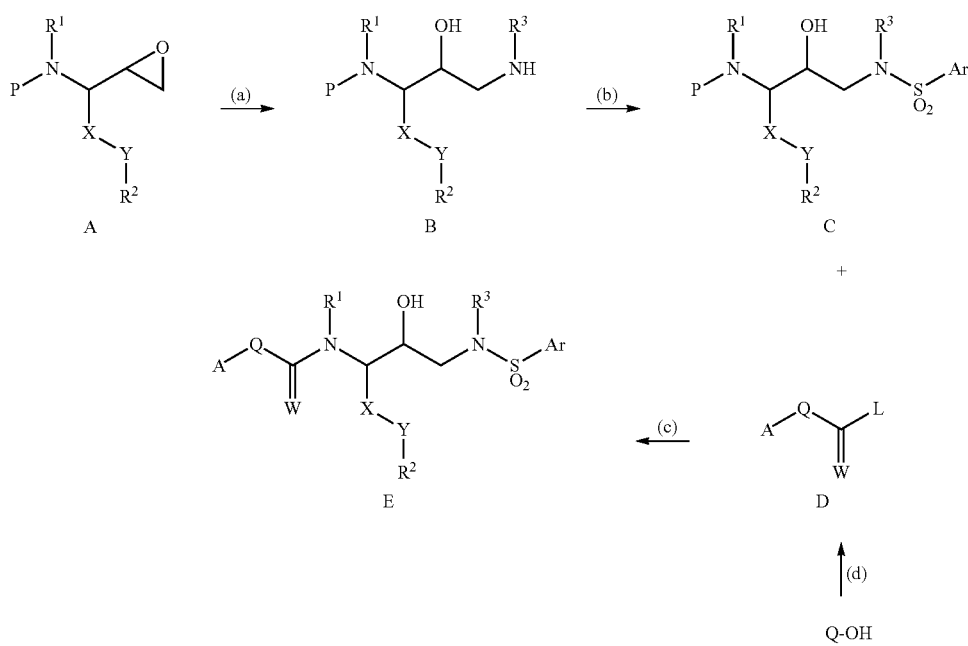

(a) R³—NH₂, i-PrOH; (b) i. Ar-sulfonyl chloride, NaHCO₃, DCM; ii. optional deprotection of Ar substituents when present (e.g. for NHBn: H₂, 10% Pd—C, MeOH); (c) i. TFA, DCM, ii active carbonyl 5 with leaving group (L) (e.g. L=O(p-NO2Ph), DIPEA, DCM or THF; (d) conversion of Q-OH to an activated acylating group (e.g. with p-nitrophenyl chloroformate, N-methylmorpholine, THF).

In the foregoing scheme, P is a protecting group, R¹, R², Y, X, R³, Ar, and A have the same meanings as described herein in the various illustrative embodiments and aspects, and L is a leaving group.

In another embodiment, R²—Y—X-substituted azido epoxides are opened with R³-substituted nucleophilic amines, as shown in the following scheme:

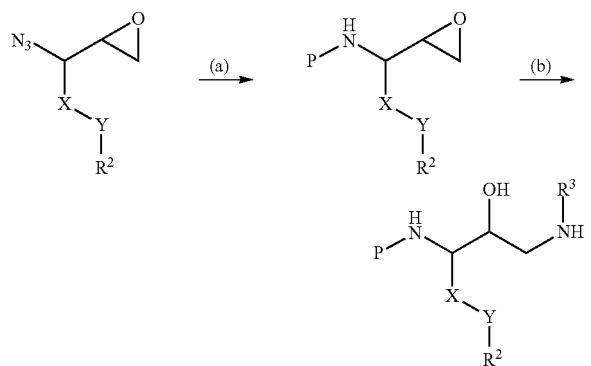

where R², Y, X, and R³ have the same meanings as described herein in the various illustrative embodiments and aspects. The R³-substituted nucleophilic amines described herein are commercially available, can be prepared by conventional reactions, or alternatively may be prepared from the corresponding alcohols according to the following scheme:

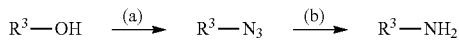

where step (a) includes conversion of the alcohol to a leaving group, such as a halo, acyloxy, alkyl or arylsulfonyloxy, and like groups, illustratively under basic conditions, followed by displacement of the leaving group with N₃ anion, such as NaN₃, in a polar aprotic solvent, such as DMF, DMA, DMSO, and the like. Step (b) includes reduction of the azide, such as catalytic reduction or hydride reduction to the corresponding amine. Illustrative hydride reducing agents include LiAlH₄, AlH₃, NaBH₄, NaCN(BH₃), BF₃(ET₂O), and the like. It is appreciated that where R³ includes functional groups that are not stable to the reaction steps described herein, additional conventional protection/deprotection steps may be included in the general syntheses described herein.

In another embodiment, the compounds described herein are prepared from sulfonyl chlorides by reaction with the R³-substituted amino group in the presence of an organic or inorganic base, or a combination thereof. In one aspect, the sulfonyl chlorides are prepared from the corresponding aryl compounds by reaction with amino sulfonic acid to prepare the corresponding arylsulfonic acid, then with a chlorinating agent, such as thionyl chloride, oxalyl chloride, and the like to prepare the arylsulfonyl chlorides.

The compounds and compositions described herein are useful in treating the various human immunodeficiency virus (HIV) families, HIV-1, HIV-2, and resistant and multi-drug resistant strains and mutants, acquired immune deficiency syndrome (AIDS), AIDS-related virus (ARV), lymphadenopathy-associated virus (LAV), and other AIDS-related diseases and disorders.

EXAMPLES

Compound Examples

All reagents were used as purchased from commercial suppliers unless otherwise noted. All evaporations and concentrations were performed under reduced pressure unless otherwise noted. Additional details for the syntheses of the compounds described herein are disclosed in Ghosh et al., *J. Med. Chem.*, 1996, 39, 3278; Ghosh et al., *Biorg. Med. Chem. Lett.*, 1998, 8, 979; Chen et al., *Chinese Journal of Chemistry*, 2003, 21, 937; and Ami et al., *Tetrahedron Lett.* 2002, 43, 2931, the disclosures of which are incorporated herein by reference.

General process for ring opening of epoxide. To a stirred solution of commercial (Aldrich Chemical company) tert-butyl[S—(R,R)-(−)-(1-oxiranyl-2-phenyl)carbamate 1 (1 mmol) in 2-propanol (10 mL) at 23° C. was added amine (1.1 mmol). The resulting mixture was heated at reflux for 6 h. After this period, the reaction mixture was concentrated under reduced pressure and the residue was purified by column chromatography in silica gel (MeOH in CHCl₃ as the eluent) to provide amine 2 in 75-92% yield.

General process for sulfonylation reaction with 4-methoxybenzenesulfonyl chloride. To a stirred solution of amine (1 mmol) in a mixture of CH₂Cl₂ (15 mL) and saturated aqueous sodium bicarbonate (15 mL) at 23° C. was added 4-methoxybenzenesulfonyl chloride (3 mmol). The resulting mixture was stirred at 23° C. for 12 h. the mixture was then extracted with CH₂Cl₂ and dried over anhydrous Na₂SO₄. Removal of solvent under reduced pressure, followed by column chromatography over silica gel provided sulfonamide 3 in 80-95% yield.

General sulfonylation reaction with 4-nitrobenzenesulfonyl chloride. To a stirred solution of amine (1 mmol) in dichloromethane (10 mL) and N,N-diisopropylethylamine (1.2 mmol) at 0° C. was added 4-nitrobenzenesulfonyl chloride (1.1 mmol) or 4-nitrobenzenesulfonyl chloride (1.1 mmol). The resulting mixture was stirred at 23° C. for 4 h. the mixture was diluted with dichloromethane and washed with water and brine. The combined organic extracts were dried over anhydrous Na₂SO₄. Removal of solvent under reduced pressure, followed by column chromatography over silica gel provided sulfonamide 4 in 80-95% yield.

General process for the deprotection of a Boc group followed by coupling. A solution of Boc protected amine (1 mmol) in a mixture of 30% trifluoroacetic acid in CH₂Cl₂ (3 mL, (1:2) was stirred at 23° C. for 40 min. After this period, the reaction mixture was concentrated under reduced pressure and the residue was redissolved in CH₂Cl₂ (3 mL). To this solution were added mixed carbonate 5 (1.1 mmol) and N,N-diisopropylethylamine (6 mmol). The resulting mixture was stirred at 23° C. for 8 h. The reaction mixture was then concentrated under reduced pressure. And the residue was purified by column chromatography over silica gel to provide the ligand coupled product in 75-88% yield.

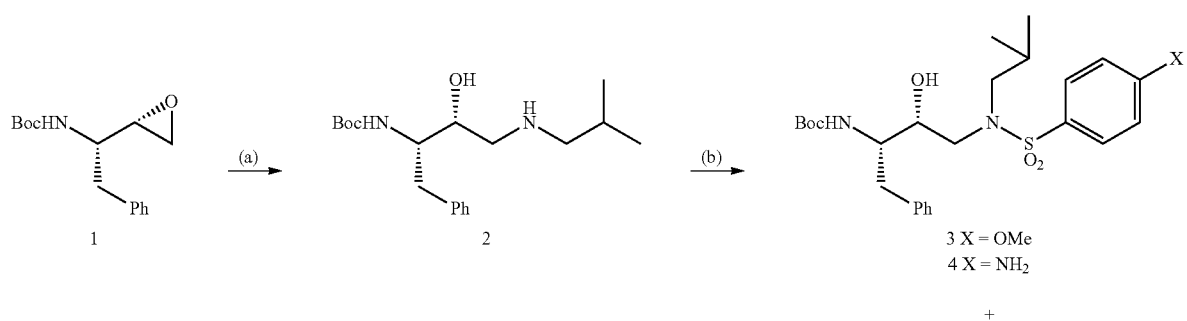
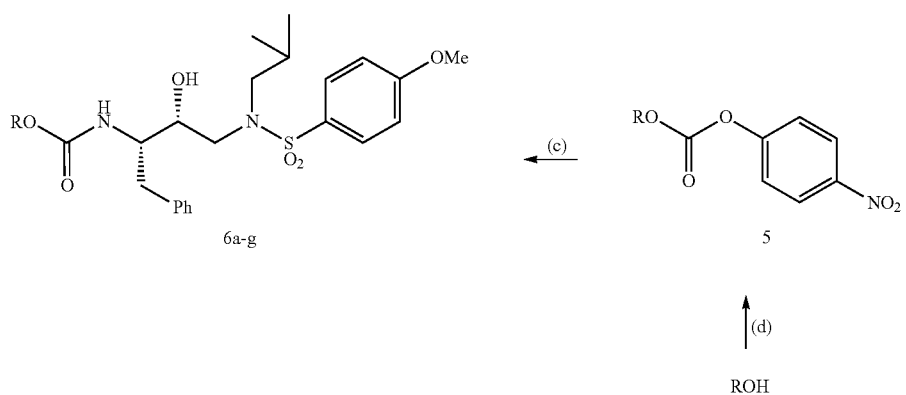
(a) i-butylamine, i-PrOH; (b) p-Methoxybenzenesulfonyl chloride, NaHCO$_3$, DCM, or i. p-benzoylaminobenzenesulfonyl chloride, NaHCO$_3$, DC; ii. H2, 10% Pd—C, MeOH; (c) i) TFA, DCM, ii) active carbonate 5, DIPEA, DCM or THF; (d) p-nitrophenyl chloroformate, N-methylmorpholine, THF.
Preparation of Compounds 6a and 6b:
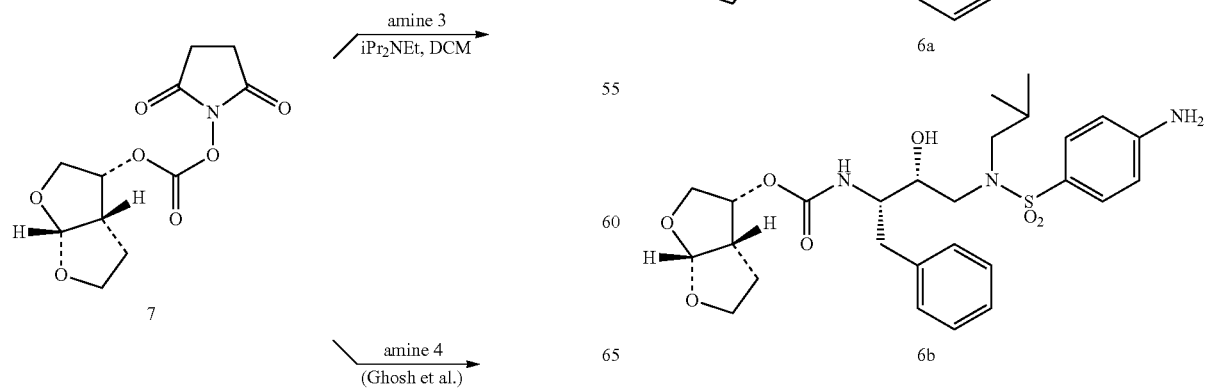
-continued
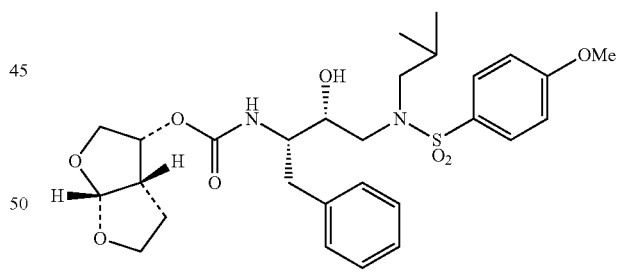
6a
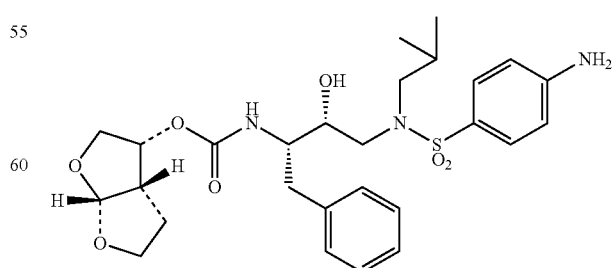
6b Succinimidyl carbonate 7: To a stirred solution of [3R, 3aS,6aR]-3-hydroxyhexahydrofuro[2,3-b]furan (650 mg, 5 mmol; prepared according to the procedure of Ghosh et. al. in dry CH₃CN (50 mL) at 23° C. were added disuccinimidyl carbonate (1.92 g, 7.5 mmol) and triethylamine (2.5 mL). The resulting mixture was stirred at 23° C. for 12 h. The reaction was quenched with saturated aqueous NaHCO₃ (20 mL) and the mixture was concentrated under reduced pressure. The residue was extracted with CH₂Cl₂ (2×50 mL) and the combined organic layers were washed with brine (10 mL) and dried over anhydrous Na₂SO₄. Evaporation of the solvent under reduced pressure gave a residue which was chromatographed over silica gel (50% ethyl acetate/hexane) to furnish (3R,3aS,6aR) 3-hydroxyhexahydrofuro[2,3-b] furanyl-succinimidyl carbonate 6 (840 mg) as a white solid (m.p. 129-131° C.).

Compound 6a: A solution of above amine 3 (75 mg) in a mixture of 30% trifluoroacetic acid in CH₂Cl₂ (10 mL) was stirred 23° C. for 40 min. After this period, the reaction mixture was concentrated under reduced pressure and the residue was redissolved in CH₂Cl₂ (10 mL). To this solution were added (3R,3aS,6aR)-3-hydroxyhexahydrofuro[2,3-b] furanyl succinimidyl carbonate 7 (45 mg, 0.17 mmol) and triethylamine (155 µL, 1.51 mmol). The resulting mixture was stirred at 23° C. for 3 h. The reaction mixture was then concentrated reduced pressure and the residue was purified by column chromatography over silica gel (2% MeOH in CHCl₃ as the eluent) to provide compound 6a (78 mg, 90%) as a white amorphous solid. ¹H-NMR (CDCl₃, 400 MHz): δδ 7.71 (d, 2H, J=8.5 Hz), 7.29-7.20 (m, 5H), 6.98 (d, 2H, J=7.0 Hz), 5.65 (d, 1H, J=5.2 Hz), 5.01 (m, 2H), 3.95-3.82 (m, 7H), 3.69 (m, 2H), 3.0-2.7 (m, 6H), 1.85 (m, 1H), 1.64-1.45 (m, 3H), 0.92 (d, 3H, J=6.5 Hz), 0.89 (d, 3H, J=6.6 Hz).

Compound 6b: A solution of above amine 4 (74 mg, 0.151 mmol) in a mixture of 30% trifluoroacetic acid in CH₂Cl₂ (10 mL) was stirred 23° C. for 40 min. After this period, the reaction mixture was concentrated under reduced pressure and the residue was redissolved in CH₂Cl₂ (10 mL). To this solution were added (3R,3aS,6aR)-3-Hydroxyhexahydrofuro[2,3-b]furanyl succinimidyl carbonate 7[1, 2] (45 mg, 0.17 mmol) and triethylamine (155 µL, 1.51 mmol). The resulting mixture was stirred at 23° C. for 3 h. The reaction mixture was then concentrated reduced pressure and the residue was purified by column chromatography over silica gel (2% MeOH in CHCl₃ as the eluent) to provide compound 6b (75 mg, 89%) as a white amorphous solid. ¹H-NMR (500 MHz, CDCl₃) δ 0.81 (d, 3H, J=6.6 Hz), 0.90 (d, 3H, J=6.6 Hz), 1.42-1.46 (M, 1H), 1.57-1.65 (m, 1H), 1.79-1.85 (m, 1H), 2.75-2.81 (m, 2H), 2.87-2.98 (m, 3H), 3.05-3.16 (m, 2H), 3.64-3.71 (m, 2H), 3.82-3.88 (m, 3H), 3.92-3.96 (m, 1H), 4.97-5.01 (m, 2H), 5.63 (d, 1H, J=5.14 Hz), 6.67 (d, 2H, J=8.6 Hz), 7.18-7.28 (m, 5H), 7.53 (d, 2H, J=8.6 Hz).

Compounds 6c and 6d: Using known mixed carbonate 8 (Ghosh, A. K.; Kincaid, J. F.; Walters, D. E.; Chen Y.; Chaudhuri N. C.; Thompson W. J.; Culberson C.; Fitzgerald P. M. D.; Lee H. Y.; McKee S. P.; Munson P. M.; Duong T. T.; Darke P. L.; Zugay J. A.; Schleif W. A.; Axel M. G.; Lin J.; Huff J. R.; *J. Med. Chem.*, 39, 3278 (1996)) compounds 6c and 6d were synthesized as described above.

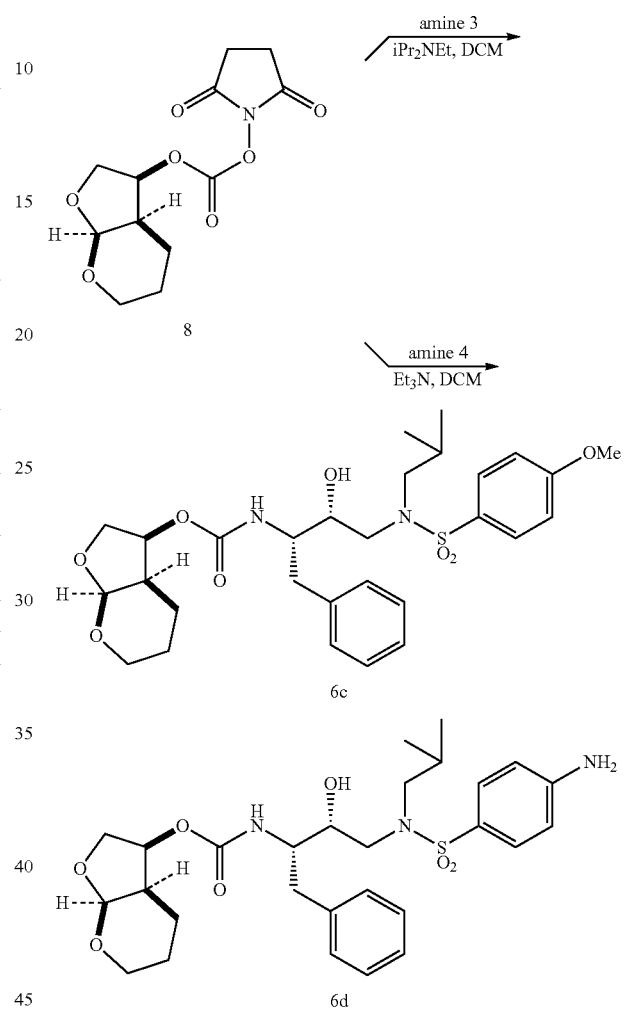

Compounds 6e and 6f: Using known mixed carbonate 9, compounds 6e and 6f were synthesized as described above.

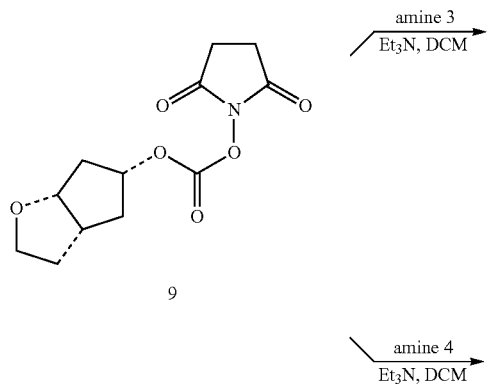

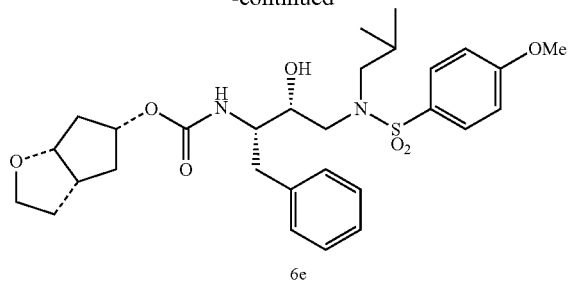

6e

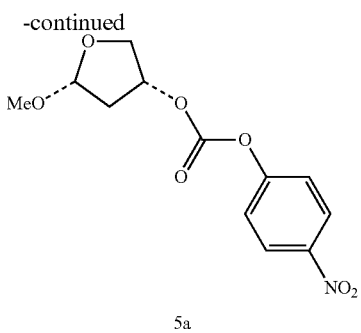

5a

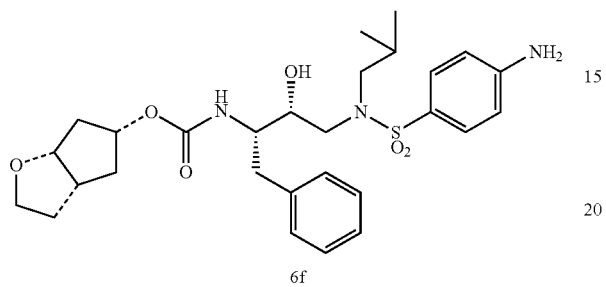

6f

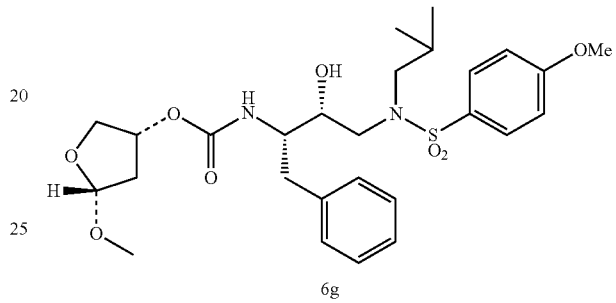

6g

Compound 6g: Compound 11 has been synthesized according to the literature procedure (Chen, X.; Wu, Y.; Chen, D.; *Chinese Journal of Chemistry*, 2003, 21, 937). Synthesis of mixed carbonate 5a followed by reaction with amine derived from 3 provided compound 6g.

Compound 11: $^1$H NMR (500 MHz, CDCl$_3$): 5.12 (t, 1H, J=4 Hz), 4.44 (m, 1H), 3.86 (dd, 1H, J=4 Hz, J=9.5 Hz), 3.73 (d, 1H, J=9.5 Hz), 3.30 (s, 3H), 2.04 (t, 2H, J=4.5 Hz). $^{13}$C NMR (125 MHz, CDCl$_3$): 105.2, 73.5, 70.5, 54.7, 41.8.

Compound 12: $^1$H NMR (300 MHz, CDCl$_3$): 8.31 (d, 2H, J=9 Hz), 7.49 (d, 2H, J=9 Hz), 5.35 (m, 1H), 5.22 (t, 1H, J=3.6 Hz), 4.07 (m, 2H), 3.36 (s, 3H), 2.34 (t, 2H, J=4.8 Hz). $^{13}$C NMR (75 MHz, CDCl$_3$): 155.2, 152.1, 145.8, 125.5, 121.6, 104.5, 79.5, 70.4, 55.1, 39.5.

Compound 6g: $^1$H NMR (400 MHz, CDCl$_3$): 7.70 (d, 2H, J=8.8 Hz), 7.21-7.31 (m, 5H), 6.97 (d, 2H, J=8.8 Hz), 5.10 (m, 2H), 4.84 (d, 1H, J=10 Hz), 3.66-4.12 (m, 7H), 3.32 (s, 3H), 3.11 (m, 1H), 2.91-2.98 (m, 4H), 2.77 (dd, 1H, J=8 Hz, J=16.5 Hz), 2.09 (m, 2H), 1.80 (m, 1H), 0.91 (d, 3H, J=6.5 Hz), 0.86 (d, 3H, J=6.5 Hz).

Compound 6h: Compound 15 has been synthesized according to Scheme 6. Synthesis of mixed carbonate 5b followed by reaction with amine derived from 3 provided compound 6h as described above.

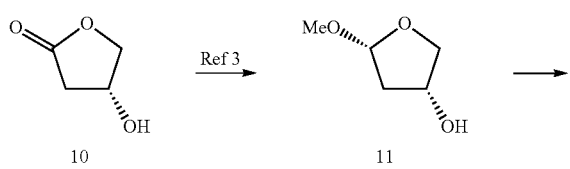

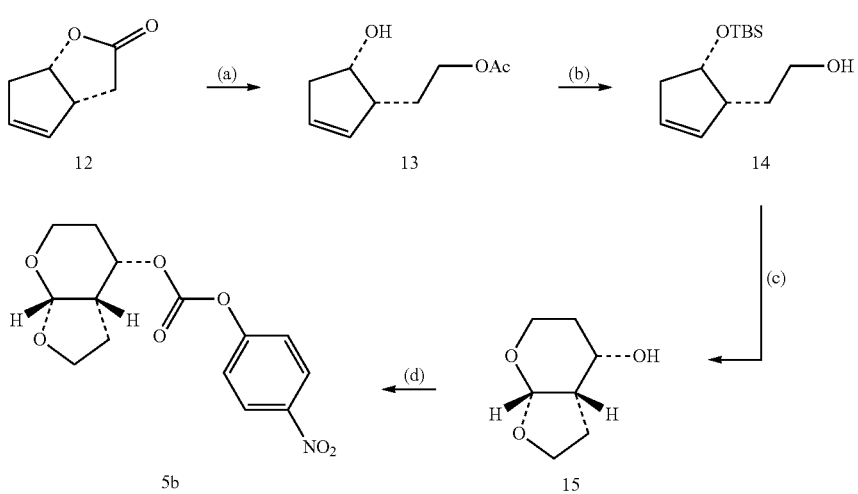

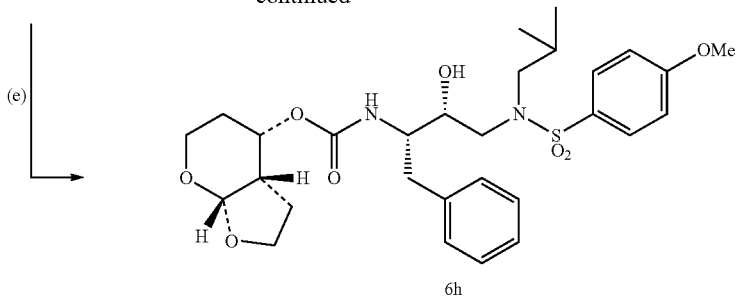

Compound 13: To a stirred suspension of lithium aluminum hydride (93 mg, 2.45 mmol) in dry Et$_2$O (6 mL) was added dropwise a solution of commercially available (1S, 5R)-(−)-2-oxabicyclo[3.3.0]oct-6-en-3-one 12 (150 mg, 1.19 mmol) in Et$_2$O (4 mL+1 mL rinse) at 0° C. under Ar. The reaction mixture was vigorously stirred at this temperature for 1.5 h. Water (0.1 mL) was then carefully added followed by addition of 3M NaOH (0.1 mL) then water (0.3 mL). The solution was stirred until formation of a white precipitate was complete. EtOAc (3 mL) then Na$_2$SO$_4$ were added and the resulting suspension was filtered out. The white solid was washed several time with EtOAc (5×5 mL). The combined organic layers were dried over Na$_2$SO$_4$, filtered and concentrated in vacuo. The crude oil was purified by flash chromatography on silica gel using hexanes:EtOAc (1:1) as eluent to give the desired diol (145 mg, 95%) as a colorless oil.

To a stirred solution of diol (76 mg, 0.59 mmol) in CH$_2$Cl$_2$ (3 mL) was added 2,4,6-collidine (1.2 mmol, 155 µL) followed by acetyl chloride (50 µL, 0.71 mmol) at −78° C. under Ar. The resulting solution was stirred at this temperature for 5 h at which point additional acetyl chloride (0.25 µL, 0.24 mmol) was added. The solution was stirred for an additional 2 h then saturated aqueous sodium bicarbonate solution was added. The two layers were separated and the aqueous layer was washed with CH$_2$Cl$_2$ (3×5 mL). The combined organic layers were washed with brine, dried over Na$_2$SO$_4$, filtered and concentrated in vacuo. The crude oil was purified by flash chromatography on silica gel using hexanes:EtOAc (6:1 then 4:1) as eluent to give the monoacetate 13 (88 mg, 87%) as a colorless oil.

Compound 14: To a stirred solution of acetate 13 (54 mg, 0.32 mmol) and 2,6-lutidine (74 µL, 0.63 mmol) in CH$_2$Cl$_2$ (1 mL) was added tert-butyldimethylsilyl trifluoromethanesulfonate (125 mg, 108 µL) at −78° C. under argon. The mixture was stirred for 5 min at which point TLC showed reaction completion. Saturated aqueous sodium carbonate solution (1 mL) and additional CH$_2$Cl$_2$ (2 mL) were added. The two layers were separated and the aqueous layer was further washed with CH$_2$Cl$_2$ (2×2 mL). The combined organic layers were washed with brine, dried over MgSO$_4$, filtered and concentrated in vacuo. The crude oil was purified by flash chromatography on silica gel using hexanes:ethyl acetate (20:1) as eluent to afford the silylated product (90 mg, quant. yield) as a colorless oil.

To a stirred solution of silyl ether (76 mg, 0.27 mmol) in MeOH (2 mL) was added K$_2$CO$_3$ (37 mg, 0.27 mmol) at once. The solution was stirred at 23° C. for 2 h then saturated aqueous ammonium chloride solution (2 mL) was added to the mixture. Ethyl acetate was added and the two layers were separated. The aqueous layer was washed with EtOAc (4×3 mL). The combined organic layers were washed with brine, dried over Na$_2$SO$_4$, filtered and concentrated in vacuo. The resulting oil was purified by flash chromatography on silica gel using hexanes:EtOAc (7:1) as eluent to give alcohol 14 (63 mg, 98%) as a colorless oil.

Compound 15: A stream of ozonized oxygen was bubbled through a solution of alcohol 14 (20.2 mg, 0.084 mmol) in CH$_2$Cl$_2$ (5 mL) at −78° C. until the blue color persisted (2 min). After the solution was flushed with nitrogen, Me$_2$S (0.2 mL) was added. The solution was warmed to 0° C. and stirred over a period of 2 h after which anhydrous Na$_2$SO$_4$ was added. The solution was left at room temperature overnight then filtered and concentrated in vacuo. The resulting solid was quickly passed through a short column of silica gel using hexanes:EtOAc (3:1) as eluent affording the corresponding hemiacetal as a white solid mixture of isomers which was submitted directly to the next step. TLC (SiO$_2$, hexanes:ethyl acetate=3:1). To a ice-cold solution of the crude hemiacetal 5 (0.084 mmol) and triethylsilane (54 µL, 0.34 mmol) in CH$_2$Cl$_2$ (1 mL) under Ar was slowly added BF$_3$-Et$_2$O (21 µL). The mixture was stirred at 0° C. for 10 min. Saturated aqueous sodium bicarbonate solution (2 mL) and additional CH$_2$Cl$_2$ were added. The two phases were separated and the aqueous layer was further washed with CH$_2$Cl$_2$ (3×2 mL). The combined organic layers were washed with brine, dried over MgSO$_4$, filtered and concentrated in vacuo. The crude oil was purified by flash chromatography on silica gel using hexanes:ethyl acetate (7:1) as eluent to give bicyclic compound 15 (19.8 mg, 90%) as a white solid.

Mixed carbonate 5b: $^1$H-NMR (CDCl$_3$, 300 MHz) δ 1.90-2.05 (m, 3H), 2.0-2.30 (m, 1H), 2.68-2.80 (m, 1H), 3.37-3.47 (m, 1H), 3.95-4.04 (m, 1H), 4.28 (dt, 1H, 3 Hz), 5.07 (d, 1H, J=2.7 Hz), 5.19-5.30 (m, 1H), 7.39 (dt, 2H, J=1.8, 7.2 Hz), 8.29 (dt, 2H, J=1.8, 7.2 Hz).

Compound 6h: $^1$H-NMR (CDCl$_3$, 300 MHz) δ 0.87 (d, 3H, J=6.9 Hz), 0.92 (d, 3H, J=5.7 Hz), 1.25-1.96 (m, 6H), 2.32-2.48 (m, 1H), 2.78-2.90 (m, 2H), 2.90-3.22 (m, 4H), 3.31 (t, 1H, J=11.7 Hz), 3.76-3.98 (m, 3H), 3.87 (s, 3H), 4.15 (dt, 1H, J=2.4, 9 Hz), 4.84 (d, 1H, J=8.4 Hz), 4.93 (d, 1H, J=3.6 Hz), 4.90-5.05 (m, 1H), 6.97 (d, 1H, 8.9 Hz), 7.17-7.33 (m, 5H), 7.71 (d, 1H, J=8.9 Hz).

Compounds 18 and 19: Racemic carboxylic acid 17 was prepared as previously described in the literature. Coupling of acid 17 with amine derived from 3 afforded 1:1 mixture of diastereomers. These diastereomers were separated by silica gel chromatography to provide compounds 18 and 19.

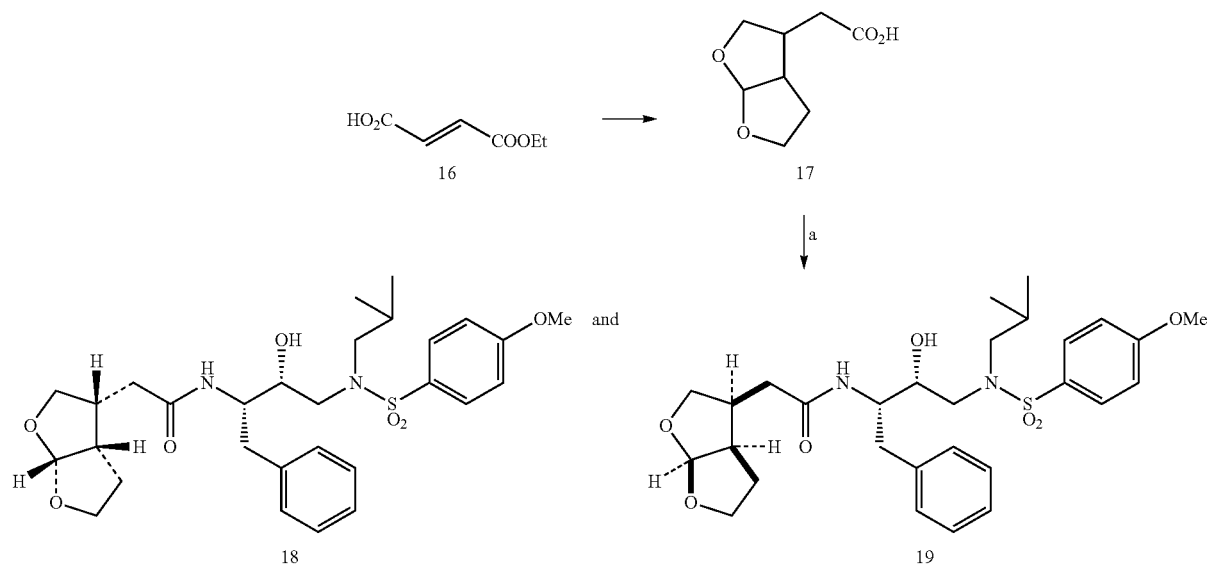

(a) DIPEA, EDC, Amine from above, CH$_2$Cl$_2$.

Compounds 18 and 19: $^1$H NMR (400 MHz, CDCl$_3$): 7.70 (d, 2H, J=8.8 Hz), 7.21-7.31 (m, 5H), 6.97 (d, 2H, J=8.8 Hz), 5.10 (m, 2H), 4.84 (d, 1H, J=10 Hz), 3.66-4.12 (m, 7H), 3.32 (s, 3H), 3.11 (m, 1H), 2.91-2.98 (m, 4H), 2.77 (dd, 1H, J=8 Hz, J=16.5 Hz), 2.09 (m, 2H), 1.80 (m, 1H), 0.91 (d, 3H, J=6.5 Hz), 0.86 (d, 3H, J=6.5 Hz).

Mixed Carbonate 26:

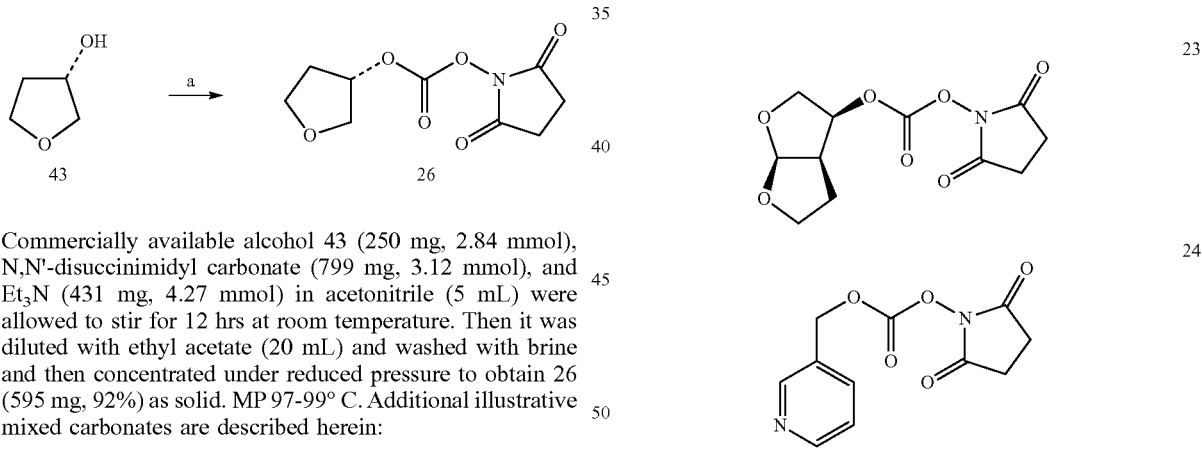

Commercially available alcohol 43 (250 mg, 2.84 mmol), N,N'-disuccinimidyl carbonate (799 mg, 3.12 mmol), and Et$_3$N (431 mg, 4.27 mmol) in acetonitrile (5 mL) were allowed to stir for 12 hrs at room temperature. Then it was diluted with ethyl acetate (20 mL) and washed with brine and then concentrated under reduced pressure to obtain 26 (595 mg, 92%) as solid. MP 97-99° C. Additional illustrative mixed carbonates are described herein:

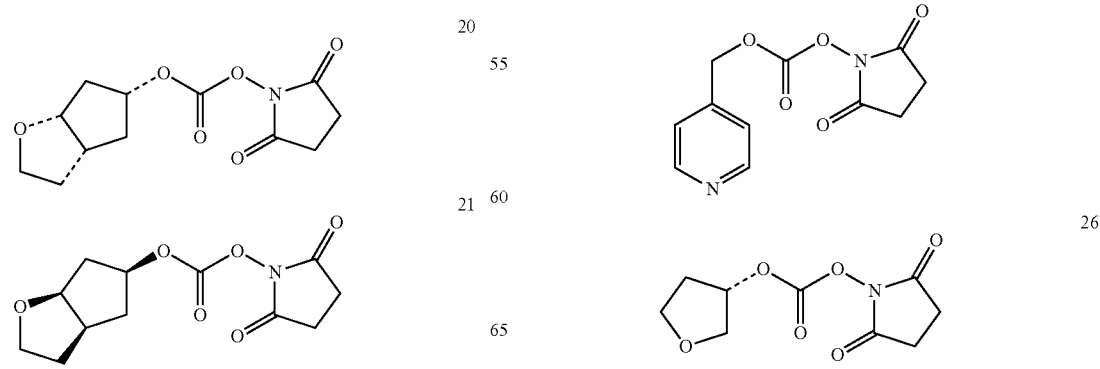

-continued
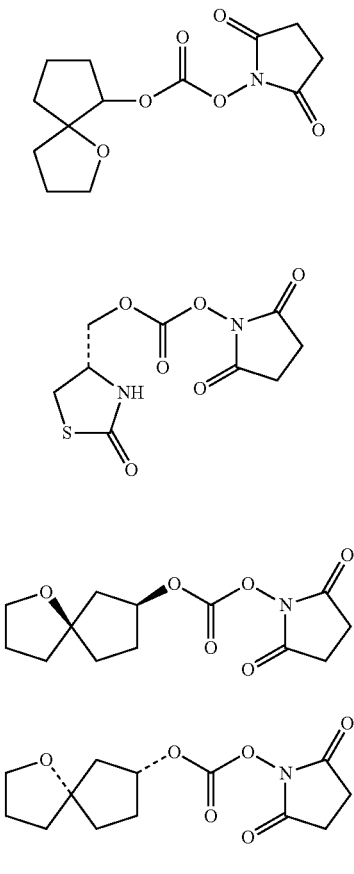
and may be prepared using the same or similar procedures described herein.
Illustrative amines are described herein:
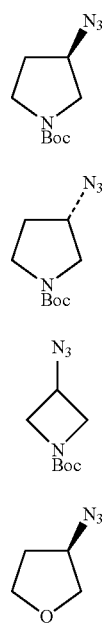
Illustrative sulfonyl chlorides are described herein:
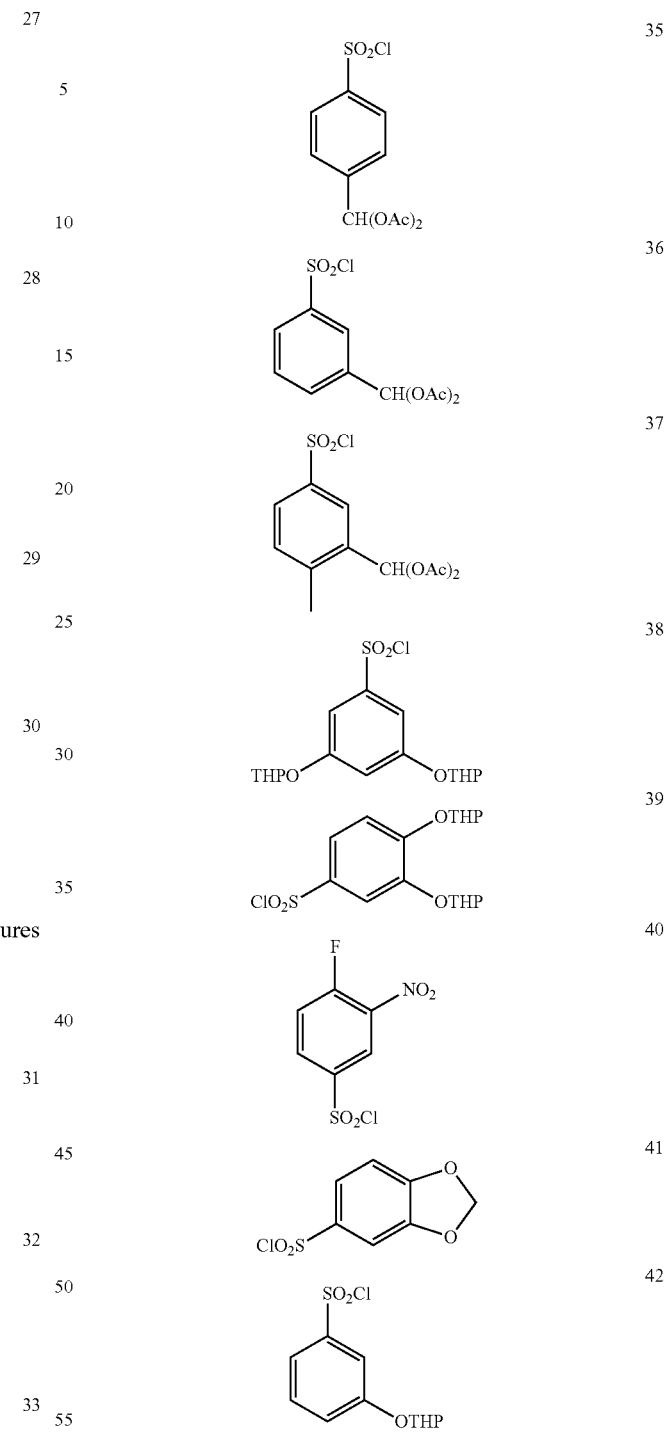
Compound 47 is prepared as follows:
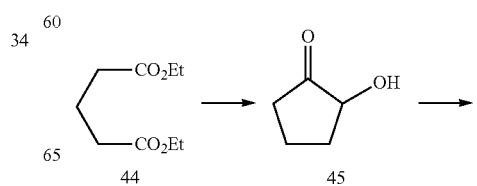

-continued

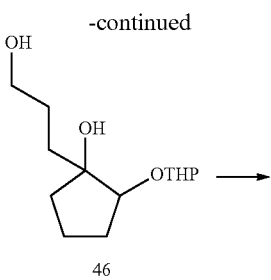

46

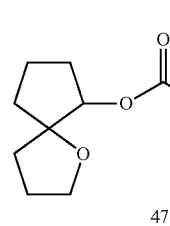

47

The known* alcohol 45 (1.13 g, 13 mmol), DHP (1.42 g, 16.9 mmol), in CH$_2$Cl$_2$ (25 mL) were stirred for 1.5 hrs. Aq. NaHCO$_3$ (10 mL) was added and the reaction was extracted with CH$_2$Cl$_2$ (10 mL). The combined extracts were dried over anhydrous Na$_2$SO$_4$ and concentrated under reduced pressure. Purification of the crude by silica gel column provided THP protected hydroxy ketone (540 mg, 63%) as an oil. $^1$H-NMR (CDCl$_3$, 200 MHz): δ 5.9 (m, 1H), 5.1 (m, 2H), 4.7 (m, 1H), 3.9 (m, 2H), 3.5 (m, 1H), 2.1-2.5 (m, 2H), 1.3-2.0 (m, 12H).

The above ketone (500 mg, 2.7 mmol) in THF (10 mL) was cooled to 0° C. and ally magnesium bromide (5.4 mL, 5.4 mmol) was added dropwise. After 3 hrs at room temperature it was treated with aq. NH$_4$Cl (10 mL) and then diluted with ethyl acetate (20 mL). The organic layer was washed with brine and dried over anhydrous Na$_2$SO$_4$. Solvents were evaporated under reduced pressure and the crude was purified by silicagel column to obtain mixture of diastereomers (443 mg, 73%) as an oil.

The above mixture (260 mg, 1.15 mmol), 9BBN (9.2 mL, 4.6 mmol, 0.5M solution), in THF at 0° C. were allowed to stir for 12 hrs at room temperature. MeOH (0.3 mL), H$_2$O$_2$ (2.5 mL, 30%), NaOH (7 mL, 30%), were heated at 65° C. for 1 hr. Cooled to room temperature and the solvents were evaporated under reduce pressure and the crude was purified by silica gel column to obtain 46 (191 mg, 68%,) as an oil. $^1$H-NMR (CDCl$_3$, 400 MHz): δ 4.7 (m, 1H), 3.8, 3.7. and 3.5 (three m, 5H), 2.5 (br s, 2H), 1.4-2 (m, 16H).

Mixed carbonate 47: The above diol 46 (170 mg, 0.69 mmol), pyridine (1 mL) was added MsCl (103 mg, 0.9 mmol) was allowed to stir for 12 hrs. Then it was diluted with ethyl acetate (10 mL) and the organic layer was washed with brine. It was dried over anhydrous Na$_2$SO$_4$ and concentrated under educed pressure. The crude cyclic ether was purified by silica gel column to obtain (111 mg, 71%) of the cyclic product. $^1$H-NMR (CDCl$_3$, 400 MHz): 5.71 (m, 1H), 3.95 (m, 4H), 3.87 (m, 1H), 1.6-2 (m, 16H).

The above ether (110 mg, 0.48 mmol), in MeOH (5 mL) was added TsOH (16 mg), After being stirred for 30 min. solvent was evaporated and the crude was extracted with ethyl acetate (2×10 mL) and the organic layers were washed with brine (10 mL) and concentrated. Purification by silicagel column provided spiro alcohol (41 mg, 60%) as an oil. $^1$H-NMR (CDCl$_3$, 400 MHz); 34.1 (m, 1H), 3.7 (m, 2H), 1.5-2 (m, 10H).

The above spiro alcohol (27 mg, 0.19 mmol), N,N'-disuccinimidyl carbonate (52 mg, 0.204 mmol), Et$_3$N (25 mg, 0.25 mmol) in acetonitrile (5 mL) was allowed to stir for 12 hrs, following the same conditions as described for 26 to obtain 47 (22 mg, 40%). $^1$H-NMR (CDCl$_3$, 200 MHz): δ 4.7 (m, 1H), 3.8 (m, 2H), 2.8 (s, 4H), 1.5-2.1 (m, 10H).

Alcohol 49:

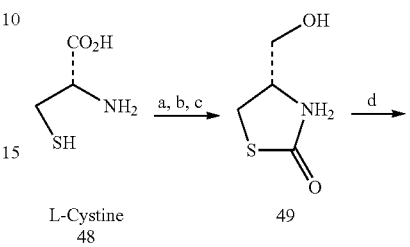

L-Cystine
48

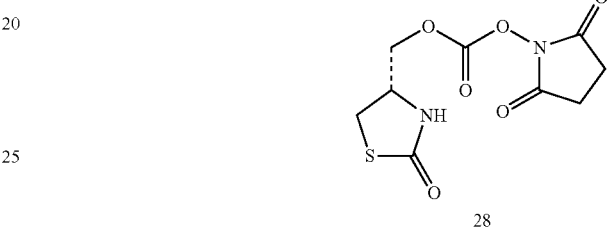

28

L-Cystine 48 (2.42 g, 20 mmol), KOH (40%, 5 mL), in water (30 mL), at 0° C. was added (COCl)$_2$ (13 mL, 20%). After being stirred for 2 hrs, the biphasic layer was placed in separating funnel, organic layer was discarded and the aqueous layer was washes with ether (10 mL). It was then acidified to pH 1 with by adding 10% HCl (20 mL), and water was evaporated under reduced pressure. The solid residue was extracted with hot ethanol (4×25 mL), the ethanol layer was concentrated to 20 mL. 0.2 mL of conc. HCl was added and it was stirred for 12 hrs. Ethanol was then evaporated and the crude was extracted with ethyl acetate (2×25 mL). Concentration and purification by silica gel column provided ethyl ester (668 mg, 20%, two steps) as an oil.

Sulfonyl Chloride 42:

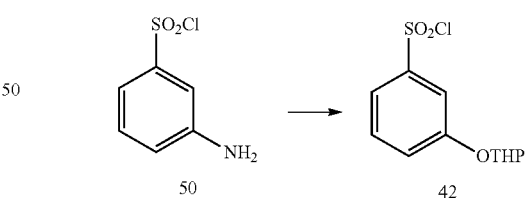

50    42

To a solution of commercial amine 50 (5 g, 29 mmol), H$_2$SO$_4$ (8.6 g, 88 mmol), in H$_2$O (100 mL) at 0° C. was added NaNO$_2$ (2.2 g, 32 mmol) in portions. Then the reaction mixture was allowed to stir for 30 minutes at room temperature. Then the reaction mixture was allowed to boil for 20 minutes. The red solution was concentrated under reduced pressure. The resulting crude was extracted with hot ethanol (2×100 mL) and all extractions were concentrated and treated with aq.NaOH solution until basic and again concentrated to provided sodium salt of crude 3-hydroxy benzene sulfonic acid.

The above salt (5.6 g, 29 mmol), SOCl$_2$ (15 mL) refluxed and DMF (0.1 mL) was added and refluxing continued for 4 hrs. The reaction mixture was cooled to room temperature. Then the reaction mixture was diluted with diluted with ethyl acetate (100 mL) and the organic layer washed with brine (2×50 mL). The combined organic layer was dried over anhydrous Na$_2$SO$_4$ and evaporated under reduced pressure. Purification of the resulting crude by flash silica gel chromatography provided the hydroxy benzene sulfonyl chloride.

The above alcohol (1 g, 5.2 mmol), DHP (0.87 g, 10 mmol), in CH$_2$Cl$_2$ (25 mL) was added PPTS (100 mg). The reaction mixture was allowed to stir for 1 hours at room temperature. Then the reaction mixture was diluted with diluted with CH$_2$Cl$_2$ (20 mL) and the organic layer washed with aq.NaHCO$_3$ solution (20 mL) and brine (2×20 mL). The combined organic layer was dried over anhydrous Na$_2$SO$_4$ and evaporated under reduced pressure. Purification of the resulting crude by flash silica gel chromatography provided the title compound 42 (670 mg, 56%). $^1$H-NMR (CDCl$_3$, 200 MHz) δ 7.67 (m, 1H), 7.55 (m, 1H), 7.4 (m, 1H), 5.5 (m, 1H), 3.9, and 3.6 (two m, 2H), 1.5-2 (m, 6H).

Sulfonyl Chlorides 35 & 36:

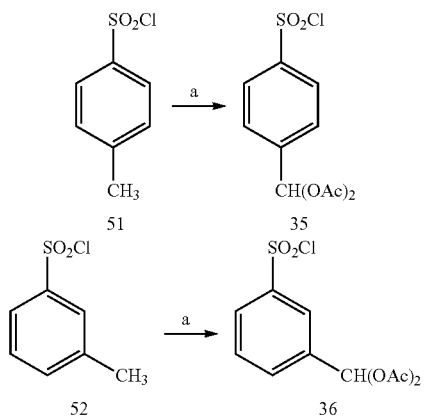

Commercial p-tosyl 51 (2 g, 10.5 mmol), H$_2$SO$_4$ (2 g, 21 mmol), in Ac$_2$O (8 mL), AcOH (8 mL) at 0° C.-5° C. was added CrO$_3$ (2.1 g, 21 mmol) in portions. The resulting reaction mixture was monitored by TLC. When the reaction was 50% complete, ice cold water (50 mL) was added and extracted with ethyl acetate. and the organic layer washed with brine (2×20 mL) and then aq. NaHCO$_3$ solution. The combined organic layer was dried over anhydrous Na$_2$SO$_4$ and evaporated under reduced pressure. Purification of the resulting crude by flash silica gel chromatography provided the title compound 35 (1.09 g, 33%). $^1$H-NMR (CDCl$_3$, 200 MHz): δ 8.0 (d, 2H, J=6.7 Hz), 7.78 (m, 3H), 2.15 (s, 6H).

Same procedure was followed for the preparation of 36 starting with m-toluene sulfonyl chloride (52). $^1$H-NMR (CDCl$_3$, 200 MHz): δ 8.19 (m, 1H), 8.1 (m, 1H), 7.9 (m, 1H), 7.65 (m, 1H), 2.16 (s, 6H).

Sulfonyl Chloride 38:

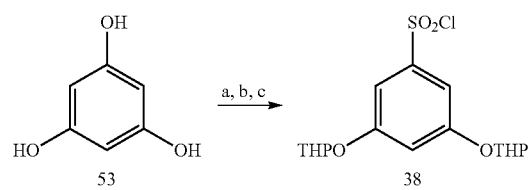

To a suspension of NaHCO$_3$ (10 g, 119 mmol), in water (30 mL), was bubbled SO$_2$ gas. Bubbling continued until NaHCO$_3$ went into solution (6 hrs). To this yallow solution (exit gases have Ph 1-2) was added phloroglucin 37 (5 g, 30.8 mmol). The reaction mixture was refluxed for four days, then cooled to r.t., and solvent evaporated, and the resulting solid was dried to obtain 3,5-dihydroxybenzene sulfonic acid.

The above crude acid (500 mg, 2.35 mmol), SO2Cl (7 mL) were refluxed in the presence of DMF (0.1 mL) for 40 minutes. The resulting reaction mixture was with ethyl acetate (50 mL) and the organic layer washed with brine (2×20 mL) and aq.NaHCO$_3$ solution. The combined organic layer was dried over anhydrous Na$_2$SO$_4$ and evaporated d under reduced pressure. Purification of the resulting crude by flash silica gel chromatography provided the dihydroxy benzene sulfonyl chloride (246 mg, 50%) as an oil. $^1$H-NMR (CDCl$_3$, 200 MHz): δ 7.1 (m, 2H), 6.8 (m, 1H).

The above dihydroxy compound (222 mg, 1.06 mmol), DHP (224 mg, 2.66 mmol), in CH$_2$CL$_2$ (10 mL), PPTS (50 mg) were allowed to stir for 30 minutes at room temperature. Then the reaction mixture was diluted with diluted with CH$_2$Cl$_2$ (20 mL) and the organic layer washed with brine (2×20 mL). The combined organic layer was dried over anhydrous Na$_2$SO$_4$ and evaporated d under reduced pressure. Purification of the resulting crude by flash silica gel chromatography provided the title compound 2 (237 mg, 67%) as an oil. $^1$H-NMR (CDCl$_3$, 300 MHz): δ 7.3 (m, 2H), 7 (m, 1H), 5.4 (m, 2H), 3.8 and 3.6 (two m, 4H), 1.4-2 (m, 12H).

Sulfonyl Chloride 40:

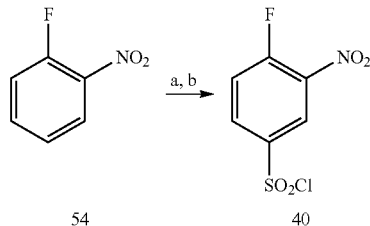 [SMILES: O=[N+]([O-])c1ccccc1F ; O=[N+]([O-])c1cc(S(=O)(=O)Cl)ccc1F]

To nitro compound 54 (7 g, 5 mmol), was carefully added fuming H$_2$SO$_4$ (60 mL) and was heated to 60° C. for 30 minutes. Then this hot mixture was slowly and very carefully poured into beaker containing KCl (30 g) and ice. The white solid obtained was recrystallised from hot water to give 4-fluoro-3-nitro benzene sulfonic acid in quantitative yield.

The above acid (2 g, 7.7 mmol), PCl$_5$ (1.8 g, 7.5 mmol), in POCl$_3$ (60 mL), were refluxed for 6 hrs. The resulting mixture was cooled to r.t., and concentrated. To the oily residue was added crushed ice. The solid was filtered and washed with water (2×50 mL), dried to obtain 40 (99%). $^1$H-NMR (CDCl$_3$, 500 MHz): δ 8.8 (m, 1H), 8.36 (m, 1H), 7.6 (m, 1H).

Preparation of Amine 31:

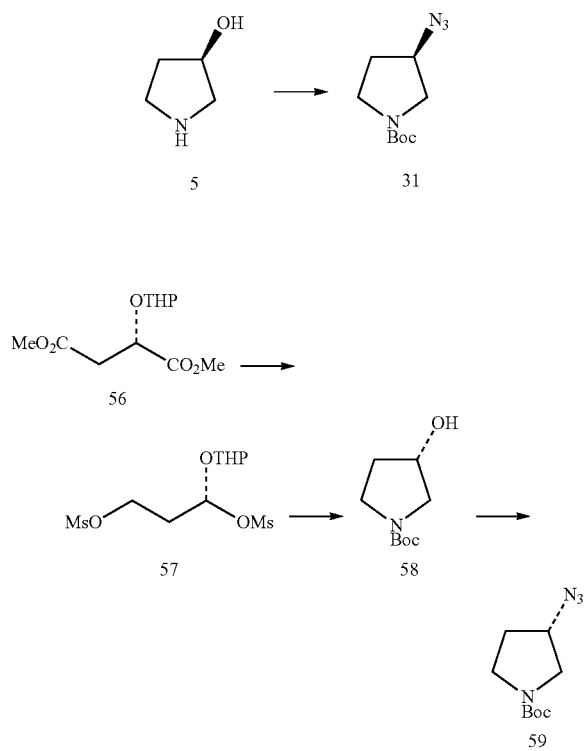

Azide 31: Commercial alcohol 55 (775 mg, 9 mmol), Boc₂O (2.33 g, 10.6 mmol), in CH₂Cl₂ (40 mL), were allowed to stir for 2 hours 30 minutes at room temperature. Then the reaction mixture was diluted with diluted with CH₂Cl₂ (20 mL) and the organic layer washed with brine (2×20 mL). The combined organic layer was dried over anhydrous Na₂SO₄ and evaporated. Purification of the resulting crude by flash silica gel chromatography provided N-Boc pyrrolidinol as an oil.

The above alcohol (7.3 g, 39 mmol), p-TsCl (8.2 g, 43 mmol), Et₃N (9.8 g, 97 mmol), DMAP (240 mg) in CH₂Cl₂ (100 mL) were allowed to stir for 8 hours at room temperature. Then the reaction mixture was washed with brine (100 mL). The organic layer was dried over anhydrous Na₂SO₄ and evaporated. Purification of the resulting crude by flash silica gel chromatography provided the ester in quantitative yield The above sulfonate ester (12.5 g, 38 mmol), NaN₃ (3.7 g, 57 mmol), in DMF (70 mL) were heated at 80° C. for 4 hrs. After cooling to room temperature Then the reaction mixture was diluted with ethyl acetate (200 mL) and the organic layer washed with brine (2×100 mL). The combined organic layer was dried over anhydrous Na2SO4 and evaporated. Purification of the resulting crude by flash silica gel chromatography provided the title compound 31 (7.43 g, 92%) as an oil. ¹H-NMR (CDCl₃, 300 MHz): δ 4.12 (m, 1H), 3.5 (m, 4H), 2 (m, 2H), 1.45 (s, 9H)

Azide 32: Bis-ester 56 (8.4 g, 34 mmol), in THF (130 mL) was added LiAlH₄ (7.6 g, 206 mmol), was added in portions. Then it was heated at 55° C. for 24 hrs. After cooling to room temperature H₂O (7.2 ml), NaOH (7.2 mL, 20%), H₂O (14.4 mL) were sequentially added and stirred for 12 hrs. The solid filtered and the filtrate concentrated. Purification of the resulting crude by flash silica gel chromatography provided the diol (3.66, 55%) as an oil. ¹H-NMR (CDCl₃, 400 MHz) δ 4.6 (m, 1H), 4 (m, 1H), 3.5-3.9 (m, 6H), 2.92 (s, 2H), 1.4-1.82 (m, 8H), (s, 9H).

The above diol (3.66 g, 19 mmol), Et₃N (5.23 g, 51 mmol), in CH₂Cl₂ (80 mL) at 0° C. was added MsCl (5.48 g, 48 mmol). The resulting reaction mixture was allowed to stir for 45 minutes at room temperature. Then the reaction mixture was diluted with diluted with CH₂Cl₂ (50 mL) and the organic layer washed with brine (2×20 mL). The combined organic layer was dried over anhydrous Na₂SO₄ and evaporated. Purification of the resulting crude by flash silica gel chromatography provided the title compound 57 (6 g, 90%) as an oil. ¹H-NMR (CDCl₃, 300 MHz): δ 4.6 (m, 1H), 4.2-4.4 (m, 4H), 3.8-4.1 (m, 2H), 3 (m, 6H), 2 (m, 2H), 1.75 (m, 2H), 1.45 (m, 4H).

Above compound 57: (6 g, 17 mmol), BnNH₂ (6.5 g, 60 mmol) in THF (150 mL) were refluxed for 12 hrs. Then BnNH₂ (6.5 g, 60 mmol) was again added and refluxing continued for 24 hrs. were allowed to cool to room temperature. Then the reaction mixture was diluted with diluted with ethyl acetate (100 mL) and the organic layer washed with brine (2×20 mL). The combined organic layer was dried over anhydrous Na₂SO₄ and evaporated. Purification of the resulting crude by flash silica gel chromatography provided the pyrrolidine compound (4.4 g) as an oil. ¹H-NMR (CDCl₃, 300 MHz): δ 7.2 (m, 5H), 4.55 (m, 1H), 4.38 (m, 1H), 3.8 (m, 1H), 3.6 (m, 2H), 3.41 (m, 1H), 2.4-2.7 (m, 4H), 2.1 (m, 1H), 1.4-1.9 (m, 7H)

The above amino compound (4.4 g, 17 mmol), in MeOH (50 mL) was hydrogenated over Pd (OH)₂ (1 g, 20%) for 18 hrs. Boc₂O (4.4 g, 20 mmol), Et₃N (3 g, 21 mmol) were added and allowed to stir for 8 hours at room temperature. Then the reaction mixture was diluted with diluted with ethyl acetate (100 mL) and the organic layer washed with brine (2×20 mL). The combined organic layer was dried over anhydrous Na₂SO₄ and evaporated. Purification of the resulting crude by flash silica gel chromatography provided the Boc compound (3.9 g, 85%).

The above THP ether (3.9 g, 14.3 mmol), in MeOH (60 mL) was added TsOH (140 mg) were allowed to stir for 1 hours at room temperature. Then the reaction mixture was diluted with diluted with ethyl acetate (100 mL) and the organic layer washed with brine (2×20 mL). The combined organic layer was dried over anhydrous Na₂SO₄ and evaporated. Purification of the resulting crude by flash silica gel chromatography provided the title compound 58 (2.56, 96%). [a]_D25: +24.2o, c, 2.1; CHCl₃. 1H-NMR (CDCl₃, 300 MHz): δ 4.4 (m, 1H), 3.4 (m, 3H), 3.3 (m, 1H), 1.89 (m, 2H), 1.4 (m, 9H).

To the above alcohol (g, 10.7 mmol), Et₃N (2.15 g, 21 mmol), in CH₂Cl₂ (50 mL) at 0° C. was added MsCl (1.46 g, 12.8 mmol), were allowed to stir for 10 minutes room temperature Then the reaction mixture was diluted with diluted with CH₂Cl₂ (50 mL) and the organic layer washed with brine (2×50 mL). The combined organic layer was dried over anhydrous Na₂SO₄ and evaporated. Purification of the resulting crude by flash silica gel chromatography provided the dimesolate compound (2.9 g) as an oil.

The above mesolate (2.9 g, 11 mmol), NaN₃ (1 g, 16 mmol), in DMF (20 mL) were allowed to stir for 6 hours at 60° C. Then the reaction mixture was diluted with diluted with ethyl acetate (50 mL) and the organic layer washed with brine (2×20 mL). The combined organic layer was dried over anhydrous Na₂SO₄ and evaporated. Purification of the resulting crude by flash silica gel chromatography provided the title azide 32 (1.87 g, 81%) as an oil. $^1$H-NMR (CDCl$_3$, 400 MHz): δ 4.12 (m, 1H), 3.4 (m, 4H), 2 (m, 2H), 1.45 (s, 9H).

Azide 33:

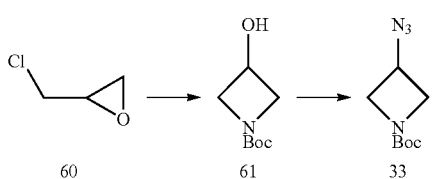 [SMILES: ClCC1CO1 ; CC(C)(C)OC(=O)N1CC(O)C1 ; CC(C)(C)OC(=O)N1CC(N=[N+]=[N-])C1]

Epichlorohydrin (60) (5 g, 54 mmol), benzhydrylamine (10 g, 53 mmol), in MeOH (25 mL), left standing for 72 hrs was then refluxed for 72 hrs. It was then cooled to room temperature, concentrated to obtain crude solid.

The above crude (1.7 g, 7 mmol), in MeOH, EtOH (10+10 mL) was hydrogenated in presence of Pd (OH)$_2$ (500 mg, 20%) for 12 hrs. It was then filtered and Boc$_2$O (2.3 g, 10 mmol), sat. NaHCO$_3$ solution (10 mL) were allowed to stiff for 24 hours at room temperature. Then the reaction mixture was diluted with diluted with ethyl acetate (50 mL) and the organic layer washed with brine (2×20 mL). The combined organic layer was dried over anhydrous Na$_2$SO$_4$ and evaporated. Purification of the resulting crude by flash silica gel chromatography provided 61 (1.35 g). $^1$H-NMR (CDCl$_3$, 300 MHz): δ 4.5 (m, 1H), 4.04 (m, 2H), 3.7 (dd, 2H, J=), 1.45 (s, 9H).

Alcohol 61 (928 mg, 5.3 mmol), Et$_3$N (1 g, 10.7 mmol), in CH$_2$Cl$_2$ (20 mL), was added MsCl (733 mg, 6.4 mmol), were allowed to stir for 1 hours at room temperature. Then the reaction mixture was diluted with diluted with CH$_2$Cl$_2$ (20 mL) and the organic layer washed with brine (20 mL). The combined organic layer was dried over anhydrous Na2SO4 and evaporated. Purification of the resulting crude by flash silica gel chromatography provided the mesolate compound (1.11 g, 83%) as an oil.

To the above meslate (1.11 g, 4.4 mmol), NaN$_3$ (574 mg, 8.8 mmol), in DMF (10 mL), were allowed to stir for 72 hours at 70° C. Then the reaction mixture was diluted with diluted with ethyl acetate (20 mL) and the organic layer washed with brine (2×20 mL). The combined organic layer was dried over anhydrous Na$_2$SO$_4$ and evaporated. Purification of the resulting crude by flash silica gel chromatography provided the title compound 33 in quantitative yield. $^1$H-NMR (CDC$_{l3}$, 300 MHz): δ 4.15 (m, 3H), 3.82 (m, 2H), 1.4 (s, 9H).

Azide 34:

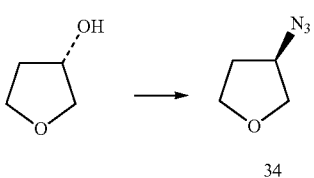 [SMILES: O[C@H]1CCOC1 ; [N-]=[N+]=N[C@@H]1CCOC1]

The same reaction conditions were followed as for the compound 33 to obtain 34 in quantitative yield. Satisfactory NMR was obtained for this compound.

Sulfonyl Chloride 39:

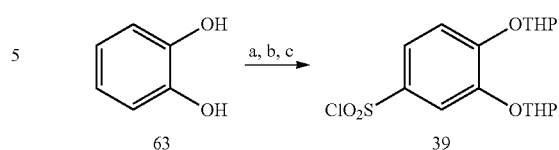

Diol 63 (25 g, 220 mmol), was heated at 180-200° C. and then amino sulfonic acid (9.7 g, 100 mmol) added portionwise. The resulting slurry was stirred was heated at same temperature for 1.5 hrs, and then cooled, dissolved in minimum amount of water. The clear solution was treated with decolorizing charcoal and filtered. The filtrate washed with ether (2×50 mL), and the aqueous layer concentrated to minimum volume (20 mL). Upon standing crystals separated which were dried to obtain 3,4-dihydroxy benzene sulfonic acid (7.56 g, 40%). Mp. 254-255° C., lit. 260° C.

The above sulfonic acid (7 g, 38 mmol), was added SOCl$_2$ (15 mL) and DMF (0.1 mL) following the same conditions as described for 39 to obtain sulfonyl chloride (3.6 g, 44%) as an oil.

The above chloride (3.5 g, 16.8 mmol), DHP (3.1 g, 37 mmol), PPTS (200 mg), in CH$_2$Cl$_2$ (50 mL) were allowed to stir for 2 hours at room temperature. Then the reaction mixture was diluted with CH$_2$Cl$_2$ (20 mL) and the organic layer washed with NaHCO$_3$ (20 mL) and then brine (2×20 mL). The combined organic layer was dried over anhydrous Na$_2$SO$_4$ and evaporated. Purification of the resulting crude by flash silica gel chromatography provided the title compound 39 (3.2 g, 56%) as an oil. $^1$H-NMR (CDCl$_3$, 200 MHz): δ 8 (d, 1H, J=2 Hz), 7.63 (m, 1H), 7.25 (d, 1H, J=8.4 Hz), 5.58 (m, 2H,), 3.4-4.2 (m, 4H), 1.4-2.2 (m, 12H).

Mixed carbonate 29 and 30: Following the procedure for 47, carbonates 29 and 30 were prepared.

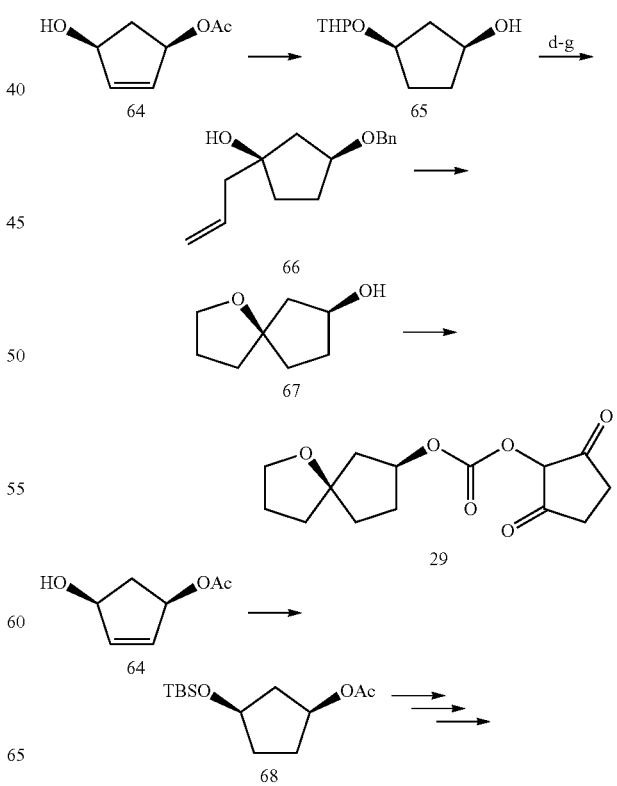

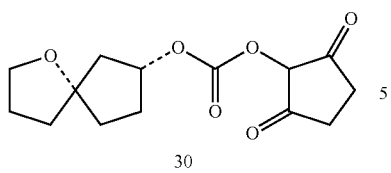
30
Preparation of compounds 72-82: Optically active epoxide 69* was converted to compounds 72-82 using similar reaction steps as Scheme I.
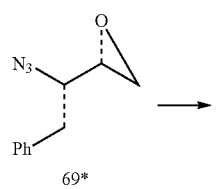
69*
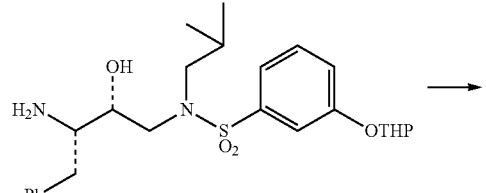
70
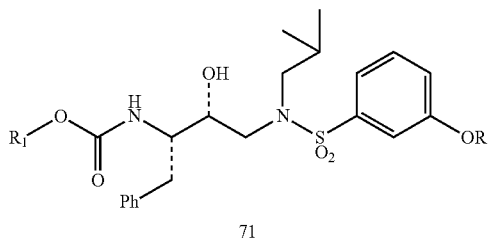
71
Variation of P2 Ligands of
3-hydroxybenzenesulfonamide isosteres
| Compound # | Structure |
|---|---|
| 72 | ![structure 72] |
| 73 | ![structure 73] |
| 74 | ![structure 74] |
| 75 | ![structure 75] |

-continued
| Compound # | Structure |
|---|---|
| 76 | 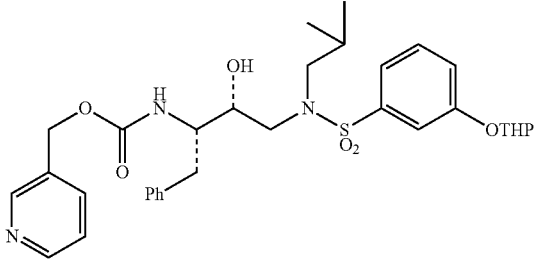 |
| 77 | 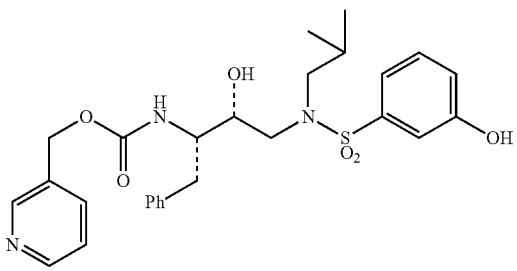 [SMILES: CC(C)CN(C[C@@H](O)[C@H](Cc1ccccc1)NC(=O)OCc1cccnc1)S(=O)(=O)c1cccc(O)c1] |
| 78 | 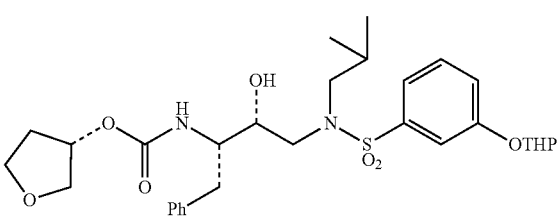 |
| 79 | 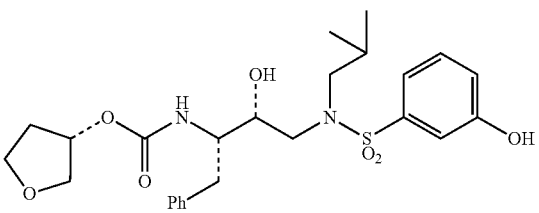 |
| 80 | 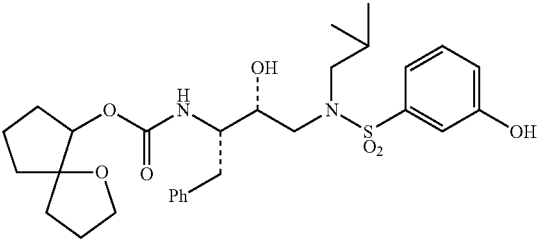 [SMILES: CC(C)CN(C[C@@H](O)[C@H](Cc1ccccc1)NC(=O)OC1CCCC12CCCO2)S(=O)(=O)c1cccc(O)c1] |
| 81 | 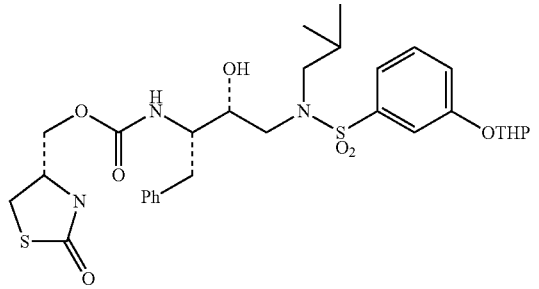 |

| Compound # | Structure |
|---|---|
| 82 | 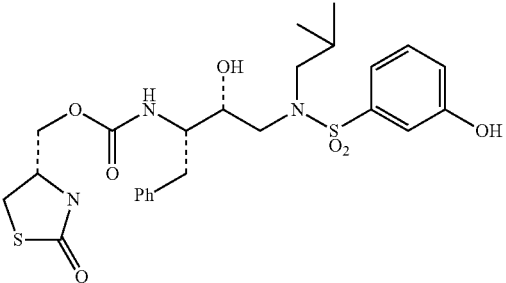 [SMILES: CC(C)CN(C[C@@H](O)[C@H](Cc1ccccc1)NC(=O)OC[C@H]1CSC(=O)N1)S(=O)(=O)c1cccc(O)c1] |
| 83 | 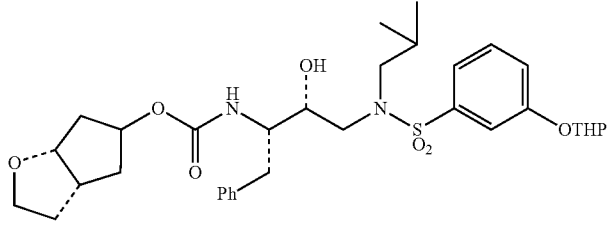 |
| 84 | 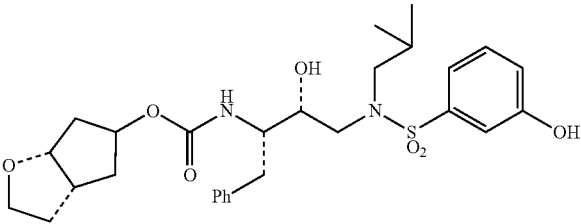 |

Compound 72: Acid 22 (7.07 mg, 0.05 mmol), EDC (10.6 mg, 0.055 mmol), HOBt (7.5 mg, 0.055 mmol), in methylene chloride:DMF (9:1, 0.5 mL), were stirred for 10 minutes, and then amine 70 (20 mg, 0.05 mmol), in methylene chloride (0.5 mL), was added followed by EtNiPr$_2$ (2.0 equiv.) and were allowed to stir for 6 hours at room temperature. Then the reaction mixture was diluted with methylene chloride (20 mL) and the organic layer washed with brine (2×20 mL). The combined organic layer was dried over anhydrous Na$_2$SO$_4$ and evaporated. Purification of the resulting crude by flash silica gel chromatography provided the title compound 72 (9 mg) as a solid. $^1$H-NMR (CDCl$_3$, 300 MHz): δ 7.2-7.5 (m, 9H), 6.9 (m, 1H), 6.76 (d, 1H, J=7.9 Hz), 6.54 (m, 1H), 6.05 (m, 1H), 5.8 (s, 1H), 5.43 (d, 1H, J=17 Hz), 4.35 (m, 1H), 4, 3.78, and 3.55 (three m, 3H), 3.21 and 2.98 (two m, 6H), 1.96 (s, 3H), 1.85 (m, 3H), 1.27 (m, 4H), 0.91 (m, 6H).

Compound 73: Compound 72 (6.8 mg, 0.011 mmol), p-TsOH (2 mg), in MeOH (0.5 mL) were allowed to stir for 10 minutes at room temperature. Then the reaction mixture was diluted with ethyl acetate (10 mL) and the organic layer washed with brine (2×20 mL). The combined organic layer was dried over anhydrous Na$_2$SO$_4$ and evaporated. Purification of the resulting crude by flash silica gel chromatography provided the title compound 73 (4.3 mg) as solid. $^1$H-NMR (CDCl$_3$, 200 MHz δ δ 7.19 (m, 9H), 7 (m, 1H), 6.93 (d, 1H, J=7.7 Hz), 6.76 (d, 1H, J=7.8 Hz), 6.54 (d, 1H, J=7.4 Hz), 6.15 (d, 1H, J=8.6 Hz), 4.36 (m, 1H), 3.96 (m, 1H), 3.26, and 2.86 (two m, 6H), 1.89 (s, 3H), 1.82 (m, 1H), 0.89 (dd, 6H, J=4 Hz, 6.4 Hz)

Compound 74: Amine 70 (48 mg, 0.12 mmol), 7 (39 mg, 0.14 mmol), Et$_3$N (2 equiv.), in methylene chloride (1 mL), were allowed to stir for 6 hours at room temperature. Then the reaction mixture was diluted with methylene chloride (10 mL) and the organic layer washed with brine (2×20 mL). The combined organic layer was dried over anhydrous Na$_2$SO$_4$ and evaporated. Purification of the resulting crude by flash silica gel chromatography provided the title compound 74 (44 mg) as solid. $^1$H-NMR (CDCl$_3$, 400 MHz): δ 7.4 (m, 1H), 7.25 (m, 8H), 5.63 (d, 1H, J=5.16 Hz), 5.46 (m, 1H), 5.05 (m, 1H), 4.88 (m, 1H), 3.8 (m, 6H), 3.61 (m, 2H), 3.2, 3.06, and 2.86 (three m, 6H), 2, 1.8, 1.54-1.78 (three m, 10H), 0.92 and 0.88 (ABq 6H, J=6.5 Hz).

Compound 75: Above (15 mg, 0.023 mmol), p-TsOH (5 mg), in MeOH (1 mL), were subjected to same conditions as described above for 73 to obtain title compound 75 in quantitative yield as solid. (prolong stirring may leads to decomposition of the reaction). M.p. 90-93° C. [a]D25: −7o, c, 0.42, MeOH. $^1$H-NMR (CDCl$_3$, 200 MHz): δ 7.26 (m, 9H), 5.7 (d, 1H, J=5.2 Hz), 5.29 and 5 (two m, 2H), 3.89 (m, 6H), 2.81-3.41 (m, 7H), 1.6-2 (m, 4H), 0.9 (dd, 6H, J=3.9 Hz, 6.4 Hz).

Compound 76: 70 (50 mg, 0.12 mmol), 18 (47 mg, 0.19 mmol), Et$_3$N (2 equiv.), in methylene chloride (1 mL) were subjected to same conditions as described above for 69 to obtain title compound 76 as solid. $^1$H-NMR (CDCl$_3$, 400 MHz): δ 8.54 (m, 2H), 7.17-7.54 (m, 12H), 5.47 (m, 1H), 5.01 (m, 2H), 3.85 (m, 3H), 3.57 (m, 1H), 2.8-3.2 (m, 6H), 1.55-2.1 (m, 7H), 0.87 (m, 6H).

Compound 77: 76 (15 mg, 0.02 mmol), p-TsOH (5 mg), in MeOH (1 mL), were subjected to same conditions as described above for 73 to obtain title compound 77 as solid. $^1$H-NMR (CDCl$_3$, 300 MHz): δ (m, H), (m, H), (m, H), (d, H), (m, H), (m, H), (m, H), (m, H), (m, H), (s, H), (m, H), (m, H), (m, H), Compound 78: 70 (55 mg, 0.13 mmol), 22 (34 mg, 0.015 mmol), Et$_3$N (2 equiv.), in methylene chloride (1 mL) were subjected to same conditions as described above for 74 to obtain title compound 78 (52 mg) as solid. $^1$H-NMR (CDCl$_3$, 200 MHz): δ 7.1-7.5 (m, 9H), 5.47 (m, 1H), 5.1 (m, 1H), 4.8 (m, 1H), 3.5-4 (m, 8H), 2.8-3.2 (m, 6H), 1.5-2.1 (m, 8H), 0.88 (dd, 6H, J=6.6 Hz, 9.3 Hz).

Compound 79: 78 (30 mg, 0.05 mmol), p-TsOH (10 mg), in MeOH (1 mL) were subjected to same conditions as described above for 73 to obtain title compound 79 (15 mg) as solid. $^1$H-NMR (CDCl$_3$, 300 MHz): δ (m, H), (m, H), (m H), (d, H), (m, H), (m, H), (m, H), (m, H), (s, H), (m, H), (m, H), (m, H), Compound 80: 70 and 27 were subjected to same conditions as described above for 74 to obtain THP ether which was further were subjected to same conditions as described above for 73 to obtain title compound 80 (5 mg) as solid. $^1$H-NMR (CDCl$_3$, 00 MHz): δ 8.3 (s, 1H), 7-7.4 (m, 9H), 5.05 (m, 1H), 4.68 (d, 1H, 4 Hz), 3.8-4 (m, 3H), 3.6 (m, 1H), 2.6-3.1 (m, 6H), 1.5-2.1 (m, 1H), 0.93 (m, 6H).

Compound 81: 70 (52 mg, 0.13 mmol), 28 (43 mg, 0.15 mmol), Et$_3$N (2 equiv.) in methylene chloride (1 mL) were subjected to same conditions as described above for 74 to obtain title compound 81 as solid. $^1$H-NMR (CDCl$_3$, 400 MHz): d 7.15-7.5 (m, 9H), 5.7 (m, 1H), 5.5 (m, 1H), 5.1 (m, 1H), 4.12 (m, 1H), 3.9 (m, 4H), 3.65 (m, 1H), 3.4 (m, 1H), 2.8-3.2 (m, 8H), 1.5-2.1 (m, 7H), 0.88 (m, 6H).

Compound 82: 81 (52 mg, 0.08 mmol), p-TsOH (15 mg), in MeOH (1 mL), were subjected to same conditions as described above for 73 to obtain title compound 82 (25 mg) as solid. $^1$H-NMR (CDCl$_3$, 200 MHz): δ 7.8 (s, 1H), 7-7.74 (m, 9H), 6.3 (s, 1H), 5.3 (d, 1H, J=8.7 Hz), 4.37 (m, 1H), 3.8-4.1 (m, 4H), 2.8-3.5 (m, 9H), 1.9 (m, 1H), 0.9 (d, 6H, J=6.1 Hz).

Compound 83: 70 (22 mg, 0.055 mmol), 21 (18 mg, 0.066 mmol), Et$_3$N (2 equiv.) in methylene chloride (1 mL) were subjected to same conditions as described above for 74 to obtain title compound 83 (23 mg) as solid. $^1$H-NMR (CDCl$_3$, 400 MHz): δ 7.2-7.5 (m, 9H), 5.5 (m, 1H), 4.86 (m, 2H), 4.4 (m, 1H), 3.6-3.8 (m, 6H), 2.8-3.2 (m47 6H), 2.6 (m, 1H), 1.4-2.1 (m, 13H), 0.96 (ABq, 6H, J=6.5 Hz).

Compound 84: 83 (19 mg, 0.03 mmol), p-TsOH (6 mg), in MeOH (1 mL), were subjected to same conditions as described above for 73 to obtain title compound 84 (12 mg) as solid. $^1$H-NMR (CDCl$_3$, 400 MHz): δ 8.9 (s, 1H), 7.1-7.4 (m, 8H), 7.03 (d, 1H, J=6.9 Hz), 5.29 (m, 1H), 5 (d, 1H, J=8.8 Hz), 4.6 (t, 1H, J=6.1 Hz), 4.1 (m, 1H), 3.85-4 (m, 2H), 3.75 (q, 1H, J=7.9 Hz), 3.53 (dd, 1H, J=3 Hz, 15 Hz), 3.1 (m, 1H), 2.91 (dd, 1H, J=5.2 Hz, 14 Hz), 2.82 (m, 1H), 2.65 (dd, 1H, J=7.6 Hz, 14.9 Hz), 2.59 (dd, 1H, J=4.6 Hz, 13.1 Hz), 1.7-2.2 (m, 7H), 0.98 and 0.88 (ABq, 6H, J=6.4 Hz).

Using the procedure of 69-71, following compounds 85-92 were prepared using the amines and mixed carbonates described herein.

Variation of P2 Ligands of
2,4-dihydroxybenzenesulfonamide isosteres

| Compound # | Structure |
| --- | --- |
| 81 | 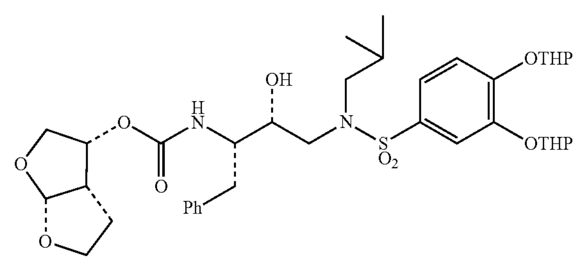 |
| 82 | 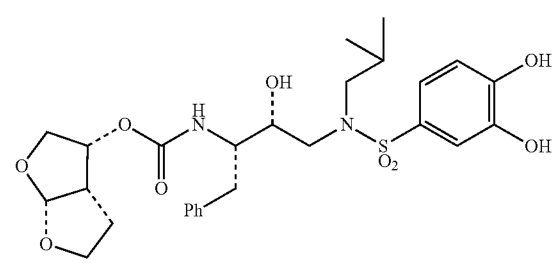 |
| 83 | 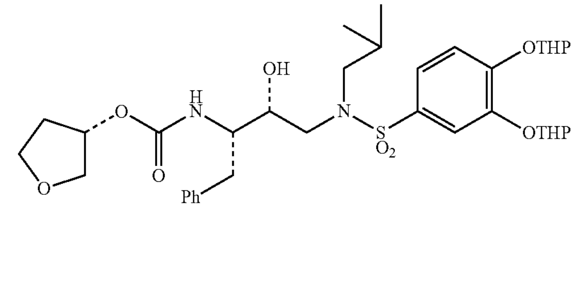 |

| Compound # | Structure |
|---|---|
| 84 | 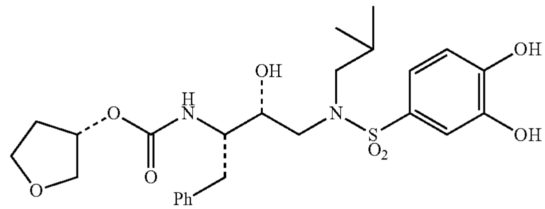 |
| 85 | 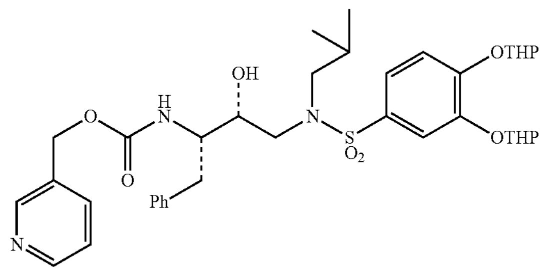 |
| 86 | 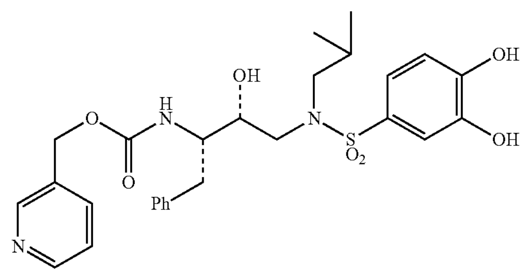 [SMILES: CC(C)CN(C[C@@H](O)[C@H](Cc1ccccc1)NC(=O)OCc1cccnc1)S(=O)(=O)c1ccc(O)c(O)c1] |
| 87 | 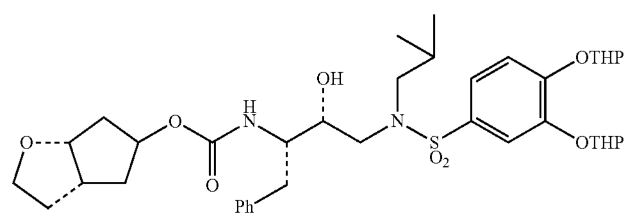 |
| 88 | 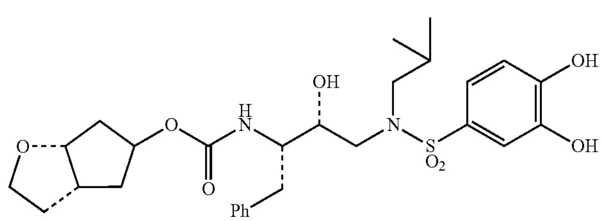 |

Compound 85: $^1$H-NMR (CDCl$_3$, 300 MHz): δ (m, H), (m, H), (m, H), (m, H), (d, H), (m, H), (m, H), (m, H), (m, H), (m, H), (s, H), (m, H), (m, H), (m, H), Compound 86: $^1$H-NMR (CDCl$_3$, 300 MHz): δ (m, H), (m, H), (m, H), (m, H), (d, H), (m, H), (m, H), (m, H), (m, H), (m, H), (s, H), (m, H), (m, H), (m, H), Compound 87: $^1$H-NMR (CDCl$_3$, 300 MHz): δ (m, H), (m, H), (m, H), (m, H), (d, H), (m, H), (m, H), (m, H), (m, H), (m, H), (s, H), (m, H), (m, H), (m, H), Compound 88: $^1$H-NMR (CDCl$_3$, 300 MHz): δ (m, H), (m, H), (m, H), (m, H), (d, H), (m, H), (m, H), (m, H), (m, H), (m, H), (s, H), (m, H), (m, H), (m, H), Compound 89: $^1$H-NMR (CDCl$_3$, 200 MHz): δ 8.5 (m, 2H), 7.1-7.7 (m, 10H), 5.45 (m, 2H), 5 (m, 2H), 3.93 (m, 5H), 3.59 (m, 1H), 2.8-3.2 (m, 6H), 1.5-2.2 (m, 12H), 0.86 (m, 6H).

Compound 90: $^1$H-NMR (CDCl$_3$, 400 MHz): δ 8.4 (s, 2H), 7.55 (m, 1H), 7.2 (m, 9H), 6.7 (s, 1H), 4.96 (m, 2H), 3.78 (m, 2H), 2.76-3.04 (m, 6H), 1.75 (m, 1H), 0.78 (d, 6H, J=5.7 Hz).

Compound 91: $^1$H-NMR (CDCl$_3$, 00 MHz): δ 7.2-7.5 (m, 8H), 5.56 (m, 2H), 4.86 (m, 2H), 4.3 (m, 1H), 3.5-4 (m, 8H), 2.8-3.2 (m, 6H), 2.6 (m, 1H), 1.6-2.1 (m, 19H), 0.86 (ABq, 6H, J=6.3 Hz).

Compound 92: ¹H-NMR (CDCl₃, 400 MHz): δ 9.5 (s, 1H), 7.2 (m, 7H), 7 (d, 1H, J=8.3 Hz), 6 (s, 1H), 5.03 (t, 1H, J=5.2 Hz), 4.91 (d, 1H, J=8.9 Hz), 4.58 (t, 1H, J=6.2 Hz), 4.18 (dd, 1H, J=6.5 Hz, 7.7 Hz), 3.9 (m, 2H), 3.82 (m, 1H), 3.51 (dd, 1H, J=3.5 Hz, 15 Hz), 3.25 (m, 1H), 3.1 (m, 2H), 2.95 (dd, 1H, J=8.2 Hz, 14 Hz), 2.87 (m, 1H), 2.58 (m, 1H), 2.49 (dd, 1H, J=4.3 Hz, 13 Hz), 1.9-2.2 (m, 4H), 1.75 (d, 1H, J=14.2 Hz), 1.02 and 0.87 (ABq, 6H, 6.4 Hz).
Amine 93 was prepared as described above and converted to compounds 94-104.
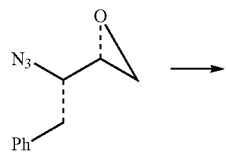
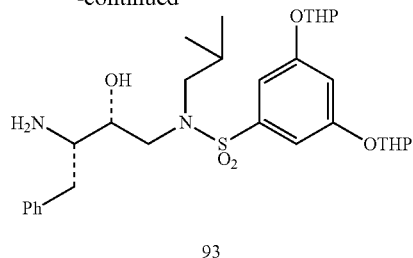
Incorporation of Various P2-Ligands to 3,5-dihydroxy benzene sulfonamide isostere
| Compound # | Structure |
|---|---|
| 94 | 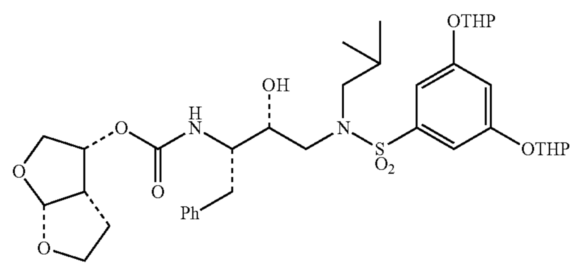 |
| 95 | 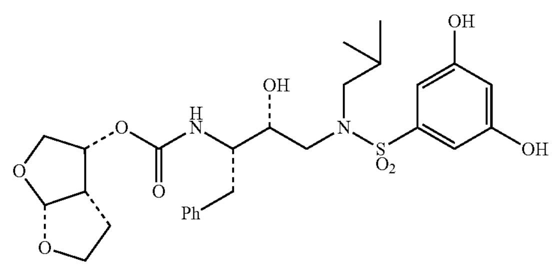 |
| 96 | 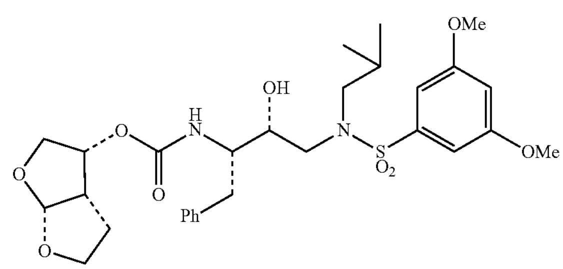 |
| 97 | 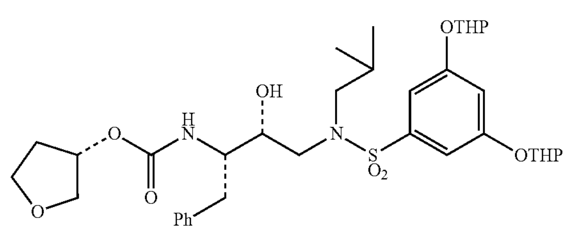 |

-continued
| Compound # | Structure |
|---|---|
| 98 | 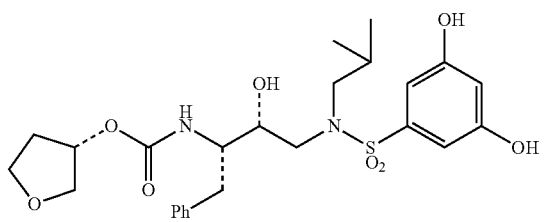 |
| 99 | 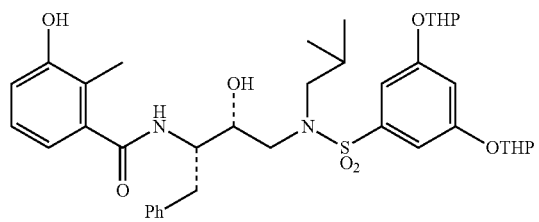 |
| 100 | 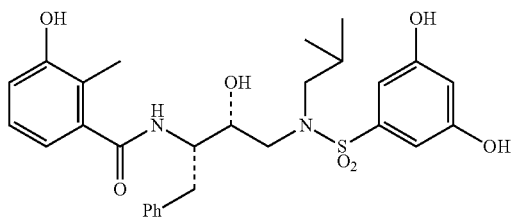 [SMILES: Cc1c(O)cccc1C(=O)N[C@@H](Cc1ccccc1)[C@H](O)CN(CC(C)C)S(=O)(=O)c1cc(O)cc(O)c1] |
| 101 | 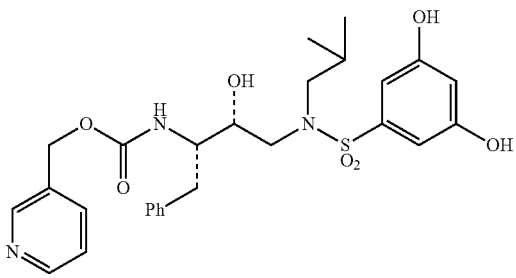 [SMILES: CC(C)CN(C[C@@H](O)[C@H](Cc1ccccc1)NC(=O)OCc1cccnc1)S(=O)(=O)c1cc(O)cc(O)c1] |
| 102 | 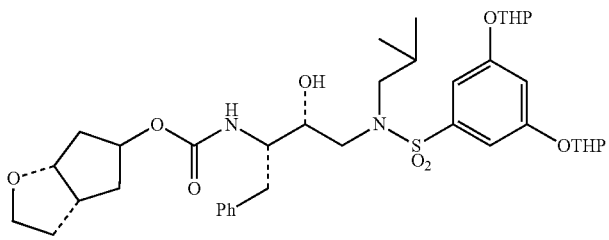 |
| 103 | 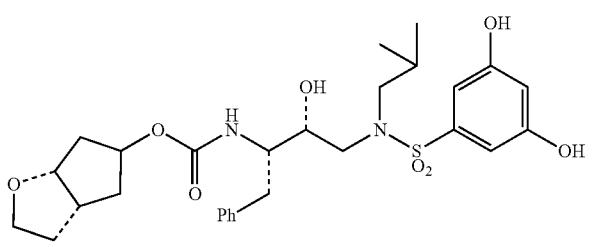 |

Compound 94: $^1$H-NMR (CDCl$_3$, 300 MHz): δ 7.5 (m, 5H), 7.02 (s, 2H), 6.9 (s, 1H), 5.56 (d, 1H, J=5.2 Hz), 5.4 (m, 2H), 5 (m, 2H), 3.4-3.9 (m, 10H), 2.6-3.2 (m, 7H), 1.4-2 (m, 15H), 0.83 (ABq, 6H, J=6.4 Hz).

Compound 95: $^1$H-NMR (CDCl$_3$, 300 MHz): δ 7.12 (m, 5H), 6.59 (s, 2H), 6.37 (s, 1H), 5.47 (d, 1H, J=5.1 Hz), 4.83 (m, 1H), 4.6 (m, 1H), 4 (m, 1H), 3.4-3.8 (m, 6H), 2.6-3.2 (m, 6H), 2.48 (m, 1H), 1.77 (m, 1H), 1.41 (m, 1H), 1.15 (m, 2H), 0.73 (ABq, 6H, J=6.4 Hz).

Compound 96: $^1$H-NMR (CDCl$_3$, 200 MHz): δ 7.25 (m, 5H), 6.89 (d, 2H, J=2.2 Hz), 6.63 (m, 1H), 5.65 (d, 1H, J=5.2 Hz), 4.95 (m, 2H), 3.8-4 (m, 3H), 3.83 (s, 6H), 3.65 (m, 3H), 2.75-3.25 (m, 7H), 1.45, 1.63 and 1.82 (three m, 3H), 0.92 (ABq, 6H, J=6.6 Hz).

Compound 97: $^1$H-NMR (CDCl$_3$, 400 MHz): δ 7.25 (m, 5H), 7.06 (m, 2H), 6.94 (m, 1H), 5.41 (m, 2H), 5.06 (m, 2H), 3.75 (m, 7H), 3.57 (m, 3H), 3.16 (m, 2H), 3 (m, 2H), 2.85 (m, 2H), 1.6 and 1.95 (two m, 15H), 0.84 (ABq, 6H, J=6.4 Hz).

Compound 98: $^1$H-NMR (CDCl$_3$, 300 MHz): δ 7.16 (m, 5H), 6.6 (s, 2H), 6.4 (s, 1H), 4.98 (m, 2H), 3.6-3.8 (m, 5H), 3.46 (m, 1H), 2.6-3.1 (m, 6H), 1.72-2.08 (m, 3H), 0.81 (d, 6H, J=6.3 Hz).

Compound 99: $^1$H-NMR (CDCl$_3$, 300 MHz): δ 7.2 (m, 5H), 7.14 (s, 2H), 6.88 (s, 1H), 6.82 (m, 1H), 6.65 (m, 1H), 6.45 (m, 1H), 6.06 (m, 1H), 5.35 (m, 2H), 4.25 (br s, 1H), 4.07, 3.9 (two m, 2H), 3.76, 3.5 (two m, 4H), 2.88-3.3 (m, 6H), 1.4-2.5 (m, 16H), 0.84 (m, 6H).

Compound 100: $^1$H-NMR (CDCl$_3$, 200 MHz): δ 7.2 (m, 5H), 6.86 (t, 1H, J=7.7 Hz), 6.66 (m, 3H), 6.45 (m, 2H), 4.27 (m, 1H), 3.87 (m, 1H), 3.27 (dd, 2H, J=3.1 Hz, 15 Hz), 3.16 (dd, 2H, J=7.5 Hz, 16.2 Hz), 2.87 (d, 1H, J=7.4 Hz), 2.75 (dd, 1H, J=10.7 Hz, 14.2 Hz), 2.51 (s, 3H), 1.87 (m, 1H), 0.85 (d, 6H, J=6.5 Hz).

Compound 101: $^1$H-NMR (CDCl$_3$, 400 MHz): δ 8.4 (m, 2H), 7.5 (m, 1H), 7.2 (m, 6H), 6.7 (s, 2H), 6.51 (s, 1H), 5.67 (d, 1H, J=8.2 Hz), 5.04, 4.9 (ABq, 2H, J=13 Hz), 3.8 (m, 2H), 3.22 (d, 1H, J=14.4 Hz), 3 (m, 2H), 2.82 (d, 1H, J=7.3 Hz), 2.73 (m, 1H), 1.79 (m, 1H), 0.84 (ABq, 6H, J=6 Hz).

Compound 102: $^1$H-NMR (CDCl$_3$, 400 MHz): δ 7.25 (m, 5H), 7.09 (s, 2H), 6.96 (s, 1H), 5.43 (m, 2H), 4.78 (m, 2H), 4.39 (m, 1H), 3.9 (m, 5H), 3.65 (m, 3H), 3.15 (m, 2H), 3.05 (m, 1H), 2.87 (m, 2H), 2.6 (m, 1H), 2.02, 1.85 and 1.7 (three m, 18H), 0.92 and 0.87 (ABq, 6H, J=6.4 Hz).

Compound 103: $^1$H-NMR (CDCl$_3$, 200 MHz): δ 8.08 (s, 2H), 7.23 (m, 5H), 6.78 (s, 2H), 6.54 (s, 1H), 5.21 (d, 1H, J=8 Hz), 4.93 (m, 1H), 4.52 (m, 1H), 3.8-4.1 (m, 3H), 3.68 (dd, 1H, J=7 Hz, 14.5 Hz), 3.5 (m, 2H), 2.5-3.1 (m, 7H), 1.5-2.2 (m, 7H), 0.92 and 0.89 (ABq, 6H, J=6.4 Hz).

Using amines 104 and 105, compounds 106-114 were prepared.

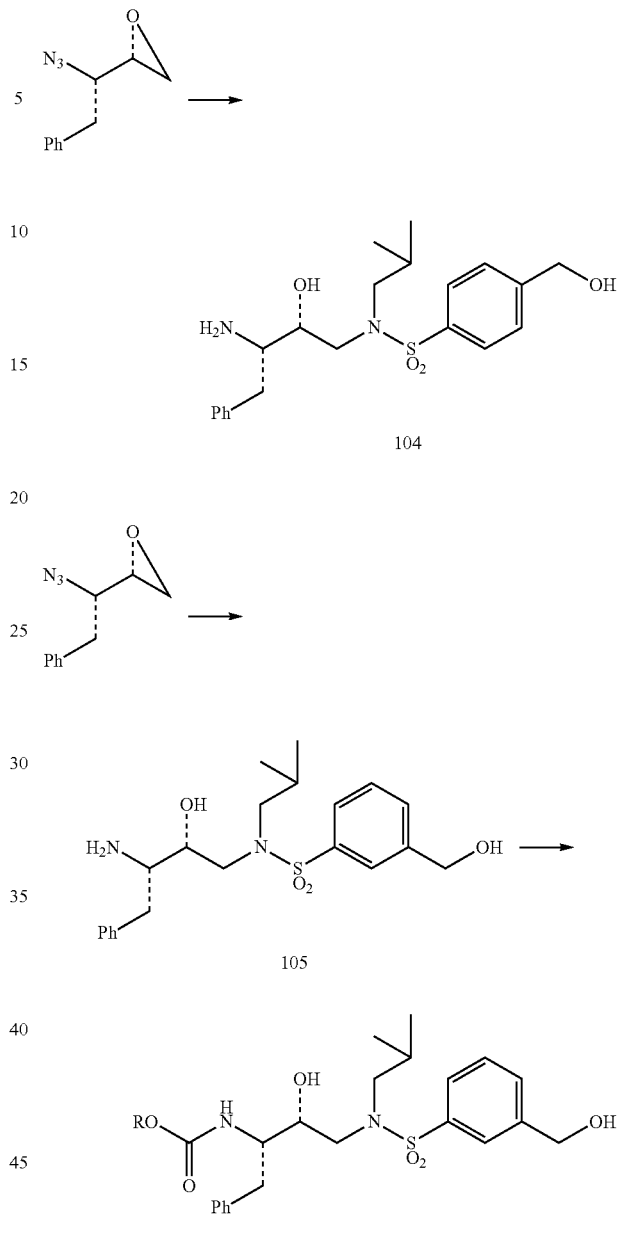

Incorporation of High Affinity P2-Ligands into the Hydroxyethylamine Isostere

| Compound # | Structure |
|---|---|
| 106 | 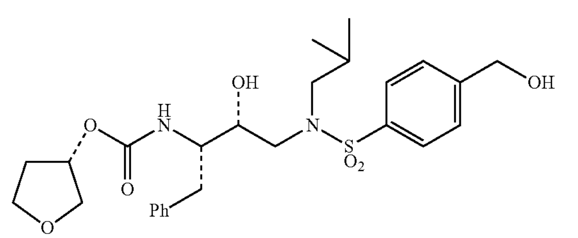 |

| Compound # | Structure |
|---|---|
| 107 | 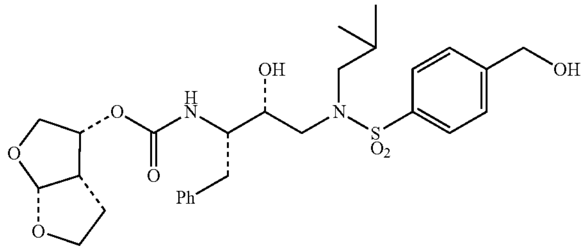 |
| 108 | 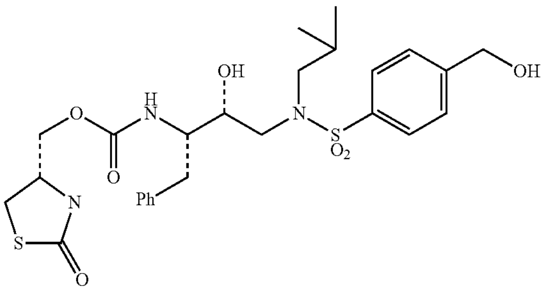 |
| 109 | 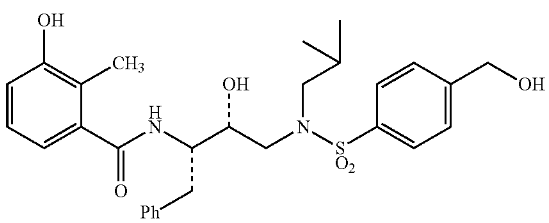 [SMILES: Cc1c(O)cccc1C(=O)N[C@@H](Cc1ccccc1)[C@H](O)CN(CC(C)C)S(=O)(=O)c1ccc(CO)cc1] |
| 110 | 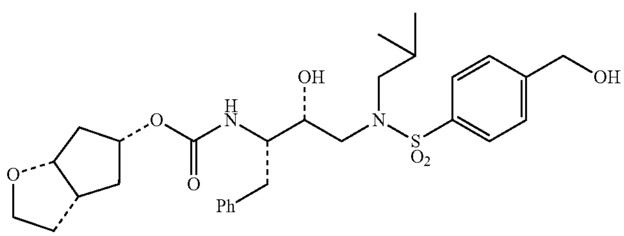 |
| 111 | 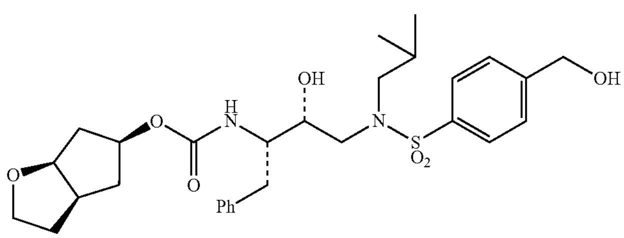 [SMILES: CC(C)CN(C[C@@H](O)[C@H](Cc1ccccc1)NC(=O)O[C@H]1C[C@H]2CCO[C@H]2C1)S(=O)(=O)c1ccc(CO)cc1] |

Compound 106: ¹H-NMR (CDCl₃, 400 MHz): δ 7.76 (d, 2H, J=8 Hz), 7.52 (d, 2H, J=8 Hz), 7.28 (m, 5H), 5.11 (m, 1H), 4.87 (d, 1H, J=8.4 Hz), 4.79 (s, 2H), 3.77 (m, 5H), 3.61 (m, 1H), 3.12 (dd, 1H, J=8.4 Hz, 15.2 Hz), 2.75-3 (m, 5H), 2.1, 1.93, and 1.82 (three m, 3H), 0.88 (ABq, 6H, J=6.4 Hz).

Compound 107: ¹H-NMR (CDCl₃, 400 MHz): δ 7.76 (d, 2H, J=8.4 Hz), 7.52 (d, 2H, J=8 Hz), 7.26 (m, 5H), 5.64 (d, 1H, J=5.2 Hz), 4.95 (m, 2H), 4.79 (d, 2H, J=5.6 Hz), 3.59-3.92 (m, 6H), 2.75-3.2 (m, 7H), 2.21 (s, 1H), 1.84 and 1.49 (two m, 2H), 0.89 (ABq, 6H, J=6.4 Hz).

Compound 108: ¹H-NMR (CDCl₃, 400 MHz): δ 7.76 (d, 2H, J=), 7.52 (d, 2H, J=), 7.27 (m, 5H), 6.17 (s, 1H), 5.21 (d, 1H, J=), 4.77 (d, 2H, J=), 4.14 (m, 1H), 3.87 (m, 5H), 3.38 (m, 1H), 2.8-3.15 (m, 6H), 0.89 (ABq, 6H, J=6.4 Hz).

Compound 109: ¹H-NMR (CDCl₃, 200 MHz): δ 7.69 (d, 2H, J=8.2 Hz), 7.42 (d, 2H, J=8.2 Hz), 2.25 (m, 5H), 6.87 (t, 1H, J=7.8 Hz), 6.71 (d, 1H, J=8 Hz), 6.42 (dd, 1H, J=7.2 Hz, 8.6 Hz), 4.64 (s, 2H), 4.28 (m, 1H), 3.89 (m, 1H), 3.15 (m, 3H), 2.92 (d, 2H, J=7.6 Hz), 2.82 (dd, 1H, J=14 Hz, 10 Hz), 2.5 (s, 3H), 1.98 (m, 1H), 0.88 (d, 6H, J=6.4 Hz).

Compound 110: ¹H-NMR (CDCl₃, 400 MHz): δ 7.75 (d, 2H, J=), 7.5 (d, 2H, J=), 4.85 (s, 1H), 4.76 (m, 3H), 4.37 (m, 1H), 3.6-3.9 (m, 4H), 2.8-3.15 (m, 6H), 2.6 (m, 1H), 2 (m, 2H), 1.8 (m, 2H), 1.69, 1.55 and 1.44 (three m, 3H), 0.89 (ABq, 6H, J=6.4 Hz).

Compound 111: ¹H-NMR (CDCl₃, 300 MHz): δ 7.76 (d, 2H, J=8 Hz), 7.42 (d, 2H, J=8.1 Hz), 7.2 (m, 5H), 4.8 (m, 1H), 4.77 (s, 2H), 4.66 (m, 1H), 4.35 (m, 1H), 3.6-3.82 (m, 4H), 2.71-3.05 (m, 6H), 2.6 (m, 1H), 1.4-2.1 (m, 6H), 0.82 (ABq, 6H, J=6.4 Hz).

Compound 112: ¹H-NMR (CDCl₃, 300 MHz): δ 7.8 (s, 1H), 7.61 (d, 1H, J=10 Hz), 7.44 (m, 2H), 7.21 (m, 5H), 4.92 (d, 1H, J=10.8 Hz), 4.81 (m, 1H), 4.71 (s, 2H), 4.38 (m, 1H), 3.6-3.91 (m, 3H), 3.39 (m, 1H), 3.01 (m, 3H), 2.92 (d, 2H, J=10 Hz), 2.5-2.8 (m, 2H), 1.78-2.02 (m, 5H), 1.4-1.65 (m, 2H), 0.91 (ABq, 6H, J=6.3 Hz).

Compound 113: ¹H-NMR (CDCl₃, 400 MHz): δ 7.15-7.65 (m, 9H), 5.6 (d, 1H, J=5.1 Hz), 5.54 (d, 1H, J=9.2 Hz), 4.96 (m, 1H), 4.69 (s, 2H), 3.57-3.83 (m, 6H), 2.72-3.2 (m, 7H), 1.9, 1.32 and 1.26 (three m, 3H), 0.88 (ABq, 6H, J=6.4 Hz).

Compound 114: ¹H-NMR (CDCl₃, 200 MHz): δ 7.68 (s, 1H), 7.57 (d, 1H, J=7.27 Hz), 7.39 (m, 2H), 7.13 (m, 5H), 6.89 (d, 1H, J=8.8 Hz), 6.81 (dd, 1H, 7.6 Hz, 7.8 Hz), 6.66 (d, 1H, J=8 Hz), 6.4 (d, 1H, J=7.4 Hz), 4.51 (s, 2H), 4.16 (m, 1H), 3.72 (m, 1H), 3.25 (dd, 1H, J=3 Hz, 15.2 Hz), 2.55-3.15 (m, 5H), 1.79 (m, 1H), 1.76 (s, 3H), 0.79 (ABq, 6H, J=6.4 Hz).

Compounds 116-121 were prepared according to the procedures described herein.

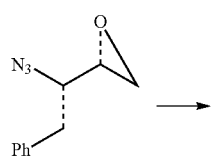

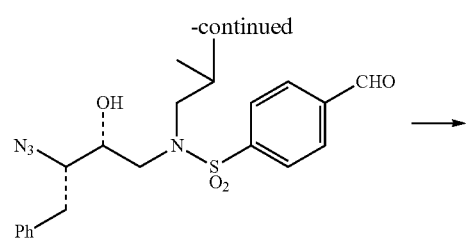

115

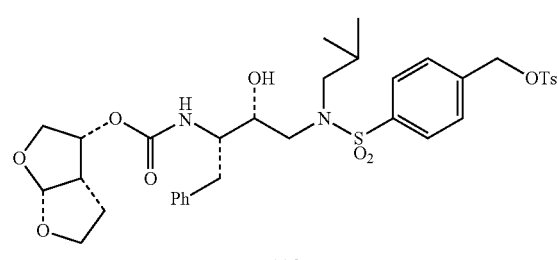

116

Bis-THF as P2 Ligand in Hydroxyethylsulfonamide Isosteres with Variation at P1' Region

| Compound # | Structure |
|---|---|
| 116 | ![structure 116] |
| 117 | ![structure 117] |
| 118 | ![structure 118] |

| Compound # | Structure |
|---|---|
| 119 | 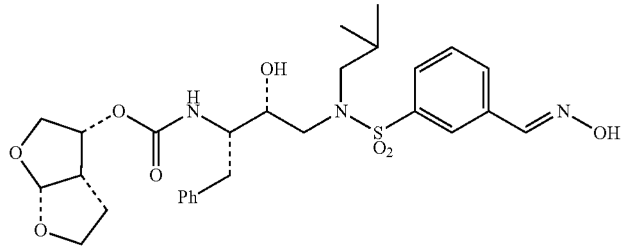 |
| 120 | 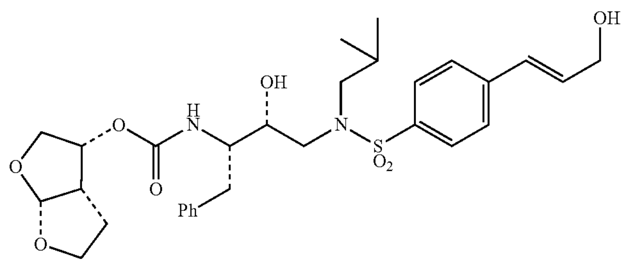 |

Compound 116: 115 (prepared from above epoxide and sulfonyl chloride 33) was subjected to NaBH₄ reduction and the resulting alcohol was treated with pTsCl in pyridine to obtain 116 as an oil. ¹H-NMR (CDCl₃, 400 MHz): δ 7.79 (d, 2H, J=8 Hz), 7.74 (d, 2H, J=8.4 Hz), 7.43 (d, 2H, J=8 Hz), 7.36 (d, 2H, J=8.4 Hz), 7.23 (m, 5H), 5.64 (d, 1H, J=5.2 Hz), 5.1 (s, 2H), 5.02 (m, 2H), 3.8-4 (m, 3H), 3.7 (m, 2H), 3.61 (m, 1H), 2.75-3.2 (m, 7H), 2.45 (s, 3H), 1.45, 1.6 and 1.83 (three m, 3H), 0.89 (ABq, 6H, J=6.4 Hz).

Compound 117: 116 (26 mg, 0.036 mmol), NaN₃ (5 mg, 0.073 mmol), in DMF (2 mL) were allowed to stir for 30 min at 65-70° C. temperature. Then the reaction mixture was diluted with ethyl acetate (20 mL) and the organic layer washed with brine (2×20 mL). The combined organic layer was dried over anhydrous Na₂SO₄ and evaporated. Purification of the resulting crude by flash silica gel chromatography provided azido intermediate.

The above azido compound (21 mg, 0.036 mmol), Ph₃P (14 mg, 0.054 mmol) in THF:H₂O (9:1, 2 mL) were allowed to stir for 12 hours at room temperature. Then the reaction mixture was diluted with ethyl acetate (20 mL) and the organic layer washed with brine (2×20 mL). The combined organic layer was dried over anhydrous Na₂SO₄ and evaporated. Purification of the resulting crude by flash silica gel chromatography provided the title compound 117 as solid. ¹H-NMR (CDCl₃, 200 MHz): δ 7.75 (d, 2H, J=8.2 Hz), 7.51 (d, 2H, J=8 Hz), 7.23 (m, 5H), 5.65 (d, 1H, J=5.2 Hz), 4.99 (m, 2H), 3.62-4.1 (m, 6H), 2.73-3.2 (m, 7H), 1.85 (m, 1H), 1.6 (m, 2H), 0.91 (ABq, 6H, J=6.4 Hz).

Compound 118: To 115 (75 mg, 0.133 mmol), MeNH₂ (8.3 mg, 0.026 mmol), AcOH (9.5 mg, 0.015 mmol), in MeOH (5 mL) was added NaCNBH₄ (10 mg, 0.159 mmol), at r.t. were allowed to stir for 12 hours at room temperature. Then the reaction mixture was diluted with ethyl acetate (20 mL) and NaHCO₃ solution (5 mL). The organic layer washed with brine (2×20 mL). The combined organic layer was dried over anhydrous Na₂SO₄ and evaporated. Purification of the resulting crude by flash silica gel chromatography provided the title compound 118 as solid. ¹H-NMR (CDCl₃, 400 MHz): δ 7.75 (d, 2H, J=7.6 Hz), 7.75 (d, 2H, J=8 Hz), 5.64 (d, 1H, J=5.2 Hz), 5.03 (m, 2H), 3.8-4 (m, 5H), 3.88 (s, 2H), 3.67 (m, 1H), 2.75-3.2 (m, 7H), 1.44, 1.63, and 1.93 (three m, 3H), 0.89 (ABq, 6H, J=6.4 Hz).

Compound 119: The above azido epoxide was converted into corresponding aldehyde in the following sequence: i) terminal epoxide opening with isobutyl amine in iPrOH for 3 hrs. ii) treatment of resulting amine with 36 in.NHCO₃/H₂O iii) hydrolysis of the resulting bisacetoxy compound to aldehyde using K₂CO₃ in MeOH to obtain aldehyde. The resulting aldehyde (35 mg, 0.062 mmol), NH₂OH.HCl (86 mg, 0.12 mmol), Et₃N (2 eq) in MeOH (5 mL) were allowed to stir for 24 hours at room temperature. Then the reaction mixture was diluted with ethyl acetate (20 mL) and the organic layer washed with brine (2×20 mL). The combined organic layer was dried over anhydrous Na₂SO₄ and evaporated. Purification of the resulting crude by flash silica gel chromatography provided the azido oxime as an oil.

The above azido function of oxime was hydrogenated over Pd/C (10%) in MeOH for 6 hrs and the resulting amine was treated with 7 (1 eq.) Et₃N (2 eq.) in CH₂Cl₂ for 3 hrs to obtain 119 as solid. ¹H-NMR (CDCl₃, 400 MHz): δ 8.15 and 8.05 (two s, 2H), 7.77 (d, 1H, J=7.6 Hz), 7.72 (d, 1H, J=7.6 Hz), 7.54 (dd, 1H, J=7.6 Hz, 8.0 Hz), 5.67 (d, 1H, J=5.2 Hz), 5.05 (m, 2H), 3.7-4 (m, 6H), 3.19 (m, 1H), 3.1 (m, 2H), 2.95 (d, 2H, J=7.6 Hz), 2.8 (dd, 1H, J=7.6 Hz, 12.4 Hz), 1.6, 1.7 and 1.85 (three m, 3H), 0.89 (d, 6H, J=6.4 Hz).

Compound 120: To (EtO)₂P(O)CH₂CO₂Et (1.1 equiv.) in THF was added NaH ((37 mg, 0.93 mmol) were allowed to stir for 10 hours at room temperature. Then aldehyde 115 (222 mg, 0.54 mmol), in THF (2 mL) was added and were allowed to stir further 10 min at room temperature. Then the reaction mixture was diluted with ethyl acetate (20 mL) and the organic layer washed with brine (2×20 mL). The combined organic layer was dried over anhydrous Na₂SO₄ and evaporated. Purification of the resulting crude by flash silica gel chromatography provided the ester. To the above ester (50 g, 0.1 mmol), in CH₂Cl₂ (5 mL) was added DIBAL-H (1M, 0.5 mL) at −78° C. After 30 min the reaction mixture was warmed to r.t. and treated with MeOH (1 mL) to destroy excess of DIBAL-H. Cold dil. HCl (10%, 15 mL) was added cautiously and the resulting mixture was stirred until clear organic layer was obtained which was extracted with EtOAc (2×10 mL). The organic layer washed with brine (2×20 mL). The combined organic layer was dried over anhydrous Na₂SO₄ and evaporated to obtain crude amino allylic alcohol.

The above amino alcohol (1 equiv.), 7 (1 equiv.) and Et₃N (2 equiv.) in CH₂Cl₂ were allowed to stir for 3 hours at room temperature. Then the reaction mixture was diluted with ethyl acetate and the organic layer washed with brine. The combined organic layer was dried over anhydrous Na₂SO₄ and evaporated. Purification of the resulting crude by flash silica gel chromatography provided the title compound 120 as solid. ¹H-NMR (CDCl₃, 400 MHz): δ 7.72 (d, 2H, J=8 Hz), 7.5 (d, 2H, J=8 Hz), 7.29 (m, 5H), 6.69 (d, 1H, J=16 Hz), 6.51 (m, 1H), 5.6 (d, 1H, J=5.2 Hz), 5 (m, 1H), 4.95 (d, 1H, J=8.4 Hz), 4.37 (d, 2H, J=4.4 Hz), 3.86 (m, 4H), 3.65 (m, 2H), 3.15 (m, 1H), 3.1 (dd, 1H, J=4 Hz, 14.4 Hz), 3 (m, 2H), 2.81 (m, 2H), 1.45, 1.61 and 1.8 (three m, 3H), 0.91 (ABq, 6H, J=6.4 Hz)

Compound 121: Terminal azido epoxide was subjected to ring opening with isobutyl amine (2 equiv.) in isopropanol under reflux for about 3 hrs and solvents were evaporated and the resulting crude amine (1 equiv.) was coupled with acid 6 (1 equiv.) in presence of EDCI (1.2 equiv.), HOBt (1.2 equiv.), Et₃N (2 equiv.) in CH₂Cl₂:DMF (9:1) for 6 hrs and after workup and purification was obtained the benzamide derivative. The azido function was hydrogenated over Pd—C (10%) in presence of 15 (1.1 equiv.) and Et₃N (2 equiv.) in THF for 12 hrs. After filtration and purification title compound 122 was obtained in reasonable yield. ¹H-NMR (CDCl₃, 200 MHz): δ 7.3 (m, 5H), 7.1 (m, 2H), 6.78 (d, 1H, J=8 Hz), 6.2 (s, 1H), 5.65 (d, 1H, J=5.2 Hz), 5 (m, 2H), 3.8-4.15 (m, 6H), 2.8-3.3 (m, 7H), 2.6 (m, 3H), 2.2, 1.8, and 1.6 (three m, 3H), 0.78 (d, 6H, J=6.4 Hz).

Using aldehyde 115 and various mixed carbonates, compounds 122-126 were prepared.

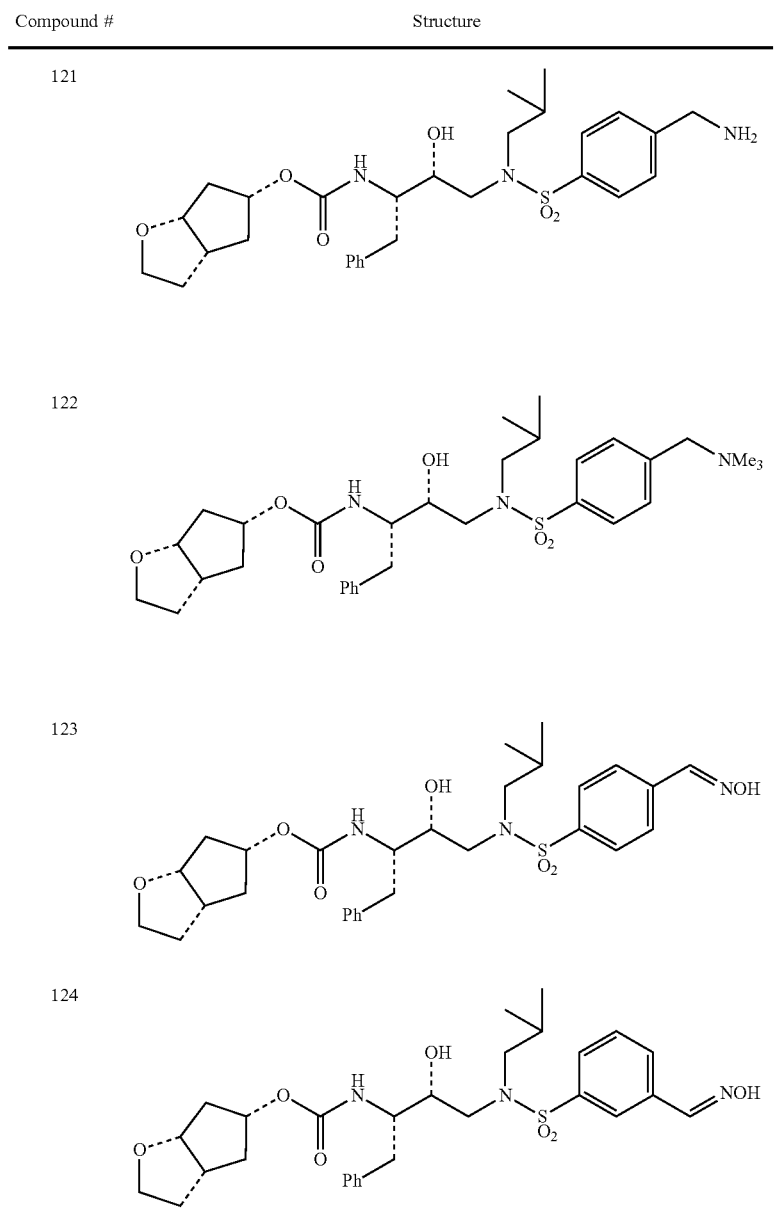

| Compound # | Structure |
|---|---|
| 121 | 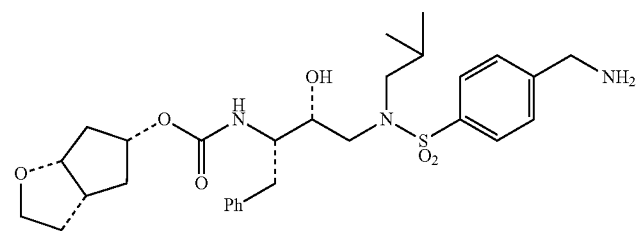 |
| 122 | 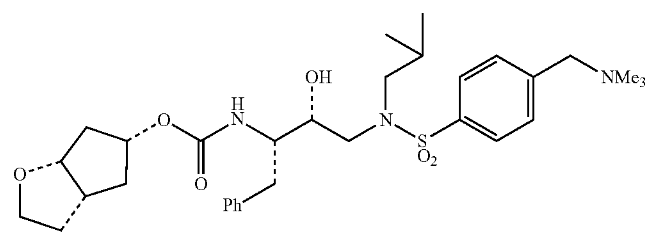 |
| 123 | 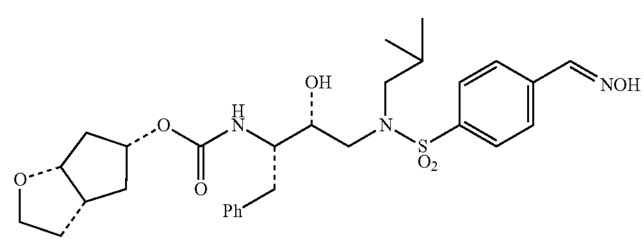 |
| 124 | 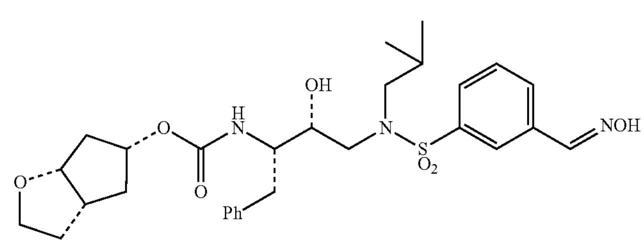 |

| Compound # | Structure |
|---|---|
| 125 | 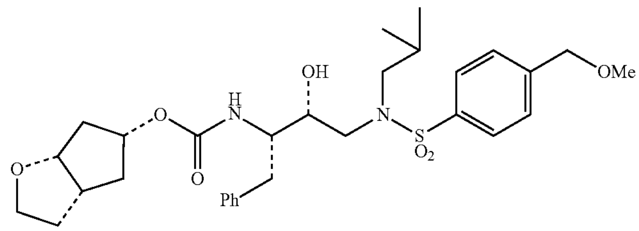 |
| 126 | 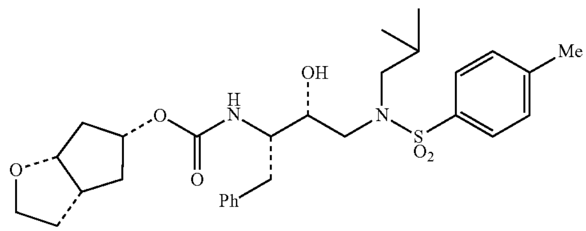 |

Compound 121: ¹H-NMR (CDCl₃, 400 MHz): δ 7.74 (d, 2H, J=8.4 Hz), 7.48 (d, 2H, J=8.4 Hz), 7.3 (m, 5H), 4.9 (m, 2H), 4.41 (m, 1H), 4 (s, 2H), 3.78 (m, 3H), 3.68 (m, 1H), 2.72-3.2 (m, 6H), 2.65 (m, 1H), 2.46 (br s, 2H), 1.8-2.1 (m, 5H), 1.4 (m, 2H), 0.88 (ABq, 6H, J=6.4 Hz).

Compound 122: ¹H-NMR (CDCl₃, 200 MHz): δ 7.78 (d, 2H, J=8.2 Hz), 7.58 (d, 2H, J=8.2 Hz), 7.25 (m, 5H), 4.84 (m, 2H), 4.39 (dt, 1H, J=6.4 Hz, 4.4 Hz), 3.6-3.85 (m, 6H), 2.75-3.2 (m, 6H), 2.6 (m, 1H), 2.38 (s, 6H), 2 (m, 3H), 1.9 and 1.5 (two m, 4H), 0.88 (ABq, 6H, J=6.4 Hz).

Compound 123: ¹H-NMR (CDCl₃, 300 MHz): δ 8.53 and 8.1 (two s, 2H), 7.73 (d, 2H, J=8.4 Hz), 7.65 (d, 2H, J=8.7 Hz), 7.2 (m, 5H), 4.83 (m, 1H), 4.79 (d, 1H, J=8.7 Hz), 4.35 (m, 1H), 3.78 (m, 3H), 3.61 (m, 1H), 2.75-3.12 (m, 6H), 2.6 (m, 1H), 1.4, 1.8 and 2 (three m, total 7H), 0.83 (ABq, 6H, J=6.4 Hz).

Compound 124: ¹H-NMR (CDCl₃, 400 MHz): δ 9.5 (s, 1H), 8.1 (s, 2H), 7.77 (d, 1H, J=8 Hz), 7.62 (d, 1H, J=7.6 Hz), 7.55 (t, 1H, J=4 Hz), 7.23 (m, 5H), 5.02 (d, 1H, J=8.8 Hz), 4.94 (m, 1H), 4.44 (m, 1H), 3.6-4 (m, 4H), 3.4, 3 and 2.83 (three m, 6H), 2.65 (m, 1H), 2.05 (m, 4H), 1.5, 1.63 and 1.9 (three m, 3H), 0.89 (ABq, 6H, J=6.4 Hz).

Compound 125: ¹H-NMR (CDCl₃, 400 MHz): δ 7.76 (d, 2H, J=8.4 Hz), 7.48 (d, 2H, J=8.4 Hz), 7.27 (m, 5H), 3.8 (m, 3H), 3.63 (m, ¹H), 3.43 (s, 3H), 3-3.15 (m, 3H), 2.95 (dd, 1H, J=13.6 Hz, 8.4 Hz), 2.83 (m, 2H), 2.63 (m, 1H), 2.05 (m, 3H), 1.81 (m, 2H), 1.49 and 1.55 (two m, 2H), 0.87 (ABq, 6H, J=6.4 Hz).

Compound 126: ¹H-NMR (CDCl₃, 400 MHz): δ 7.6 (d, 2H, J=8.4 Hz), 7.31 (d, 2H, J=8 Hz), 7.25 (m, 5H), 4.87 (m, 1H), 4.75 (m, 1H), 4.4 (m, 1H), 3.8 (m, 3H), 3.7 (m, 1H), 2.7-3.2 (m, 6H), 2.62 (m, 1H), 2.42 (s, 3H), 2.03 (m, 3H), 1.82 (m, 2H), 1.4 and 1.53 (two m, 2H), 0.87 (ABq, 6H, The following compounds are described herein:

| Compound # | Structure |
|---|---|
| 127 | 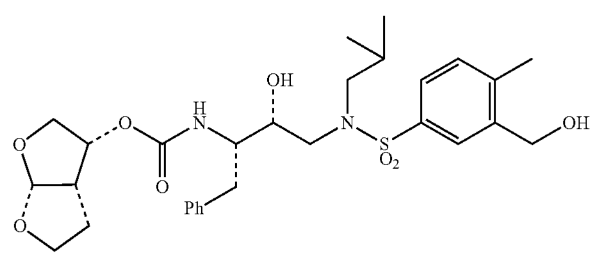 |
| 128 | 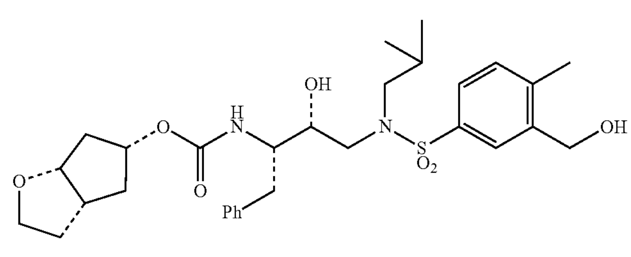 |

| Compound # | Structure |
|---|---|
| 129 | 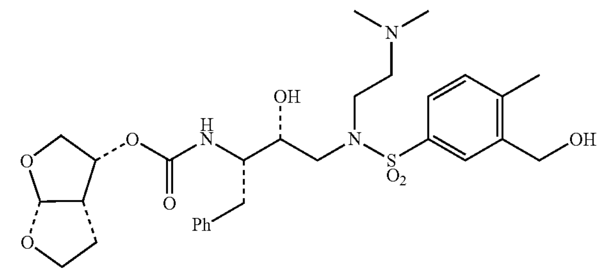 |
| 130 | 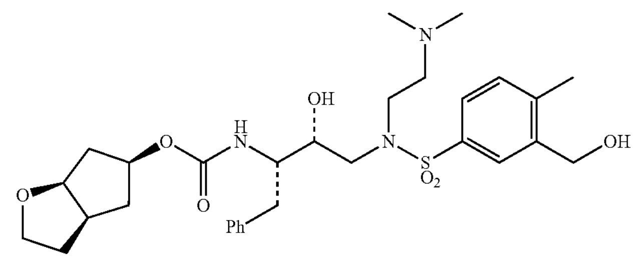 [SMILES: Cc1ccc(S(=O)(=O)N(CCN(C)C)C[C@@H](O)[C@H](Cc2ccccc2)NC(=O)O[C@H]2C[C@H]3CCO[C@H]3C2)cc1CO] |
| 131 | 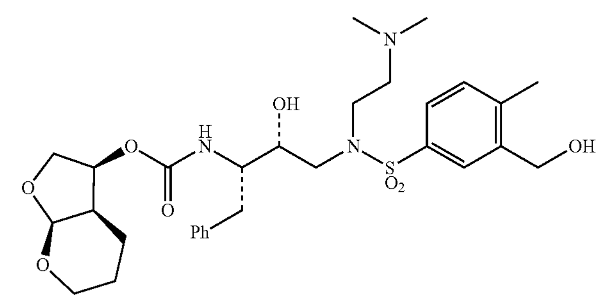 [SMILES: Cc1ccc(S(=O)(=O)N(CCN(C)C)C[C@@H](O)[C@H](Cc2ccccc2)NC(=O)O[C@@H]2CO[C@@H]3OCCC[C@@H]32)cc1CO] |
| 132 | 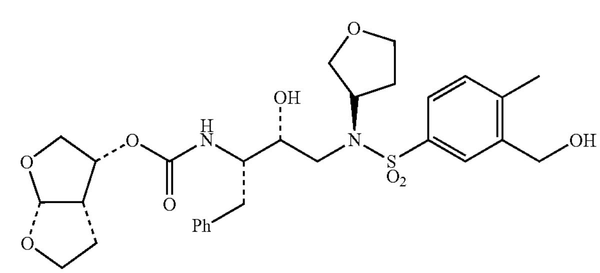 |
| 133 | 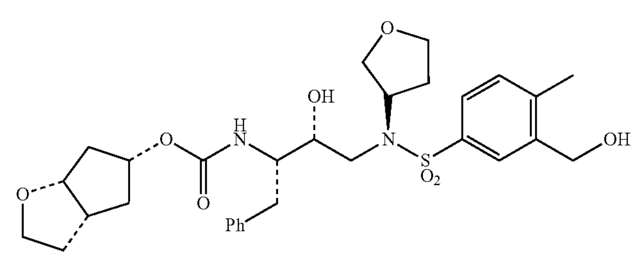 |

| Compound # | Structure |
|---|---|
| 135 | 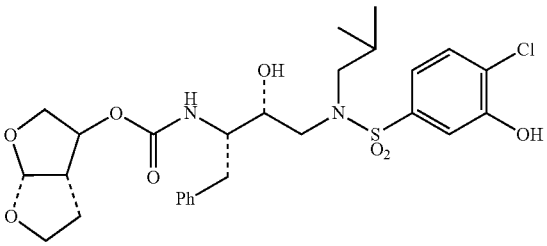 |
| 136 | 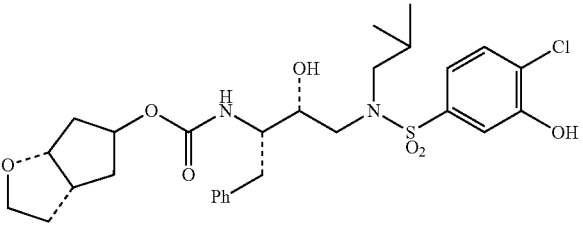 |
| 137 | 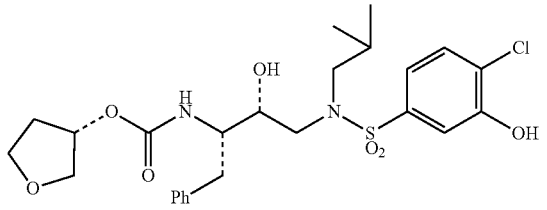 |
| 138 | 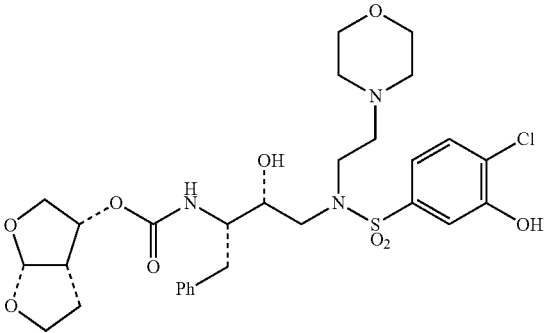 |
| 139 | 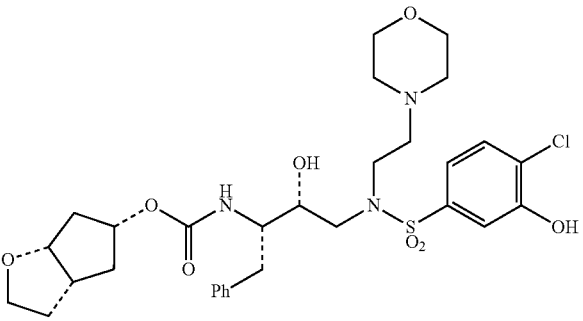 |

| Compound # | Structure |
|---|---|
| 140 | 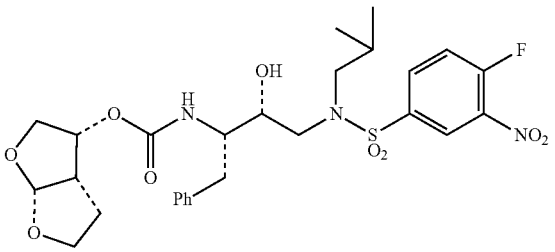 |
| 141 | 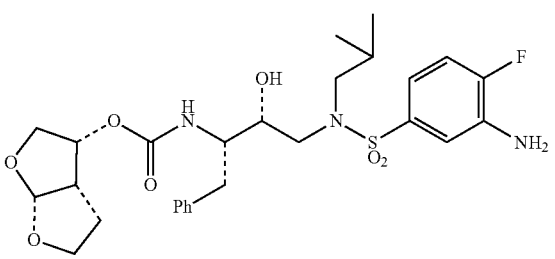 |
| 142 | 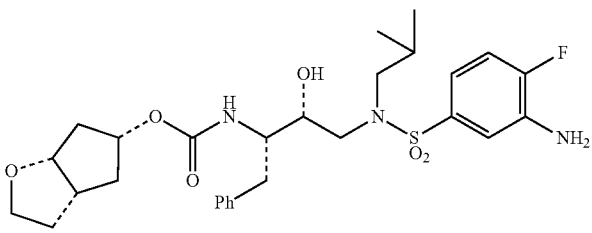 |
| 143 | 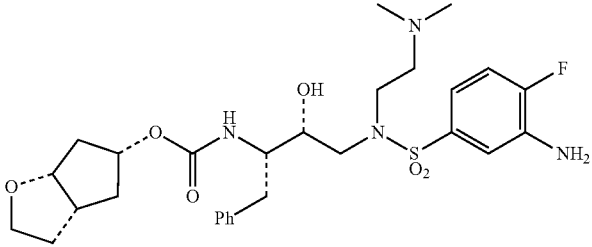 |
| 144 | 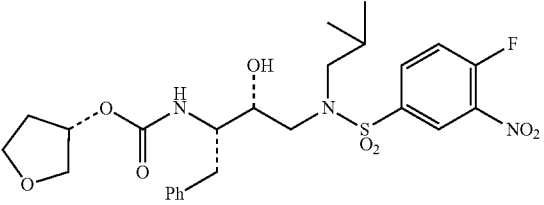 |
| 145 | 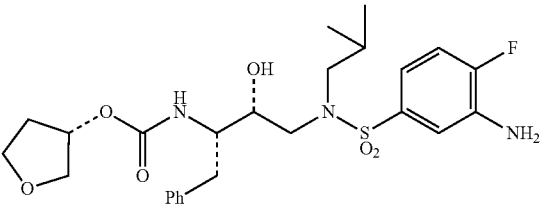 |

| Compound # | Structure |
|---|---|
| 146 | 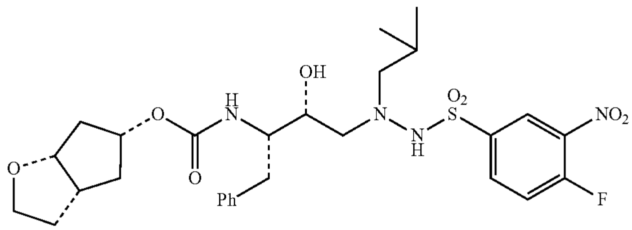 |
| 147 | 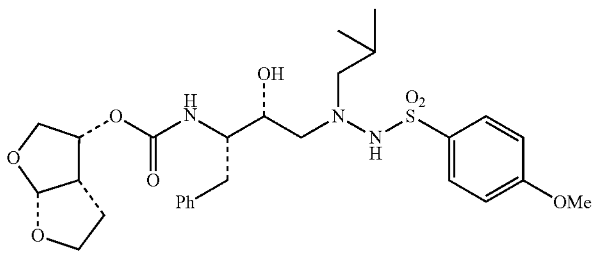 |
| 148 | 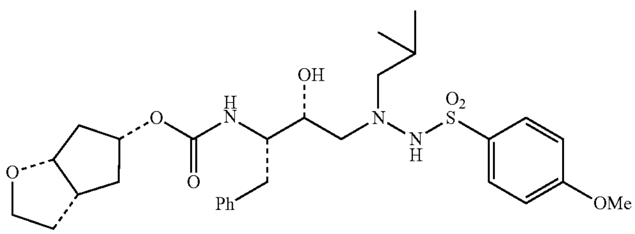 |
| 149 | 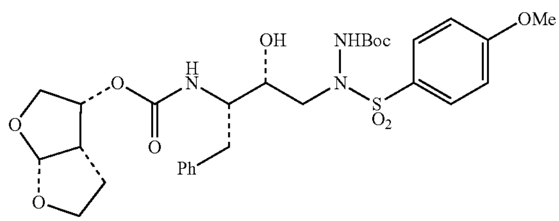 |
| 150 | 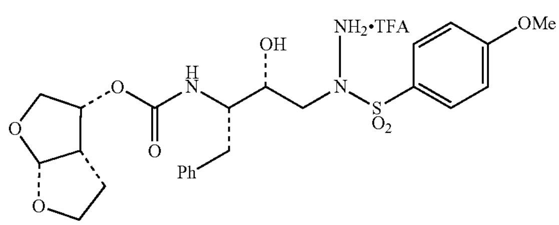 |
| 151 | 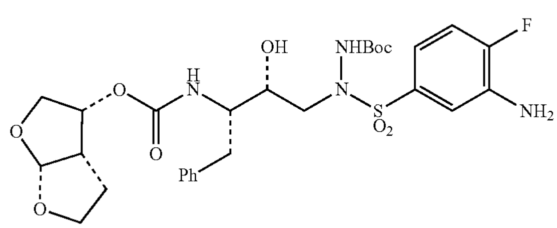 |
| 152 | 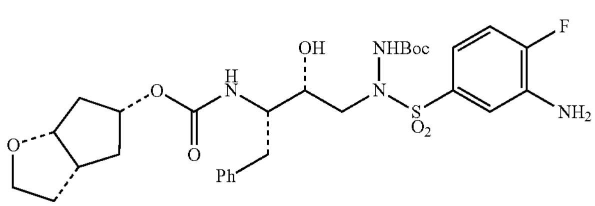 |

| Compound # | Structure |
|---|---|
| 153 | 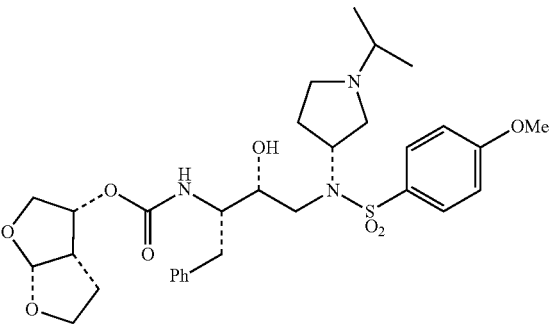 |
| 154 | 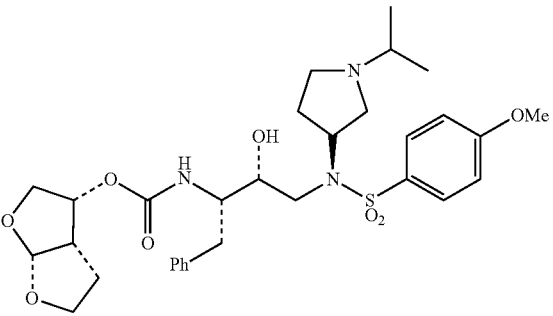 |
| 155 | 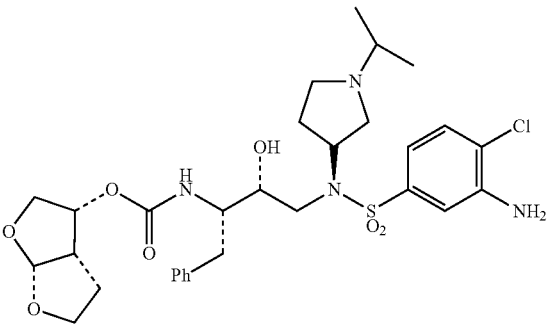 |
| 156 | 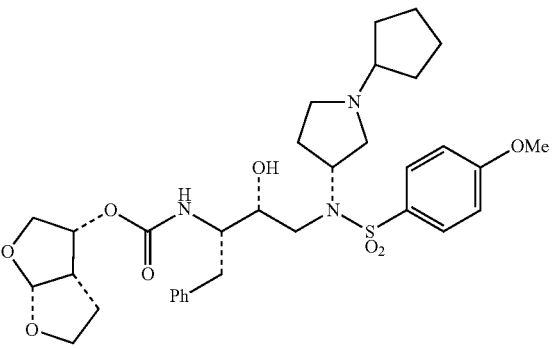 |
| 157 | 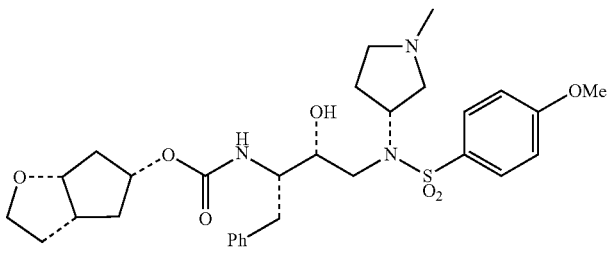 |

| Compound # | Structure |
|---|---|
| 158 | 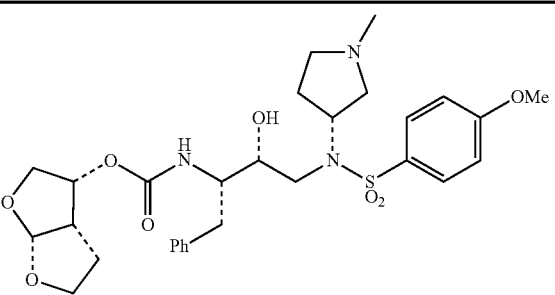 |
| 159 | 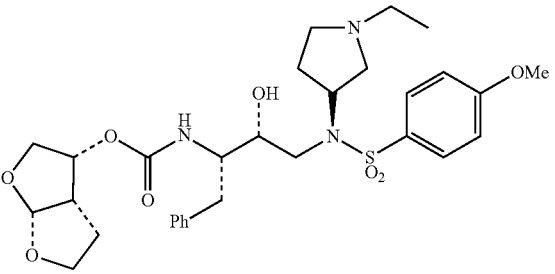 |
| Compound # | Structure |
|---|---|
| 160 | 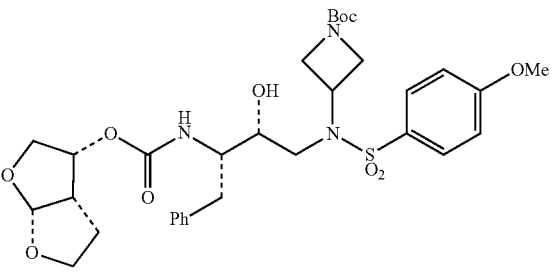 |
| 161 | 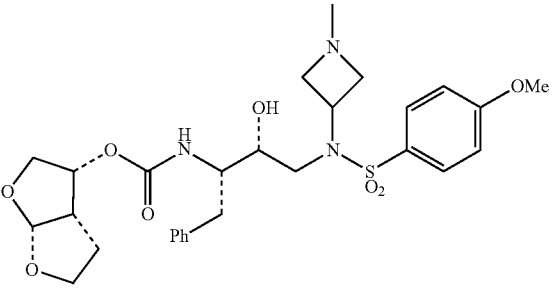 |
| 162 | 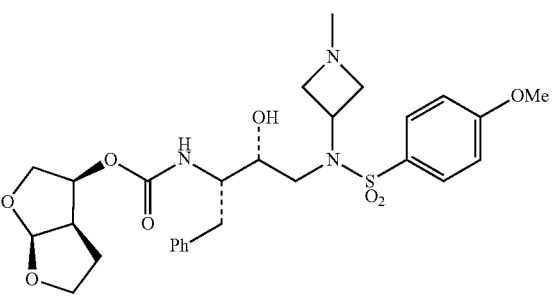 [SMILES: COc1ccc(S(=O)(=O)N(C[C@@H](O)[C@H](Cc2ccccc2)NC(=O)O[C@@H]2CO[C@@H]3OCC[C@@H]32)C2CN(C)C2)cc1] |

-continued

| Compound # | Structure |
| --- | --- |
| 163 | 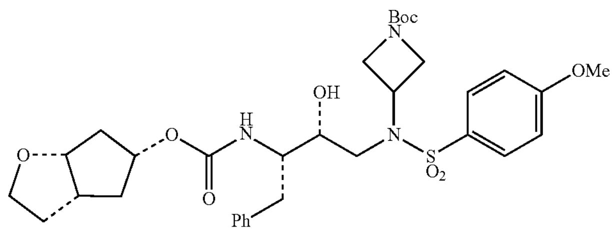 |
| 164 | 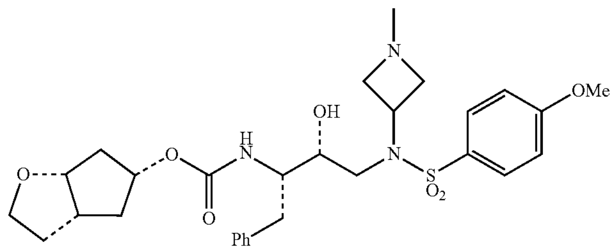 |
| 165 | 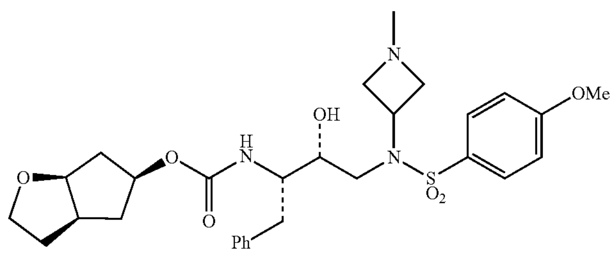 [SMILES: COc1ccc(S(=O)(=O)N(C[C@@H](O)[C@H](Cc2ccccc2)NC(=O)O[C@H]2C[C@H]3CCO[C@H]3C2)C2CN(C)C2)cc1] |
| 166 | 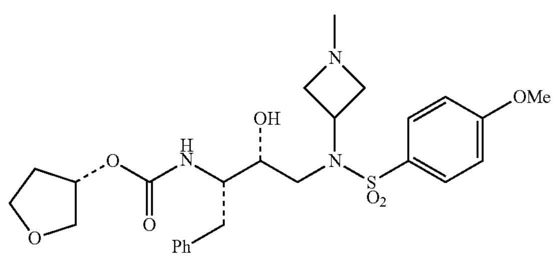 |
| 167 | 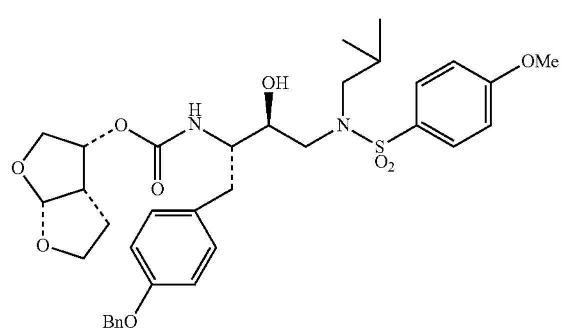 |

| Compound # | Structure |
|---|---|
| 168 | 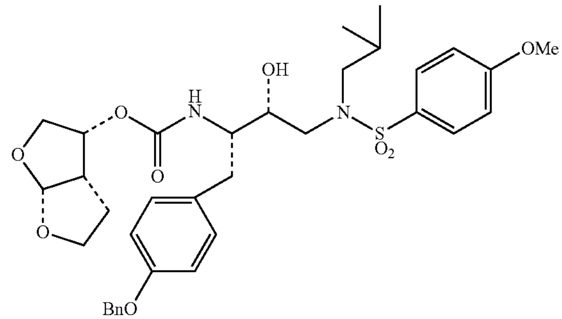 |
| 169 | 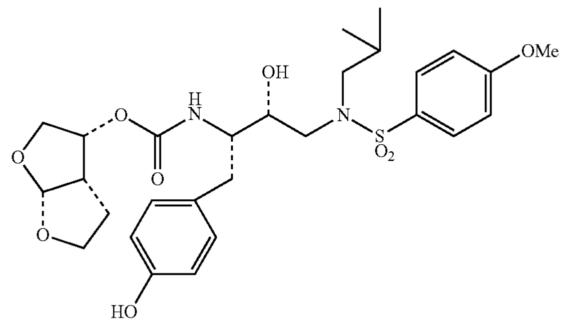 |

Synthesis of GRL-98065:

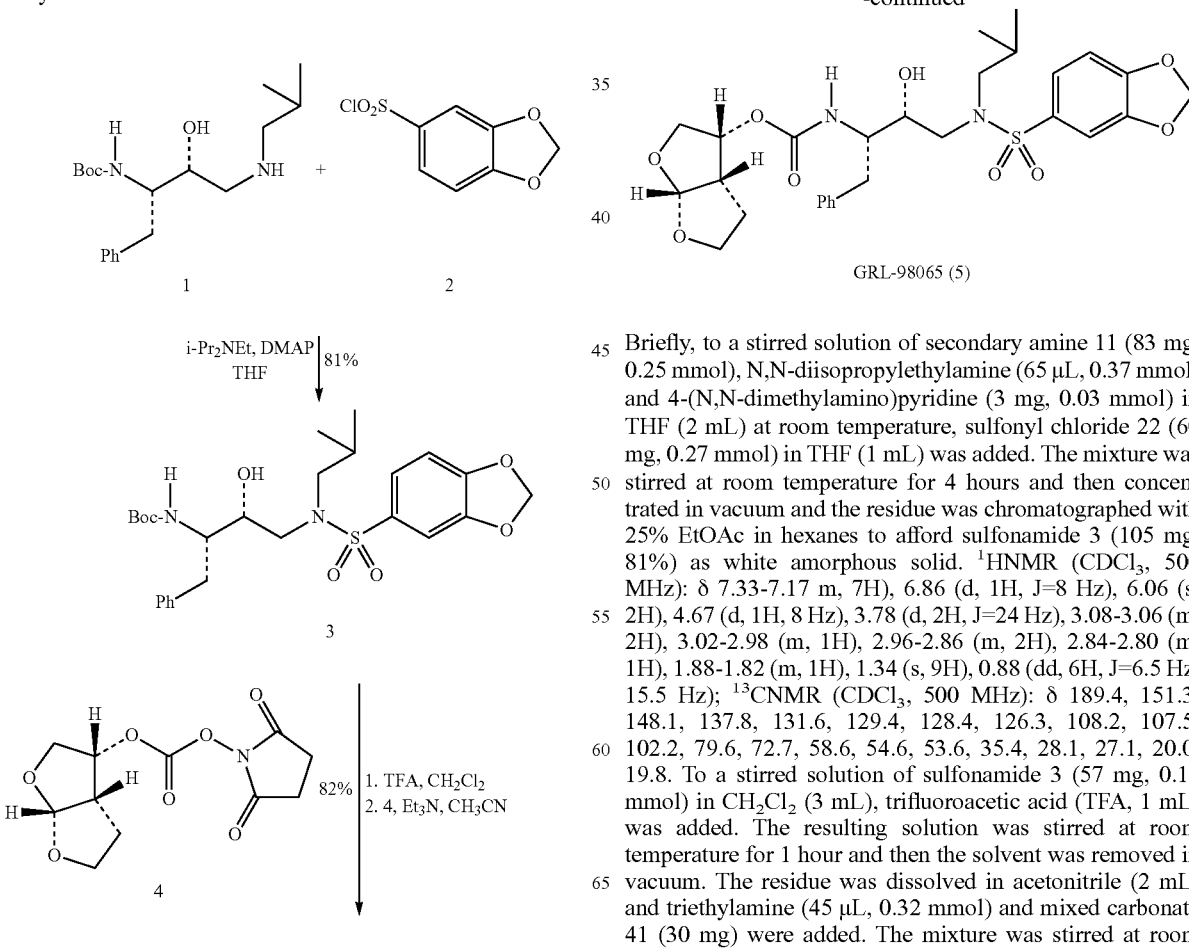

GRL-98065 (5)

Briefly, to a stirred solution of secondary amine 11 (83 mg, 0.25 mmol), N,N-diisopropylethylamine (65 µL, 0.37 mmol) and 4-(N,N-dimethylamino)pyridine (3 mg, 0.03 mmol) in THF (2 mL) at room temperature, sulfonyl chloride 22 (60 mg, 0.27 mmol) in THF (1 mL) was added. The mixture was stirred at room temperature for 4 hours and then concentrated in vacuum and the residue was chromatographed with 25% EtOAc in hexanes to afford sulfonamide 3 (105 mg, 81%) as white amorphous solid. $^1$HNMR (CDCl$_3$, 500 MHz): δ 7.33-7.17 m, 7H), 6.86 (d, 1H, J=8 Hz), 6.06 (s, 2H), 4.67 (d, 1H, 8 Hz), 3.78 (d, 2H, J=24 Hz), 3.08-3.06 (m, 2H), 3.02-2.98 (m, 1H), 2.96-2.86 (m, 2H), 2.84-2.80 (m, 1H), 1.88-1.82 (m, 1H), 1.34 (s, 9H), 0.88 (dd, 6H, J=6.5 Hz, 15.5 Hz); $^{13}$CNMR (CDCl$_3$, 500 MHz): δ 189.4, 151.3, 148.1, 137.8, 131.6, 129.4, 128.4, 126.3, 108.2, 107.5, 102.2, 79.6, 72.7, 58.6, 54.6, 53.6, 35.4, 28.1, 27.1, 20.0, 19.8. To a stirred solution of sulfonamide 3 (57 mg, 0.11 mmol) in CH$_2$Cl$_2$ (3 mL), trifluoroacetic acid (TFA, 1 mL) was added. The resulting solution was stirred at room temperature for 1 hour and then the solvent was removed in vacuum. The residue was dissolved in acetonitrile (2 mL) and triethylamine (45 µL, 0.32 mmol) and mixed carbonate 41 (30 mg) were added. The mixture was stirred at room temperature for 4 hours and then concentrated in vacuum. Column chromatography over silical gel with 30% and then 50% of EtOAc in hexanes afforded inhibitor GRL-98065 (5, 51 mg, 82%) as white amorphous solid. $^{1}$HNMR (CDCl$_3$, 500 MHz): δ 7.35-7.17 (m, 7H), 6.89 (d, 1H, J=8.5 Hz), 6.09 (s, 2H), 5.64 (d, 1H, J=5.5 Hz), 5.05-4.97 (m, 2H), 3.97-3.94 (m, 1H), 3.89-3.83 (m, 3H), 3.72-3.67 (m, 2H), 3.16-2.95 (m, 4H), 2.93-2.87 (m, 1H), 2.83-2.79 (m, 2H), 1.86-1.81 (m, 1H), 1.68-1.55 (m, 1H), 1.50-1.42 (m, 1H), 0.94-0.88 (dd, 6H, J=6.5 Hz, 21 Hz); $^{13}$CNMR (CDCl$_3$, 500 MHz): δ 155.4, 151.5, 148.3, 137.5, 131.2, 129.3, 129.2, 128.6, 126.5, 123.0, 109.2, 108.3, 107.3, 102.3, 73.0, 72.8, 70.6, 69.6, 58.8, 55.0, 53.7, 45.2, 35.5, 27.1, 25.7, 19.2, (8, 21).

Method Examples

Cells and viruses. MT-2 and MT-4 cells were grown in RPMI 1640-based culture medium supplemented with 10% fetal calf serum (FCS; PAA Laboratories GmbH, Linz, Austria) plus 50 U of penicillin and 100 µg of kanamycin per mL. The following HIV strains were used for the drug susceptibility assay: HIV-1LAI, HIV-1Ba-L, HIV-1NL4-3, HIV-2EHO, HIV-2ROD, clinical HIV-1 strains from drug-naive patients with AIDS (HIV-1ERS104pre) (28), and 6 HIV-1 clinical isolates those were originally isolated from patients with AIDS who had received to anti-HIV-1 therapy heavily (32 to 83 months) and those were genotypically and phenotypically characterized as multi-PI-resistant HIV-1 variants. HIV-1 isolates of different subtypes (subtypes A, B, C, and E) were also used.

Antiviral agents. GRL-98065 was prepared as described herein. Saquinavir (SQV) and ritonavir (RTV) were provided by Roche Products Ltd. (Welwyn Garden City, United Kingdom) and Abbott Laboratories (Abbott Park, Ill.), respectively. Amprenavir (APV) was obtained from GlaxoSmithKline, Research Triangle Park, N.C. Nelfinavir (NFV), indinavir (IDV), and lopinavir (LPV) were provided by Japan Energy Inc., Tokyo, Japan. Atazanavir (ATV) was obtained from Bristol Myers Squibb (New York, N.Y.).

Dual luciferase assay. Dual luciferase assay was established using the CheckMate™ Mammalian Two-Hybrid System (Promega Corp., Madison, Wis.). Briefly, BamHI/KpnI fragments from pCR-XL-TOPO vector containing the HIV-1 protease (PR$_{WT}$)-encoding gene excised from pHIV-1$_{NL4-3}$ was inserted into the pACT vector and pBIND vector that had been digested with BamHI and KpnI, generating pACT-PR$_{wt}$, pBIND-PR$_{wt}$, which produced an in-frame fusion of wild-type HIV-1 protease downstream of VP16 activation domain and GAL4 DNA-binding domain, respectively. Cos-7 cells were co-transfected with pACT-PR$_{wt}$, pBIND-PR$_{wt}$, and pG5luc in the absence or presence of 0.1 or 1.0 µM of DRV in white 96-well flat bottom plates (Corning, N.Y.), cultured for 48 hrs, and the intensity of firefly luminescence (Fluc) and *Renilla* luminescence (Rluc) was measured with TR717 microplate luminometer (Applied Biosystems) according to manufacturer's instructions. DRV was added to the culture medium simultaneously with plasmids to be used. Fluc/Rluc intensity ratios were determined with co-transfection of pACT-PR$_{wt}$, pBIND-PR$_{wt}$, and pG5luc in the absence of DRV, serving as maximal values. Fluc/Rluc intensity ratios determined with co-transfection of a pACT vector, a pBIND vector, and pG5luc served as minimal (background) values. Relative response ratios (RRR) were determined using the following formula: RRR=[(experimental Fluc/Rluc)−(negative control Fluc/Rluc)]/[(positive control Fluc/Rluc)−(negative control Fluc/Rluc)].

Drug susceptibility assay. The susceptibility of HIV-1LAI, HIV-2EHO, HIV-2ROD, to various drugs and the cytotoxicity of those drugs was determined by using the MTT assay. Briefly, MT-2 cells (2×10$^4$/mL) were exposed to 100 TCID50s (50% tissue culture infectious doses) of HIV-1LAI, HIV-2EHO, or HIV-2ROD in the presence or absence of various concentrations of drugs in 96-well microculture plates and were incubated at 37° C. for 7 days. After 100 µL of the medium was removed from each well, 3-(4,5-dimethylthiazol-2-yl)-2,5-diphenyltetrazolium bromide (MTT) solution (10 µL, 7.5 mg/mL in phosphate-buffered saline) was added to each well in the plate, followed by incubation at 37° C. for 4 hours. After incubation to dissolve the formazan crystals, 100 µL of acidified isopropanol containing 4% (vol/vol) Triton X-100 was added to each well and the optical density was measured in a kinetic microplate reader (Vmax; Molecular Devices, Sunnyvale, Calif.). All assays were performed in duplicate or triplicate. To determine the sensitivity of HIV-1Ba-L, HIV-1ERS104 pre, and clinical multi-drug-resistant HIV-1 isolates and different subtypes of HIV-1 isolates to drugs, phytohemagglutinin-activated peripheral blood mononuclear cells (PHA-PBMs; 10$^6$/mL) were exposed to 50 TCID50 (50% tissue infectious dose) of each HIV-1 isolate and cultured in the presence or absence of various concentrations of drugs in 10-fold serial dilutions in 96-well microtiter culture plates. To determine the drug susceptibility of certain laboratory HIV-1 strains (HIV-1NL4-3), MT-4 cells were used as target cells. MT-4 cells (10$^5$/mL) were exposed to 100 TCID50 of wild type HIV-1NL4-3 and PI-resistant HIV-1NL4-3 in the presence or absence of various concentrations of drugs and were incubated at 37° C. On day 7 of culture, the supernatant was harvested and the amount of p24 Gag protein was determined by using a fully automated chemiluminescent enzyme immunoassay system (Lumipulse F; Fujirebio Inc., Tokyo, Japan) (22). The drug concentrations that suppressed the production of p24 Gag protein by 50% (50% inhibitory concentrations; IC50) were determined by comparison with the level of p24 production in drug-free control cell cultures. All assays were performed in duplicate or triplicate.

Generation of PI-resistant HIV-1 in vitro. MT-4 cells (10$^5$/mL) were exposed to HIV-1NL4-3 (500 TCID$_{50}$) and cultured in the presence of various PIs at an initial concentration of its IC$_{50}$ values. Viral replication was monitored by determination of the amount of p24 Gag produced by MT-4 cells. The culture supernatants were harvested on day 7 and used to infect fresh MT-4 cells for the next round of culture in the presence of increasing concentrations of each drug. When the virus began to propagate in the presence of the drug, the drug concentration was generally increased two- to three-fold. Proviral DNA samples obtained from the lysates of infected cells were subjected to nucleotide sequencing. This drug selection procedure was carried out until the drug concentration reached 1 or 5 µM.

Determination of nucleotide sequences. Molecular cloning and determination of the nucleotide sequences of HIV-1 strains passaged in the presence of anti-HIV-1 agents were performed as described previously (Koh et al. 2003. Novel bis tetrahydrofuranylurethane-containing nonpeptidic protease inhibitor (PI) UIC-94017 (TMC114) with potent activity against multi-PI-resistant human immunodeficiency virus in vitro. Antimicrob Agents Chemother 47:3123-9). In brief, high molecular-weight DNA was extracted from HIV-1-infected MT-4 cells by using the InstaGene Matrix (Bio-Rad Laboratories, Hercules, Calif.) and was subjected to molecular cloning, followed by sequence determination. The primers used for the first round of PCR with the entire Gag- and protease-encoding regions of the HIV-1 genome were LTR-F1 (5'-GAT GCT ACA TAT AAG CAG CTG C-3') (SEQ ID NO: 69) and PR12 (5'-CTC GTG ACA AAT TTC TAC TAA TGC-3') (SEQ ID NO: 70). The first-round PCR mixture consisted of 1 µL of proviral DNA solution, 10 µL of Premix Taq (Ex Taq Version; Takara Bio Inc., Otsu, Japan), and 10 pmol of each of the first PCR primers in a total volume of 20 µL. The PCR conditions used were an initial 3 min at 95° C., followed by 30 cycles of 40 sec at 95° C., 20 sec at 55° C., and 2 min at 72° C., with a final 10 min of extension at 72° C. The first-round PCR products (1 µL) were used directly in the second round of PCR with primers LTR F2 (5'-GAG ACT CTG GTA ACT AGA GAT C-3') (SEQ ID NO:71) and Ksma2.1 (5'-CCA TCC CGG GCT TTA ATT TTA CTG GTA C-3') (SEQ ID NO: 72) under the PCR conditions of an initial 3 min at 95° C., followed by 30 cycles of 30 s at 95° C., 20 s at 55° C., and 2 min at 72° C., with a final 10 min of extension at 72° C. The second-round PCR products were purified with spin columns (MicroSpin S-400 HR columns; Amersham Biosciences Corp., Piscataway, N.J.), cloned directly, and subjected to sequencing with a model 3130 automated DNA sequencer (Applied Biosystems, Foster City, Calif.).

Crystallographic analysis. Recombinant HIV-1 protease was expressed and purified as described (Tie, Y., P. I. Boross, Y. F. Wang, L. Gaddis, A. K. Hussain, S. Leshchenko, A. K. Ghosh, J. M. Louis, R. W. Harrison, and I. T. Weber. 2004. High resolution crystal structures of HIV-1 protease with a potent non-peptide inhibitor (UIC-94017) active against multi-drug-resistant clinical strains. J Mol Biol 338:341-52). GRL-98065 was dissolved in dimethyl sulfoxide (DMSO). Crystals were grown by the hanging-drop vapor-diffusion method from 4.9 mg/mL protease solution buffered at pH 4.8 with 25 mM sodium acetate in the presence of 10% (w/v) sodium chloride, 6% dioxane and 10% (v/v) DMSO. The crystal was mounted in a fiber loop with 20-30% (v/v) glycerol as cryoprotectant. Diffraction data were collected at the National Synchrotron Light Source, beamline X-26C. The data were processed in the space group P21212 with unit cell parameters of a=58.25, b=85.83 and c=45.97 Å by using the HKL2000 program (Otwinowski, Z., and Minor, W. 1997. Processing of X-ray diffraction data in oscillation mode. Methods in Enzymology. 276:307-26). The structure was solved by molecular replacement with AMoRe (Navaza, J. 1994. AMoRe: An automated package for molecular replacement. Acta Crystallogr A 50:157-63) using 1FG6, from the Protein Data Bank, as the starting model. Refinement was carried out using SHELX-97 (Sheldrick, G. M., and Schneider, T. R. 1997. SHELXL: High resolution refinement. Methods in Enzymology. 277:319-43) and manual adjustment with 0 (Jones, T. A., J. Y. Zou, S. W. Cowan, and Kjeldgaard. 1991. Improved methods for building protein models in electron density maps and the location of errors in these models. Acta Crystallogr A 47 (Pt 2):110-9). Alternate conformations for protease residues, inhibitor, water and other solvent molecules were modeled when observed, as described (Tie, Y., P. I. Boross, Y. F. Wang, L. Gaddis, A. K. Hussain, S. Leshchenko, A. K. Ghosh, J. M. Louis, R. W. Harrison, and I. T. Weber. 2004. High resolution crystal structures of HIV-1 protease with a potent non-peptide inhibitor (UIC-94017) active against multi-drug-resistant clinical strains. J Mol Biol 338:341-52). Anisotropic B factors were applied, and hydrogen atoms were calculated in the last round of crystallographic refinement by SHELXL.

Analysis of GRL-98065 interactions with mutant proteases with molecular docking. A model was generated from the crystal structure. Hydrogens were added and optimized, with constraints on heavy atom positions, using OPLS2005 force field as implemented in MacroModel version 9.1. Structural figures were generated using Maestro version 7.5. The interactions of GRL-98065 with six mutant HIV-1 proteases were elucidated with molecular docking using Glide version 4.0 (Schrödinger, LLC, New York, N.Y. 2005). The crystal structures of these mutant proteases were accessed from the PDB, and the native ligand was removed. Close interaction in the protease was annealed, and the docking grid was set-up. The conformation of GRL-98065 in its complex with wild-type protease was taken as the starting ligand conformation. The conformational flexibility of GRL-98065 when it binds to protease was taken into account during the docking calculations. The extra-precision mode of Glide, which has a higher penalty for unphysical interactions, was used (Friesner, R. A., J. L. Banks, R. B. Murphy, T. A. Halgren, J. J. Klicic, D. T. Mainz, M. P. Repasky, E. H. Knoll, M. Shelley, J. K. Perry, D. E. Shaw, P. Francis, and P. S. Shenkin. 2004. Glide: a new approach for rapid, accurate docking and scoring. 1. Method and assessment of docking accuracy. J Med Chem 47:1739-49).

Antiviral activity of GRL-98065 against HIV-1LAI and HIV-2. GRL-98065 was examined for its antiviral activity against a variety of HIV-1 isolates. It was found that GRL-98065 was highly potent in vitro against a laboratory wild-type HIV-1 strain, HIV-1LAI, compared to clinically available Food and Drug Administration (FDA)-approved PIs with the $IC_{50}$ values of ~0.0005 µM as examined with the MTT assay using MT-2 target cells, while its cytotoxicity was seen only at high concentrations with the $CC_{50}$ values of 35.7 µM and the selectivity index of 71,400 (Table 1).

TABLE 1

Antiviral activity against HIV-1$_{LAI}$ and cytotoxicity of GRL-98065

| Drug | $IC_{50}$ (µM) | $CC_{50}$ (µM) | Selectivity Index |
|---|---|---|---|
| GRL-98065 | 0.0005 ± 0.0001 | 35.7 | 71400 |
| SQV | 0.008 ± 0.001 | 16.4 | 2050 |
| RTV | 0.054 ± 0.001 | 31.1 | 580 |
| IDV | 0.048 ± 0.007 | 69.8 | 1450 |
| NFV | 0.032 ± 0.004 | 8.1 | 250 |
| APV | 0.036 ± 0.002 | >100 | >2780 |
| LPV | 0.007 ± 0.001 | >100 | >14300 |
| ATV | 0.0048 ± 0.0001 | 27.6 | 5750 |

T-2 cells ($2 \times 10^3$) were exposed to 100 TCID50 of HIV-1LAI and cultured in the presence of various concentrations of PIs, and the IC50 values were determined using the MTT assay on day 7 of culture. All assays were conducted in duplicate, and the data shown represent mean values (±1 standard deviations) derived from the results of three independent experiments.

In contrast, FDA-approved PIs had IC50 values ranging from 0.0048 to 0.054 µM. The selectivity index of GRL-98065 hence proved to be very high with 71,400. GRL-98065 was also examined against two different strains of HIV-2, HIV-2EHO and HIV-2ROD. The potency of GRL-98065 against HIV-2 strains examined was less than that against HIV-1LAI, by factors of 6-9, however, its absolute IC50 values were comparable to those of three FDA-approved PIs (SQV, LPV, and ATV) which showed similar antiviral potency against HIV-1LAI and HIV-2 strains (Table 2).

TABLE 2

Antiviral activity of GRL-98065 against HIV-1$_{LAI}$, HIV-2$_{EHO}$, and HIV-2$_{ROD}$

| Virus | IC$_{50}$ (μM) | | | |
|---|---|---|---|---|
| | SQV | RTV | IDV | NFV |
| HIV-1$_{LAI}$ | 0.008 ± 0.001 | 0.054 ± 0.001 | 0.048 ± 0.007 | 0.032 ± 0.004 |
| HIV-2$_{EHO}$ | 0.0030 ± 0.0004 | 0.21 ± 0.05 | 0.024 ± 0.005 | 0.030 ± 0.006 |
| HIV-2$_{ROD}$ | 0.0043 ± 0.0002 | 0.26 ± 0.01 | 0.054 ± 0.003 | 0.240 ± 0.009 |
| Virus | APV | LPV | ATV | GRL-98065 |
| HIV-1$_{LAI}$ | 0.036 ± 0.002 | 0.007 ± 0.001 | 0.0048 ± 0.0001 | 0.0005 ± 0.0001 |
| HIV-2$_{EHO}$ | 0.25 ± 0.08 | 0.0026 ± 0.0008 | 0.005 ± 0.002 | 0.0032 ± 0.0007 |
| HIV-2$_{ROD}$ | 0.57 ± 0.01 | 0.0049 ± 0.0008 | 0.013 ± 0.006 | 0.0045 ± 0.0004 |

MT-2 cells (2×10$^3$) were exposed to 100 TCID50 of each viral isolate and cultured in the presence of various concentrations of each PI, and the IC50 values were determined by the MTT assay. All assays were conducted in duplicate, and the data shown represent mean values (±1 standard deviations) derived from the results of three independent experiments.

GRL-98065 was observed to be potent against PI-selected laboratory HIV-1 variants. GRL-98065 was also examined against a variety of HIV-1 variants in vitro selected with each of 7 FDA-approved PIs (SQV, RTV, IDV, NFV, APV, LPV, and ATV). These variants were selected by propagating HIV-1NL4-3 in the presence of increasing concentrations of each of those PIs (up to 1 or 5 μM) in MT-4 cells (18) and such variants proved to have acquired various PI resistance-associated amino acid substitutions in the protease-encoding region of the viral genome (Table 3).

TABLE 3

Antiviral activity of GRL-98065 against laboratory PI-resistant HIV-1 variants

| Virus | Amino acid substitutions in the protease-encoding region | SQV | RTV |
|---|---|---|---|
| HIV-1$_{NL43}$ | Wildtype | 0.007 ± 0.002 | 0.033 ± 0.002 |
| HIV-1$_{SQV5μM}$ | L10I/G48V/I54V/L63P/A71V/G73S/V82T | >1 (>143) | >1 (>30) |
| HIV-1$_{RTV5μM}$ | M46I/V82F/I84V | 0.010 ± 0.008 (1) | >1 (>30) |
| HIV-1$_{IDV5μM}$ | L10F/L24I/M46I/I54V/L63P/A71V/G73S/V82T | 0.059 ± 0.004 (8) | >1 (>30) |
| HIV-1$_{NFV5μM}$ | L10F/K20T/D30N/K45I/A71V/V77I | 0.024 ± 0.008 (3) | 0.051 ± 0.005 (2) |
| HIV-1$_{APV5μM}$ | L10F/M46I/I50V/A71V/I84V/L90M | 0.031 ± 0.004 (4) | 0.29 ± 0.02 (9) |
| HIV-1$_{LPV1μM}$ | L10F/M46I/I54V/V82A | 0.032 ± 0.002 (5) | >1 (>30) |
| HIV-1$_{ATV1μM}$ | L23I/K43I/M46I/I50L/G51A/A71V | 0.037 ± 0.004 (5) | 0.12 ± 0.06 (4) |

| Virus | Amino acid substitutions in the protease-encoding region | APV | LPV |
|---|---|---|---|
| HIV-1$_{NL43}$ | Wildtype | 0.026 ± 0.007 | 0.031 ± 0.009 |
| HIV-1$_{SQV5μM}$ | L10I/G48V/I54V/L63P/A71V/G73S/V82T | 0.33 ± 0.03 (13) | 0.27 ± 0.09 (9) |
| HIV-1$_{RTV5μM}$ | M46I/V82F/I84V | 0.28 ± 0.02 (11) | 0.16 ± 0.02 (5) |
| HIV-1$_{IDV5μM}$ | L10F/L24I/M46I/I54V/L63P/A71V/G73S/V82T | 0.17 ± 0.01 (7) | 0.26 ± 0.01 (8) |
| HIV-1$_{NFV5μM}$ | L10F/K20T/D30N/K45I/A71V/V77I | 0.060 ± 0.004 (2) | 0.024 ± 0.001 (1) |
| HIV-1$_{APV5μM}$ | L10F/M46I/I50V/A71V/I84V/L90M | >1 (>38) | 0.23 ± 0.02 (7) |
| HIV-1$_{LPV1μM}$ | L10F/M46I/I54V/V82A | 0.31 ± 0.02 (12) | 0.31 ± 0.02 (10) |
| HIV-1$_{ATV1μM}$ | L23I/K43I/M46I/I50L/G51A/A71V | 0.20 ± 0.07 (8) | 0.033 ± 0.006 (1) |

| Virus | Amino acid substitutions in the protease-encoding region | IDV | ATV |
|---|---|---|---|
| HIV-1$_{NL43}$ | Wildtype | 0.034 ± 0.004 | 0.0042 ± 0.0004 |
| HIV-1$_{SQV5μM}$ | L10I/G48V/I54V/L63P/A71V/G73S/V82T | >1 (>29) | 0.326 ± 0.001 (78) |
| HIV-1$_{RTV5μM}$ | M46I/V82F/I84V | 0.25 ± 0.01 (7) | 0.018 ± 0.008 (4) |
| HIV-1$_{IDV5μM}$ | L10F/L24I/M46I/I54V/L63P/A71V/G73S/V82T | >1 (>29) | 0.06 ± 0.02 (14) |
| HIV-1$_{NFV5μM}$ | L10F/K20T/D30N/K45I/A71V/V77I | 0.27 ± 0.05 (8) | 0.021 ± 0.006 (5) |
| HIV-1$_{APV5μM}$ | L10F/M46I/I50V/A71V/I84V/L90M | 0.200 ± 0.007 (6) | 0.003 ± 0.001 (1) |
| HIV-1$_{LPV1μM}$ | L10F/M46I/I54V/V82A | >1 (>29) | 0.040 ± 0.002 (10) |
| HIV-1$_{ATV1μM}$ | L23I/K43I/M46I/I50L/G51A/A71V | 0.388 ± 0.001 (11) | 0.33 ± 0.06 (79) |

TABLE 3-continued

Antiviral activity of GRL-98065 against laboratory PI-resistant HIV-1 variants

| Virus | Amino acid substitutions in the protease-encoding region | IC$_{50}$ (µM) NFV | IC$_{50}$ (µM) GRL-98065 |
|---|---|---|---|
| HIV-1$_{NL4-3}$ | Wildtype | 0.033 ± 0.007 | 0.0003 ± 0.0002 |
| HIV-1$_{SQV5µM}$ | L10I/G48V/I54V/L63P/A71V/G73S/V82T | 0.48 ± 0.04 (15) | 0.006 ± 0.003 (20) |
| HIV-1$_{RTV5µM}$ | M46I/V82F/I84V | 0.21 ± 0.05 (6) | 0.0025 ± 0.0003 (8) |
| HIV-1$_{IDV5µM}$ | L10F/L24I/M46I/I54V/L63P/A71V/G73S/V82T | 0.47 ± 0.07 (14) | 0.0037 ± 0.0007 (12) |
| HIV-1$_{NFV5µM}$ | L10F/K20T/D30N/K45I/A71V/V77I | >1 (>30) | 0.0024 ± 0.0008 (8) |
| HIV-1$_{APV5µM}$ | L10F/M46I/I50V/A71V/I84V/L90M | 0.27 ± 0.05 (8) | 0.032 ± 0.004 (107) |
| HIV-1$_{LPV1µM}$ | L10F/M46I/I54V/V82A | 0.49 ± 0.04 (15) | 0.0075 ± 0.0003 (25) |
| HIV-1$_{ATV1µM}$ | L23I/K43I/M46I/I50L/G51A/A71V | 0.22 ± 0.04 (7) | 0.0015 ± 0.0009 (5) |

MT-4 cells (10$^4$) were exposed to 100 TCID$_{50}$ of each HIV-1, and the inhibition of p24 Gag protein production by each drug was used as an endpoint. The numbers in parentheses represent the fold changes of IC$_{50}$ values for each isolate compared to the IC$_{50}$ values for wild-type HIV-1$_{NL4-3}$. All assays were conducted in duplicate or triplicate, and the data shown represent mean values (±1 standard deviations) derived from the results of three independent experiments.

Each of the variants except HIV-1LPV1 µM and HIV-1ATV1 µM was highly resistant to the PI, with which the variant was selected and showed a significant resistance with the IC50 value of >1 µM (fold differences of 29-143). HIV-1LPV 1 µM, which was only moderately resistant against LPV with the IC50 value of 0.31 µM, was highly resistant to both RTV and IDV with the IC50 value of >1 µM. HIV-1ATV1 µM was resistant to ATV with the IC50 value of 0.33 µM (79-fold difference). The activity of GRL-98065 against all the variants except HIV-1APV5 µM was found relatively well spared with fold differences of 5 to 25. Even with the 5 to 25 fold differences in the IC50 values as compared to those against the wild type HIV-1NL4-3, IC50 values were all <0.0075 µM, except against HIV-1APV5 µM. GRL-98065 was relatively less potent against HIV-1APV5 µM with the IC50 value of 0.032 µM (107-fold difference). Without being bound by theory, it is suggested that the observed activity may be due to the structural resemblance between GRL-98065 and APV, both of which contain a sulfonamide isostere (FIG. 1).

GRL-98065 exerts potent activity against highly PI-resistant clinical HIV-1 strains. Highly multi-PI-resistant primary HIV-1 strains, HIV-1MDR/TM, HIV-1MDR/MM, HIV-1MDR/JSL, HIV-1MDR/B, HIV-1MDR/C, HIV-1MDR/G, were isolated from patients with AIDS who had failed then-existing anti-HIV regimens after receiving 9 to 11 anti-HIV-1 drugs over 32 to 83 months (Yoshimura et al. 2002. A potent human immunodeficiency virus type 1 protease inhibitor, UIC-94003 (TMC-126), and selection of a novel (A28S) mutation in the protease active site. J Virol 76:1349-58). These primary strains contained 9 to 14 amino acid substitutions in the protease-encoding region which have reportedly been associated with HIV-1 resistance against various PIs (see the legend to Table 4).

TABLE 4

Antiviral activity of GRL-98065 against multi-drug resistant clinical isolates in PHA-PBMs

| Virus | IC$_{50}$ (µM) SQV | IC$_{50}$ (µM) RIV |
|---|---|---|
| HIV-1$_{ERS104pre}$ (wild-type: X4) | 0.008 ± 0.003 | 0.025 ± 0.005 |
| HIV-1$_{MDR/TM}$ (X4) | 0.18 ± 0.05 (23) | >1 (>40) |
| HIV-1$_{MDR/MM}$ (R5) | 0.14 ± 0.04 (18) | >1 (>40) |
| HIV-1$_{MDR/JSL}$ (R5) | 0.29 ± 0.05 (36) | >1 (>40) |
| HIV-1$_{MDR/B}$ (X4) | 0.27 ± 0.06 (34) | >1 (>40) |
| HIV-1$_{MDR/C}$ (X4) | 0.035 ± 0.004 (4) | >1 (>40) |
| HIV-1$_{MDR/G}$ (X4) | 0.033 ± 0.005 (4) | >1 (>40) |

| Virus | APV | LPV |
|---|---|---|
| HIV-1 ERS104pre (wild-type: X4) | 0.029 ± 0.005 | 0.007 ± 0.001 |
| HIV-1 MDR/TM (X4) | 0.30 ± 0.04 (10) | 0.36 ± 0.09 (51) |
| HIV-1 MDR/MM (R5) | 0.48 ± 0.09 (17) | 0.38 ± 0.08 (54) |
| HIV-1 MDR/JSL (R5) | 0.43 ± 0.05 (15) | 0.70 ± 0.19 (100) |
| HIV-1 MDR/B (X4) | 0.36 ± 0.09 (12) | 0.30 ± 0.03 (43) |
| HIV-1 MDR/C (X4) | 0.25 ± 0.05 (9) | 0.31 ± 0.05 (44) |
| HIV-1 MDR/G (X4) | 0.32 ± 0.02 (11) | 0.16 ± 0.04 (23) |

| Virus | IC$_{50}$ (µM) IDV | IC$_{50}$ (µM) NFV |
|---|---|---|
| HIV-1$_{ERS104pre}$ (wild-type: X4) | 0.024 ± 0.008 | 0.015 ± 0.004 |
| HIV-1$_{MDR/TM}$ (X4) | >1 (>42) | >1 (>67) |
| HIV-1$_{MDR/MM}$ (R5) | >1 (>42) | >1 (>67) |
| HIV-1$_{MDR/JSL}$ (R5) | >1 (>42) | >1 (>67) |
| HIV-1$_{MDR/B}$ (X4) | >1 (>42) | >1 (>67) |
| HIV-1$_{MDR/C}$ (X4) | >1 (>42) | 0.42 ± 0.06 (28) |
| HIV-1$_{MDR/G}$ (X4) | 0.64 ± 0.11 (27) | 0.37 ± 0.05 (25) |

| Virus | ATV | GRL-98065 |
|---|---|---|
| HIV-1 ERS104pre (wild-type: X4) | 0.0038 ± 0.0004 | 0.0005 ± 0.0002 |
| HIV-1 MDR/TM (X4) | 0.038 ± 0.009 (10) | 0.0032 ± 0.0006 (6) |
| HIV-1 MDR/MM (R5) | 0.045 ± 0.0001 (12) | 0.0038 ± 0.0006 (8) |
| HIV-1 MDR/JSL (R5) | 0.54 ± 0.20 (142) | 0.006 ± 0.002 (12) |
| HIV-1 MDR/B (X4) | 0.25 ± 0.003 (66) | 0.0039 ± 0.0005 (8) |
| HIV-1 MDR/C (X4) | 0.021 ± 0.006 (6) | 0.0027 ± 0.0003 (5) |
| HIV-1 MDR/G (X4) | 0.032 ± 0.002 (8) | 0.0034 ± 0.0003 (7) |

The amino acid substitutions identified in the protease-encoding region of HIV-1$_{ERS104pre}$, HIV-1$_{TM}$, HIV-1$_{MM}$, HIV-1$_{JSL}$, HIV-1$_B$, HIV-1$_C$, HIV-1$_G$ compared to the consensus type B sequence cited from the Los Alamos database include L63P; L10I, K14R, R41K, M46L, I54V, L63P, A71V, V82A, L90M; I93L; L10I, K43T, M46L, I54V, L63P, A71V, V82A, L90M, Q92K; L10I, L24I, I33F, E35D, M36I, N37S, M46L, I54V, R57K, I62V, L63P, A71V, G73S, V82A; L10I, K14R, L33I, M36I, M46I, F53I, K55R, I62V, L63P, A71V, G73S, V82A, L90M, I93L; L10I, I15V, K20R, L24I, M36I, M46L, I54V, I62V, L63P, K70Q, V82A, L89M; and L10I, V11I, T12E, I15V, L19I, R41K, M46L, L63P, A71T, V82A, L90M, respectively. HIV-1$_{ERS104pre}$ served as a source of wild-type HIV-1. The IC$_{50}$ values were determined by using PHA-PBMs as target cells and the inhibition of p24 Gag protein production by each drug was used as an endpoint. The numbers in parentheses represent the fold changes of IC$_{50}$ values for each isolate compared to the IC$_{50}$ values for wild-type HIV-1$_{ERS104pre}$. All assays were conducted in duplicate or triplicate, and the data shown represent mean values (±1 standard deviations) derived from the results of three independent experiments.

The IC$_{50}$ values of RTV, IDV, and NFV against clinical multi-drug-resistant HIV-1 strains were mostly >1 μM and the activity of other 4 PIs (SQV, APV, LPV, and ATV) was also significantly compromised as examined in PHA-PBMs as target cells using p24 production inhibition as an endpoint. However, GRL-98065 exerted quite potent antiviral activity and its IC$_{50}$ values against those clinical variants were as low as 0.006 μM or less (Table 4). GRL-98065 was the most potent against the six representative multi-drug-resistant clinical HIV-1 variants compared to the currently available approved PIs including the two recently approved PIs, LPV and ATV.

GRL-98065 is potent against HIV-1 strains of diverse subtypes. GRL-98065 was further examined as to whether the compound exerted antiviral activity against HIV-1 strains of diverse subtypes in vitro. It was found that GRL-98065 exerted highly potent activity against HIV-1 isolates of all subtypes (subtypes A, B, C, and E) examined (Table 5) with its IC$_{50}$ values from 0.0002 to 0.0005 μM.

TABLE 5

Antiviral activity of GRL-98065 against various subtypes

| Virus (subtype) | IC$_{50}$ (μM) SQV | IC$_{50}$ (μM) RTV |
|---|---|---|
| 92UG029 (A-X4) | 0.0048 ± 0.0005 | 0.071 ± 0.011 |
| 92UG037 (A-R5) | 0.0032 ± 0.0003 | 0.041 ± 0.008 |
| Ba-L (B-R5) | 0.0083 ± 0.0005 | 0.023 ± 0.006 |
| 97ZA003 (C-R5) | 0.0067 ± 0.0008 | 0.039 ± 0.004 |
| 92TH019 (E-R5) | 0.0030 ± 0.0001 | 0.030 ± 0.009 |
| Virus (subtype) | APV | LPV |
| 92UG029 (A-X4) | 0.046 ± 0.006 | 0.007 ± 0.001 |
| 92UG037 (A-R5) | 0.027 ± 0.005 | 0.005 ± 0.001 |
| Ba-L (B-R5) | 0.025 ± 0.006 | 0.0053 ± 0.0004 |
| 97ZA003 (C-R5) | 0.033 ± 0.005 | 0.0073 ± 0.0006 |
| 92TH019 (E-R5) | 0.021 ± 0.006 | 0.0033 ± 0.0005 |

| Virus (subtype) | IC$_{50}$ (μM) IDV | IC$_{50}$ (μM) NFV |
|---|---|---|
| 92UG029 (A-X4) | 0.044 ± 0.009 | 0.043 ± 0.006 |
| 92UG037 (A-R5) | 0.034 ± 0.003 | 0.056 ± 0.014 |
| Ba-L (B-R5) | 0.022 ± 0.005 | 0.018 ± 0.004 |
| 97ZA003 (C-R5) | 0.037 ± 0.006 | 0.037 ± 0.007 |
| 92TH019 (E-R5) | 0.021 ± 0.001 | 0.029 ± 0.004 |
| Virus (subtype) | ATV | GLR-98065 |
| 92UG029 (A-X4) | 0.006 ± 0.002 | 0.0005 ± 0.0002 |
| 92UG037 (A-R5) | 0.0025 ± 0.0002 | 0.0004 ± 0.0001 |
| Ba-L (B-R5) | 0.0013 ± 0.0004 | 0.0002 ± 0.0001 |
| 97ZA003 (C-R5) | 0.0034 ± 0.0001 | 0.0005 ± 0.0001 |
| 92TH019 (E-R5) | 0.0027 ± 0.0001 | 0.0003 ± 0.0001 |

The IC$_{50}$ values were determined by using PHA-PBMs as target cells and the inhibition of p24 Gag protein production by each drug was used as an endpoint. All assays were conducted in duplicate, and the data shown represent mean values (±1 standard deviations) derived from the results of two or three independent experiments.

It is observed that GRL-98065 is significantly more potent than SQV, LPV, and ATV, whose IC$_{50}$ values were fairly low compared with other FDA-approved PIs (RTV, IDV, NFV, and APV) by factors of 8 to 41.5 and 11 to 26.5 and 6.5 to 12, respectively.

In vitro selection of HIV-1 variants resistant to GRL-98065. HIV-1 variants were selected with GRL-98065, by propagating a laboratory HIV-1 strain, HIV-1$_{NL4-3}$, in MT-4 cells in the presence of increasing concentrations of GRL-98065 as previously described (Yoshimura et al. 2002. A potent human immunodeficiency virus type 1 protease inhibitor, UIC-94003 (TMC-126), and selection of a novel (A28S) mutation in the protease active site. J Virol 76:1349-58). HIV-1$_{NL4-3}$ was initially exposed to 0.0005 μM GRL-98065 and underwent 40 passages to be found to have acquired a 1,000-fold increase (0.5 μM), at which the virus was yet relatively well propagating. The protease-encoding region of the proviral DNA isolated from infected MT-4 cells was cloned and sequenced at passages 5, 10, 15, 20, 25, 30, 33, and 40. Individual protease sequences and their frequency at each passage are depicted in FIG. 4. By passage 10 (HIV-1$_{GRL98065p10}$), wild-type protease gene sequence was seen in 8 of 13 clones, although one or two sporadic amino acid substitutions were noted in 5 of the 13 clones. However, by passage 15 and beyond, the virus acquired K43I substitution. As the passage proceeded, more amino acid substitutions emerged. In HIV-1$_{GRL98065p25}$, K43I, M46I, V82I, I85V, and L89M were seen along with A28S (9 of 20 clones). Val82 is an active-site amino acid residue whose side chain has direct contacts with inhibitor atoms (Yoshimura et al. 1999. JE-2147: a dipeptide protease inhibitor (PI) that potently inhibits multi-PI-resistant HIV-1. Proc Natl Acad Sci USA 96:8675-80), and the V82I substitution has been shown to be effective in conferring resistance when combined with a second active site mutation such as V32I (17). By passage 30, more amino acid substitutions such as E21K and E34K were seen, while the latter was not seen in HIV-1$_{GRL98065p33}$. The A28S substitution that was first seen in HIV-1$_{GRL98065p20}$ never became predominant in the later passages and the percentage of HIV-1 carrying A28S remained around 50% (45% in HIV-1$_{GRL98065p25}$, 60% in HIV-1$_{GRL98065p30}$, 36% in HIV-1$_{GRL98065p33}$, and 64% in HIV-1$_{GRL98065p40}$). As previously described, the A28S substitution, located at the active site of the enzyme, was seen early (at passage 15) in HIV-1 selected in the presence of TMC126, the prototype of GRL-98065, and this particular mutation never disappeared but was consistently seen at frequencies of ~50%, suggesting that A28S substitution was critical in conferring resistance to TMC-126. E21K coexisted with A28S by passage 30 and beyond in 4 of 6 clones at passage 30. A substitution I50V, seen in HIV-1 resistant to APV, was not coexisted with A28S throughout the passage. This profile was previously seen in the case of TMC126-selected HIV-1 variants. The M46I substitution first emerged at passage 25 and was present in 4 of 10 clones at passage 30 (FIG. 4). Met46 is located on the flap region of the enzyme. I47V substitution reportedly emerges with viral resistance to APV, but was not seen in GRL-98065-resistant variants.

Reduced sensitivity of GRL-98065 selected HIV-1 variants to various PIs. The antiviral activity of FDA-approved PIs was examined against the in vitro generated GRL-98065-resistant HIV-1 variant (HIV-1$_{GRL98065r-40P}$: Table 6), which proved to be highly resistant to GRL-98065 with 600-fold difference in the IC$_{50}$ value 0.18 μM) as compared to that against HIV-1$_{NL4-3}$.

TABLE 6

Antiviral activity of GRL-98065 against a laboratory GRL-98065-selected HIV-1 variant $IC_{50}$ (μM)

| Virus | Amino acid substitutions in protease-encoding region | SQV | RTV |
|---|---|---|---|
| HIV-1$_{NL4-3}$ | Wild type | 0.007 ± 0.002 | 0.033 ± 0.002 |
| HIV-1$_{GRL98065r-40P}$ | E21K/A28SK43IM46I/I50V/D60N/A71V/V82I/I85V/L89M | 0.032 ± 0.002 (5) | 0.38 ± 0.09 (12) |

| Virus | Amino acid substitutions in protease-encoding region | APV | LPV |
|---|---|---|---|
| HIV-1$_{NL4-3}$ | Wild type | 0.026 ± 0.007 | 0.031 ± 0.009 |
| HIV-1$_{GRL98065r-40P}$ | E21K/A28SK43IM46I/I50V/D60N/A71V/V82I/I85V/L89M | >1 (>38) | 0.19 ± 0.07 (6) |

$IC_{50}$ (μM)

| Virus | Amino acid substitutions in protease-encoding region | IDV | NFV |
|---|---|---|---|
| HIV-1$_{NL4-3}$ | Wild type | 0.034 ± 0.004 | 0.033 ± 0.007 |
| HIV-1$_{GRL98065r-40P}$ | E21K/A28SK43IM46I/I50V/D60N/A71V/V82I/I85V/L89M | 0.28 ± 0.02 (8) | 0.34 ± 0.01 (10) |

| Virus | Amino acid substitutions in protease-encoding region | ATV | GRL-98065 |
|---|---|---|---|
| HIV-1$_{NL4-3}$ | Wild type | 0.0042 ± 0.0004 | 0.0003 ± 0.0002 |
| HIV-1$_{GRL98065r-40P}$ | E21K/A28SK43IM46I/I50V/D60N/A71V/V82I/I85V/L89M | 0.011 ± 0.007 (3) | 0.18 ± 0.03 (600) |

MT-4 cells ($10^4$) were exposed to 100 TCID$_{50}$ of each HIV-1, and the inhibition of p24 Gag protein production by each drug was used as an endpoint. The numbers in parentheses represent the fold changes of IC$_{50}$ values for HIV-1$_{GRL98065r-40P}$ compared to the IC$_{50}$ values for HIV-1$_{NL4-3}$. All assays were conducted in duplicate, and the data shown represent mean values (±1 standard deviations) derived from the results of two or three independent experiments.

However, HIV-1$_{GRL98065r-40P}$ was still sensitive to SQV and ATV with IC$_{50}$ values of 0.032 μM (5-fold difference) and 0.011 μM (3-fold difference), respectively, and moderately sensitive to IDV and LPV with IC$_{50}$ values of 0.28 μM (8-fold difference) and 0.19 μM (6-fold difference), respectively. APV was no longer active against HIV-1$_{GRL98065r-40P}$ with IC$_{50}$ value of >1 μM.

Crystal structure analysis of HIV-1 protease with GRL-98065. The crystal structure of HIV-1 protease complexed with GRL-98065 was refined to an R-factor of 0.147 at 1.6 Å resolution in order to determine the molecular basis for the inhibitor potency. The crystallographic statistics are listed in Table 7.

TABLE 7

Crystallographic data collection and refinement statistics

| | Wild-type protease |
|---|---|
| Space group | P2$_1$2$_1$2 |
| Unit cell dimensions: (Å) | |
| A | 58.25 |
| B | 85.83 |
| C | 45.97 |
| Resolution range (Å) | 50-1.60 |
| Unique reflections | 31,128 |

TABLE 7-continued

Crystallographic data collection and refinement statistics

| | Wild-type protease |
|---|---|
| R$_{merge}$ (%) overall (final shell) | 7.1 (38.8) |
| I/σ(I) overall (final shell) | 11.0 (4.7) |
| Completeness (%) overall (final shell) | 99.7 (99.4) |
| Data range for refinement (Å) | 10-1.60 |
| R (%) | 14.7 |
| R$_{free}$ (%) | 20.8 |
| No. of solvent atoms (total occupancies) | 207.7 |
| RMS deviation from ideality | |
| Bonds (Å) | 0.009 |
| Angle distance (Å) | 0.030 |
| Average B-factors (Å$^2$) | |
| Main-chain | 15.5 |
| Side-chain | 19.0 |
| Inhibitor | 10.7 |
| Solvent | 28.7 |
| Residual density (max/min) (eÅ$^{-3}$) | 0.38/−0.40 |

Figure 5A:
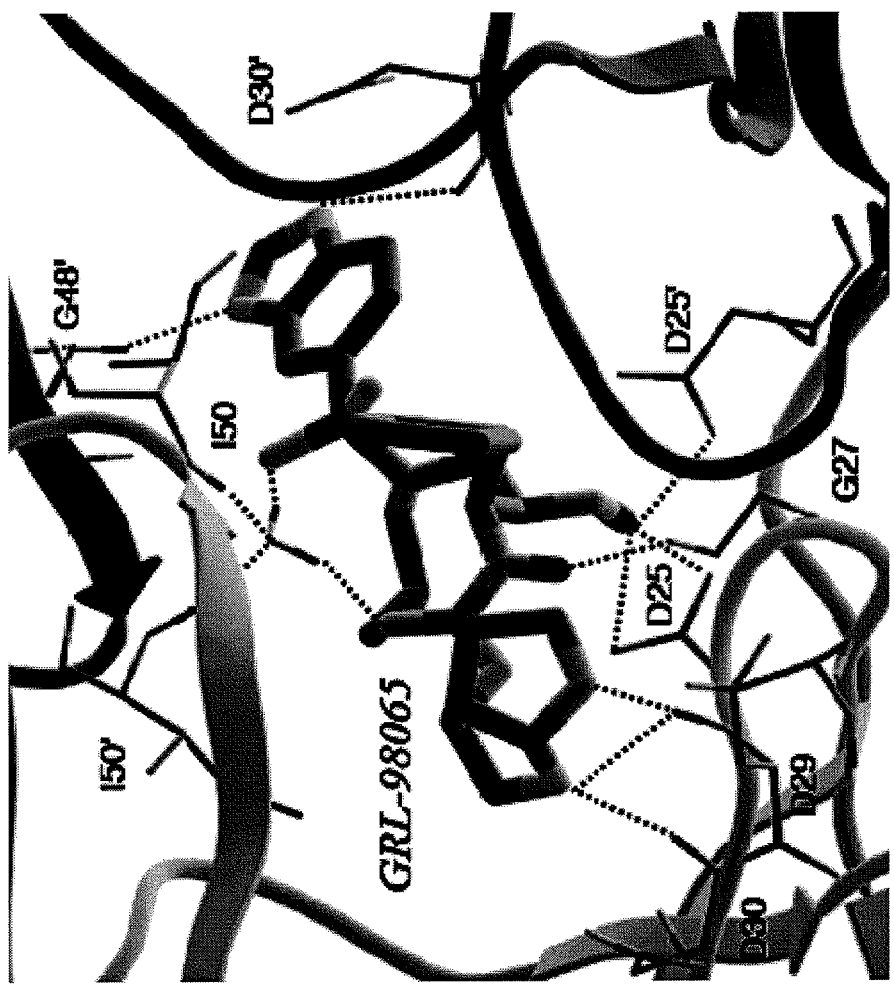
FIG. 5 shows the molecular modeling of selected hydrogen bond interactions of GRL-98065 with wild-type HIV-1 protease. Panel A: The bis-THF group forms hydrogen bond interactions with backbone atoms of Asp29 and Asp30. There is a hydrogen bond with the backbone atom of Gly27. The hydroxyl group forms hydrogen bonds with the sidechains of the catalytic aspartates. One oxygen of the benzodioxole group forms a hydrogen bond interaction with Asp30', and the other oxygen of benzodioxole group forms a water-mediated hydrogen bond interaction with Gly48'. Panel B: The molecular modeling of hydrogen bond interactions between DRV and protease (PDB ID: 1S6G) are shown. Most of the interactions between GRL-98065 and DRV are similar except the interactions with Asp30' and Gly48'. GRL-98065 interacts with the Asp30' amide while DRV interacts with the Asp30' carbonyl oxygen. The benzodioxole oxygen of GRL-98065 has a water-mediated interaction with Gly48' in the flap. This interaction appears to stabilize the binding site more for GRL-98065. Without being bound by theory, that interaction may be partly responsible for the greater anti-viral potency observed compared to DRV.
Figure 5B:
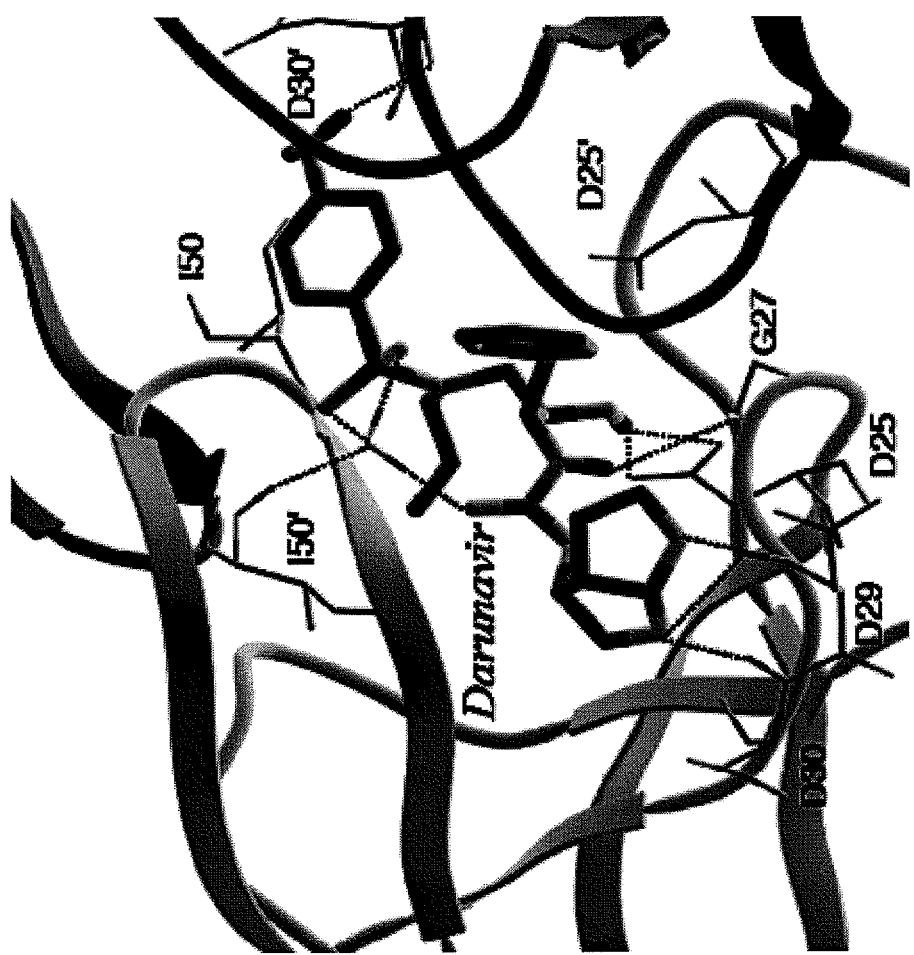

The inhibitor was found to bind in two overlapping conformations with equivalent interactions with protease, as observed for DRV (Koh et al. 2003. Novel bis tetrahydrofuranylurethane-containing nonpeptidic protease inhibitor (PI) UIC-94017 (TMC114) with potent activity against multi-PI-resistant human immunodeficiency virus in vitro. Antimicrob Agents Chemother 47:3123-9; Tie et al. 2004. High resolution crystal structures of HIV-1 protease with a potent non-peptide inhibitor (UIC-94017) active against multi-drug-resistant clinical strains. J Mol Biol 338:341-52). GRL-98065 has hydrogen bond interactions with the backbone atoms of Asp29, Asp30, Gly27, Asp30', and with the side chain atoms of Asp25, and Asp25' (FIG. 5-A). The protease formed very similar hydrogen bond interactions with GRL-98065 and DRV, with a few exceptions. The equivalent atoms of GRL-98065 and DRV superimpose with an RMSD of 0.04 Å, excluding the aniline group of DRV and 1,3-benzodioxole group of GRL-98065. The 1,3-benzodioxole group of GRL-98065 and aniline group of DRV formed a hydrogen bond each with Asp30'—however they interact with different atoms of Asp30'. GRL-98065 interacts with the Asp30' amide, while the aniline of DRV interacts with the carbonyl oxygen of Asp30' FIG. 5-B). More significantly, the other oxygen of the 1,3-benzodioxole group of GRL-98065 has formed a water-mediated interaction with the amide of the flap residue Gly48', while DRV had no equivalent interaction Gly 48'. These additional interactions of GRL-98065 with Gly48' in the flexible flap region should stabilize its binding to protease and mimic the interactions of the peptide substrates more closely than does DRV.

Structural analysis of interaction with mutant protease. Predictions can be made for the molecular interactions of GRL-98065 with a variety of mutant proteases by molecular docking. Described herein are analyses of the hydrogen bond interactions of various PIs (including DRV) with wild-type protease employing previously published coordinates for each PI complexed with wild-type protease (PDB IDs: 1S6G, 1HXB, 1HXW, 1SDT, 1OHR, 1HPV, 1MUI, and 2AQU) (Table 8).

TABLE 8

Hydrogen bond distances (in Å) of protease inhibitors with selected active site residues

| Inhibitor | PDB ID | Asp29 | Asp30 | Asp30' |
|---|---|---|---|---|
| GRL-98065 |  | 1.9/2.4 | 2.4 | 2.5 |
| DRV | 1S6G | 2.3/2.4 | 2.4 | 2.5 |
| SQV | 1HXB | 1.9 | 2.2 | NP |
| RTV | 1HXW | 2.1 | NP | 2.2 |
| IDV | 1SDT | 2.1 | NP | NP |
| NFV | 1OHR | NP | NP | NP |
| APV | 1HPV | 2.8 | 2.6 | NP |
| LPV | 1MUI | 1.7 | NP | NP |
| ATV | 2AQU | 1.9 | NP | NP |

Hydrogen atoms were added and optimized with constraints on heavy atoms using OPLS2005 force field (MacroModel version 9.1, Schrödinger, LLC). Hydrogen bond tolerances used were: 3.0 Å for H-A distance; D-H-A angle greater than 90°; and H-A-B angle greater than 60° where H is the hydrogen, A is the acceptor, D is the donor, and B is a neighbor atom bonded to the acceptor. NP (not present) denotes that hydrogen bond is not present between the inhibitor and the particular residue.

It is observed that GRL-98065 and DRV have four hydrogen bond interactions with backbone atoms of Asp29, Asp30, and Asp30'. None of the other PIs examined have more than two hydrogen bond interactions with these residues. These results should corroborate that GRL-98065 as well as DRV exert highly potent antiviral activity against wild-type HIV-1 strains. Six mutant proteases were examined with two to eleven amino acid substitutions (PDB IDs: 2FDD, 1SGU, 1HSH, 2AZC, 1B6K, 2AVV). Even though the mutations in each of these proteases did not exactly match the mutations shown in Table 3 and Table 4, they cover the range of amino acid substitutions observed in multi-drug382 resistant protease. The docking calculations show that for these mutant proteases GRL-98065 is able to maintain most of the four hydrogen bond interactions observed for the wild-type protease. In particular, we observed that the hydrogen bond interaction with Asp29 is maintained in four out of six mutant proteases. Taken together, these results may explain why GRL-98065 is able to show greater potency against a wide spectrum of multi-PI-resistant HIV-1 variants compared to other clinically approved PIs.

GRL-98065, which contains the component, 3(R),3a(S), 6a(R)-bis391 tetrahydrofuranylurethane (bis-THF) and a sulfonamide isostere, suppressed a wide spectrum of HIV-1, HIV-2, and primary HIV-1 strains of different subtypes over a very narrow spread of $IC_{50}$ values ranging from 0.0002 to 0.0045 µM (Tables 1, 2 and 5). GRL-98065 was highly potent against a variety of multi-drug-resistant clinical HIV-1 isolates with $IC_{50}$ values of 0.003 to 0.006 µM, while the existing FDA-approved PIs examined either failed to suppress the replication of those isolates or required much higher concentrations for viral inhibition (Table 4). When examined against laboratory PI-selected HIV-1 variants (except against HIV-$1_{APV5µM}$), GRL-98065 also exerted potent activity with $IC_{50}$ values ranging 0.0015 to 0.0075 µM. It is of note that GRL-98065 was less potent against APV-resistant HIV-$1_{APV5µM}$, however, it is thought that this relative cross resistance is due to the structural similarities of GRL-98065 with APV.

In contrast, although the activity of SQV against laboratory PI-selected variants except the SQV-selected variant was fairly well maintained, when SQV was examined against multi405 drug-resistant primary HIV-1 strains, high concentrations of SQV were required to suppress the replication of 4 of 6 strains tested ($IC_{50}$ values ranging 0.14 to 0.29 µM) (Table 4). In contrast, GRL-98065 exerted highly potent activity against all the 6 primary strains examined. As shown in Table 4, even the replication of the most PI409 resistant primary strain, HIV-$1_{JSL}$, against which $IC_{50}$ values of the 7 other PIs including ATV were 0.29 to >1 µM, was effectively suppressed by GRL-98065 at a fairly low concentration with an $IC_{50}$ value of 0.006 µM.

The observed greater potency of GRL-98065 over the existing FDA-approved PIs examined may stem, at least in part, from the ability of the two conformationally constrained ring oxygen atoms in its bis-THF group to form hydrogen bonds with the main chain amide hydrogen atoms of Asp29 and Asp30 in the S2 subsite (FIG. 5). Since the main chain atoms cannot be changed by viral amino acid substitutions, the interactions of GRL-98065 and the two catalytic site amino acids are less likely to be substantially affected, perhaps resulting in GRL-98065's broad spectrum of activity against multi-drug-resistant variants. When Asp30 is mutated to asparagine when HIV-1 is exposed to NFV (Patick et al. 1996. Antiviral and resistance studies of AG1343, an orally bioavailable inhibitor of human immunodeficiency virus protease. Antimicrob Agents Chemother 40:292-7), this mutation, D30N, is a primary resistance mutation for NFV that forms a hydrogen bond with the side chain of Asp30. GRL-98065 does not have direct interaction with the side chain of Asp30 (FIG. 5). Consistent with this observation, exposure of HIV-1 to GRL-98065 did not select mutations at codon 30 and GRL-98065 was active against D30N-carrying HIV-$1_{NFV5µM}$ that was highly resistant against NFV with an $IC_{50}$ value of >1 µM (Table 3).

Figure 6:
FIG. 6 shows the molecular modeling of interactions between GRL-98065 and wild-type protease. The figure shows the van der Waals surfaces of GRL-98065, Val82 and Ile85. There are strong van der Waals interactions of GRL-98065 with Val82 and Val82'. Val82 was substituted with isoleucine as a primary resistant mutation during in vitro passage of HIV-1 in the presence of GRL-98065. However, Ile85 does not have van der Waals contact with the inhibitor. Without being bound by theory, it is believed that I85V emerged as a secondary mutation during the in vitro selection with the inhibitor.

In the present HIV-1 selection experiment with GRL-98065, by passage 30 and beyond there were 10 major amino acid substitutions (E21K, A28S, K43I, M46I, I50V, D60N, A71V, V82I, I85V, and L89M) were identified. Mutation of Val82, whose side chain makes direct contacts with a number of PIs, was not seen in HIV-1 selected with TMC-126 that has bis-THF and exerts potent activity against a wide spectrum of HIV-1 strains. Without being bound by theory, it is suggested that V82I arises due to the fact that GRL-98065 has a tight and direct contact with Val82 (FIG. 6), while Ile85 does not have van der Waals contact with the inhibitor, suggesting that I85V emerged as a secondary mutation during the in vitro selection with GRL-98065 (FIG. 6). In the GRL-98065-selected HIV-1, neither of the active-site amino acid substitutions, I84V or V32I, emerged. These two substitutions are known to confer high levels of PI-resistance on HIV-1, in particular, when combined with V82I (Kaplan et al. 1994. Selection of multiple human immunodeficiency virus type 1 variants that encode viral proteases with decreased sensitivity to an inhibitor of the viral protease. Proc Natl Acad Sci USA 91:5597-601). The absence of these mutations may contribute to the observed delayed acquisition and relatively low level of resistance against GRL-98065.

During the selection with GRL-98065, the unique A28S mutation in the active site of the enzyme emerged. The A28S mutation was seen during the selection of HIV-1$_{NL4-3}$ with TMC126, where the mutation never became predominant but persisted within TMC126-selected HIV-1 variants at frequencies of ~50%. In a previous biochemical study conducted by Hong and Tang, the A28S mutation in HIV protease caused a more than 1,500-fold decrease in $k_{cat}/K_m$ values for peptide substrates. Without being bound by theory, these results suggest that A28S represents an important mutation for GRL-98065 resistance but also confers a severe replication disadvantage on the virus. However, the population size of HIV-1 in a culture is relatively small and the appearance of mutations can be affected by stochastic phenomena; i.e., rates and orders of appearance of mutations. In order to address the issue of mutation appearance, clinical studies on GRL-98065 are ultimately needed. The crystal structure reveals that GRL-98065 has a series of hydrogen bond interactions with backbone atoms of Asp29, Asp30, Asp30', and Gly27 of the protease (FIG. 5). Like other protease inhibitors, GRL98065 also has hydrogen bond interactions with the side-chain atoms of Asp25 and Asp25'. Besides the water-mediated hydrogen bond interactions with Ile50 and Ile50', there is a water-mediated hydrogen bond interaction with the flap residue Gly48'. Thus GRL-98065 makes favorable polar interactions with the Asp29 and Asp30 as well as with the flap residues.

These hydrogen bond interactions besides various favorable van der Waals contacts are likely to be responsible for the strong binding of the inhibitor and its potent antiviral activity observed in the present work. Comparison of the crystal structure of HIV-1 protease with GRL-98065 and the crystal structure of the complex with the recently approved inhibitor DRV shows that the interactions with the S2 site of the protease are shared by the two PIs, but the nature of the hydrogen bonds with residues in S2' site differs (FIG. 5). The water-mediated interaction of GRL-98065 with flap residue 48' is not observed for DRV. These differences in interactions may be partly responsible for the lower IC$_{50}$ of GRL-98065 compared to that of DRV (~3 nM in MT-2 cells). It is also suggested that there exists specific structural features, such as those present on GRL-98065, that allow it to maintain a highly favorable potency against a variety of laboratory PI-resistant HIV-1 variants and multi-drug-resistant clinical isolates. The resistance of PIs may be due to mutations arising because of possible loss of direct hydrogen bond interactions with specific residues (e.g., D30N for NFV and G48V for SQV) or loss of van der Waals contact (e.g., with V82A and I84V for first generation PIs).

Analysis of mutant protease crystal structures in comparison with wild-type protease showed that the backbone atoms of mutant protease undergo minimal conformational changes on mutation (Hong et al. 2000. Crystal structure of an in vivo HIV-1 protease mutant in complex with saquinavir: insights into the mechanisms of drug resistance. Protein Sci 9:1898-904; Kovalevsky et al. 2006. Effectiveness of nonpeptide clinical inhibitor TMC-114 on HIV-1 protease with highly drug resistant mutations D30N, I50V, and L90M. J Med Chem 49:1379-87). The loss of binding, in many cases seems to be due to loss of weaker van der Waals contacts between the inhibitor and protease. Without being bound by theory, it is suggested that if an inhibitor maintains strong hydrogen bond interactions with the wild-type protease, particularly with backbone atoms of multiple residues that are conserved (e.g., Asp29, and Gly27), then the loss of van der Waals contacts due to mutations may not result in drastic loss of binding affinity. Thus, inhibitors without multiple strong hydrogen bond interactions with wild-type protease may be more susceptible to loss of binding due to loss of weaker van der Waals contacts than inhibitors with multiple hydrogen bond interactions. In this respect, the hydrogen bond interactions of several PIs with wild-type protease were analyzed (Table 8). Only GRL-98065 and DRV have four hydrogen bond interactions with backbone atoms of Asp29 and Asp30, and Asp30'.

None of the other clinically approved PIs studied here have more than two hydrogen bond interactions with these residues. Thus, GRL-98065 may preserve the hydrogen bond interactions and bind tightly with mutant protease. Taken together, the present data suggest that GRL-98065 has several advantages: (i) it exerts potent activity against a wide spectrum of drug-resistant HIV-1 variants, presumably due to its interactions with the main chains of the active-site amino acids Asp29 and Asp30; (ii) its unique contact with HIV-1 protease differs from that of other PIs; (iii) the viral acquisition of resistance is substantially delayed; and (iv) at least several PIs including SQV, LPV, and ATV remain active in vitro against the virus selected in vitro with GRL-98065. Further development of GRL-98065 for treating patients harboring multi-PI-resistant HIV-1 is warranted.

Transfection. An assay system was established to enable the examination of the activity of test compounds to potentially block the dimerization of HIV-1 protease. Enhanced cyan fluorescent protein (CFP)- and yellow fluorescent protein (YFP)-tagged HIV-1 protease constructs were generated using BD Creator™ DNA Cloning Kits (BD Biosciences, San Jose, Calif.). First, Xho I/Hind III fragments from pCR-XL-Topo vector containing the HIV-1 protease-encoding gene excised from pHIV-1$_{NL4-3}$ was inserted into the pDNR-1r (donor vector) that had been digested with Xho I and Hind III. To transfer the protease gene from the donor vector into pLP-CFP/YFP-C1 (acceptor vector), the Cre-loxP site-specific recombination method was used according to manufacturer's instructions. Using Cre-recombinase with the lox P site, the protease gene from pDNR-1r was efficiently inserted into pLP-CFP-C1 or pLP-YFP-C1 through Cre-mediated recombination (Hoess, Proc Natl Acad Sci USA 81(4):1026-1029 (1984)), generating pPRwt tagged to ECFP (designated pPR$_{WT}^C$) and pPR$_{WT}$ tagged to EYFP (pPR$_{WT}^Y$), with which HIV-1 protease was successfully expressed as a fusion protein with ECFP and EYFP hooked at the C-terminus, respectively.

For the generation of full-length molecular infectious clones containing ECFP- or EYFP-tagged protease, the PCR-mediated recombination (PMR) method of Fang (1999) was used (Fang et al. Nat Med 5(2):239-242 (1999)). An upstream proviral DNA fragment containing Apa I site and HIV-1 protease (excised from pHIV-1$_{NL4-3}$) was amplified with a primer pair: Apa-PRO-F (5'-TTG CAG GGC CCC TAG GAA AAA GG-3') SEQ ID NO:73) plus PR-5Ala-R (5'-GGC TGC TGC GGC AGC AAA ATT TAA AGT GCA GCC AAT CT-3') (SEQ ID NO:74), a middle proviral DNA fragment containing ECFP (excised from pECFP-C1) or EYFP (excised from pEYFP-C1) (Clontech, Mountain View, Calif.) with a primer pair: CFPYFP-5Ala-F (5'-GCT GCC GCA GCA GCC GTG AGC AAG GGC GAG GAG CTG-3') (SEQ ID NO:75) plus CFPYFP-FP-R (5'-ACT AAT GGG AAA CTT GTA CAG CTC GTC CAT GCC G-3') SEQ ID NO:76), and a downstream proviral DNA fragment containing 5'-DNA fragment of RT and Sma I site from pHIV-1$_{NLSma}$ (Gatanaga et al. J Biol Chem 277(8): 5952-5961 (2002)), which had been created to have a Sma I site by changing two nucleotides (2590 and 2593) of pHIV-1$_{NL4-3}$ with a primer pair: FRT-F (5'-TTT CCC ATT AGT CCT ATT GAG ACT GTA-3') (SEQ ID NO:77) plus NL4-3-RT263-R (5'-CCA GAA ATC TTG AGT TCT CTT ATT-3') (SEQ ID NO:78). A spacer consisting of five alanines was inserted between protease and fluorescent protein and the phenylalanine-proline site that HIV-1 protease cleaves had been inserted between fluorescent protein and RT. Thus obtained three DNA fragments were subsequently joined by using the PMR reaction performed under the standard condition for ExTaq polymerase (Takara Bio Inc., Otsu, Japan) with 10 pmoles of Apa-PRO-F (5'-TTG CAG GGC CCC TAG GAA AAA GG-3') (SEQ ID NO:79) and NL4-3-RT263-R (5'-CCA GAA ATC TTG AGT TCT CTT ATT-3') (SEQ ID NO:80) and the three DNA fragments (100 ng each) in a 20 µl reaction solution. Thermal cycling was carried out as follows: 94° C. for 3 min, followed by 35 cycles of 94° C. for 50 sec, 53° C. for 50 sec, and 72° C. for 2 min, and finally by 72° C. for 15 min. The amplified PCR products were cloned into pCR-XL-Topo vector according to the manufacturer's instructions (Gateway Cloning System; Invitrogen, Carlsbad, Calif.). PCR products were generated with pCR-XL-Topo vector as templates, followed by digestion by both ApaI and SmaI, and the ApaI-SmaI fragment was introduced into pHIV-1$_{NLSma}$ (Gatanaga et al. J Biol Chem 277(8):5952-5961 (2002)), generating pPR$_{WT}^{C}$ and pPR$_{WT}^{Y}$ (also referred to as pHIV-PRWT CFP and pHIV-PRWT YFP), respectively).

Figures 1, 2A:
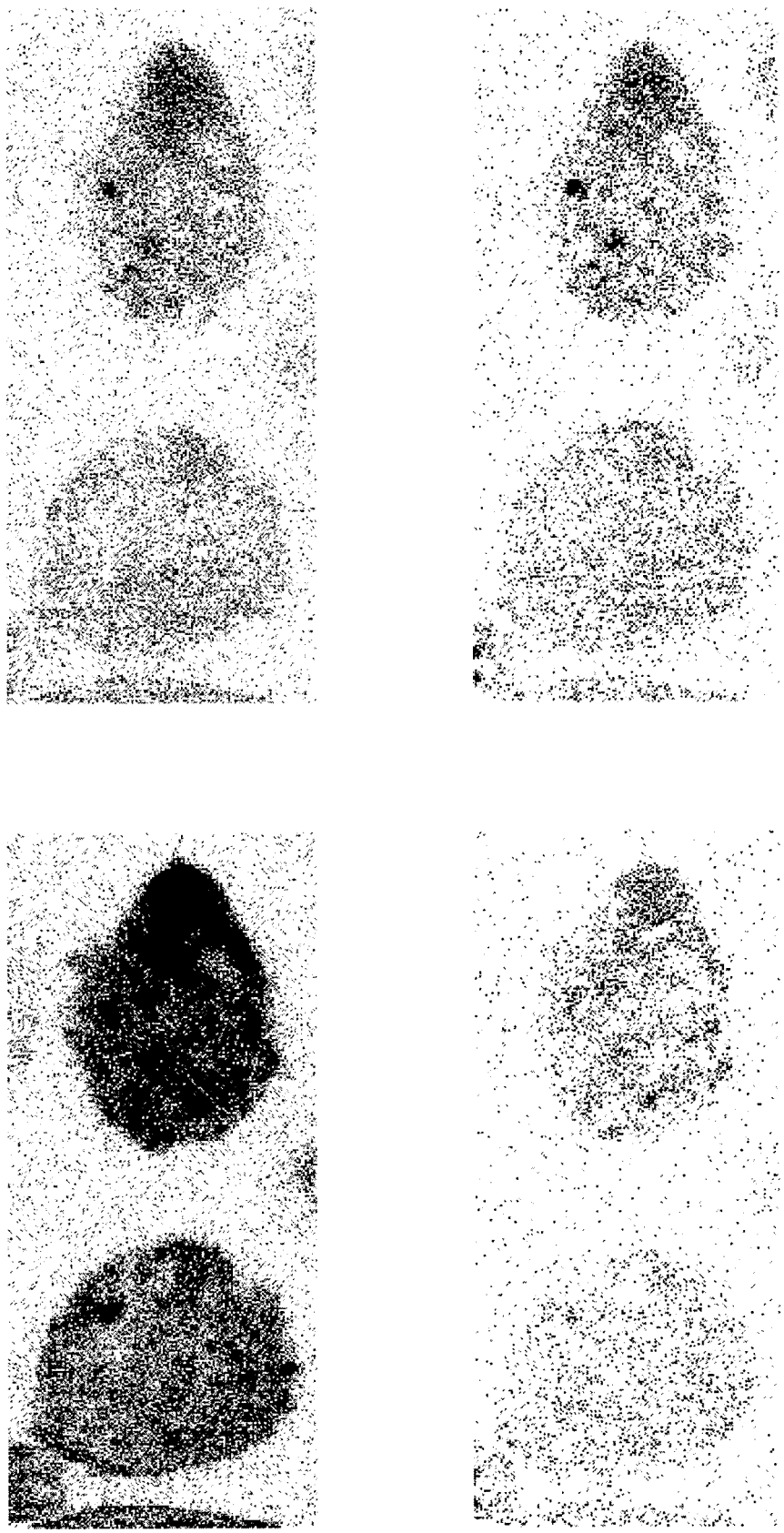
Figures 2, 2A:
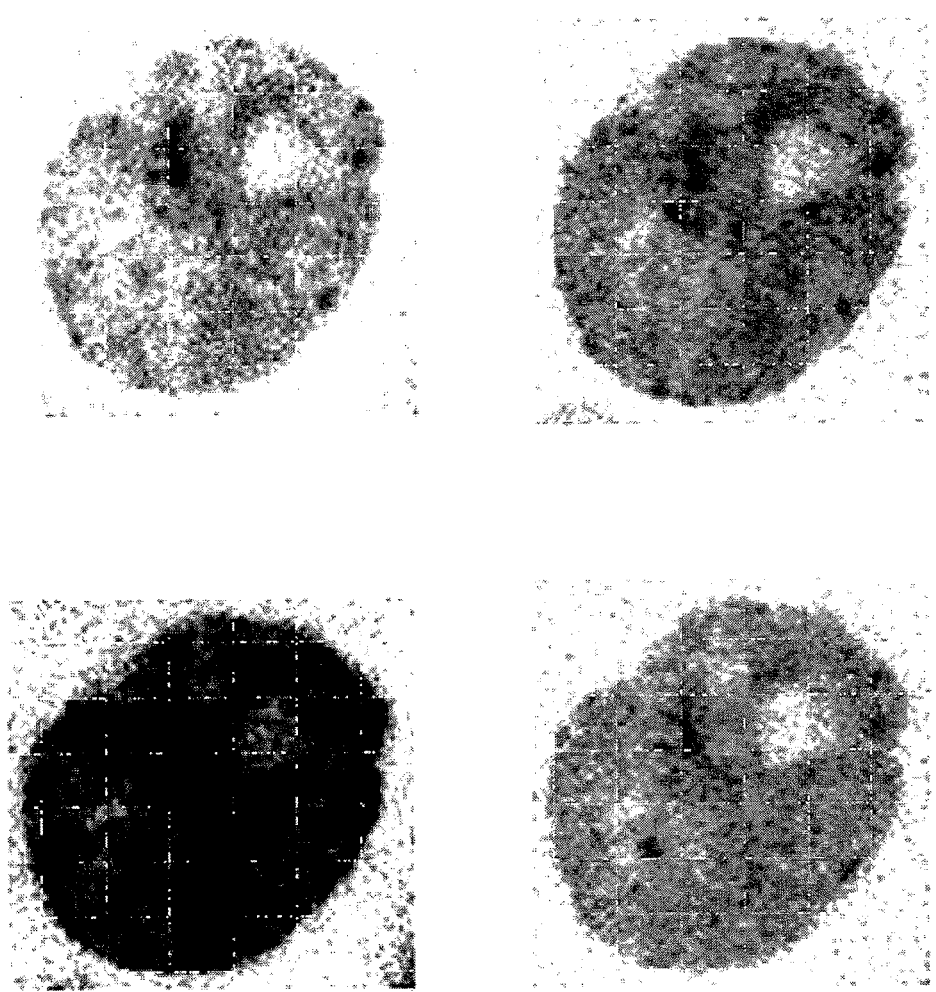

When Cos-7 cells were transfected with two plasmids, pNLPRwt-CFP and pNLPRwt-YFP, cultured and analyzed under confocal scanning microscope, both NL-PRwt-CFP and NL-PRwt-YFP proteins were well visualized. The fluorescence pattern of the proteins was diffuse and a slightly punctate staining pattern was seen mostly in the cytoplasm; the fluorescein was not seen concentrated at the plasma membrane (FIG. 2-a). Photobleaching of the cells dramatically reduced YFP fluorescence and increased CFP emission from NL-PRwt-CFP, strongly suggesting that both YFP- and CFP-tagged protease subunits were dimerized. When Cos-7 cells were co-transfected with wild-type NL-PR-CFP and NL-PR-YFP plasmids, cultured, and examined with confocal laser scanning microscope, the FRET efficiency determined following acceptor photobleaching [Bastiaens et al., EMBO 1996; Siegel et al., Science's stke 2000; Firulli et al., Nature genetics, 2005; Szczesna et al., JBC 2003], the ratio of intensities of CFP fluorescence after photobleaching to CFP fluorescence prior to photobleaching was 1.19±0.05. All these FRET assays were performed double-blind, the preparation of cells (and drugs) and co-transfection were performed blind and the FRET determination was also conducted blind. The virions containing YFP- and CFP-tagged protease subunits produced by Cos-7 cells were comparably infectious as compared to the virions containing untagged wild-type protease produced in Cos-7 cells similarly co-transfected with wild-type protease-containing HIV-1 plasmids.

A network of interaction around the active site and termini of the mature protease are reportedly critical for the dimerization of protease (Lapatto 1989, Nature 342, 299-302; Wlodawer, 1989, Science 245, 616-621). It has been suggested that the intramonomer contact formed by the conserved Asp-29 and Arg87 are essential to the dimerization of the protease and the introduction of amino acid substitutions to the protease including D29N and R87K substitutions destabilizes the dimer through the disruption of the dimer interface contacts (Ishima, 2003, JBC 278, 43311-43319; Ishima, 2001, JBC 276, 49110-49116). Thus, such amino acid substitutions were introduced to both NL-PR-CFP and NL-PRYEP, co-transfected Cos-7 cells with mutant NL-PR-CFP and NL-PR-YFP plasmids, and examined whether the FRET was seen. As shown in FIG. 2-b, when Cos-7 cells were co-transfected with wild-type NL-PR-CFP and -YFP plasmids, FRET was observed to occur since the ratios of more than 1 indicate that association (i.e., dimerization) of CFP- and YFP-tagged protease subunits took place. However, when the cells were transfected with the plasmids containing D29N, D29A, or R87K substitution, no FRET was seen in the assay. In the cells co-transfected with the plasmids with an amino acid substitution (A28S or D30N) in the proximity to Asp-29, FRET was seen as expected from the previous observations that HIV-1 variants containing A28S (Yoshimura, 2002) or D30N remain replicative. These data, taken together, suggest that the absence of FRET in this system denotes that the dimerization of CFP- and YFP-tagged protease subunits did not occur within Cos-7 cells.

Enzyme kinetics. The chromogenic substrate Lys-Ala-Arg-Val-Nle-p-nitroPhe-Glu-Ala-Nle-amide (Sigma, St. Louis, Mo.) was used to determine the kinetic parameters (Kovalevsky et al. J Mol Biol 363(1):161-173 (2006), Ghosh et al. J Med Chem 49(17):5252-5261 (2006)). Wild-type PR at final concentrations of 160-190 nM were added to varying concentrations of substrate (100-400 µM) maintained in 50 mM sodium acetate (pH 5.0), 0.1 M NaCl, 1 mM EDTA, and assayed by monitoring the decrease in absorbance at 310 nm using a Varian Cary 100Bio UV-Vis spectrophotometer. The $k_{cat}$ and Km values were obtained employing standard data fitting techniques for a reaction obeying Michaelis-Menten kinetics. The data curves were fitted using SigmaPlot 8.0.2 (SPSS Inc., Chicago, Ill.). The active enzyme concentrations were calculated from the intercept of the linear fit to the $IC_{50}$ versus [S] plots with the $IC_{50}$ axis. The $K_i$ values were obtained from the $IC_{50}$ values estimated from an inhibitor dose-response curve with the spectroscopic assay using the equation $K_i=(IC_{50}-[E]/2)/(1+[S]/Km)$, where [E] and [S] are the PR and substrate concentrations, respectively (Maibaum & Rich J Med Chem 31(34):625-629 (1988)). The $K_i$ values were measured at four to five substrate concentrations. The measurement was repeated at least three times to produce the average values.

Assay for effects of darunavir on dimerized mature protease. To examine whether the representative dimerization inhibitor DRV could dissociate mature protease that had already been dimerized, Cos-7 cells were co-transfected with a pair of plasmids encoding HIV-PR$_{WT}^{CFP}$ and HIV-PR$_{WT}^{YFP}$ and exposed to a protein synthesis inhibitor cycloheximide (50 µg/ml, Sigma, St. Louis, Mo.) at 24, 48, 72, and 96 hrs of culture following transfection. The cells were then exposed to DRV (1 µM) on day 5 of culture, and the values of the CFP$^{A/B}$ ratio were determined at various time points. When the CFP$^{A/B}$ ratios determined were greater than 1.0, it was determined that HIV-1 protease had been generated and dimerization had occurred. The production of HIV-1 was monitored every 24 hours following transfection by determining levels of p24 Gag protein produced into culture medium as described by Koh et al. *Antimicrob Agents Chemother* 47:3123-9 (2003).

Figure 7A:
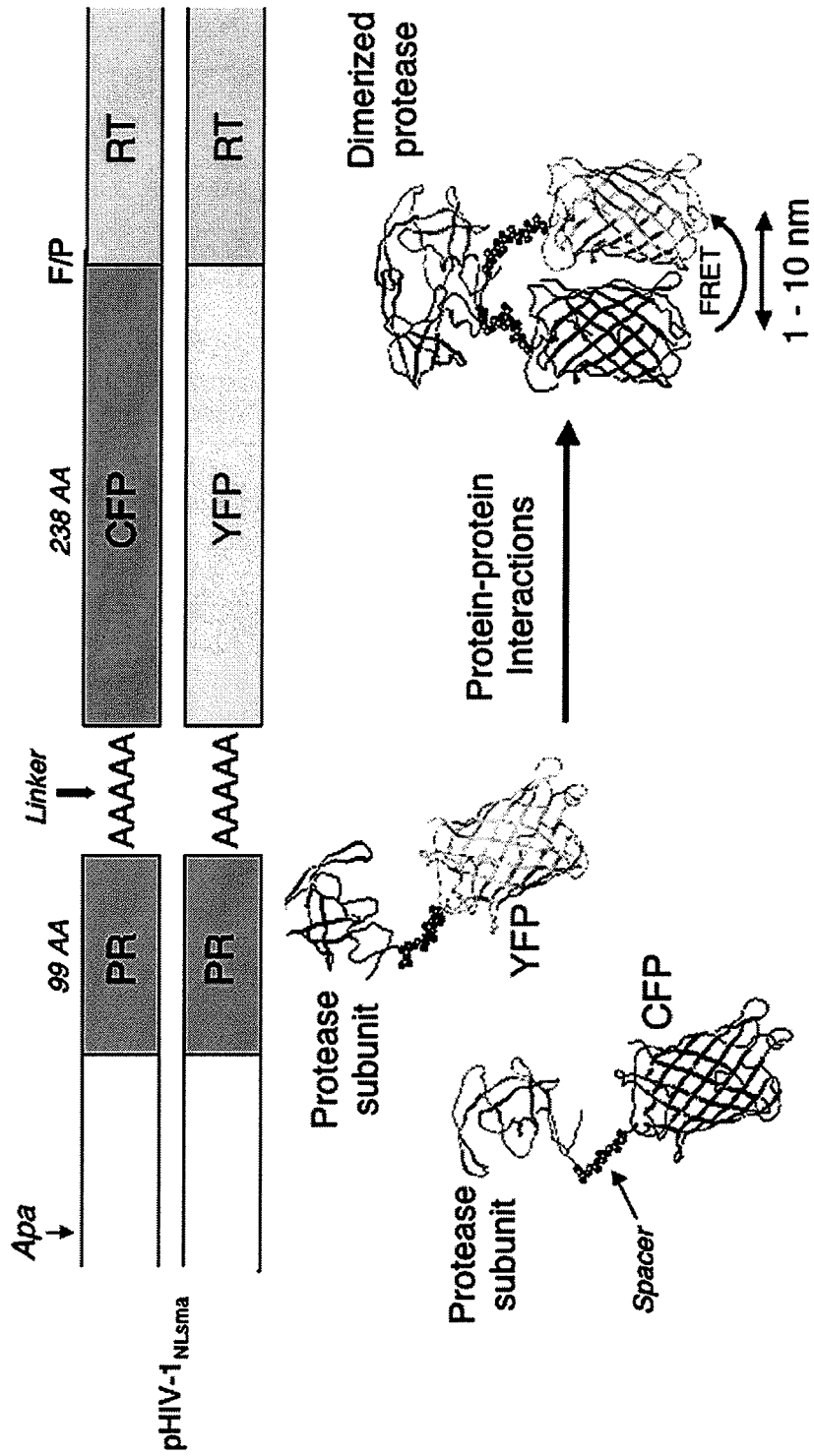
FIG. 7 shows the FRET-based HIV-1 expression system. (A) Generation of FRET-based HIV-1 expression system. Various plasmids encoding full-length molecular infectious HIV-1 (HIV-1$_{NL4-3}$) clones producing CFP- or YFP-tagged protease using the PCR-mediated recombination method were prepared. A linker consisting of five alanines was inserted between protease and fluorescent protein and the phenylalanine-proline site that HIV-1 protease cleaves were also inserted between fluorescent protein and RT. Shown are structural representations of protease monomers and dimer in association with the linker atoms and fluorescent proteins. FRET occurs only when the fluorescent proteins are 1 to 10 nm apart. (B) Expression of CFP and YFP-tagged wild-type HIV-1 protease. To confirm the presence of HIV-1 protease tagged to fluorescent protein in COS7 cells transfected with a plasmid encoding HIVWT CFP, HIVA28S CFP, HIVWT YFP or HIVA28S YFP, Western blot analysis was performed using lysates of pelleted virions. The CFP- and YFP-tagged proteases were visualized by SuperSignal WestPico Chemiluminescent Substrates using polyclonal anti-GFP antiserum and ECL Anti-rabbit IgG peroxidase-linked species-specific whole antibody. pLPYFP denotes the lysates of cells transfected with a plasmid encoding only YFP. The lysates of Cos-7 cells transfected with a plasmid encoding HIV$_{WT}$ and those of untreated Cos-7 cells serve as controls. (C) Ratios of the emission intensities before and after photobleaching. Fluorescence intensities of each cell transfected with two plasmids, pPR$_{WT}^{CFP}$ and pPR$_{WT}^{YFP}$, were measured before and after photobleaching, and ratios of the emission intensities before and after photobleaching (CFP$^{A/B}$ ratios) were determined, and plotted. The CFP values were 1.24±0.11 (n=23), while the YFPA/B ratio values 0.47±0.09 (n=23). The mean of these ratios are shown as horizontal bars.
Figure 7B:
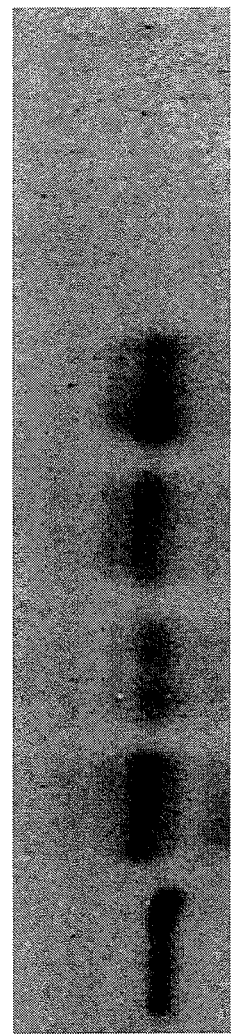

Generation of FRET-based HIV-1 expression assay. The basic concepts of the intermolecular fluorescence resonance energy transfer (FRET)-based HIV-1-expression assay (FRET-HIV-1 assay) are shown in FIG. 7. Within a plasmid (pHIV-1$_{NL4-3}$), which encodes a full-length molecular infectious HIV-1 clone, the gene encoding a cyan fluorescent donor protein (CFP) was attached to the downstream end (C-terminus) of the gene encoding an HIV-1 protease subunit through the flexible linker added (five alanines), generating pHIV-1$_{NL4-3/CFP}$ (FIG. 7A). Within the other plasmid (pHIV-1NL4-3), the gene encoding a yellow fluorescent acceptor protein (YFP) was attached to the downstream end of protease-encoding gene in the same manner, generating pHIV-1$_{NL4-3/YFP}$. Both CFP and YFP were designed to have phenylalanine and proline in the connection with reverse transcriptase so that the protease is cleaved from reverse transcriptase when two subunits dimerize and the dimerized protease acquires enzymatic activity. FIG. 7B illustrates that HIV-1 virions generated in Cos-7 cells transfected with pHIV-1$_{NL4-3/CFP}$ contained CFP-tagged protease and those in Cos-7 cells transfected with pHIV-1$_{NL4-3/YFP}$ contained YFP-tagged protease as examined in Western blotting. The HIV-1 virions produced were capable of infecting CD4$^+$ MT-4 cells when the cells were exposed to the supernatant of the transfected Cos-7 cells (data not shown), indicating that the expressed tagged protease was enzymatically and virologically functional. In the cytoplasm of Cos-7 cells co-transfected with pHIV-1$_{NL4-3/CFP}$ and pHIV-1$_{NL4-3/YFP}$, a CFP-tagged protease subunit interacts and dimerizes with a YFP-tagged protease subunit, and CFP and YFP get close because the termini are separated by only 0.5 to 1.8 nm in the dimeric form of protease [Note: the representative distance was determined by analyzing the protease-DRV crystal structure (PDB ID: 1 S6G)]. A focused laser beam excitation of CFP (triggered by Helium-Cadmium laser) results in rapid energy transfer to YFP, and most of the fluorescence photons are emitted by YFP (Miyawaki et al. *Nature* 388(6645):882-887 (1997)). If the dimerization is blocked, the average distance between CFP and YFP becomes larger and the energy transfer rate is decreased and the fraction of photons emitted by YFP is lowered.

In order to interpret the energy transfer efficiency quantitatively, an acceptor photobleaching technique was used, in which the change in CFP emission quenching is measured by comparing the value before and after selectively photobleaching YFP, which prevents problems associated with variable expression levels. In this acceptor photobleaching approach, when FRET occurs, the fluorescence of the CFP donor increases after bleaching the YFP acceptor chromophore, which is recognized as a signature for FRET (Sekar et al. *J Cell Biol* 160(5):629-633 (2003)). Thus, the analysis of the change in CFP fluorescence intensity in the same specimen regions, before and after removal of the acceptor, directly relates the energy transfer efficiency to both donor and acceptor fluorescence. FIG. 2A-2 illustrates representative images of co-transfected cells prior to and after YFP photobleaching, showing that, following photobleaching, YFP fluorescence of YFP-tagged wild-type protease subunit (PR$_{WT}^{YFP}$) was decreased, while CFP fluorescence of PR$_{WT}^{CFP}$ increased.

Figure 7C:
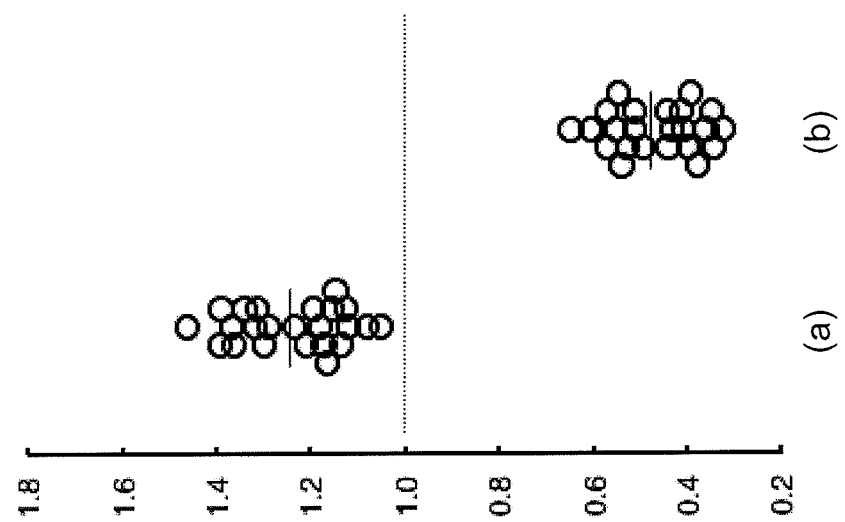

In order to further evaluate the energy transfer efficiency, the ratios of cyan fluorescence intensity were determined with a confocal laser scanning microscope, after photobleaching over that before photobleaching (hereafter referred to as CFP$^{A/B}$ ratios). Also determined were the YFP$^{A/B}$ ratios in the same manner. If the CFP$^{A/B}$ ratios are greater than 1.0, it is thought the energy transfer (or FRET) took place (13), signifying that dimerization of PR$_{WT}^{CFP}$ and PR$_{WT}^{YFP}$ subunits occurred. FIG. 7C shows that in the co-transfected Cos-7 cells (n=23), the CFP$^{NB}$ ratios were all greater than 1.0 (CFP$^{A/B}$ ratios, 1.24±0.11; while YFP$^{A/B}$ ratios 0.47±0.09), demonstrating that dimerization of protease subunits occurred.

Figure 8A:
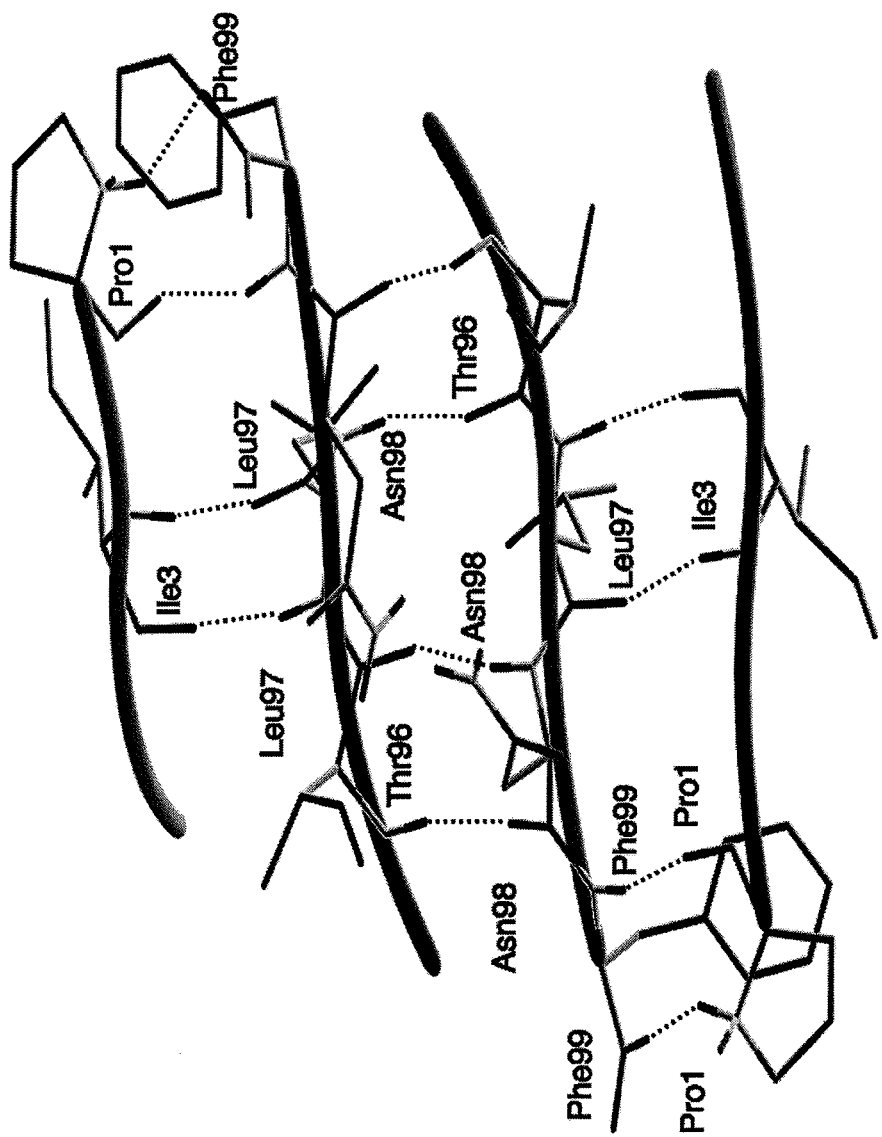
FIG. 8 shows the molecular modeling of certain amino acid residues that may be available for protease dimerization. (A) Four stranded antiparallel beta-sheets involving the N- and C-termini of both monomer subunits. Two HIV-1 protease monomer subunits are connected by four stranded antiparallel beta-sheets involving the N- and C-termini of both monomer subunits. As viewed from the top, the first and third ribbons represent one monomer subunit, and the second and fourth ribbons represent the other monomer subunit. It is appreciated that a molecule disrupting these inter-protease hydrogen bond contacts may also disrupt their dimerization. (B and C) Intermolecular hydrogen bonds between two HIV-1 protease monomer subunits. The figure shows the intermolecular hydrogen bonds between two protease monomer subunits. The hydrogen bond interactions between protease monomer A (left) and monomer B (right) are D29-R8'; R87-L5'; L24-T26'; and T26-T26'. The corresponding amino acids of monomer B also form hydrogen bonds with monomer A (i.e. D29'-R8 etc.). Intra-molecular hydrogen bond interaction between D29 and R87 are shown by the dotted lines. The residues forming intermolecular contacts between two monomer subunits are shown. Only polar hydrogens are shown. The corresponding residues of chain B are labeled with a prime. Without being bound by theory, these interactions provide a structural explanation for the FRET experimental data, which show that mutations L5, D29, D26, and R87 prevent formation of a protease dimer. (D) Potential binding sites of the small molecule dimerization inhibitors. The figure shows one of the potential binding sites of the dimerization inhibitors. Residues D29, R87 and T26 are spatially close enough to form binding interactions with the dimerization inhibitor and prevent the other protease monomer from interacting with these residues.

Changes in fluorescence emission with amino acid substitutions in protease. First, it was determined whether the above-described FRET-HIV-1 assay could be used to detect the disruption of HIV-1 protease dimerization. Five amino acids at the amino-terminus and those at the carboxyl-terminus have been shown to be critical for protease dimerization (Babe et al. *Protein Sci* 1(10):1244-1253 (1992)). As shown in FIG. 8A, two protease monomer subunits are connected by four stranded antiparallel beta-sheets involving the N- and C-termini of both subunits. It is of note that mature dimerized protease has as many as 12 hydrogen bonds in this N- and C-terminal region. Thus, we introduced a Pro-1 to Ala substitution (P1A), Q2A, I3A, T4A, L5A, T96A, L97A, N98A, or F99A substitution into the replication-competent HIV-1$_{NL4-3}$, and found that I3A, L5A, T96A, L97A, and F99A disrupted protease dimerization, although other substitutions did not disrupt the dimerization. Several amino acid substitutions outside the amino- and carboxyl-termini have also been known to play a role in HIV-1 protease dimerization.

Figure 2B:
FIG. 2B shows changes in emission intensity ratios upon amino acid substitution. COS7 cells were co-transfected with various pairs of HIV-$PR^{CFP}$ and HIV-$PR^{YFP}$: (a) WT, (b) Pro1Ala, (c) Glu2Ala, (d) Ile3Ala, (e) Thr4Ala, (f) Leu5Ala, (g) Asp25Ala, (h) Thr26Ala, (i) Ala28Ser, (j) Asp29Ala, (k) Asp29Asn, (l) Asp30Asn, (m) Arg87Lys, (n) Thr96Ala, (o) Leu97Ala, (p) Asn98Ala or (q) Phe99Ala, and $CFP^{A/B}$ ratios were determined. All the experiments were conducted in a blind fashion. A $CFP^{A/B}$ ratio that is greater than 1 signifies a protease dimer, whereas a ratio that is less than 1 signifies disruption of protease dimerization. It is observed that residues (such as Ile-3 or Asp-29) whose mutation results in disruption of dimerization had intermolecular hydrogen bonds contact with the other protease monomer as shown in FIG. 8A-C.
Figure 2C:
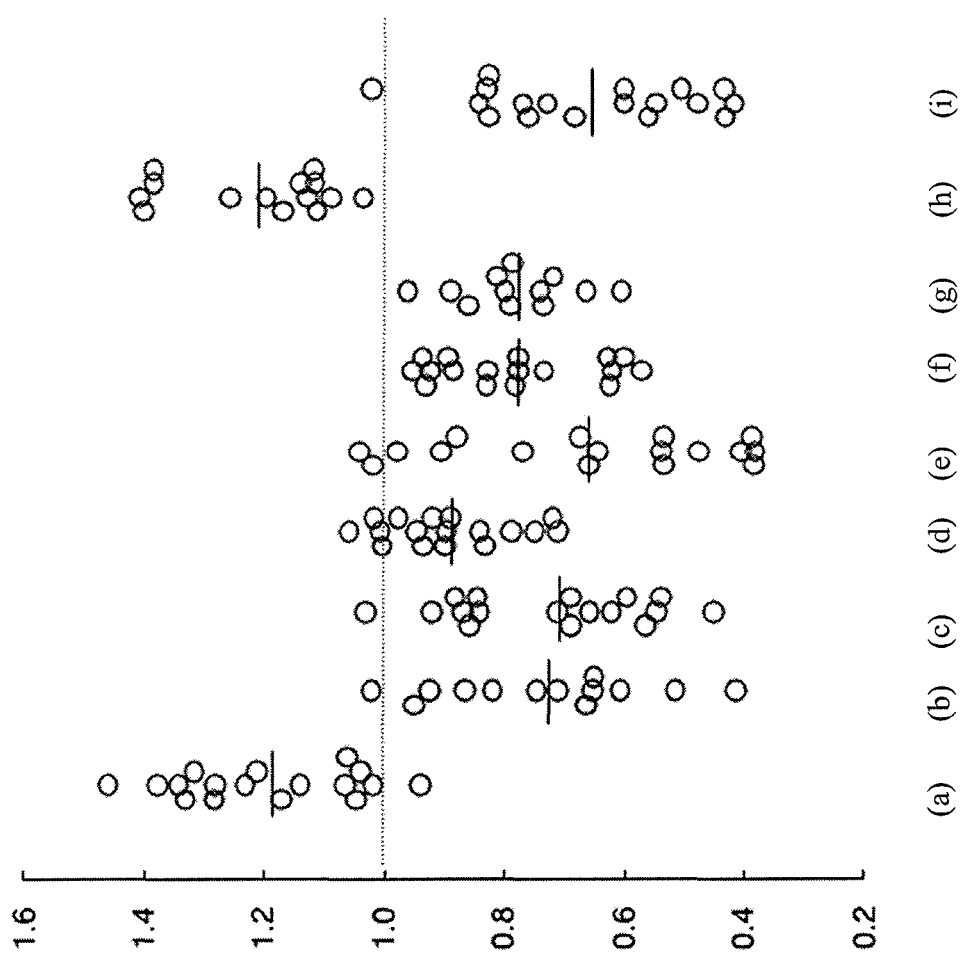
FIG. 2C shows the inhibition of protease dimerization by non-peptidyl and peptidyl compounds. Cos-7 cells were exposed to each of the agents (control (a), 1 µM of (b) GRL-0036A, (c) GRL-06579A, (d) GRL-98065, (e) TMC126, (f) DRV and (g) BCV and (h) 10 µM of P9 and (i) P27) and subsequently co-transfected with $pPR_{WT}^{CFP}$ and $pPR_{WT}^{YFP}$. After 72 hr, cultured cells were examined in the FRET-HIV-1 assay system using confocal microscopy Fluoview FV500 confocal laser scanning microscope, and $CFP^{A/B}$ were determined and plotted. The mean of these ratios obtained are shown as horizontal bars. The FRET efficiency was determined following acceptor photobleaching as previously described (Bastiaens et al., EMBO 1996; Siegel et al., Science's stke 2000; Firulli et al., Nature genetics, 2005; Szczesna et al., JBC 2003). Dequenching of the donor CFP by selective photobleaching of the acceptor YFP was performed by first obtaining YFP and CFP images at the same focal plane, followed by illuminating for 3 min the same image at wavelength of 488 nm with a laser power set at the maximum intensity to bleach YFP and re-capturing the same CFP and YFP images. The changes in the CFP and YFP fluorescence intensity in the images of selected regions were examined and quantified using Olympus FV500 Image software system. Background values were obtained from the regions where no cells were present and were subtracted from the values for the cells examined in all calculations. For each chimeric protein, the data were obtained from at least three independent experiments. FRET efficiency was determined using the formula: $ET=(1-(I_{DA}/I_D))\times 100$, where $I_{DA}$ and $I_D$ represent the steady-state donor fluorescence in the presence and absence of the acceptor, respectively. Digitized image data obtained from the experiment were prepared for presentation using Photoshop 6.0 (Adobe systems, Mountain View, Calif.). Ratios of intensities of ECFP fluorescence after photobleaching to ECFP fluorescence prior to photobleaching were determined. The ratios of more than 1 indicate that dimerization of CFP- and YFP-tagged protease subunits occurred and those of less than 1 indicate that dimerization was blocked by the test agent.
Figure 2D:
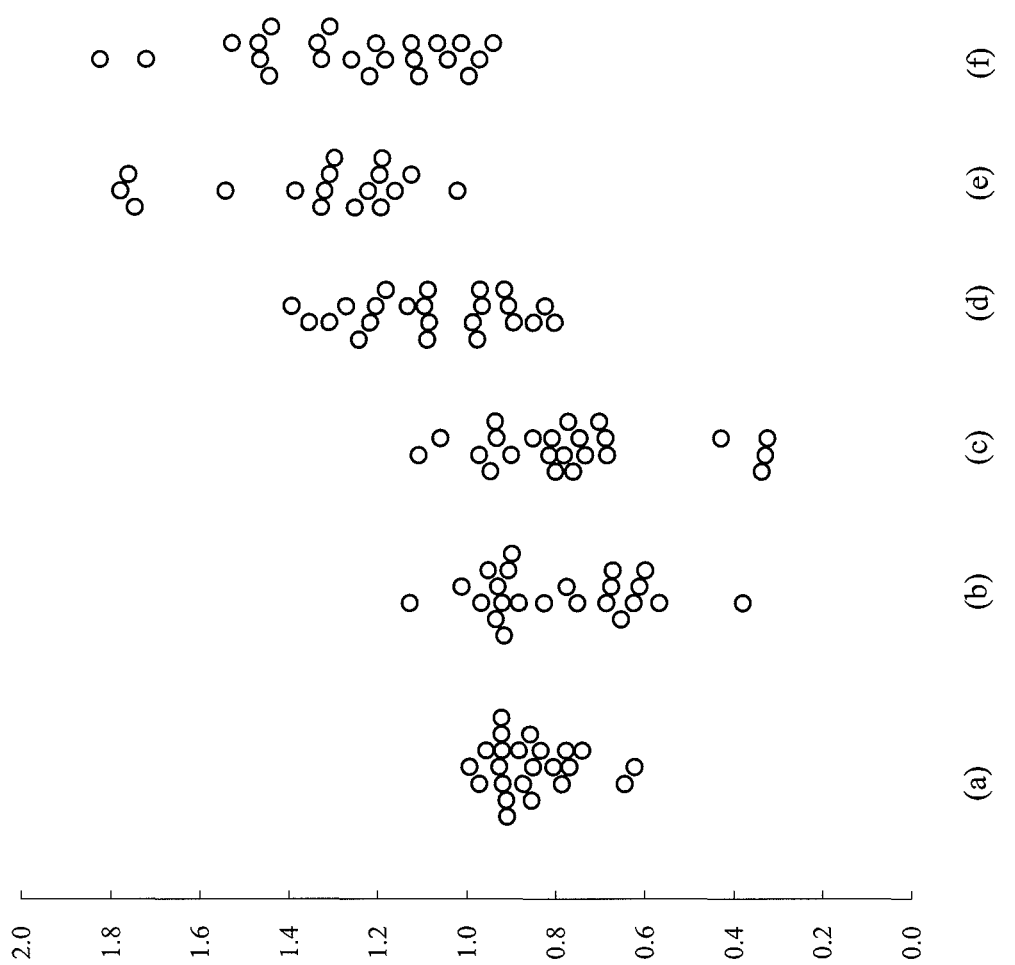
FIG. 2D shows the dose-responsive dimerization inhibition by TMC114 at (a) 10 µM (0.85±0.09); (b) 1 µM (0.80±0.18); (c) 0.1 µM (0.76±0.22); (d) 0.01 µM (1.08±0.17); (e) 0.001 µM (1.35±0.23); and in the absence of drug (f) (1.27±0.24). Cos-7 cells were exposed to various concentrations of TMC114, co-transfected with NL-PRwt-ECFP and NL-PRwt-EYFP, and ratios of intensities of ECFP fluorescence after photobleaching to ECFP fluorescence prior to photobleaching were determined.

Ishima and Louis and their colleagues have demonstrated that the introduction of T26A, D29N, D29A or R87K to HIV-1 protease disrupts the dimer interface contacts and destabilizes protease dimer, causing the inhibition of protease dimerization (Ishima et al. *J Biol Chem* 278(44): 43311-43319 (2003); Ishima *J Biol Chem* 276(52):49110-49116 (2001); Louis et al. *J Biol Chem* 278(8):6085-6092 (2003)). FIGS. 2B and 2C shows the locations of intermolecular hydrogen bonds formed by such amino acids between two monomer subunits. The hydrogen bond interactions between two subunits occur between Asp-29-Arg-8', Arg-87-Leu-5', Leu-24-Thr-26', and Thr-26-Thr-26'. There are also intra-molecular hydrogen bond interactions between Asp-29 and Arg-87 as shown in FIGS. 2B-D. Thus, mutations in those amino acids were introduced into HIV-PR$_{WT}^{CFP}$ and HIV-PR$_{WT}^{YFP}$, generating HIV-PR$_{T26A}^{CFP}$, HIV-PR$_{T26A}^{YFP}$, HIV-PR$_{D29N}^{CFP}$, HIV-PR$_{D29N}^{YFP}$, HIV-PR$_{D29A}^{CFP}$, HIV-PR$_{D29A}^{YFP}$, HIV-PR$_{R87K}^{CFP}$, and HIV-PR$_{R87K}^{YFP}$. Co-transfection of Cos-7 cells with a pair of CFP- and YFP-tagged protease-carrying HIV-1-encoding plasmids demonstrated that these four amino acid substitutions disrupted protease dimerization (the average CFPA/B ratios were all <1.0; FIG. 2B). Substitutions of two amino acids adjacent to Asp-29 were also introduced, generating HIV-PR$_{A28S}^{CFP}$, HIV-PR$_{A28S}^{YFP}$, HIV-PR$_{D30N}^{CFP}$ and HIV-PR$_{D30N}^{YFP}$. Both A28S and D30N are known primary amino acid substitutions, conferring resistance to TMC-126 and nelfinavir on HIV-1, respectively (Yoshima et al. *J Viol* 76(3):1349-1358 (2002); Patick et al. *Antimicrob Agents Chemother* 40(2):292-297 (1996)). The fact that A28S- or D30N-containing HIV-1 is infectious and replication-competent indicates that these two amino acid substitutions would not disrupt protease dimerization. HIV-1 virions generated in COS7 cells transfected with HIV-PR$_{A28S}^{CFP}$ and HIV-PR$_{A28S}^{YFP}$ were confirmed to contain CFP-tagged protease and YFP-tagged protease in Western blotting, respectively (FIG. 7B). As expected, neither substitution disrupted the dimerization as examined in the FRET-HIV-1 assay (FIG. 2B). Another mutation D25A, which is adjacent to Asp-26 and is known to abrogate replicative activity of HIV-1 (Konvalinka et al. *J Viol* 69(11):7180-7186 (1995)), failed to disrupt protease dimerization, indicating that the inability of D25A mutation-carrying HIV-1 to replicate is not due to dimerization disruption, but due to the loss of proteolytic activity of dimerized HIV-1 protease. Analysis of these data indicated that the FRET-HIV-1 assay system is a reliable tool to evaluate agents for their potential to inhibit protease dimerization.

Figure 9A:
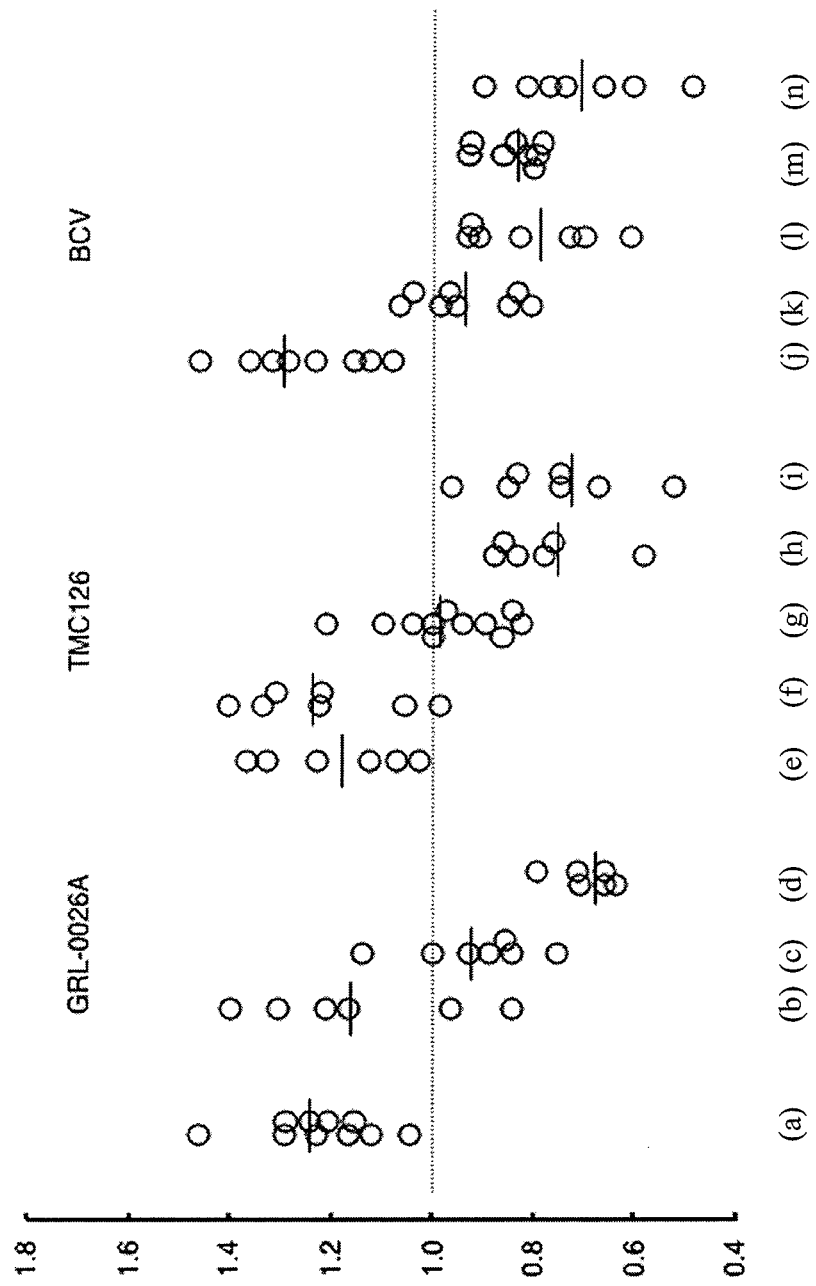
FIG. 9 shows inhibition of protease dimerization. (A) Dose-responsive dimerization inhibition by various non-peptidyl compounds. Compared to control (a), Cos-7 cells were exposed to various concentrations (μM) of GRL-0026A (b) 0.1, (c) 1, (d) 10; TMC126 (e) 0.001, (f) 0.01, (g) 0.1, (h) 1, (i) 10; and BCV (j) 0.001, (k) 0.01, (l) 0.1, (m) 1, (n) 10, co-transfected with pPR$_{WT}^{CFP}$ and pPR$_{WT}^{YFP}$, and cultured for 72 hrs. At the end of the culture, CFP$^{A/B}$ ratio values were determined. (B) Failure of a high concentration of four clinically available protease inhibitors to inhibit HIV-1 protease dimerization. Compared to control (a), Cos-7 cells were co-transfected with p PR$_{WT}^{CFP}$ and p PR$_{WT}^{YFP}$ in the presence of four known protease inhibitors, (b) saquinavir, (c) amprenavir, (d) nelfinavir, (e) atazanavir, and (f) darunavir, at a higher concentration of 10 μM, cultured for 72 hr, and CFP$^{A/B}$ ratios were determined. All the CFP$^{A/B}$ ratio values were greater than 1.0 except for those of DRV. (C) Various approved anti-HIV-1 agents failed to inhibit HIV-1 protease dimerization. Compared to (a) control, Cos-7 cells were co-transfected with pPR$_{WT}^{CFP}$ and pPR$_{WT}^{YFP}$ in the presence of the nucleoside and non-nucleoside reverse transcriptase inhibitors (b) zidovudine, (c) lamivudine, (d) abacavir, (e) nevirapine and (f) efavirenz, (g) CCR5 inhibitor aplaviroc, and soluble (h) CD4, and A/B ratios were determined. (D) Protease dimerization inhibition by DRV on Dual luciferase assay. Cos-7 cells were co-transfected with pACT-PR$_{WT}$, pBIND-PR$_{WT}$, and pG5luc in the absence (a) or presence of 0.1 μM (b) or 1.0 μM (c) of DRV, cultured for 48 hrs, and the intensity of firefly luminescence (Fluc) and Renilla luminescence (Rluc) was measured with TR717 microplate luminometer. DRV was added to the culture medium simultaneously with plasmids to be used. Fluc/Rluc intensity ratios were determined with co-transfection of pACT-PR$_{WT}$, pBIND-PR$_{WT}$, and pG5luc in the absence of DRV, serving as maximal values.

Assay results. Compounds described herein blocked the dimerization of HIV protease subunits. FIG. 2C shows representative 6 such compounds (TMC114, TMC126, GRL-06579A, GRL-98065, GRL-0036A, and GRL-0037A). All of these 6 compounds were potent against HIV-1$_{LAI}$ in vitro with 0.0003 to 0.003 μM. When the cells were exposed to each compound and transfected with the wild-type plasmids, the ratios were significantly less than in the control cells transfected with the plasmids without drug exposure, indicating that the dimerization was effectively blocked by these agents. To corroborate the above observation, a dose-response was determined, and the dimerization inhibition could be seen when the cells were exposed to various concentrations of TMC114. As shown in FIG. 2D, TMC114 effectively blocked FRET at concentrations of 0.1 to 10 μM, while the value with 0.001 μM was greater than 1, indicating that FRET occurred, and the value with 0.01 μM was close to 1.0, the threshold. In addition, a TMC126-congener GRL-0026A (FIG. 1) was examined that is substantially less potent than TMC126 against HIV-1 with IC$_{50}$ of 0.48 μM, along with TMC126 and BCV for their dose response dimerization inhibition in the FRET-HIV-1 assay and found that the inhibition was similarly dose-responsive (FIG. 9A).

Figure 2E:
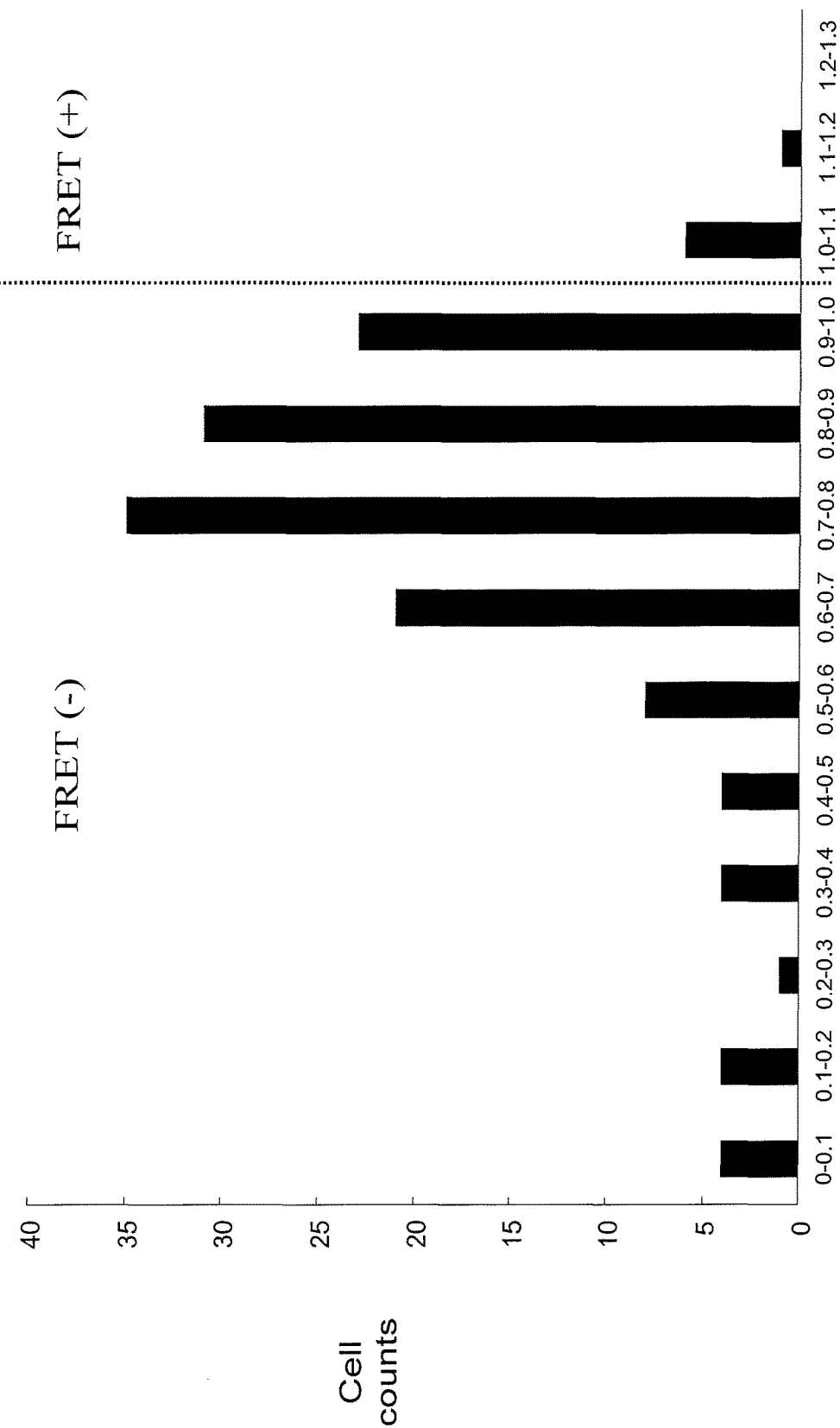
FIG. 2E shows the cell distribution of FRET ratio for 143/173 cells treated with 1 µM TMC114; Average CFP 0.73±0.17 (n=143). Distribution of the values of intensity values (ECFP fluorescence after photobleaching/ECFP fluorescence before photobleaching) in the presence of 1 µM TMC114. One hundred seventy three cells were examined and the ratio values were plotted, derived from seven independent experiments. The average ratio value was 0.73 (±0.22) and indicates that TMC114 blocked protease dimerization. All the determinations were conducted in a double-blind fashion.
Figure 2F:
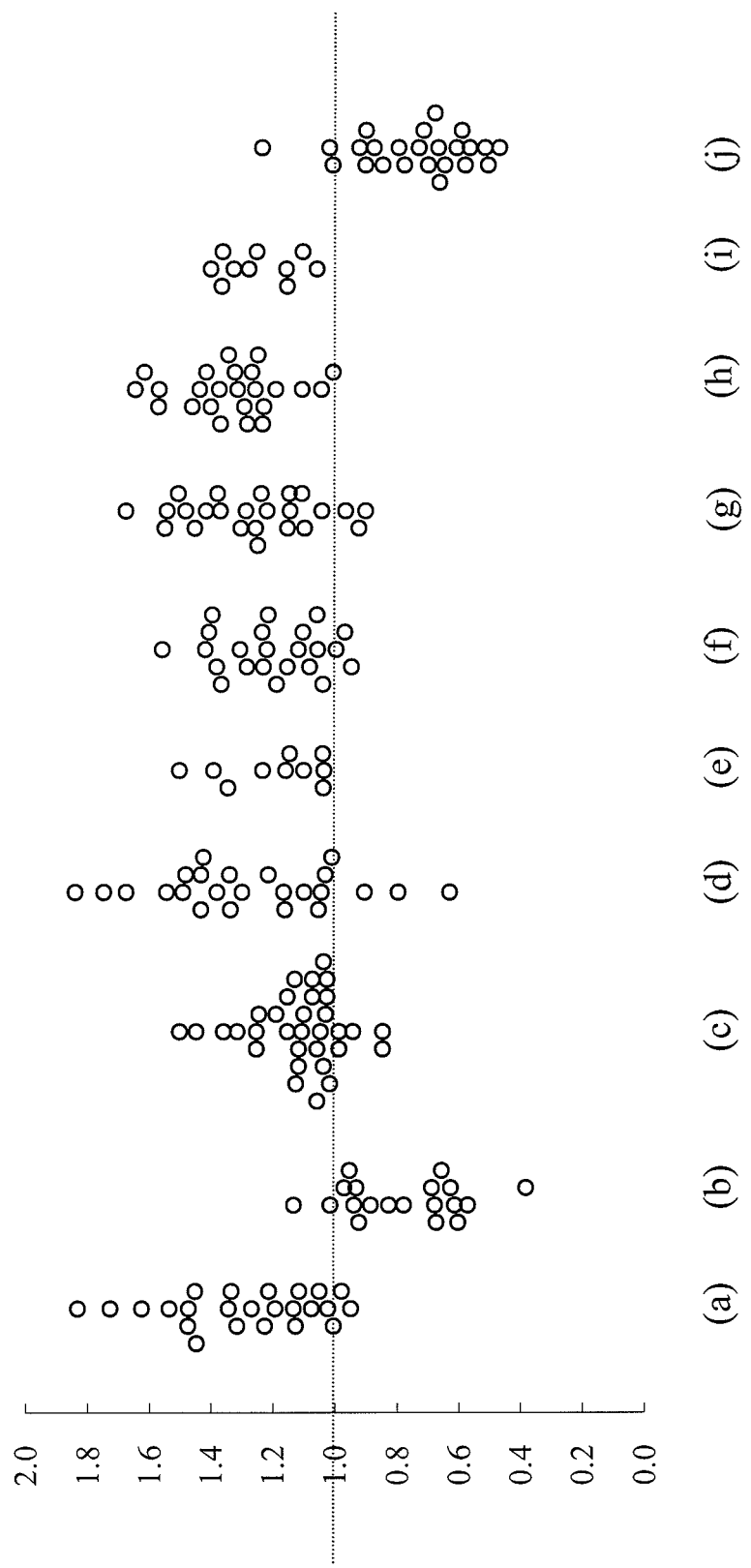
FIG. 2F shows the FRET ratio results for 9 known HIV drugs, each administered at 1 µM, in inhibiting protease dimerization; (a) No drug (1.29±0.24); (b) TMC114 (0.78±0.19); (c) SQV (1.11±0.15); (d) NFV (1.27±0.30); (e) APV (1.20±0.17); (f) IDV (1.21±0.17); (g) RTV (1.27±0.21); (h) LPV (1.34±0.17); (i) ATZ (1.25±0.12); (j) TPV (0.75±0.19). All existing clinically available protease inhibitors except tipranavir (TVP) failed to inhibit the dimerization of CFP- and YFP-tagged protease subunits. Cos-7 cells were co-transfected with NL-PRwt-ECFP and NL-PRwt-EYFP in the presence of various anti-HIV-1 agents (FIG. 9C). (a) no drug, (b) Azidothymidine (AZT, 1 µM), (c) lamivudine (3TC, 10 µM), (d) abacavir (ABC, 10 µM), (e) nevirapine (NVP, 1 µM), (f) efavirenz (EFV, 1 µM), and (g) aplaviroc (1 µM) failed to inhibit the dimerization of protease subunits. Soluble CD4 (h) (sCD4) also failed to inhibit the dimerization at 5 mg/ml.
Figure 3:
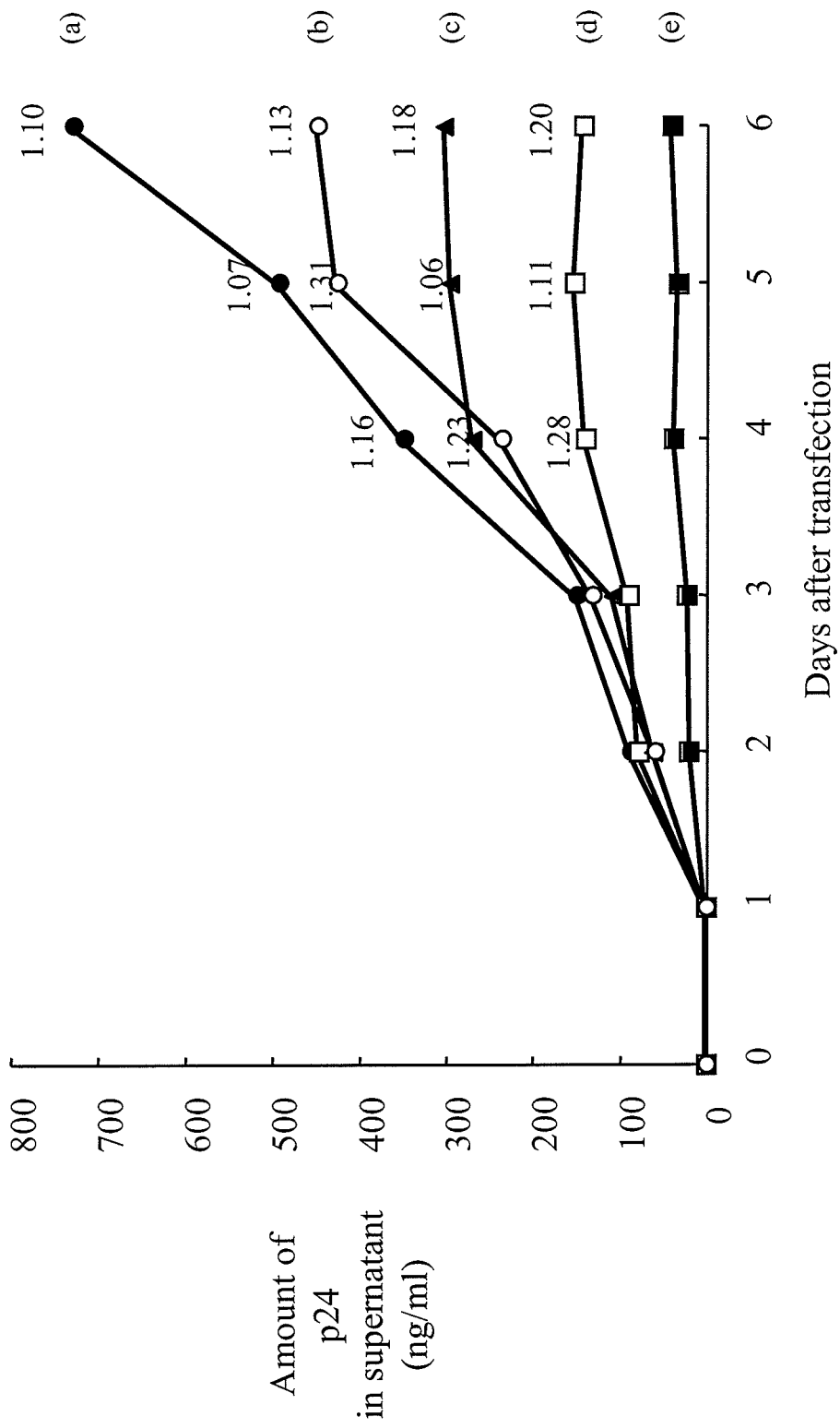
FIG. 3 shows the effect of TMC114 on pre-dimerized HIV protease; (a) No drug; (b) day4-chx-day5 TMC114 1 µM; (c) day3-chx-days TMC114 1 µM; (d) day2-chx-day5 TMC114 1 µM; (e) day1-chx 50 ug/ml. Once dimerization has occurred, the compounds tested did not appear to reverse the dimerization in cells producing infectious HIV-1 virions. Cos-7 cells were co-transfected with two plasmids, pNL-PRwt-CFP and pNLPRwt-YFP (also referred to as pPRwt-CFP and pPRwt-YFP, respectively), exposed to cycloheximide (50 mg/ml) in 24, 48, 72, and 96 hrs of culture and beyond. Cellular protein synthesis was monitored every 24 hours by determining levels of p24 Gag protein produced into culture medium using the fully automated chemiluminescent enzyme immunoassay system (Lumipulse F; Fujirebio Inc., Tokyo, Japan). The cells were exposed to TMC114 (1 µM) on day 5 and beyond of culture and analyzed under Fluoview FV500 confocal laser scanning microscope (OLYMPUS Optical Corp) at room temperature.
Figure 9B:
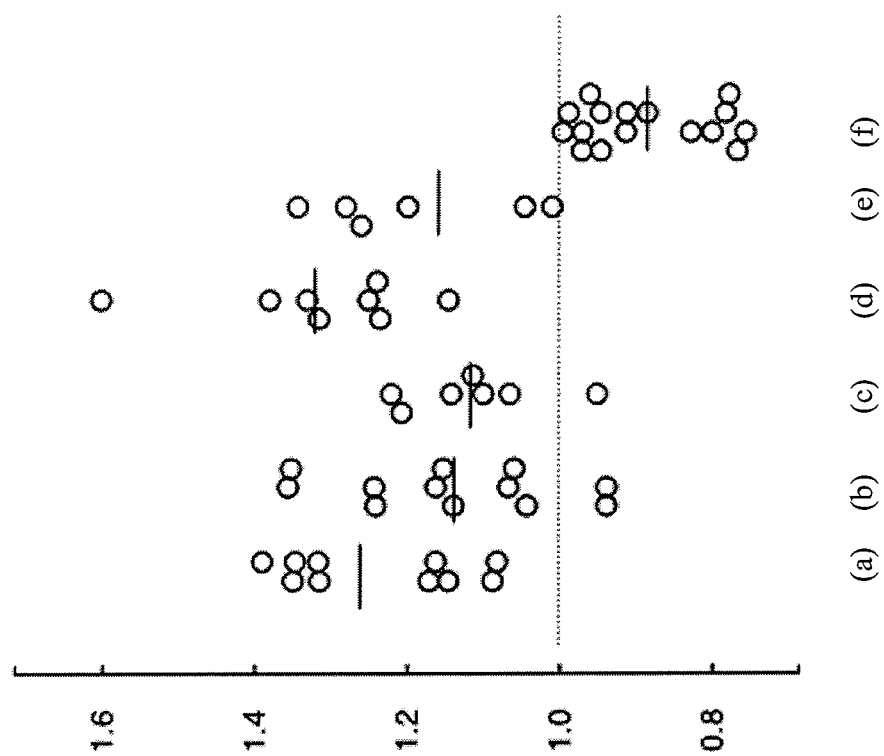
Figure 9C:
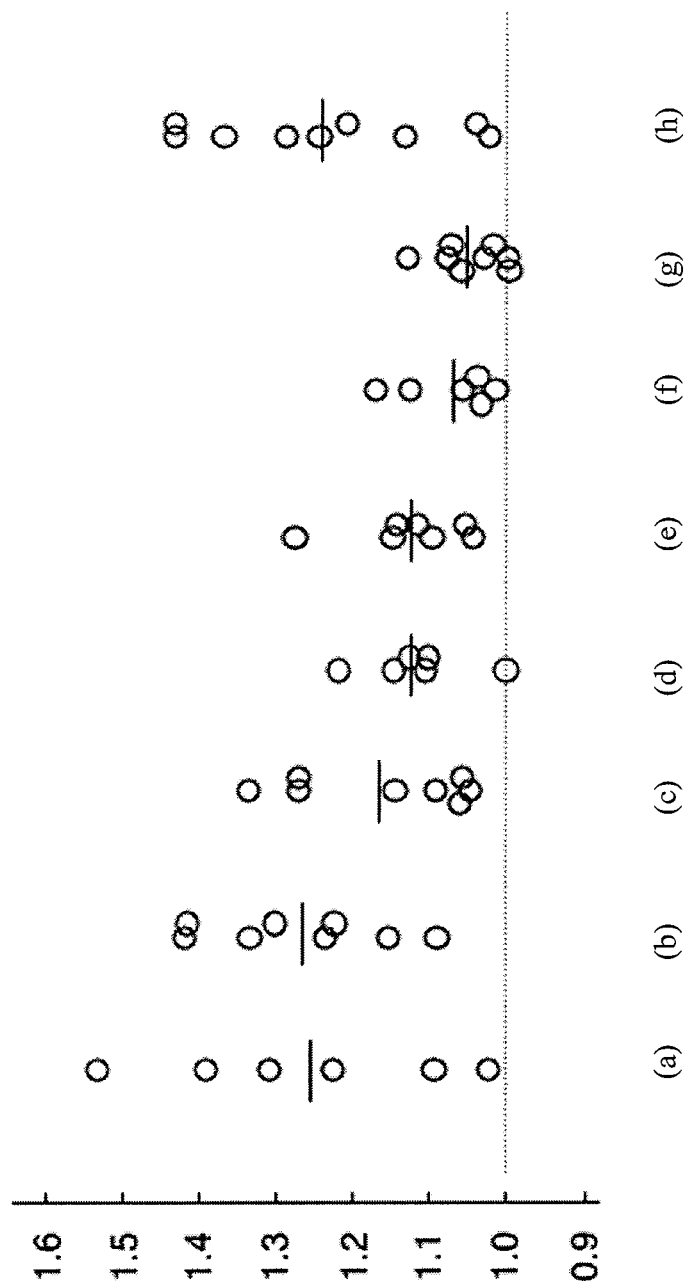

Inhibition of protease dimerization by non-peptidyl and peptidyl compounds. After establishing the validity of the FRET-HIV-1 assay to detect protease dimerization inhibition, we evaluated various newly generated non-peptidyl small molecule agents including the currently available anti-HIV-1 drugs for their ability to inhibit protease dimerization in a blind manner, where agents examined were identified only under code in conducting the FRET-HIV-1 assay. Six different non-peptidyl small molecule agents [GRL-0036A, GRL-06579A (Ghosh et al. *J Med Chem* 49(17):5252-5261), TMC126 (Yoshimura et al. *J Virol* 76(3):1349-1358)), GRL-98065 (Amano et al. *Antimicrob Agents Chemother* In Press), DRV (Koh et al. *Antimicrob Agents Chemother* 47(10):3123-3129 (2004)), and brecanavir (BCV) (Miller et al. *Bioorg Med Chem Lett* 16(7):1788-1794 (2006)); M.W., ranging 547-704: FIG. 1] were found to disrupt protease dimerization at concentration of 1 μM in the assay (FIG. 2C). All of these agents had potent inhibitory activity against HIV-1 protease with Ki values of 29, 3.5, 10, 14, 16, and 6.8 pM, respectively, as examined in the assay previously described (Kovalevsky et al. *J Mol Biol* 363(1): 161-173 (2006), Ghosh et al. *J Med Chem* 49(17):5252-5261), and were highly potent against HIV-1$_{LAI}$ in acute HIV-1 infection assays using target CD4$^+$ MT-2 cells (19) with IC$_{50}$ values of 0.0002 to 0.005 μM (See each IC$_{50}$ value in the legend to FIG. 1). In addition to small molecule agents, we examined various peptides in the FRET-HIV-1 assay. A 27-amino acid peptide containing the dimer interface sequences amino acids 1-5 and amino acids 95-99 (P27:PQITLRKKRRQRRRPPQVSFNFATLNF), (SEQ ID NO:81) which blocks HIV-1 infectivity and replication as a peptidyl protease dimerization inhibitor (Davis et al. *Antiviral Res* 72(2):89-99 (2006)), also inhibited protease dimerization. Another peptide P9 (RKKRRQRRRP-PQVSFNF) (SEQ ID NO:82) that lacks the dimer interface sequences and is not active against HIV-1 (Davis et al. *Antiviral Res* 72(2):89-99 (2006)) failed to inhibit protease dimerization in the FRET-HIV-1 assay. These data again corroborated the utility of the assay to evaluate protease dimerization. The distribution of the values of the ratio in a total of 143 cells was further examined (FIG. 2E), resulting in confirming that the deviation was appreciably small with the average ratio of 0.73±0.17, the data are highly reproducible and the data support a theory that TMC114 blocks the protease dimerization. These data, taken together, indicate that there was a dose response in TMC114's FRET blockade in this assay. None of 7 known PIs (saquinavir, nelfinavir, amprenavir, indinavir, ritonavir, lopinavir, and atazanavir) inhibited protease dimerization at 1 μM concentration, while only TMC114 and tipranavir blocked the dimerization as shown in FIG. 2F. Further, nucleoside and non-nucleoside reverse transcriptase inhibitors (zidovudine, lamivudine, abacavir, nevirapine and efavirenz), CCR5 inhibitor aplaviroc (Maeda, 2004), and soluble CD4 did not block the dimerization of protease. Considering that DRV is generally more potent against HIV-1 in vitro than most currently existing PIs (Koh et al. *Antimicrob Agents Chemother* 47(10):3123-3129 (2004)), four PIs (saquinavir, amprenavir, nelfinavir, and atazanavir) were examined in the FRET-HIV-1 assay at a higher concentration, 10 μM, however, none of these 4 PIs inhibited protease dimerization (FIG. 9B).

Dissociation of already formed dimer. TMC114 was examined for its ability to dissociate the protease once dimerized within cells producing infectious HIV-1 virions. Cos-7 cells were co-transfected with wild-type pNLPR-CFP and -YFP plasmids, exposed to cycloheximide (50 μg/mL) in 24, 48, 72, and 96 hrs of culture and beyond, the cells exposed to 1 μM TMC114 on day 5 of culture and beyond, cellular protein synthesis was monitored every 24 hours by determining levels of p24 Gag protein produced into culture medium, and the values of the ratio were determined at various time points. When the cells were treated with cycloheximide on day 1, no p24 Gag protein was seen in the medium. In contrast, the cells were exposed on day 2 and beyond significant amounts of p24Gag protein were produced. Even when TMC114 was added to the culture on day 5, no inhibition of FRET was detected when the cells were examined on day 6 of culture (FIG. 4). These data suggest that dadrunavir (TMC114) does not dissociate the protease once dimerized with the cells producing infectious HIV-1 virions.

Analysis of inter- and intra-molecule interactions of protease subunits. Analysis of inter- and intra-molecule interactions of protease subunits was conducted by employing the crystal structure of DRV with HIV-1 protease (PDB ID: 1S6G). Hydrogens were added, and minimized using OPLS2005 force field with constraints on heavy atom positions. The calculation was performed using MacroModel 9.1 from Schrödinger, LLC. Hydrogen bonds were assigned when the following distance and angle cut-off was satisfied: 3.0 Å for H-A distance; D-H-A angle greater than 90°; and H-A-B angle greater than 60° where H is the hydrogen, A is the acceptor, D is the donor, and B is a neighbor atom bonded to the acceptor. The representative distance between the termini of two monomers was determined by analyzing the protease-DRV crystal structure (PDB ID: 1 S6G). The distance between the alpha carbons at the N-termini and C-termini is around 0.5 nm while distance between the alpha carbons of the N-termini ends of two monomers is around 1.8 nm.

FRET efficiency. Cos-7 cells plated on EZ view coverglass bottom culture plate (IWAKI, TOKYO, JAPAN) were transfected with the indicated plasmid constructs using Lipofectamine 2000 (Invitrogen, Carlsbad, Calif.) according to manufacturer's instructions in the presence of various concentrations of each compound, cultured for 48 to 72 hrs, and analyzed under confocal microscopy Fluoview FV500 confocal laser scanning microscope (OLYMPUS Optical Corp, Tokyo) at room temperature. When the effect of each compound was analyzed by FRET, test compounds were added to the culture medium simultaneously with plasmid transfection.

Results of FRET were determined by quenching of CFP (donor) fluorescence and an increase in YFP (acceptor) fluorescence (sensitized emission), since part of the energy of CFP is transferred to YFP instead of being emitted. This phenomenon can be measured by bleaching YFP, which should result in an increase in CFP fluorescence. This technique, also known as acceptor photobleaching, is a well-established method of determining the occurrence of FRET. Dequenching of the donor CFP by selective photobleaching of the acceptor YFP was performed by first obtaining YFP and CFP images at the same focal plane, followed by illuminating for 3 min the same image at wavelength of 488 nm with a laser power set at the maximum intensity to bleach YFP and re-capturing the same CFP and YFP images. The changes in the CFP and YFP fluorescence intensity in the images of selected regions were examined and quantified using Olympus FV500 Image software system (OLYMPUS Optical Corp). Background values were obtained from the regions where no cells were present and were subtracted from the values for the cells examined in all calculations. For each chimeric protein, the data were obtained from at least three independent experiments. Digitized image data obtained from the experiment were prepared for presentation using Photoshop 6.0 (Adobe Systems, Mountain View, Calif.). Ratios of intensities of CFP fluorescence after photobleaching to CFP fluorescence prior to photobleaching (CFP$^{A/B}$ ratios) were determined. It is well established that the CFP$^{A/B}$ ratios of greater than 1.0 indicate that association of CFP and YFP-tagged proteins occurred, and it was interpreted that the dimerization of protease subunits occurred. When the CFP$^{A/B}$ ratios were less than 1 indicate that the association of the two subunits did not occur and it was interpreted that protease dimerization was inhibited.

Figure 9D:
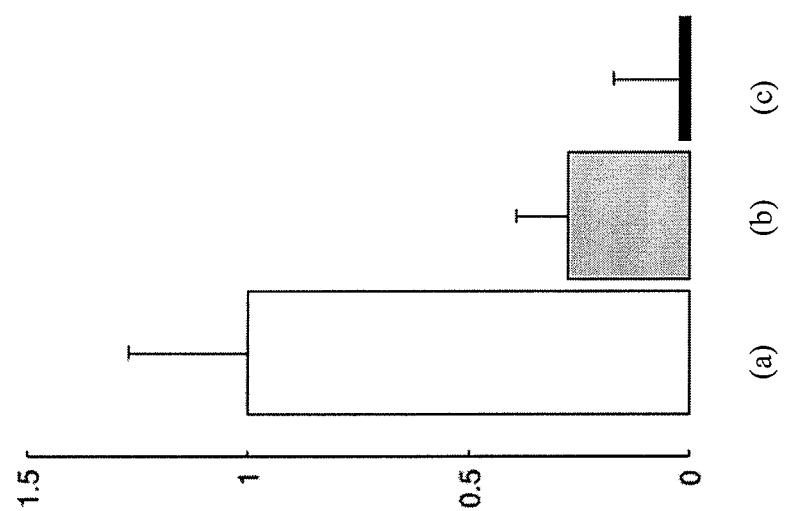

Darunavir blocks protease dimerization as examined in dual luciferase assay. This invention also established a dual luciferase assay using the CheckMate™ Mammalian Two-Hybrid System in order to examine whether DRV blocked protease dimerization in a different assay system. We generated pACT-PRwt, producing PRwt whose N-terminus is connected to the herpes simplex virus VP16 activation domain; and pBIND-PRwt, producing PRwt whose N-terminus is connected to GAL4 DNA-binding domain. In this system, interactions between two different PRwt result in an increase in firefly luciferase expression produced by the pG5luc vector. In addition, the pBIND vector expresses *Renilla* luciferase under the control of the SV40 promoter, allowing the user to normalize for the differences in transfection efficiency. Thus, when VP 16 and GAL4 closely interact upon protease dimerization, the ratio of the intensity of firefly luminescence (Fluc) over that of *Renilla* luminescence (Rluc) increases, and its decrease indicates the disruption of protease dimerization. As shown in FIG. 9D, in the presence of 0.1 and 1 µM of DRV, the relative response ratios significantly decreased, further corroborating that DRV blocks protease dimerization.

Described herein is an intermolecular fluorescence resonance energy transfer (FRET)-based HIV-1-expression assay has been developed that employed cyan or yellow fluorescent protein-tagged HIV-1 protease monomers. Using this assay, a group of non-peptidyl small molecule inhibitors of HIV-1 protease dimerization (M.W. 547-704) was identified. Dimerization of HIV-1 protease subunits is an essential process for the acquisition of proteolytic activity of HIV-1 protease, which plays a critical role in the replication cycle of HIV-1. Hence, the inhibition of dimerization of HIV-1 protease subunits represents a unique target for potential intervention of HIV-1 replication.

The strategy to target protease dimerization as a possible anti-HIV-1 modality has been explored (Bowman et al. Chem Biol 12(4):439-444 (2005); Frutos et al. Biopolymers 88(2):164-173 (2007); Bannwarth et al. J Med Chem 49(15): 4657-4664 (2006); Levy et al. J Mol Biol 340(1):67-69 (2004)) and certain compounds have been reported as potential protease dimerization inhibitors. However, no direct evidence of dimerization inhibition by such compounds has been documented. The present report represents the first demonstration that non-peptidic small molecule agents can disrupt protease dimerization. The structural feature that is in common to the four dimerization inhibitors [TMC126 (Yoshimura et al. J Virol 76(3):1349-1358), GRL-98065 (Amano et al. Antimicrob Agents Chemother In Press), DRV (Koh et al. Antimicrob Agents Chemother 47(10):3123-3129 (2004)), and BCV (Miller et al. Bioorg Med Chem Lett 16(7):1788-1794 (2006))] is that all of these agents contain the structure-based designed privileged cyclic ether-derived non-peptidyl P2 ligand, 3(R),3a(S),6a(R)-bis-tetrahydrofuranylurethane (bis-THF) and a sulfonamide isostere (17, 18). GRL-0036A and GRL-06579A (21) have bis-THF-related ligand instead of bis-THF. Crystallographic data of dimerized protease complexed with three DIs [GRL-98065 (Amano et al. Antimicrob Agents Chemother. In press (2007))), TMC-126 (unpublished), and DRV (Tie et al. J Mol Biol 338(2):341-352 (2004))] have revealed that bis-THF forms three tight hydrogen bond interactions with Asp-29 and Asp-30, two highly conserved catalytic site amino acids.

TPV has the ability to disrupt protease dimerization. TPV, which does not possess the bis-THF component, also has interactions with both Asp-29 and Asp-30, through its pyridinesulfonamide group, as shown in crystallographic analysis of a dimerized protease complexed with TPV (Thaisrivongs et al. J Med Chem 39(22):4349-4353 (1996)). Thus, the inhibition of protease dimerization is not inherent only to the bis-THF component. It is of note that the D30N-carrying HIV-1 variant is infectious and replication-competent (Patick et al. Antimicrob Agents Chemother 40(2):292-297 (1996)). Structural studies do not show any hydrogen bond interactions between two monomer proteases mediated through Asp-30, and the FRET-HIV-1 expression assay showed that D30N mutant did not disrupt protease dimerization. Without being bound by theory, it is believed that this observation suggests that Asp-30 is not a critical residue for disrupting protease dimerization, and the potential interaction of these inhibitors with Asp-30 is not linked to the observed dimerization inhibition. However, potential interactions involving Asp-29 could be critical since D29N and D29A mutations disrupted protease dimer formation (FIG.

Figure 8B:
Figure 8C:
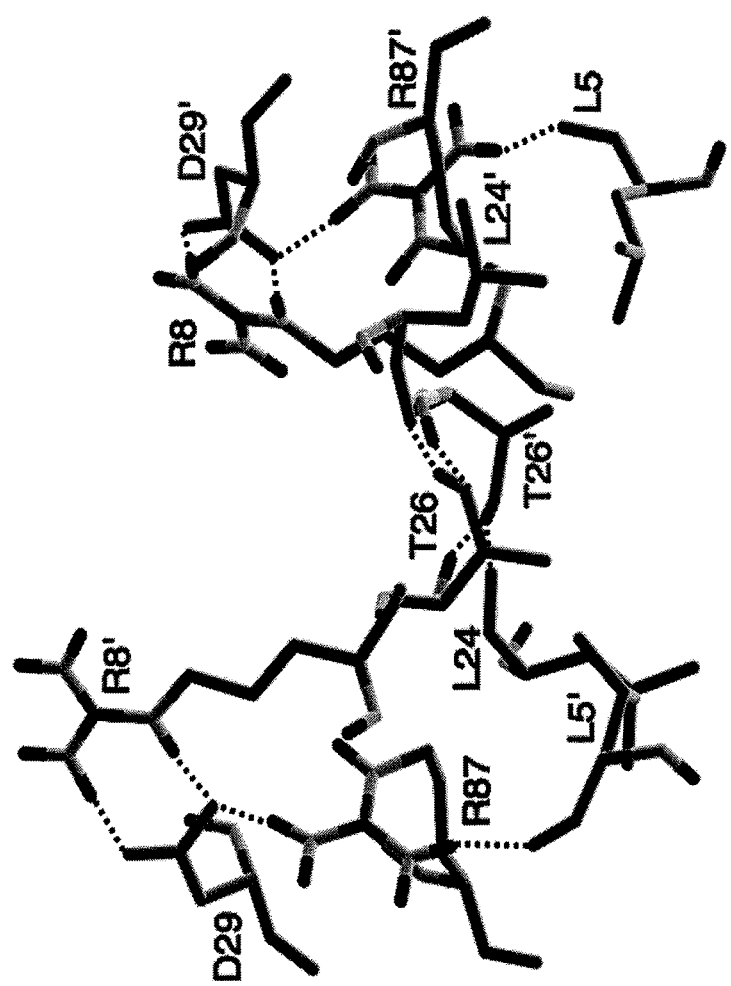
Figure 8D:
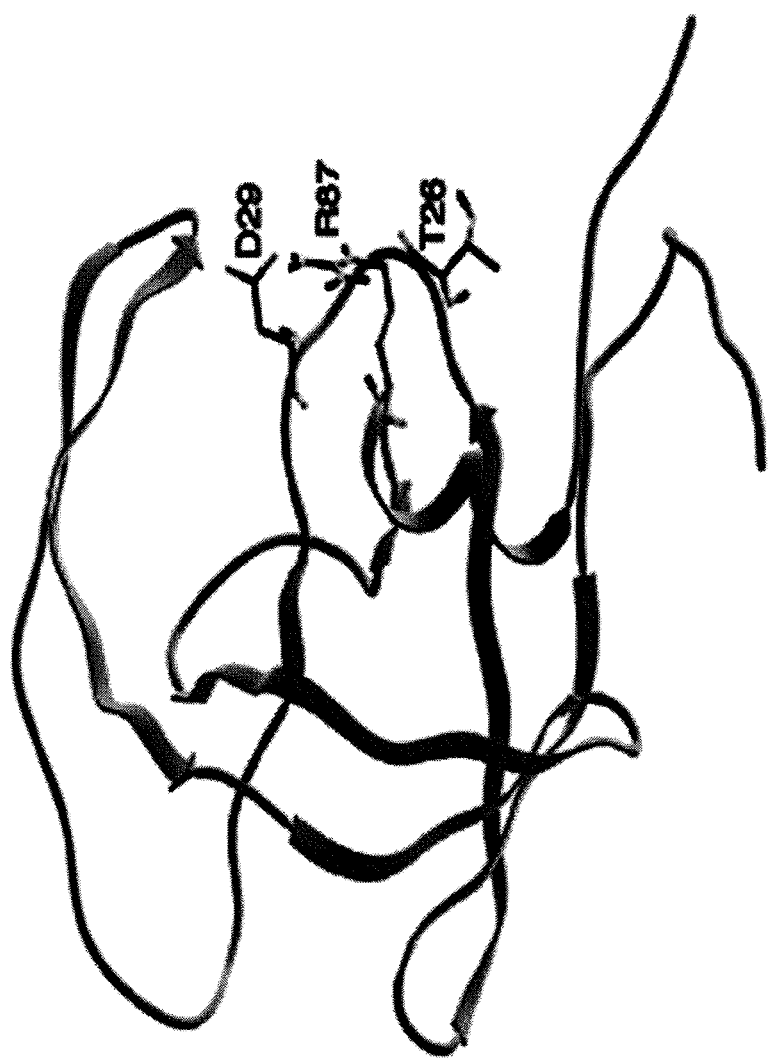

2B). The analysis described herein using the FRET-HIV-1 expression assay revealed that the introduction of T26A and R87K to HIV-1 protease also disrupted protease dimerization (the average CFPA/B ratios were all <1.0; FIG. 2B). If the protease monomer takes a configuration comparable to that in the dimerized protease, it is possible that the hydrogen bonding of the inhibitors with Asp-29, and/or with Thr-26 and Arg-87 which are in the vicinity of Asp-29 and could be critical for dimerization, could be associated with the disruption of dimerization process through affecting the intermolecular and/or intramolecular hydrogen bond network (FIG. 8B-D). In this regard, Ishima et al. have shown that a truncated protease monomer takes a configuration similar to the one in the mature dimerized protease (Ishima et al. J Biol Chem 278(44):43311-43319 (2003)); however, it is unknown whether the untruncated monomer subunit takes a similar mature configuration. Furthermore, it is not known as to what stage of protease maturation (before dimerization) the dimerization inhibitors reported here bind to the monomer subunit.

Another possible mechanism of the dimerization inhibition by the agents reported here is that they might interact with another dimerization interface formed by an interdigitation of the N- and C-terminal portions of each monomer (residues 1-5 and 95-99; FIG. 8A). In this regard, when a Pro-1 to Ala substitution was introduced as follows (P1A), Q2A, I3A, T4A, L5A, T96A, L97A, N98A, or F99A substitution into the replication-competent HIV-1NL4-3, five substitutions (I3A, L5A, T96A, L97A, and F99A) disrupted protease dimerization. These data confirmed the five amino acids at the amino-terminus and those at the carboxyl-terminus are critical for protease dimerization (Ishima et al. J Biol Chem 278(44):43311-43319 (2003); Ishima J Biol Chem 276(52):49110-49116 (2001); Louis et al. J Biol Chem 278(8):6085-6092 (2003)).

There are no polar interactions involving Q2A or T4A, so it is not surprising that these mutations did not affect dimer formation. However, the failure of P1A and N98A to disrupt dimerization does not necessarily indicate that these amino acids are not critical for protease dimerization. It is suggested herein that conversion to a residue other than alanine may disrupt dimerization. DRV failed to dissociate mature protease dimer (FIG. 5). The mature dimerized protease has as many as 12 hydrogen bonds in the N- and C-terminal region, which may explain in part why DRV failed to dissociate two subunits of mature protease. These data also suggest that protease dimerization is inhibited before the association of two protease subunits occurs probably when protease is in the form of nascent Gag-Pol polyprotein. However, the absence of structural data of nascent forms of protease subunit-containing polyprotein makes it difficult to conclusively predict how the dimerization inhibitors inhibit protease dimerization.

The D25N substitution which is known to render HIV-1 protease enzymatically inactive (Prabu-Jeyabalan et al. J Virol 80(7):3607-3616 (2006)) failed to disrupt dimerization (FIG. 2B), showing that catalytically inactive subunits are still capable of undergoing dimerization. Thus, this observation indicates that the dimerization inhibition is a differing event than acquiring catalytic activity of two protease monomer subunits. DRV has a potent activity against a wide spectrum of HIV-1 isolates including highly multi-protease-inhibitor-resistant HIV-1 variants. The emergence of DRV-resistant HIV-1 seems to be substantially delayed both in vitro (De Meyer et al Antibmicrob Agents Chemother 49(6): 2314-2321 (2005)) and clinical settings (Poveda et al Aids 20(11):1558-1560 (2006); Youle et al. HIV Clin Trials 7(2):86-96 (2006)).

It is further suggested that DRV inhibits protease dimerization, leaving catalytically inert monomers, but if certain monomers escape from DRV and achieve the mature dimer form, DRV again blocks the proteolytic action of mature protease as a conventional protease inhibitor. This dual anti-HIV-1 function of DRV may explain why DRV is such a highly effective anti-HIV-1 therapeutic and differentiates it from many of the currently available protease inhibitors (Poveda et al Aids 20(11):1558-1560 (2006); Youle et al. HIV Clin Trials 7(2):86-96 (2006)). The plasma concentrations of DRV achieved in those receiving DRV and ritonavir remain over 2 µg/ml or ~3.66 µM (Hoetelmans et al. 10th Conference on Tetroviruses and Opportunistic Infections (CRO1), February 10-14, 549 (2003)-Abstract). These concentrations substantially exceed the concentration of DRV effectively disrupting protease dimerization (0.1 µM in culture as shown in FIG. 2C). Hence, the dimerization inhibition by DRV should be in operation in the clinical settings.

Furthermore, DRV could more efficiently disrupt protease dimerization in individuals with HIV-1 infection receiving DRV and ritonavir, since the protease expression levels upon transfection in this study appear to be considerably greater than the protease expression levels in vivo, considering that the p24 production levels could be as high as 500-1500 ng/ml by 5 days following transfection of Cos-7 cells with plasmids used in the FRET-HIV-1 expression assay. The inhibition of HIV-1 protease dimerization by non-peptidyl small molecule agents represents a unique mechanism of HIV-1 intervention and the dually functional inhibitors reported here might serve as potential candidates as a new class of therapeutic agents for HIV-1 infection and AIDS.

What is claimed is:

1. A method for treating a patient with HIV, AIDS, or an AIDS-related disease, the method comprising administering to the patient a therapeutically effective amount of at least one compound having protease dimerization inhibitory activity and protease inhibitory activity, wherein the compound is:

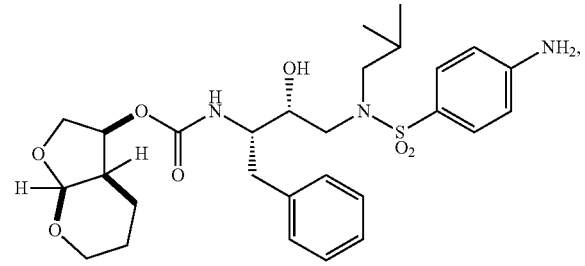

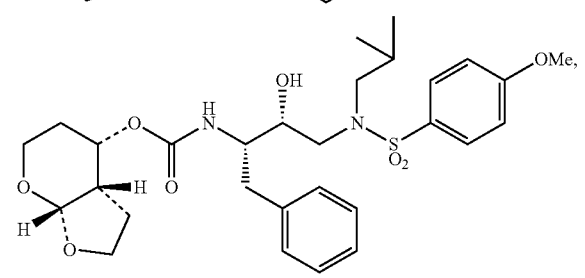

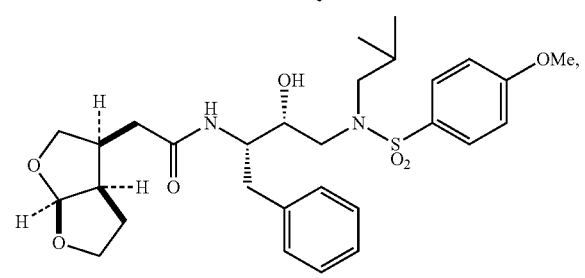

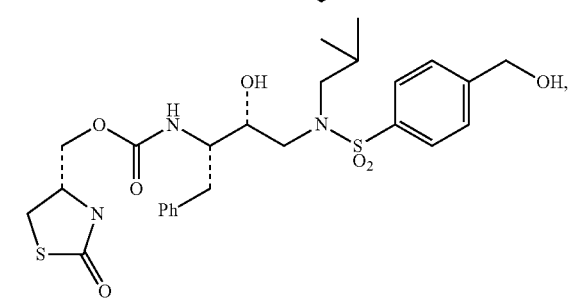

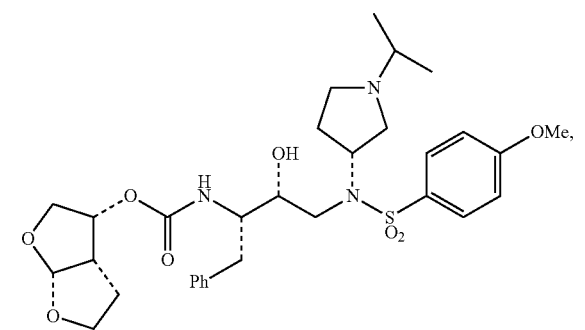

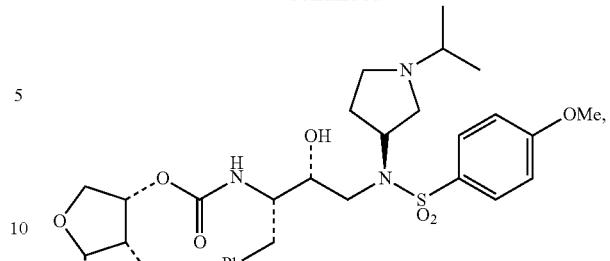

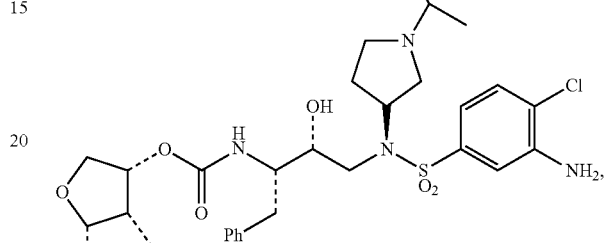

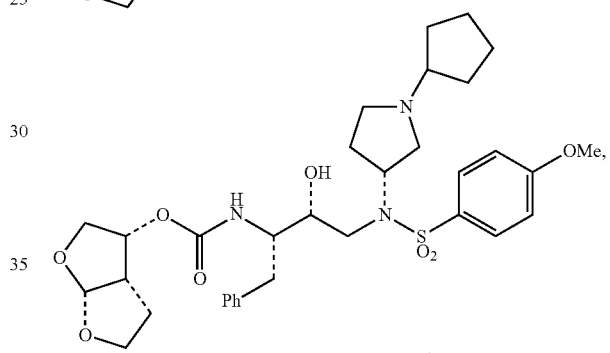

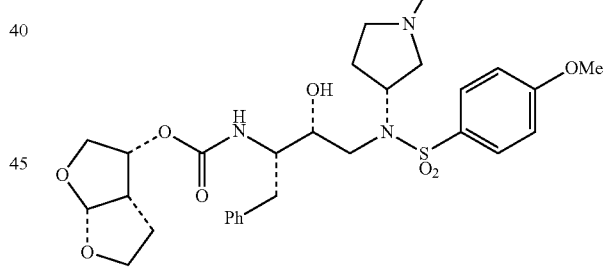

or

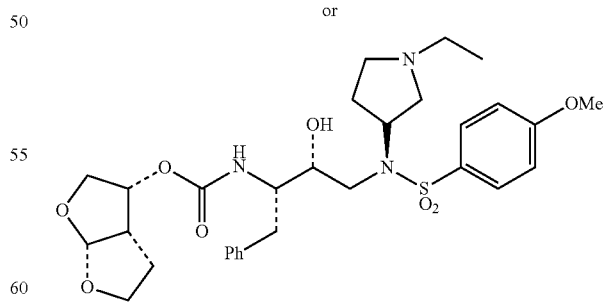

and pharmaceutically acceptable salts thereof.

2. The method of claim 1, wherein the compound having protease dimerization inhibitory activity and protease inhibitory activity is the sole therapeutic agent.

* * * * *